US010479983B2

(12) United States Patent
Douglas et al.

(10) Patent No.: US 10,479,983 B2
(45) Date of Patent: Nov. 19, 2019

(54) VARIANT ENZYMES

(71) Applicant: DANISCO US INC, Palo Alto, CA (US)

(72) Inventors: Nicholai Douglas, Menlo Park, CA (US); Maria Foukaraki, Rotterdam (NL); Ronaldus Wilhelmus Hommes, Haarlem (NL); Thijs Kaper, Half Moon Bay, CA (US); Bradley R. Kelemen, Menlo Park, CA (US); Slavko Kralj, Oegstgeest (NL); Suzanne E. Lantz, San Carlos, CA (US); Jonathan K. Lassila, San Francisco, CA (US); Igor Nikolaev, Noordwijk (NL); Daniel Esteban Torres-Pazmino, Leiden (NL); Wilhelmus Van Der Kley, The Hague (NL); Johannes Franciscus Thomas Van Lieshout, Utrecht (NL); Sander Van Stigt Thans, Zevenbergen (NL)

(73) Assignee: DANISCO US INC, Palo Alto, CA (US)

( * ) Notice: Subject to any disclaimer, the term of this patent is extended or adjusted under 35 U.S.C. 154(b) by 683 days.

(21) Appl. No.: 14/909,041

(22) PCT Filed: Jul. 24, 2014

(86) PCT No.: PCT/US2014/048067
§ 371 (c)(1),
(2) Date: Jan. 29, 2016

(87) PCT Pub. No.: WO2015/017254
PCT Pub. Date: Feb. 5, 2015

(65) Prior Publication Data
US 2016/0186155 A1   Jun. 30, 2016

Related U.S. Application Data

(60) Provisional application No. 61/859,630, filed on Jul. 29, 2013, provisional application No. 61/859,666, filed on Jul. 29, 2013, provisional application No. 61/859,680, filed on Jul. 29, 2013, provisional application No. 61/859,704, filed on Jul. 29, 2013, provisional application No. 61/859,712, filed on Jul. 29, 2013, provisional application No. 61/859,721, filed on Jul. 29, 2013, provisional application No. 61/859,735, filed on Jul. 29, 2013.

(51) Int. Cl.
| | |
|---|---|
| *C12N 9/14* | (2006.01) |
| *C12N 15/09* | (2006.01) |
| *C12N 9/42* | (2006.01) |
| *C12N 9/02* | (2006.01) |
| *C12P 19/02* | (2006.01) |
| *C12P 19/14* | (2006.01) |
| *C12N 9/24* | (2006.01) |
| *A61K 38/00* | (2006.01) |

(52) U.S. Cl.
CPC ........ *C12N 9/2437* (2013.01); *C12N 9/0083* (2013.01); *C12N 9/2402* (2013.01); *C12N 9/2434* (2013.01); *C12P 19/02* (2013.01); *C12P 19/14* (2013.01); *C12Y 302/01004* (2013.01)

(58) Field of Classification Search
None
See application file for complete search history.

(56) References Cited

U.S. PATENT DOCUMENTS

| | | | |
|---|---|---|---|
| 4,435,307 A | 3/1984 | Barbesgaard et al. | |
| 5,246,853 A | 9/1993 | Clarkson et al. | |
| 5,648,263 A | 7/1997 | Schulein et al. | |
| 5,691,178 A | 11/1997 | Schulein et al. | |
| 5,776,757 A | 7/1998 | Schulein et al. | |
| 5,874,276 A | 2/1999 | Fowler et al. | |
| 6,268,196 B1 | 7/2001 | Fowler et al. | |
| 6,407,208 B1 | 6/2002 | Chen et al. | |
| 6,562,340 B1 | 5/2003 | Bedford et al. | |
| 6,620,605 B2 | 9/2003 | Fowler et al. | |
| 7,005,128 B1 | 2/2006 | Bedford et al. | |
| 8,715,647 B2 | 5/2014 | Bedford et al. | |
| 8,877,474 B2 | 11/2014 | Yang et al. | |
| 9,145,569 B2 | 9/2015 | Brown et al. | |
| 10,081,802 B2 * | 9/2018 | Foukaraki | C12N 9/2434 |
| 2002/0164774 A1 | 11/2002 | Fowler et al. | |
| 2006/0005279 A1 | 1/2006 | Dotson et al. | |

(Continued)

FOREIGN PATENT DOCUMENTS

| | | |
|---|---|---|
| CA | 2818659 A1 | 7/2012 |
| CN | 103966252 A | 8/2014 |

(Continued)

OTHER PUBLICATIONS

NCBI reference (2018, updated) "Trichoderma saturnisporum type IV endoglucanase mRNA",\ www.ncbi.nlm.nih.gov/nuccore/GU290062, pp. 1-2.*

(Continued)

*Primary Examiner* — Paul J Holland
*Assistant Examiner* — Samuel W Liu

(57) ABSTRACT

Disclosed are glycosyl hydrolase enzyme variants, particularly variants of certain oxidoreductases of glycosyl hydrolase family 61. Nucleic acids encoding the glycosyl hydrolyase variants, compositions including the glycosyl hydrolase variants, methods of producing the variants, and methods of using the variants are also described.

4 Claims, 5 Drawing Sheets
Specification includes a Sequence Listing.

(56) References Cited

U.S. PATENT DOCUMENTS

| | | |
|---|---|---|
| 2006/0193897 A1 | 8/2006 | Bedford et al. |
| 2007/0077630 A1 | 4/2007 | Harris et al. |
| 2010/0003367 A1 | 1/2010 | Francois et al. |
| 2010/0124769 A1 | 5/2010 | Brown et al. |
| 2011/0086236 A1 | 4/2011 | Catchmark et al. |
| 2011/0283421 A1 | 11/2011 | Harris et al. |
| 2012/0009300 A1* | 1/2012 | Schnorr ............... A21D 2/24 426/20 |
| 2012/0083019 A1* | 4/2012 | Baidyaroy ............. C12N 9/242 435/99 |
| 2013/0018172 A1 | 1/2013 | Stowell Laurence et al. |
| 2013/0052694 A1 | 2/2013 | Montalibet et al. |
| 2013/0052698 A1 | 2/2013 | Yang et al. |
| 2013/0143277 A1 | 6/2013 | Gutierrez et al. |
| 2013/0177947 A1 | 7/2013 | Bower et al. |
| 2013/0210086 A1* | 8/2013 | Vaaje-Kolstad .......... C12P 7/10 435/99 |
| 2013/0219568 A1 | 8/2013 | Sweeney et al. |
| 2013/0280764 A1 | 10/2013 | Emalfarb et al. |
| 2014/0099444 A1 | 4/2014 | Catchmark et al. |
| 2014/0099678 A1* | 4/2014 | Puranen ............... C12P 19/14 435/99 |
| 2014/0106408 A1 | 4/2014 | Mitchinson et al. |
| 2014/0134677 A1 | 5/2014 | Mitchinson et al. |
| 2015/0007369 A1* | 1/2015 | Lin ..................... C12N 9/0071 800/298 |
| 2015/0082493 A1 | 3/2015 | Lin et al. |
| 2015/0210991 A1 | 7/2015 | Schnorr et al. |
| 2015/0307562 A1 | 10/2015 | Basu et al. |
| 2015/0329841 A1 | 11/2015 | Hill et al. |
| 2016/0168550 A1 | 6/2016 | Foukaraki et al. |
| 2016/0177279 A1 | 6/2016 | Bower et al. |
| 2016/0177281 A1 | 6/2016 | Foukaraki et al. |
| 2016/0177283 A1 | 6/2016 | Brevnova et al. |
| 2016/0186155 A1 | 6/2016 | Foukaraki et al. |
| 2016/0201043 A1 | 7/2016 | Scott et al. |
| 2017/0088859 A1 | 3/2017 | Bosch Tubert et al. |
| 2017/0088869 A1 | 3/2017 | Quinlan et al. |
| 2017/0096651 A1 | 4/2017 | Mitchinson et al. |

FOREIGN PATENT DOCUMENTS

| | | |
|---|---|---|
| EP | 0137280 B1 | 3/1992 |
| EP | 2993230 A1 | 3/2016 |
| FR | 2957922 A | 9/2011 |
| GB | 1368599 A | 10/1974 |
| GB | 2094826 A | 9/1982 |
| GB | 2095275 A | 9/1982 |
| JP | 2006515506 A | 6/2006 |
| JP | 2009085831 A | 4/2009 |
| JP | 2009296958 A | 12/2009 |
| JP | 2010046034 A | 3/2010 |
| JP | 2012039968 A | 3/2012 |
| JP | 2012528598 A | 11/2012 |
| RU | 2378372 C2 | 9/2009 |
| WO | 9117244 A1 | 11/1991 |
| WO | 9206209 A1 | 4/1992 |
| WO | 9428117 A1 | 12/1994 |
| WO | 9516782 A1 | 6/1995 |
| WO | 9623928 A1 | 8/1996 |
| WO | 9720025 A1 | 6/1997 |
| WO | 0248350 A1 | 6/2002 |
| WO | 03052055 A2 | 6/2003 |
| WO | 03106490 A1 | 12/2003 |
| WO | 2004/016760 A2 | 2/2004 |
| WO | 2005030998 A2 | 4/2005 |
| WO | 2005074647 A2 | 8/2005 |
| WO | 2005074656 A2 | 8/2005 |
| WO | 2007095335 A2 | 8/2007 |
| WO | 2009035537 A1 | 3/2009 |
| WO | 2009117689 A1 | 9/2009 |
| WO | 2009132008 A2 | 10/2009 |
| WO | 2009138877 A2 | 11/2009 |
| WO | 2010005551 A2 | 1/2010 |
| WO | 2010059413 | 5/2010 |
| WO | 2010059424 A2 | 5/2010 |
| WO | 2010080407 | 7/2010 |
| WO | 2010080408 | 7/2010 |
| WO | 2010080532 A1 | 7/2010 |
| WO | 2010096673 A1 | 8/2010 |
| WO | 2010096931 A1 | 9/2010 |
| WO | 2010/141779 A1 | 12/2010 |
| WO | 2010138754 A1 | 12/2010 |
| WO | 2011000949 A1 | 1/2011 |
| WO | 2011038019 A2 | 3/2011 |
| WO | 2011047047 A2 | 4/2011 |
| WO | 2011069106 A1 | 6/2011 |
| WO | 2011094530 A2 | 8/2011 |
| WO | 2011097713 A1 | 8/2011 |
| WO | 2011117728 A2 | 9/2011 |
| WO | 2012000892 A1 | 1/2012 |
| WO | 2012006642 A1 | 1/2012 |
| WO | 2012019151 A1 | 2/2012 |
| WO | 2012024698 A1 | 2/2012 |
| WO | 2010/036810 A2 | 3/2012 |
| WO | 2012061382 A1 | 5/2012 |
| WO | 2012068509 A1 | 5/2012 |
| WO | 2012069593 A2 | 5/2012 |
| WO | 2012125925 A2 | 9/2012 |
| WO | 2012125937 A2 | 9/2012 |
| WO | 2012125951 A1 | 9/2012 |
| WO | 2012135719 A1 | 10/2012 |
| WO | 2012138772 A1 | 10/2012 |
| WO | 2012139086 A2 | 10/2012 |
| WO | 2012149344 A1 | 11/2012 |
| WO | 2013028701 A1 | 2/2013 |
| WO | 2013028927 A1 | 2/2013 |
| WO | 2013037933 A2 | 3/2013 |
| WO | 2013110242 A1 | 8/2013 |
| WO | 2013119302 A2 | 8/2013 |
| WO | 2013156443 A2 | 10/2013 |
| WO | 2013163590 A2 | 10/2013 |
| WO | 2013177714 A1 | 12/2013 |
| WO | 2014019219 A1 | 2/2014 |
| WO | 2014081884 A1 | 5/2014 |
| WO | 2014092832 A2 | 6/2014 |
| WO | 2014130812 A1 | 8/2014 |
| WO | 2014202711 A1 | 12/2014 |
| WO | 2014202716 A1 | 12/2014 |
| WO | 2015004098 A1 | 1/2015 |
| WO | 2015017254 A1 | 2/2015 |
| WO | 2015017255 A1 | 2/2015 |
| WO | 2015017256 A1 | 2/2015 |
| WO | 2015035029 A1 | 3/2015 |
| WO | 2015048332 A2 | 4/2015 |
| WO | 2015105835 A1 | 7/2015 |
| WO | 2015165951 A1 | 11/2015 |
| WO | 2015175308 A1 | 11/2015 |
| WO | 2016025825 A1 | 2/2016 |
| WO | 2016029107 A1 | 2/2016 |

OTHER PUBLICATIONS

Harris et al., 'Stimulation of lignocellulosic biomass hydrolysis by proteins of glycoside hydrolase family 61: structure and function of a large, enigmatic family,' Biochemistry, American Chemical Society, Apr. 1, 2010, vol. 49, No. 15, pp. 3305-3316, XP002608645.

Hemmpel, 'The surface modification of woven and knitted cellulose fibre fabrics by enzymatic degradation,' ITB Dyeing/Printing/Finishing, 1991, 7 pages.

Hemsworth et al., 'The copper active site of CBM33 Polysaccharide oxygenases,' Journal of the American Chemical Society, 2013, vol. 135, pp. 6069-6077.

Hemsworth et al., 'Discovery and characterization of a new family of lytic polysaccharide mono-oxygenases,' Nat Chem Biol., Feb. 2014, vol. 10(2), pp. 122-126.

Henikoff et al., 'Amino acid substitution matrices from protein blocks,' PNAS, Nov. 1992, vol. 89, pp. 10915-10919.

Herr et al., 'Purification and properties of an extracellular β-glucosidase from Lenzites trabea,' European J. Appl. Microbiol., 1978, vol. 5, pp. 29-36.

(56) References Cited

OTHER PUBLICATIONS

Higuchi, 'Recombinant PCR,' PCR Protocols: A Guide to Methods and Applications, 1990, pp. 177-183.
Hu et al., 'Antibodies specific for the human retinoblastoma protein identify a family of related polypeptides,' Molecular and Cellular Biology, 1991, vol. 11, No. 11, pp. 5792-5799.
Hynes et al., 'Isolation of genomic clones containing the amdS gene of Aspergillus nidulans and their use in the analysis of structural and regulatory mutations,' Molecular and Cellular Biology, Aug. 1983, vol. 3, No. 8, pp. 1430-1439.
Ihaka et al., 'R: a language for data analysis and graphics,' J. Comput. Graphical Statistics, 1996, vol. 5(3), pp. 299-314.
Ilmen et al., 'Regulation of cellulase gene expression in the filamentous fungus Trichoderma reesei,' Applied and Environmental Microbiology, Apr. 1997, vol. 63, No. 4, pp. 1298-1306.
Jakobovits et al., 'Production of antigen-specific human antibodies from mice engineered with human heavy and light chain YACs,' Annals New York Academy of Sciences, 1995, vol. 764, pp. 525-535.
Jakobovits et al., 'Production of fully human antibodies by transgenic mice,' Curr Opin Biotechnol, 1995, vol. 6(5), pp. 561-566.
Jones et al., 'Replacing the complementarity-determining regions in a human antibody with those from a mouse,' Nature, 1986, vol. 321, pp. 522-525.
Karkehabadi et al., 'The first structure of a glycoside hydrolase family 61 member, Cel61B from hypocrea jecorina, at 1.6 A resolution,' Journal of Molecular Biology, Oct. 31, 2008, vol. 383, No. 1, pp. 144-154, XP025433363.
Karlin et al., 'Applications and statistics for multiple high-scoring segments in molecular sequences,' Proc. Natl. Acad. Sci., Jun. 1993, vol. 90, pp. 5873-5877.
Karlsson et al., 'Homologous expression and characterization of Cel61A (EV IV) of Trichoderma reesei,' Eur. J. Biochem., 2001, vol. 268, pp. 6498-6507.
Kawaguchi et al., 'Cloning and sequencing of the cDNA encoding β-glucosidase 1 from Aspergillus aculeatus,' Gene, 1996, vol. 173, pp. 287-288.
Knowles et al., 'Cellulase families and their genes,' TIBTECH, 1987, vol. 5, pp. 255-261.
Kohler et al., 'Continous cultures of fused cells secreting antibody of predefined specificity,' Nature, 1975, vol. 256, pp. 495-497.
Kolbe et al., 'The streptomyces reticuli α-chitin-binding protein CHB2 and its gene,' Microbiology, 1998, vol. 144, pp. 1291-1297.
Krishna et al., 'Simultaneoud saccharification and fermentation of lignocellulosic wastes to ethanol using a thermotolerant yeast,' Bioresource Technology, 2001, vol. 77, pp. 193-196.
Kumar et al., 'Optimizing the use of cellulase enzymes in finishing cellulosic fabrics,' Textile Chemist and Colorist, 1997, vol. 29, pp. 37-42.
Kunkel, 'Rapid and efficient site-specific mutagenesis without phenotypic selection,' Proc. Natl. Acad. Sci., Jan. 1985, vol. 82, pp. 488-492.
Leggio et al., 'A structural overview of GH61 proteins—fungal cellulosedegrading polysaccharide monooxyenases,' Computational and Structural Biotechnology Journal, Sep. 2012, vol. 2(3), e201209019, 8 pgs.
Lehtio et al., 'Directed immobilaztion of recombinant staphylococci on cotton fibers by functional display of a fungal cellulose-binding domain,' FEMS Microbiology Letters, 2001, vol. 195, pp. 197-204.
Levasseur et al., 'Expansion of the enzymatic repertoire of the CAZy database to integrate auxiliary redox enzymes,' Biotechnology for Biofuels, 2013, vol. 6, 14 pgs.
Li et al., Expression of Aureobasidium pullulans xynA in, and secretion of the Xylanase from, *Saccharomyces cerevisiae*, Applied and Environmental Microbiology, 1996, vol. 62, pp. 209-213.
Li et al., 'Increased crystalline cellulose activity via combinations of amino acid changes in the family 9 catalytic domain and family 3c cellulose binding module of thermobifida fusca Cel9A' Applied and Environmental Microbiology, Apr. 2010, vol. 76, No. 8, pp. 2582-2588.

Li et al., 'Structural basis for substrate targeting and catalysis by fungal polysaccharide monooxygenases,' Structure, Jun. 2012, vol. 20, pp. 1051-1061.
Liang et al., 'Engineered pentafunctional minicellulosome for simultaneous saccharification and ethanol fermentation in *Saccharomyces cerevisiae*,' Applied and Environmental Microbiology, Nov. 2014, vol. 80, No. 21, pp. 6677-6684.
Linder et al., 'The roles and function of cellulose-binding domains,' Journal of Biotechnology, 1997, vol. 57, pp. 15-28.
Lockington et al., 'Cloning and characterization of the ethanol utilization regulon in Aspergillus nidulans,' Gene, 1985, vol. 33, pp. 137-149.
Lo Leggio et al., 'Structure and boosting activity of a starch-degrading lytic polysaccharide monooxygenase,' Nature Communications, 2015, 6:5961, DOI: 10.1038, 9 pgs.
Long et al., 'Identification of a genomic region containing a novel promoter resistant to glucose repression and over-expression of [beta]-glucosidase gene in hypocrea orientaliz EU7-22,' International Journal of Molecular Sciences, Apr. 17, 2013, vol. 14, No. 4, pp. 8479-8490, XP055149086.
Lorito et al., 'Biolistic transformation of Trichoderma harzianum and Gliocladium virens using plasmid and genomic DNA,' Current Genetics, 1993, vol. 24, pp. 349-356.
Martinez et al., 'Genome sequencing and analysis of the biomass-degrading fungus Trichoderma reesei (syn. Hypocrea jecorina),' Nature Biotechnology, 2008, vol. 26, pp. 553-560.
McKnight et al., 'Nucleotide sequence of the triosephosphate isomerase gene from Aspergillus nidulans: implications for a differential loss of introns,' Cell, Jul. 4, 1896, vol. 46, pp. 143-147.
Medve et al., 'Ion-exchange chromatographic purification and quantitative analysis of Trichoderma reesei cellulases cellbiohydrolase I, II and endoglucanase II by fast protein liquid chromatography,' Journal of Chromatography A, 1998, vol. 808, pp. 153-165.
Mekasha et al., 'Structural and functional characterization of a small chitin-active lytic polysaccharide monooxygenase domain of a multi-modular chitinase from Jonesia denitrificans,' FEBS Letter, 2016, vol. 590, pp. 34-42.
Mildvan et al., 'Inverse thinking about double mutants of enzymes +', Biochemistry, Nov. 1, 2004, vol. 43, No. 46, pp. 14517-14520, XP55412813.
Mildvan et al., 'Quantitative interpretations of double mutations of enzymes,' Archives of Biochemistry and Biophysics, May 1, 1992, vol. 294, No. 2, pp. 327-340, XP024762280.
Mullaney et al., 'Primary structure of the trpC gene from Aspergillus nidulans,' Mol. Gen. Genet., 1985, vol. 199, pp. 37-45.
Murzin et al., 'SCOP: a structural classification of proteins database for the investigation of sequences and structures,' J. Mol. Biol., 1995, vol. 247, pp. 536-540.
Needleman et al., 'A general method applicable to the search for similiarities in the amino acid sequence of two proteins,' J. Mol. Biol., 1970, vol. 48, pp. 443-453.
Nevalainen et al., 'Molecular Biology of Cellulolytic Fungi,' The Mycota II, 1995, pp. 303-319.
Nunberg et al., 'Molecular cloning and characterization of the glucoamylase gene of Aspergillus awamori,' Mollecular and Cellular Biology, Nov. 1984, vol. 4, pp. 2306-2315.
Ohmiya et al., 'Structure of cellulases and their applications,' Biotechnol. Gen. Engineer Rev., 1997, vol. 14, pp. 365-414.
Ooi et al., Complete nucleotide sequence of a gene coding for Aspergillus aculeatus cellulase (FI-CMCase), Nucleic Acids Research, 1990, vol. 18, p. 5884.
Ortega et al., 'Kinetics of cellulose saccharification by Trichoderma reesei cellulases,' International Biodeterioration & Biodegradation, 2001, vol. 47, pp. 7-14.
Pearson et al., 'Improved tools for biological sequence comparison,' Proc. Natl. Acad. Sci., Apr. 1988, vol. 85, pp. 2444-2448.
Penttila et al., 'Expression of two Trichoderma reesei endoglucanases in the yeast *Saccharomyces cerevisiae*,' Yeast, 1987, vol. 3, pp. 175-185.
Penttila et al., 'Efficient secretion of two fungal cellobiohydrolases by *Saccharomyces cerevisiae*,' Gene, 1988, vol. 63, pp. 103-112.

(56) References Cited

OTHER PUBLICATIONS

Pentilla et al., 'A versatile transformation system for the cellulolytic filamentous fungus Trichoderma reesei,' Gene, 1987, vol. 61, pp. 155-164.
Pere et al., 'Use of purified enzymes in mechanical pulping,' 1996, in Proc. Tappo Pulping Conf., Nashville, TN, 27-31, pp. 693-696.
Pourquie et al., 'Scale up of cellulase production and utilization,' Biochemistry and Genetics of Cellulose Degradation, 1988, pp. 72-85.
Quinlan et al., 'Insights into the oxidative degradation of cellulose by a copper metalloenzyme that exploits biomass components,' PNAS, Sep. 13, 2011, vol. 108, No. 37, pp. 15079-15084.
Riechmann et al., 'Reshaping human antibodies for therapy,' Nature, 1988, pp. 323-327.
Rothstein et al., 'Synthesis and secretion of wheat α-amylase in *Saccharomyces cerevisiae*,' Gene, 1987, vol. 55, pp. 353-356.
Saarilahti et al., 'Cels: a novel endoglucanase identified from *Erwinia carotovora* subsp. Carotovora,' Gene, 1990, vol. 90, pp. 9-14.
Sakamoto et al., 'Cloning and sequencing of cellulase cDNA from Aspergillus kawachii and its expression in *Saccharomyces cerevisiae*,' Curr Genet., 1995, vol. 27, pp. 435-439.
Saloheimo et al., 'EGIII, a new endoglucanase from Trichoderma reesei: the characterization of both gene and enzymes,' Gene, 1988, vol. 63, pp. 11-21.
Saloheimo et al., 'cDNA cloning of a Trichoderma reesei cellulase and demonstration of endoglucanase activity by expression in yeast,' Eur. J. Biochem., 1997, vol. 249, pp. 584-591.
Schell et al., 'Dilute-sulfuric acid pretreatment of corn stover in pilot-scale reactor,' Applied Biochemistry and Biotechnology, 2003, vol. 105, pp. 69-85.
Schulein, 'Cellulases of Trichoderma reesei,' Methods Enzymology, 1988, vol. 160, pp. 234-243.
Scopes et al., 'Purification of all glycolytic enzymes from one muscle extract,' Methods Enzymology, 1982, vol. 90, pp. 479-490.
Sheir-Neiss et al., 'Characterization of the secreted cellulases of Trichoderma reesei wild type and mutants during controlled fermentations,' Appl Microbiol Biotechnol, 1984, vol. 20, pp. 46-53.
Shoemaker et al., 'Enzymic activities of endo-1,4-β-D-glucanases purified from Trichoderma Viride,' Biochimica et Biophysica Acta, 1978, vol. 523, pp. 133-146.
Siloto et al., 'Site saturation mutagenesis: methods and applications in protein engineering,' Biocatalysis and Agricultural Biotechnology, Jul. 1, 2012, vol. 1, No. 3, pp. 181-189, XP55412897.
Smith, 'Comparison of biosequences,' Advances in applied mathematics, 1981, vol. 2, pp. 482-489.
Sorensen et al., 'Temperature effects on kinetic parameters and substrate affinity of Cel7A cellobiohydrolases,' Journal of Biological Chemistry, Sep. 4, 2015, vol. 290, No. 36, pp. 22193-22202.
Spilliaert et al., 'Cloning and sequencing of a Rhodothermus marinus gene, bglA, coding for a thermostable 8-glucanase and its expression in *Escherichia coli*,' Eur J. Biochem., 1994, vol. 224, pp. 923-930.
Stahlberg et al., 'A new model for enzymatic hydrolysis of cellulose based on the two-domain structure of cellobiohydrolase I,' Bio Technol., 1991, vol. 9, pp. 286-290.
Stahlberg et al., 'Activity studies and crystal structures of catalytically deficient mutants of cellobiohydrolase I from Trichoderma reesei,' J. Mol. Biol., 1996, vol. 264, pp. 337-349.
Suurnakki et al., 'Trichoderma reesei cellulases and their core domains in the hydrolysis and modification of chemical pulp,' Cellulose, 2000, vol. 7, pp. 189-209.
Tange et al., 'Recombinant expression of Trichoderma reesei Cel61A in Pichia pastoris: Optimizing yield and N-terminal processing,' Mol. Biotechnology, Aug. 19, 2015, 8 pgs.
Te'O et al., 'Codon optimization of xylanase gene xynB from the thermophilic bacterium Dictyoglomus termophilum for expression in the filamentous fungus Trichoderma reesei,' FEMS Microbiology Letters, 2000, vol. 190, pp. 13-19.

Thompson et al., 'CLUSTAL W: improving the sensitivity of progressive multiple sequence alignment through sequence weighting, position-specific gap penalties and weight matrix choice,' Nucleic Acids Research, 1994, vol. 22, No. 22, pp. 4673-4680.
Timberlake et al., 'Organization in a gene cluster expressed specifically in the asexual spores of A. nidulans,' Cell, 1981, vol. 1, pp. 29-37.
Tomaz et al., 'Studies on the chromatographic fractionation of Trichoderma reesei cellulases by hydrophobic interaction,' Journal of Chromatography A., 1999, vol. 865, pp. 123-128.
Tomme et al., 'Studies of the cellulolytic system of Trichoderma reesei QM 9414,' Eur. J. Biochem., 1988, vol. 170, pp. 575-581.
Tormo et al., 'Crystal structure of a bacterial family-III cellulose-binding domain: a general mechanism for attachment to cellulose,' The EMBO Journal, 1996, vol. 15, pp. 5739-5751.
Tyndall, 'Improving the softness and surface appearance of cotton fabrics and garments by treatment with cellulase enzymes,' Textile Chemist and Colorist, 1992, vol. 24, pp. 23-26.
Vaaje-Kolstad et al., 'The non-catalytic chitin-binding protein CBP21 from Serratia marcescens is essential for chitin degradation,' The Journal of Biological Chemistry, 2005, vol. 280, No. 31, pp. 28492-28497.
Vaaje-Kolstad et al., 'Characterization of the chitinolytic machinery of Enterococcus faecalis V583 and high-resolution structure of its oxidative CBM33 enzyme,' Journal of Molecular Biology, 2012, vol. 416, pp. 239-254.
Vaaje-Kolstad et al., 'Structural diversity of lytic polysaccharide monooxygenases,' Current Opinion in Structural Biology, 2017, vol. 44, pp. 67-76.
Vaaje-Kolstad et al., 'Crystal structure and binding properties of the Serratia marcescens chitin-binding protein CBP21,' The Journal of Biological Chemistry, 2005, vol. 280, No. 12, pp. 11313-11319.
Vallette et al., 'Construction of mutant and chimeric genes using the polymerase chain reaction,' Nucleic Acids Research, 1989, vol. 17, pp. 723-732.
Van Den Hondel et al., 'Heterologous gene expression in filamentous fungi,' More Gene Manipulations in Fungi, Academic Press, 1991, pp. 396-428.
Van Rensburg et al., 'Engineering yeast for efficient cellulose degradation,' Yeast, 1998, vol. 14, pp. 67-76.
Van Tilbeurgh et al., 'Separation of endo- and exo-type cellulases using a new affinity chromatography method,' FEBS Ltt., 1984, vol. 169, pp. 215-218.
Van Tilbeurgh et al., 'Limited proteolysis of the cellobiohydrolase I from Trichoderma reesei,' FEBS Lett., 1986, vol. 204, pp. 223-227.
Verhoeyen et al., 'Reshaping human antibodies: grafting an antilysozyme activity,' Science, 1988, vol. 239, pp. 1534-1536.
Ward et al., 'Use of Aspergillus overproducing mutants, cured for integrated plasmid, to overproduce heterologous proteins,' Appl Microbiol Biotechnol., 1993, vol. 39, pp. 738-743.
Warrington et al., 'A radiation hybrid map of 18 growth factor, growth factor receptor, hormone receptor, or neurotransmitter receptor genes on the distal region of the long arm of chromosome 5,' Genomics, 1992, vol. 13, pp. 803-808.
Wells et al., 'Cassette mutagenesis: an efficient method for generation of multiple mutations at defined sites,' Gene, 1985, vol. 34, pp. 315-323.
Wells et al., 'Importance of hydrogen-bond formation in stabilizing the transition state of subtilisin,' Phil. Trans. R. Soc. Lond. A., 1986, vol. 317, pp. 415-423.
Wilson, 'Microbial diversity of cellulose hydrolysis,' Current Opinion in Microbiology, 2011, vol. 14, pp. 259-263.
Wong et al., 'The Vibrio cholerae colonization factor GbpA possesses a modular structure that governs binding to different host surfaces,' PLOS Pathogens, Jan. 2012, vol. 8, e1002373, 12 pgs.
Wood et al., 'Properties of cellulolytic enzyme systems,' Biochem. Soc. Trans., 1985, vol. 13, pp. 407-410.
Wood et al., 'Methods for measuring cellulase activities,' Methods in Enzymology, 1988, vol. 160, pp. 87-112.
Wu et al., 'Crystal structure and computational characterization of the lytic polysaccharide monooxygenase GH61D from the Basidi-

(56) References Cited

OTHER PUBLICATIONS omycota Fungus Phanerochaete chrysosporium,' The Journal of Biological Chemistry, May 3, 2013, vol. 288, No. 18, pp. 12828-12839.
Yelton et al., 'Transformation of Aspergillus nidulans by using a trpC plasmid,' Proc. Natl. Acad. Sci., Mar. 1984, vol. 81, pp. 1470-1474.
Zoller et al., 'Oligonucleotide-directed mutagenesis using M13-derived vectors: an efficient and general procedure for the production of point mutations in any fragment of DNA,' Nucleic Acids Research, 1982, vol. 10, pp. 6487-6500.
International Search Report issued for PCT/US2014/048077 dated Dec. 11, 2014.
Written Opinion issued for PCT/US2014/048077 dated Dec. 11, 2014.
International Search Report issued for PCT/US2014/048075 dated Dec. 11, 2014.
Written Opinion issued for PCT/US2014/048075 dated Dec. 11, 2014.
International Search Report issued for PCT/US2014/048067 dated Oct. 28, 2014.
Written Opinion issued for PCT/US2014/048067 dated Oct. 28, 2014.
U.S. Appl. No. 15/647,775, filed Jul. 12, 2017.
Gregory et al., 'Activity, stability and 3-D structure of the Cu(ii) form of a chitin-active lytic polysaccharide monooxygenase from Bacillus amyloliquefaciens,' Dalton Transactions, 2016, vol. 45, No. 42, pp. 16904-16912.
Marinai, 'Exploring methods for functional studies of CBM33-type lytic polysaccharide monooxygenases,' Norwegian University of Life Sciences, 2013, Master Thesis, 143 pgs.
Aachmann et al., 'NMR structure of a lytic polysaccharide monooxygenase provides insight into copper binding, protein dynamics, and substrate interactions,' PNAS, Nov. 13, 2012, vol. 109, No. 46, pp. 18779-18784.
Altschul et al., 'Basic local alignment search tool,' J. Mol. Biol., 1990, vol. 215, pp. 403-410.
Altschul et al., 'Gapped BLAST and PSI-BLAST: a new generation of protein database search programs,' Nucleic Acids Research, 1997, vol. 25, No. 17, pp. 3389-3402.
Arfi et al., 'Integration of bacterial lytic polysaccharide monooxygenases into designer cellulosomes promotes enhanced cellulose degradation,' PNAS, Jun. 24, 2014, vol. 111, No. 25, pp. 9109-9114.
Aro et al., 'ACEII, a novel transcriptional activator involved in regulation of cellulase and xylanase genes of trichoderma reesei,' The Journal of Biological Chemistry, 2001, vol. 276, No. 26, pp. 24309-24314, DOI 10.1074/M003624200.
Aubert et al., 'Biochemistry and genetics of cellulose degradation,' Academic Press, 1988, pp. 136-151.
Bajar et al., 'Identification of a fungal cutinase promoter that is inducible by a plant signal via a phosphorylated trans-acting factors,' PNAS, Sep. 1991, vol. 88, pp. 8208-8212.
Baldwin et al., 'A comparison of gel-based, nylon filter and microarray techniques to detect differential RNA expression in plants,' Curr. Opin. Plant Biol., 1999, vol. 2, pp. 96-103.
Barclay et al., 'Efficient Transformation of Dictyostelium Discoideum Amoebae,' Molecular and Cellular Biology, Dec. 1983, vol. 3, No. 12, pp. 2117-2130.
Baulcombe, 'Viruses and gene silencing in plants,' Arch Virol. Suppl, 1999, vol. 15, pp. 189-201.
Bhikhabhai et al., 'Isolation of cellulolytic enzymes from Trichoderma reesei QM 9414,' Journal of Applied Biochemistry, 1984, vol. 6, pp. 336-345.
Boel et al., 'Two different types of intervening sequences in the glucoamylase gene from Aspergullus niger,' The EMBO Journal, 1984, vol. 3, No. 7, pp. 1581-1585.
Boer et al., 'The relationship between thermal stability and pH optimum studied with wild-type and mutant Trichoderma reesei cellobiohydrolase Cel7A.' Eur. J. Biochem., 2003, vol. 270, pp. 841-848.

Borisova et al., 'Structural and functional characterization of a lytic polysaccharide monooxygenase with broad substrate specificity,' The Journal of Biological Chemistry, Sep. 18, 2015, vol. 290, No. 38, pp. 22955-22969.
Brigidi et al., 'Genetic transformation of intact cells of Bacillus subtilis by electroporation,' FEMS Microbiology Letters, 1990, vol. 67, pp. 135-138.
Brumbauer et al., 'Fractionation of cellulase and β-glucosidase in a Trichoderma reesei culture liquid by use of two phase partitioning,' Bioseparation, 1999, vol. 7, pp. 287-295.
Campbell et al., 'Improved transformation efficiency of Aspergillus niger using the homologous niaD gene for nitrate reductase,' Current Genetics, 1989, vol. 16, pp. 53-56.
Carter et al., 'Improved oligonucleotide site-directed mutagenesis using M13 vectors,' Nucleic Acids Research 1985, vol. 13, pp. 4431-4443.
Chaplin et al., 'Heterogeneity in the histidine-brace copper coordination sphere in auxiliary activity family 10 (AA10) lytic polysaccharide monooxygenases,' The Journal of Biological Chemistry, Jun. 10, 2016, vol. 291, No. 24, pp. 12838-12850.
Chen et al., 'Purification and characterization of two extracellular β-glucosidases from Trichoderma reesei,' Biochimica et Biophysica Acta, 1992, vol. 1121, pp. 54-60.
Chiu et al., 'Structural basis for the enhancement of virulence by viral spindles and their in vivo crystallization,' PNAS, Mar. 31, 2015, vol. 112, No. 13, pp. 3973-3978.
Collen et al., 'Genetically engineered peptide fusions for improved protein partitioning in aqueous two-phase systems effect of fusion localization on endoglucanase I of Trichoderma reesei,' Journal of Chromatography A, 2001, vol. 910, pp. 275-284.
Coughlin et al., Comparative biochemistry of fungal and bacterial cellulolytic enzyme systems, Biochemistry and Genetics of Celluose Degradation, 1988, 12 pgs.
Crouch et al., 'The contribution of non-catalytic carbohydrate binding modules to the activity of lytic polysaccharide monooxygenases,' The Journal of Biological Chemistry, Apr. 1, 2016, vol. 291, No. 14, pp. 7439-7449.
Cummings et al., 'Secretion of Trichoderma reesei β-glucosidase by *Saccharomyces cerevisiae*,' Curr Genet, 1996, vol. 29, pp. 227-233.
Danneels et al., 'A quantitative indicator diagram for lytic polysaccharide monooxygenases reveals the role of aromatic surface residues in HjLPMO9A regioselectivity,' PLOS ONE, 2017, https://doi.org/10.1371/journal.pone.0178446, 15 pgs.
Databse UniProt, "SubName: Full=Endoglucanase IV" May 16, 2012, XP002731687, retrieved from EBI accession No. UNIPROT:H9C5T5.
Databse UniProt, "SubName: Full=Endoglucanase IV" Nov. 4, 2008, XP002731688, retrieved from EBI accession No. UNIPROT:B5TYI4.
Databse UniProt, "SubName: Full=Type IV Endoglucanase" Mar. 23, 2010, XP002731689, retrieved from EBI accession No. UNIPROT:D3JTC4.
Databse EMBL, "*Trichoderma* sp. SSL endoglucanase IV mRNA, complete cds." Sep. 22, 2008, XP002731680, retrieved from EBI accession No. EMBL:FJ040192.
Databse EMBL, "Hypocrea orientalis strain EU7-22 endoglucanase IV (EGIV) gene, complete cds." Mar. 20, 2012, XP002731691, retrieved from EBI accession No. EMBL:JQ238609.
Databse EMBL, "Trichoderma saturnisporum type IV endoglucanase mRNA, complete cds." Feb. 2, 2010, XP002731692, retrieved from EBI accession No. EMBL:GU290062.
Dayhoff et al., 'A model of evolutionary change in proteins,' Atlas of Protein Sequence and Structure, 1978, vol. 5, Suppl 3, Chapter 22, pp. 345-352.
Deutscher, 'Rethinking your purification procedure,' Methods Enzymol., 1990, vol. 182, pp. 779-780.
Druzhinina et al., 'Molecular phylogeny and species delimitation in the section of Longibrachiatum of Trichoderma,' Fungal Genetics and Biology, Feb. 13, 2012, vol. 49, No. 5, pp. 358-368.
Ellouz et al., 'Analytical separation of trichoderma reesei cellulases by ion-exchange fast protein liquid chromatography,' Journal of Chromatography, 1987, vol. 396, pp. 307-317.

(56) References Cited

OTHER PUBLICATIONS

Fields et al., 'A novel genetic system to detect protein-protein interactions,' Nature, 1989, vol. 340, pp. 245-246.

Filho and Ximenes, 'Purification and characterization of a β-glucosidase from solid-state cultures of *Humicola grisea* var. thermoidea,' Can J. Microbiol., 1996, vol. 42, pp. 1-5.

Fliess et al., 'Characterization of cellulases by HPLC separation,' Eur J Appl Microbiol Biotechnol., 1983, vol. 17, pp. 314-318.

Forsberg et al., 'Comparative study of two chitin-active and two cellulose-active AA10-type lytic polysaccharide monooxygenases,' Biochemistry, 2014, 3 pgs.

Forsberg et al., 'Structural and functional characterization of a conserved pair of bacterial cellulose-oxidizing lytic polysaccharide monooxygenases,' PNAS, Jun. 10, 2014, vol. 111, No. 23, pp. 8446-8451.

Forsberg et al., 'Structural and functional analysis of a lytic polysaccharide monooxygenase important for efficient utilization of chitin in Cellvibrio japonicus,' The Journal of Biological Chemistry, Apr. 1, 2016, vol. 291, No. 14, pp. 7300-7312.

Frandsen et al., 'Lytic polysaccharide monooxygenases: a crystallographer's view on a new class of biomass degrading enzymes,' IUCRJ, 2016, vol. 3, pp. 448-467.

Freer, 'Kinetic characterization of a β-glucosidase from a yeast, Candida wickerhamii,' The Journal of Biological Chemistry, 1993, vol. 268, No. 13, pp. 9337-9342.

Goedegebuur et al., 'Cloning and relational analysis of 15 novel fungal endoglucanases from family 12 glycosyl hydrolase,' Curr Genet., 2002, vol. 41, pp. 89-98.

Goldman et al., 'Transformation of Trichoderma hardianum by high-voltage electric pulse,' Current Genetics, 1990, vol. 17, pp. 169-174.

Goyal et al., 'Characteristics of fungal cellulases,' Bioresource Technology, 1991, vol. 36, pp. 37-50.

Gudmundsson et al., 'Structural and electronic snapshots during the transition from a Cu(OO) to Cu(I) metal center of a lytic polysaccharide monooxygenase by X-ray photoreduction,' The Journal of Biological Chemistry, Jul. 4, 2014, vol. 289, No. 27, pp. 18782-18792.

Hakkinen et al., 'Re-annotation of the CAZy genes of Trichoderma reesei and transcription in the presence of lignocellulosic substrates,' Microbial Cell Factories, Oct. 4, 2012, 11:134, DOI:10.1186/1475-2859-11-134, 26 pgs.

Halldorsdottir et al., 'Cloning, sequencing and overexpression of a Rhodothermus marinus gene encoding a thermostable cellulase of glycosyl hydrolase family 12,' Appl Microbiol Biotechnol., 1998, vol. 49, pp. 277-284.

\* cited by examiner

SEQ ID NO:1 (Top); SEQ ID NO:2 (Bottom: signal sequence underlined)

```
1      atgatccagaagctttccaacctccttgtcaccgcactggcggtggctactggcgttgtc
1       M  I  Q  K  L  S  N  L  L  V  T  A  L  A  V  A  T  G  V  V 61     ggacatggacatattaatgacattgtcatcaacggggtgtggtatcaggcctatgatcct
21      G  H  G  H  I  N  D  I  V  I  N  G  V  W  Y  Q  A  Y  D  P 121    acaacgtttccatacgagtcaaaccccccatagtagtgggctggacggctgccgacctt
41      T  T  F  P  Y  E  S  N  P  P  I  V  V  G  W  T  A  A  D  L 181    gacaacggcttcgtttcacccgacgcataccaaaaccctgacatcatctgccacaagaat
61      D  N  G  F  V  S  P  D  A  Y  Q  N  P  D  I  I  C  H  K  N 241    gctacgaatgccaaggggcacgcgtctgtcaaggccggagacactattctcttccagtgg
81      A  T  N  A  K  G  H  A  S  V  K  A  G  D  T  I  L  F  Q  W 301    gtgccagttccatggccgcaccctggtcccattgtcgactacctggccaactgcaatggt
101     V  P  V  P  W  H  P  G  P  I  V  D  Y  L  A  N  C  N  G 361    gactgcgagaccgttgacaagacgacgcttgagttcttcaagatcgatggcgttggtctc
121     D  C  E  T  V  D  K  T  T  L  E  F  F  K  I  D  G  V  G  L 421    ctcagcggcggggatccgggcacctgggcctcagacgtgctgatctccaacaacaacacc
141     L  S  G  G  D  P  G  T  W  A  S  D  V  L  I  S  N  N  N  T 481    tgggtcgtcaagatccccgacaatcttgcgccaggcaattacgtgctccgccacgagatc
161     W  V  V  K  I  P  D  N  L  A  P  G  N  Y  V  L  R  H  E  I 541    atcgcgttacacagcgccgggcaggcaaacggcgctcagaactaccccagtgcttcaac
181     I  A  L  H  S  A  G  Q  A  N  G  A  Q  N  Y  P  Q  C  F  N 601    attgccgtctcaggctcgggttctctgcagcccagcggcgttctagggaccgacctctat
201     I  A  V  S  G  S  G  S  L  Q  P  S  G  V  L  G  T  D  L  Y 661    cacgcgacggaccctggtgttctcatcaacatctacaccagcccgctcaactacatcatc
221     H  A  T  D  P  G  V  L  I  N  I  Y  T  S  P  L  N  Y  I  I 721    cctggaccctaccgtggtatcaggcctgccaacgagtgttgcccaggggagctccgccgcg
241     P  G  P  T  V  V  S  G  L  P  T  S  V  A  Q  G  S  S  A  A 781    acggccaccgccagcgccactgttcctggaggcggtagcggcccgaccagcagaaccacg
261     T  A  T  A  S  A  T  V  P  G  G  G  S  G  P  T  S  R  T  T 841    acaacggcgaggacgacgcaggcctcaagcaggcccagctctacgcctcccgcaaccacg
281     T  T  A  R  T  T  Q  A  S  S  R  P  S  S  T  P  P  A  T  T 901    tcggcacctgctggcggcccaacccagactctgtacggccagtgtggtggcagcggttac
301     S  A  P  A  G  G  P  T  Q  T  L  Y  G  Q  C  G  G  S  G  Y 961    agcgggcctactcgatgcgcgccgccagccacttgctctaccttgaaccctactacgcc
321     S  G  P  T  R  C  A  P  P  A  T  C  S  T  L  N  P  Y  Y  A 1021   cagtgccttaac
341     Q  C  L  N
```

FIG. 1

```
SEQ ID NO:48 : HGHVTQVIINGVAYGGYLSTSFPLQRKPPVVLGWTIEQRDNGFVSPDKYD : 50
SEQ ID NO:49 : HGHVDEIIVNGVSYQGYGSTDFPYMQDPPVVAGWTIEQADNGFVSPDKYD : 50
SEQ ID NO:50 : HGHVDEIIVNGVSYQGYGSTDFPYMQDPPVVAGWTIEQADNGFVSPDKYD : 50
SEQ ID NO:47 : HGHVSNIVVNGVFYPGYDVTKYPWQPNAPTVVGWSATNTDNGFVEPNNFG : 50
SEQ ID NO:46 : HGHVSKVIVNGVEYQNYDPAVFPYLSNPPTVIGWTADQKDNGFVSPDAFG : 50
SEQ ID NO:42 : HGHVSKVIVNGVEYQNYDPTSFPYNSNPPTVIGWTIDQKDNGFVSPDAFD : 50
SEQ ID NO:43 : HGHVSKVIVNGVEYQNYDPTSFPYNSNPPTVIGWTIDQKDNGFVSPDAFD : 50
SEQ ID NO:45 : HGHVSKVIVNGVEYQNYDPTSFPYNSNPPTVIGWTIDQKDNGFVSPDAFD : 50
SEQ ID NO:34 : HGHINDIVINGVWYQAYDPTTFPYESNPPIVVGWTAADLDNGFVSPDAYQ : 50
SEQ ID NO:35 : HGHINDIVINGVWYQAYDPTTFPYESNPPIVVGWTAADLDNGFVSPDAYQ : 50
SEQ ID NO:36 : HGHINNIVINGVYYQAYDPTSFPYESNPPIVVGWTAADLDNGFVSPDAYG : 50
SEQ ID NO:37 : HGHINNIVVNGVYYQGYDPTSFPYESDPPIVVGWTAADLDNGFVSPDAYQ : 50
SEQ ID NO:38 : HGHINNIVVNGVYYQGYDPTSFPYESDPPIVVGWTAADLDNGFVSPDAYQ : 50
SEQ ID NO:40 : HGHVNNIVVNGAYYQGYDPTLFPYEPNPPIVVGWTASDTDNGFVAPDAYQ : 50
SEQ ID NO:39 : HGHVNNIVVNGVYYQGYDPTSFPYMPDPPIVVGWTAADTDNGFVSPDAYQ : 50
SEQ ID NO:41 : HGHVSNIVINGVSYQGYDPTSFPYMQNPPIVVGWTAADTDNGFVAPDAFA : 50
SEQ ID NO:44 : HGHVTNIVINGVSYQNFDPFTHPYMQNPPTVVGWTASNTDNGFVGPESFS : 50

SEQ ID NO:48 : HPDIICHRDATPAQGHVQVAAGDTITIKWSS-WPENHRGPVMDYLANC-N : 98
SEQ ID NO:49 : DPDIICHRDATPAKGHIELAAGDTLTLRWSG-WPENHSGPILNYLANC-N : 98
SEQ ID NO:50 : DPDIICHRDATPAKGHIELAAGDTLTLRWSG-WPENHSGPILNYLANC-N : 98
SEQ ID NO:47 : HPDIICHRGAQPAKGHARVRAGDKILLQWDT-WPESHKGPVLDYLARC-P : 98
SEQ ID NO:46 : TPDIICHRSATPAGGHATVKAGDKISLKWDPVWPDSHKGPVIDYLAAC-N : 99
SEQ ID NO:42 : SGDIICHKSATPAGGHATVKAGDKISLQWDQ-WPESHKGPVIDYLAAC-D : 98
SEQ ID NO:43 : SGDIICHKSATPAGGHATVKAGDKISLQWDQ-WPESHKGPVIDYLAAC-D : 98
SEQ ID NO:45 : SGDIICHKSAKPAGGHATVKAGDKISLQWDQ-WPESHKGPVIDYLAAC-D : 98
SEQ ID NO:34 : NPDIICHKNATNAKGHASVKAGDTILFQWVP-VPWPHPGPIVDYLANC-N : 98
SEQ ID NO:35 : NPDIICHKNATNAKGHASVKARDTILFQWVP-VPWPHPGPIVDYLANC-N : 98
SEQ ID NO:36 : SPDIICHKNATNAKGHASVRAGDTVLFQWVP-LPWPHPGPIVDYLANC-N : 98
SEQ ID NO:37 : SPDIICHKNATNAKGHASVKAGDTILFQWVP-VPWPHPGPIVDYLANC-N : 98
SEQ ID NO:38 : SPDIICHKNATNAKGHASVKAGDTIPLQWVP-VPWPHPGPIVDYLANC-N : 98
SEQ ID NO:40 : SPDIICHRNATNARGHASVMAGSSVLIQWVP-IPWPHPGPVLDYLANC-N : 98
SEQ ID NO:39 : TPDIVCHKNGTNAKGHASVKAGDSVLFQWVP-VPWPHKSTVVDYLANC-N : 98
SEQ ID NO:41 : SGDIICHKNATNAKGHAVVAAGDKIFIQWNT-WPESHHGPVIDYLASCGS : 99
SEQ ID NO:44 : SPDIICHKSATNAGGHAVVAAGDKVFIQWDT-WPESHHGPVIDYLADCGD : 99
```

FIG. 2A

```
SEQ ID NO:48 : GPCETVDKTKLEFFKIDGMGLISQDR-PGKYADGALRENGYTWSVRIPSN : 147
SEQ ID NO:49 : GPCERVDKTKLEFFKIDGLGLLEQGT-PGRYADKVLQDNGDRWNVRIPKN : 147
SEQ ID NO:50 : GPCERVDKTKLEFFKIDGLGLLEQGT-PGRYADKVLQDNGDRWNVRIPKN : 147
SEQ ID NO:47 : GDCETVDKTALRFFKIGEGSYISGAA-PGHWAADVLLGNGFSWVVQIPED : 147
SEQ ID NO:46 : GDCETVDKTSLRFFKIDGAGYN-----NGVWAADALVNNGNSWLVQIPAD : 144
SEQ ID NO:42 : GDCESVDKTALKFFKIDGAGYDATN---G-WASDVLIKDGNSWVVEIPEN : 144
SEQ ID NO:43 : GDCESVDKTALKFFKIDGAGYDATN---G-WASDVLIKDGNSWVVEIPEN : 144
SEQ ID NO:45 : GDCESVDKTALKFFKIDGAGYDATN---G-WASDTLIKDGNSWVVEIPES : 144
SEQ ID NO:34 : GDCETVDKTTLEFFKIDGVGLLSGGD-PGTWASDVLISNNNTWVVKIPDN : 147
SEQ ID NO:35 : GDCETVDKTTLEFFKIDGVGLLSGGD-PGTWASDVLISNNNTWVVKIPDN : 147
SEQ ID NO:36 : GDCETVDKTSLEFFKIDGVGLISGGD-PGNWASDVLIANNNTWVVKIPDD : 147
SEQ ID NO:37 : GDCETVDKTSLEFFKIDGVGLISGGD-PGNWASDVLIANNNTWVVKIPED : 147
SEQ ID NO:38 : GDCETVDKTSLEFFKIDGVGLISGGD-PGNWASDVLIANNNTWVVKIPED : 147
SEQ ID NO:40 : GDCETVDKTTLEFFKIDGIGLISGGN-PGRWASDVLIGNNGTWVVQIPAD : 147
SEQ ID NO:39 : GPCETVDKTTLEFFKIDGIGLLSGGN-PGTWGSDVLIGNNNTWVIQIPED : 147
SEQ ID NO:41 : ASCETVDKTKLEFFKIDEVGLVDGSSAPGVWGSDQLIANNNSWLVEIPPT : 149
SEQ ID NO:44 : AGCEKVDKTTLKFFKISESGLLDGTNAPGKWASDTLIANNNSWLVQIPPN : 149

SEQ ID NO:48 : IAPGNYVLRHEIIALHSGLERNGAQNYPQCFNLKITGSGSDNPPGYLGTE : 197
SEQ ID NO:49 : IAPGNYVLRHEIIALHNALDKGGAQNYPQCFNLKITGDGSDSPSGYLGTE : 197
SEQ ID NO:50 : IAPGNYVLRHEIIALHNALDKGGAQNYPQCFNLKITGDGSDSPSGYLGTE : 197
SEQ ID NO:47 : VAPGNYVLRHEIIALHGSPNPNGAQAYPQCFNLEISGSGSRQPAGVAGTS : 197
SEQ ID NO:46 : LKPGNYVLRHEIIALHGAGSANGAQAYPQCFNLKVEGSGNNLPSGVP--- : 191
SEQ ID NO:42 : IKPGNYVLRHEIIALHSAGQANGAQNYPQCFNLKVEGSGSTVPAGVAGTE : 194
SEQ ID NO:43 : IKPGNYVLRHEIIALHSAGQANGAQNYPQCFNLKVEGSGSTVPAGVAGTE : 194
SEQ ID NO:45 : IKPGNYVLRHEIIALHSAGQANGAQNYPQCFNLKVEGSGSTVPAGVAGTE : 194
SEQ ID NO:34 : LAPGNYVLRHEIIALHSAGQANGAQNYPQCFNIAVSGSGSLQPSGVLGTD : 197
SEQ ID NO:35 : LAPGNYVLRHEIIALHSAGQANGAQNYPQCFNIAVSGSGSLQPSGVLGTD : 197
SEQ ID NO:36 : LAPGNYVLRHEIIALHSAGQANGAQNYPQCFNLAVSGSGSLKPSGVKGTA : 197
SEQ ID NO:37 : LAPGNYVLRHEIIALHSAGQADGAQNYPQCFNLAVSGSGSLQPSGVKGTA : 197
SEQ ID NO:38 : LAPGNYVLRHEIIALHSAGQADGAQNYPQCFNLAVPGSGSLQPSGVKGTA : 197
SEQ ID NO:40 : LETGNYVLRHELIALHSAGSVDGAQNYPQCFNLAVTGTGSLQPTGVLGTK : 197
SEQ ID NO:39 : LQTGNYVLRHELIALHSAEQADGAQNYPQCFNLAVTGTGSLQPSGVLATD : 197
SEQ ID NO:41 : IAPGNYVLRHEIIALHSAENADGAQNYPQCFNLQITGTGTATPSGVPGTS : 199
SEQ ID NO:44 : IAPGNYVLRHEIIALHSAGQQNGAQNYPQCFNLQVTGSGTQKPSGVLGTE : 199
```

FIG. 2B

```
SEQ ID NO:48 : LYDANDPGILVNIYGNLPNYQVPGPTIVSGGVSSVRQSPSRATTTAKCTT : 247
SEQ ID NO:49 : LYDAADPGILVNVYSSSVDYEVPGPTICEGGVSSVEQKPSEATTTAKCTT : 247
SEQ ID NO:50 : LYDAADPGILVNVYSSSVDYEVPGPTICEGGVSSVEQKPSEATTTAKCTT : 247
SEQ ID NO:47 : LYRAGDPGIHFPLYNSPIVYPVPGPALIPGVPSTVAQVSTRATATSSPFL : 247
SEQ ID NO:46 : LYKATDAGILFNMYQNDFTYPVPGPALIAGAVSSIPQSSSAATATASATV : 241
SEQ ID NO:42 : LYKATDAGILFDIYKNDISYPVPGPSLIAGASSSIAQSKMAATATASATL : 244
SEQ ID NO:43 : LYKATDAGILFDIYKNDISYPVPGPSLIAGASSSIAQSKMAATATASATL : 244
SEQ ID NO:45 : LYKATDAGILFDIYKNDISYPVPGPSLIAGASSSIAQSKMAATATASATL : 244
SEQ ID NO:34 : LYHATDPGVLINIYTSPLNYIIPGPTVVSGLPTSVAQGSSAATATASATV : 247
SEQ ID NO:35 : LYHATDPGVPINIYTSPLNYIIPGPTVVSGLPTSVAQGSSAATATASATA : 247
SEQ ID NO:36 : LYHATDPGVLINIYTSPLNYIIPGPTVVSGLPTSVAQRSSAATATASATL : 247
SEQ ID NO:37 : LYHSDDPGVLINIYTSPLAYTIPGPSVVSGLPTSVAQGSSAATATASATV : 247
SEQ ID NO:38 : LYHSDDPGVLINIYTSPLAYTIPGPSVVSGLPTSVAQGSSAATATASATV : 247
SEQ ID NO:40 : LYQESDPGILFNIYTSPLTYTIPGPTVVSGLPSSVTQRSSTATATSIATV : 247
SEQ ID NO:39 : LYHETDPGILFNIYTSPLTYIIPGPTVVSGLPSSVAQASSAATATSSATV : 247
SEQ ID NO:41 : LYTPTDPGILVNIYSAPITYTVPGPALISGAV-SIAQSSSAITASGTALT : 248
SEQ ID NO:44 : LYKATDAGILANIYTSPVTYQIPGPAIISGA-SAVQQTTSAITASASAIT : 248

SEQ ID NO:48 : RS : 249
SEQ ID NO:49 : RY : 249
SEQ ID NO:50 : RY : 249
SEQ ID NO:47 : PG : 249
SEQ ID NO:46 : PG : 243
SEQ ID NO:42 : PG : 246
SEQ ID NO:43 : PG : 246
SEQ ID NO:45 : PG : 246
SEQ ID NO:34 : PG : 249
SEQ ID NO:35 : PG : 249
SEQ ID NO:36 : PG : 249
SEQ ID NO:37 : PG : 249
SEQ ID NO:38 : PG : 249
SEQ ID NO:40 : PG : 249
SEQ ID NO:39 : SG : 249
SEQ ID NO:41 : GS : 250
SEQ ID NO:44 : GS : 250
```

FIG. 2C

```
SEQ ID NO:51 : PTQTLYGQCGGSGYS--GPTRCAPPATCSTLNPYYAQCL :
SEQ ID NO:64 : --QPLYGQCGGLNWPPESPTECVPGARCSTINPYYAQC- :
SEQ ID NO:65 : PLQSKWGQCGGVGYT--GASVCSPTATCSTLNPYYAQCL :
SEQ ID NO:63 : PTQKMYGQCGGVAYM--GPTQCPAYATCSTVNPYYAQC- :
SEQ ID NO:56 : GSQTVYGQCGGTGWT--GPTACVASATCTTLNPYYAQCL :
SEQ ID NO:60 : QTQTVWGQCGGQGYS--GPTNCASGSACSTLNPYYAQCI :
SEQ ID NO:67 : ATQTHYGQCGGMSYT--GPTVCASPYTCQVQNPYYSQCL :
SEQ ID NO:59 : PTQTHYGQCGGIGYS--GPTQCVSGTTCQVLNPYYSQCL :
SEQ ID NO:62 : PTQSHYGQCGGIGYS--GPTVCASGTTCQVLNPYYSQCL :
SEQ ID NO:57 : PTQTHYGQCGGIGYS--GPTVCASGTTCQVLNPYYSQCL :
SEQ ID NO:58 : PTQTHYGQCGGIGYS--GPTVCASGSTCQVLNPYYSQCL :
SEQ ID NO:54 : GTQSLYGQCGGTGWA--GPTACAPPATCKVLNQYYSQCL :
SEQ ID NO:66 : ATQTHYGQCGGTGWT--GPTRCASGFTCQVLNPFYSQCL :
SEQ ID NO:55 : ATQTLYGQCGGSGWT--GPTACASGATCKVLNPYYSQCL :
SEQ ID NO:61 : ATQTLYGQCGGSGWT--GPTACASGATCKVLNSYYSQCL :
SEQ ID NO:53 : GVQSEYGQCGGSGYS--GPTACAAPYACSTLNPYYAQCL :
SEQ ID NO:52 : PSQTLYGQCGGSGYS--GPTICASPAVCSTLNPYYAQCL :
```

FIG. 3

VARIANT ENZYMES

CROSS REFERENCE TO RELATED APPLICATIONS

This application is the National Stage Entry of International Application No. PCT/US2014/048067 filed on 24 Jul. 2014 which claims benefit of priority from U.S. Provisional Patent Applications Ser. Nos. 61/859,630; 61/859,666; 61/859,680; 61/859,704; 61/859,712; 61/859,721; and 61/859,735, all filed on 29 Jul. 2013, the contents of all of which are incorporated herein by reference in their entirety.

GOVERNMENT RIGHTS

This invention was made with government support under Conditional Award No: De-Fc36-08go18078 awarded by the Department of Energy. The government has certain rights in this invention.

FIELD OF THE INVENTION

The present disclosure generally relates to glycosyl hydrolase enzyme variants, particularly variants of certain oxidoreductases of glycosyl hydrolase family 61. Nucleic acids encoding the glycosyl hydrolyase variants, compositions including the glycosyl hydrolase variants, methods of producing the variants, and methods of using the variants are also described.

SEQUENCE LISTING

The content of the electronically submitted sequence listing in ASCII text (File Name: NB40508USPCT_SeqList_ST25.txt; Size: 193,936 bytes; and date of creation Jan. 27, 2016) is incorporated herein by reference in its entirety.

BACKGROUND OF THE INVENTION

Cellulose and hemicellulose are the most abundant plant materials produced by photosynthesis. They can be degraded and used as an energy source by numerous microorganisms, including bacteria, yeast and fungi, that produce extracellular enzymes capable of hydrolysis of the polymeric substrates to monomeric sugars (Aro et al., 2001). As the limits of non-renewable resources approach, the potential of cellulose to become a major renewable energy resource is enormous (Krishna et al., 2001). The effective utilization of cellulose through biological processes is one approach to overcoming the shortage of foods, feeds, and fuels (Ohmiya et al., 1997).

Cellulases are enzymes that hydrolyze cellulose (beta-1, 4-glucan or beta D-glucosidic linkages) resulting in the formation of glucose, cellobiose, cellooligosaccharides, and the like. Cellulases have been traditionally divided into three major classes: endoglucanases (EC 3.2.1.4) ("EG"), exoglucanases or cellobiohydrolases (EC 3.2.1.91) ("CBH"), and beta-glucosidases (β-D-glucoside glucohydrolase; EC 3.2.1.21) ("BG"). (Knowles et al., 1987; Shulein, 1988). Endoglucanases act mainly on the amorphous parts of the cellulose fiber, whereas cellobiohydrolases are also able to degrade crystalline cellulose (Nevalainen and Penttila, 1995). Beta-glucosidase acts to liberate D-glucose units from cellobiose, cellooligosaccharides, and other glucosides (Freer, 1993).

Cellulases are known to be produced by a large number of bacteria, yeast and fungi. Certain fungi produce a complete cellulase system capable of degrading crystalline forms of cellulose, such that the cellulases are readily produced in large quantities via fermentation. Filamentous fungi play a special role since many yeast, such as *Saccharomyces cerevisiae*, lack the ability to hydrolyze cellulose. (See, e.g., Aro et al., 2001; Aubert et al., 1988; Wood et al., 1988, and Coughlan, et al.)

The fungal cellulase classifications of CBH, EG and BG can be further expanded to include multiple components within each classification. For example, multiple CBHs, EGs and BGs have been isolated from a variety of fungal sources including *Trichoderma reesei* which contains known genes for 2 CBHs, e.g., CBH I (also known as Cel7A or glycosyl hydrolase family (GH)7A) and CBH II (also known as Cel6A or GH6A), a number of EGs, e.g., EG I (also known as Cel7B or GH7B), EG II (also known as Cel5A or GH5A), EG III (also known as Cel12A or GH12A), EGV (also known as Cel45A or GH45A), EGVI (also known as Cel74A or GH74A), EGVII (also known as Cel61B or GH61 b) and EGVIII, and a series of BGs, e.g., BG1, BG3, and BG5.

In order to efficiently convert crystalline cellulose to glucose, a complete cellulase system comprising components or enzymatic activities from each of the CBH, EG and BG classifications is typically required, with isolated components less effective in hydrolyzing crystalline cellulose (Filho et al., 1996). A synergistic relationship has been observed amongst cellulase components from different classifications. In particular, the EG-type cellulases and CBH-type cellulases synergistically interact to more efficiently degrade cellulose. (See, e.g., Wood, 1985.).

Cellulases are known in the art to be useful in the treatment of textiles for the purposes of enhancing the cleaning ability of detergent compositions, for use as a softening agent, for improving the feel and appearance of cotton fabrics, and the like (Kumar et al., 1997).

Cellulase-containing detergent compositions with improved cleaning performance (U.S. Pat. No. 4,435,307; GB App. Nos. 2,095,275 and 2,094,826) and for use in the treatment of fabric to improve the feel and appearance of the textile (U.S. Pat. Nos. 5,648,263, 5,691,178, and 5,776,757; GB App. No. 1,358,599; The Shizuoka Prefectural Hammamatsu Textile Industrial Research Institute Report, Vol. 24, pp. 54-61, 1986), have been described.

Cellulases are further known in the art to be useful in the conversion of cellulosic feedstocks into ethanol. This process has a number of advantages, including the ready availability of large amounts of feedstock that is otherwise discarded (e.g., burning or land filling the feedstock). Other materials that consist primarily of cellulose, hemicellulose, and lignin, e.g., wood, herbaceous crops, and agricultural or municipal waste, have been considered for use as feedstock in ethanol production. In recent years, new classes of glycosyl hydrolases have been identified that provide further auxiliary effects that enhance or augment the enzymatic hydrolysis of cellulosic materials, although the mechanisms of action of many of these new auxiliary enzymes have not been fully elucidated. One such family of glycosyl hydrolases, which had earlier been annotated as GH61 family (see, e.g., Harris et al. "Stimulation of Lignocellulosic Biomass Hydrolysis by Proteins of Glycoside Hydrolase Family 61: Structure and Function of a Large, Enigmatic Family" Biochemistry 2010, vol. 49, pp. 3305-3316), had been repeatedly re-annotated, most recently to Auxiliary Activity (AA) Family 9 after the discovery that some family members are lytic polysaccharide monooxygenases (Levasseur A. et al, "Expansion of the enzymatic repertoire of the CAZy database to integrate auxiliary redox enzymes" Biotechnol Biofuels 2013, vol 6, issue 1, pp. 41). At least two GH61 enzymes are present in the *T. reesei* (Saloheimo M., "cDNA cloning of a *Trichoderma reesei* cellulase and demonstration of endoglucanase activity by expression in yeast" Eur J Biochem. 1997 vol. 249, issue 2: pp. 584-91; Karlsson et al., Homologous expression and characterization of Cel61A (EG IV) of *Trichoderma reese?'* Eur. J. Biochem. 2001 vol. 268, pp. 6498-6507; Karkehabadi et al., "The first structure of a glycoside hydrolase family 61 member, Cel61B from *Hypocrea jecorina*, at 1.6 A resolution" J Mol Biol. 2008, vol. 383 issue 1: pp 144-154; Martinez et al., "Genome sequencing and analysis of the biomass-degrading fungus *Trichoderma reesei* (syn. *Hypocrea jecorina*)" Nature Biotechnology 2008, vol. 26, pp. 553-560). In the very recent past, it was reported that up to four more of these glycosyl hydrolases have been identified in the *Trichoderma reesei* genome (Hakkinen M. et al, "Re-annotation of the CAZy genes of *Trichoderma reesei* and transcription in the presence of lignocellulosic substrates" 2012, Microb Cell Fact. Vol 4, issue 11, pp. 134).

It would be an advantage in the art to provide a set of GH61 enzyme variants with improved capacity, when combined with one or more cellulases, and optionally also one or more hemicellulases, to augment the efficacy and efficiency of hydrolyzing lignocellulosic biomass substrates to monosaccharides, disaccharides, and polysaccharides. Improved properties of the variant GH61 polypeptide include, but are not limited to: altered temperature-dependent activity profiles, thermostability, pH activity, pH stability, substrate specificity, product specificity, and chemical stability.

BRIEF SUMMARY OF THE INVENTION

The present disclosure describes isolated variant polypeptides having glycosyl hydrolase family 61 (GH61) activity, nucleic acids encoding such enzymes, host cells containing GH61-encoding polynucleotides (e.g., host cells that express the GH61 polypeptides), compositions containing the GH61 polypeptides, and methods for producing and using the same.

As such, aspects of the present invention provide variants of a parent GH61 enzyme, where the variant has cellulase augmenting activity, has at least 80% sequence identity to SEQ ID NO:3, and has at least one improved property or performance over the parent GH61 enzyme selected from: (a) expression (yield), (b) Thermostability and/or Tm, (c) Whole Hydrolysate Dilute Acid Pretreated Corn Stover (whPCS) Hydrolysis Assay activity, and (d) Dilute Ammonia Pretreated Corn Stover (daCS) Hydrolysis Assay activity. In certain embodiment, the GH61 enzyme is a GH61A enzyme.

In certain aspects of the present invention, GH61 variants have an amino acid substitution that falls within two stretches of amino acid residues spanning amino acids 111-114 and 144-163 in the GH61A mature enzyme (SEQ ID NO: 3) (i.e., at least one of the two stretches has an amino acid substitution; multiple substitutions within these two stretches of amino acids is also disclosed). These stretches of residues have been reported in the literature as conserved among certain members of the GH61A family and/or are key to the functions of fungal GH61A enzymes. Harris et al., "*Stimulation of Lignocellulosic Biomass Hydrolysis by Proteins of Glycoside Hydrolase Family 61: Structure and Function of a Large, Enigmatic Family*" 2010 Biochemistry, 49:3305-16; Busk et al., "*Function-based Classification of Carbohydrate-Active Enzymes by Recognition of Short, Conserved Peptide Motifs.*" App. Env. Microbiol., 2013, 79(11):3380-3391. Based on the known 3D crystal structure of GH61B of *Trichoderma reesei* (see, Karkehabadi, S. et al. *The first structure of a glycoside hydrolase family 61 member, Cel61B* from Hypocrea jecorina, *at 1.6 A resolution*. J. Mol. Biol. 2008, 383, 144-154), it can be postulated that the residues spanning positions 111-114 of SEQ ID NO:3 are part of a short loop and beta-sheet located quite a distance (at least 20 angstrom) away from the active site of the GH61A, but are partially exposed to the surface of the enzyme. The residues spanning positions 144-163 of SEQ ID NO:3 are, on the other hand, part of a short loop and a long beta-sheet. The residues in the loop are exposed to the solvent to a certain extent to the other side of the enzyme active site. The histidine at position 163 is located at or near the active site of the enzyme. Based on the structure of GH61B of *T. reesei*, it can be further postulated that there might be an internal salt bridge between residue number 156, an arginine, and 158, a glutamic acid, and potentially also another salt bridge between the residue at position 113, a lysine and certain backbone oxygen atoms. Because those residues can be understood as important to the structural integrity or stability of GH61A, as well as to its function, it is surprising that certain mutants at those residues resulted in either no reduced property or, in certain cases, at least one improved property as compared to the parent GH61 enzyme as described herein.

Given the potential importance of the conserved amino acid residues spanning amino acids 111-114 and 144-163 in the GH61 mature enzyme (SEQ ID NO: 3), there are a number of amino acid substitutions in these positions that result in a reduced property as compared to the parent GH61. Thus, certain aspects of the invention include GH61 variants having a first amino acid substitution and at least one additional amino acid substitution, where (1) the first amino acid substitution falls within the amino acid residues spanning amino acids 111-114 and 144-163 and, when in a GH61 that does not have the at least one additional amino acid substitution, results in a GH61 having a reduced property as compared to the parent GH61, and (2) the at least one additional amino acid substitution results in a GH61 having an improvement in the reduced property as compared to the GH61 that has the first amino acid substitution but does not have the at least one additional amino acid substitution. For example, the reduced production exhibited by a GH61 variant having a substitution at a position within amino acids 111-114 and 144-163 (as compared to the parent GH61) is improved by introducing a substitution in this GH61 variant at a second position in the GH61 enzyme (it is noted that the resulting compensatory mutation does not necessarily return the reduced property to wild-type levels; it simply improves the reduced property exhibited by the variant with the first amino acid substitution). The relationship between the first amino acid substitution and the at least one additional amino acid substitution as described above is sometimes referred to herein as compensatory. Therefore, aspects of the present invention include GH61 variants that have compensatory amino acid substitutions. Compensatory amino acid substitutions may also be referred to as rescuing each other, e.g., a second amino acid substitution in a GH61 variant rescues a first amino acid substitution that resulted in a reduced property of the GH61 enzyme. In some instances, a compensatory amino acid substitution is said to have rescued a property of a variant GH61 that had a reduction in that property as compared to the parent GH61. Such terminology is well understood by those of ordinary skill in the art. In certain embodiments, such compensatory substitutions are designed based on the crystal structure of the GH61A enzyme and/or on the crystal structure of one or more closely related GH61 enzymes. For example, substitutions at position 112 that reduce GH61 expression (e.g., F112A and F112V) are rescued by substitutions at positions 94 or 148 (see the Example 4 below). Thus, aspects of the subject invention include combinatorial GH61 variants having compensatory amino acid substitutions at (1) positions 112 and 94 and (2) positions 112 and 148. Examples of these combinatorial and compensatory variants include, but are not limited to: L94I-F112A; L94V-F112I; F112I-L148I; and L94I-F112V.

In certain embodiments, a GH61 variant has a few mutations, where by "a few" is meant from 1 to 10 mutations (e.g., from 1 to 10 amino acid substitutions as compared to a parent GH61 enzyme).

GH61 variants according to aspects of the present invention include, but are not limited to, the following:

1. A variant of a parent glycoside hydrolase family 61 (GH61) enzyme, where said variant has cellulase activity, has at least 80% sequence identity to SEQ ID NO:3, and has at least one improved property over said parent GH61 enzyme selected from: (a) expression, (b) thermostability and/or Tm, (c) performance in a Whole Hydrolysate Dilute Acid Pretreated Corn Stover (whPCS) hydrolysis assay, and (d) performance in a Dilute Ammonia Pretreated Corn Stover (daCS) hydrolysis assay, wherein said variant comprises at least one amino acid substitution at one or more position corresponding to amino acids 111 to 114 and 144 to 163 of SEQ ID NO:3.

2. The variant of 1, wherein said variant has improved thermostability and/or Tm and wherein said at least one amino acid substitution is selected from the group consisting of: I144G, D146F, L148P, A149P, G151Q, G151V, N152F, N152G, N152Q, N152S, N152Y, L155M, R156S, H157W, E158W, E158Y, I159Q, I160D, I160F, A161E, A161L, A161Y, L162A, L162F, H163L, H163R, H163Y, and combinations thereof.

3. The variant of 1 or 2, wherein said variant has improved performance in a whPCS hydrolysis assay and wherein said at least one amino acid substitution is selected from the group consisting of: I144K, I144R, I144S, P145G, P145H, P145I, P145K, P145R, P145S, P145V, D146A, D146C, D146E, D146F, D146K, D146M, D146Q, D146T, D146Y, N147F, N147M, L148K, L148V, A149C, A149D, A149F, A149G, A149I, A149N, A149V, P150A, P150C, P150D, P150E, P150F, P150G, P150H, P150I, P150K, P150L, P150Q, G151E, G151F, G151H, G151I, G151K, G151M, G151P, G151Q, G151S, G151V, G151W, G151Y, N152E, N152F, N152G, N152H, N152K, N152P, Y153F, Y153K, Y153L, Y153M, Y153P, Y153Q, Y153R, Y153S, Y153V, V154A, V154C, V154D, V154E, V154G, V154H, V154K, V154N, V154P, V154Q, V154R, V154T, L155C, L155F, L155K, L155M, L155N, R156A, R156C, R156D, R156E, R156F, R156H, R156I, R156K, R156L, R156M, R156P, R156Q, H157D, E158A, E158C, E158D, E158F, E158H, E158I, E158L, E158M, E158N, E158P, E158S, E158T, E158W, A161C, L162I, L162N, H163A, H163C, H163D, H163E, H163F, H163G, H163I, H163K, H163M, H163P, H163R, H163T, H163V, H163W, H163Y, and combinations thereof.

4. The variant of 1, 2 or 3, wherein said variant has improved performance in a daCS hydrolysis assay and wherein said at least one amino acid substitution is selected from the group consisting of: F112V, K113L, K113M, K113N, K113R, K113S, I114F, I114V, I144F, I144V, P145A, Y153F, V154T, H163D, H163Y, and combinations thereof.

5. The variant of 1 to 4, wherein said variant further comprises at least one second amino acid substitution selected from the group consisting of: F112M, F112W, K113P, K113T, I114L, I114M, I114T, I144A, I144C, I144D, I144E, I144H, I144N, I144P, I144Q, I144T, I144W, I144Y, P145C, P145D, P145E, P145F, P145L, P145M, P145N, P145Q, P145T, P145W, P145Y, D146G, D146H, D146I, D146L, D146N, D146P, D146R, D146S, D146V, D146W, N147A, N147C, N147D, N147E, N147G, N147H, N147I, N147K, N147L, N147P, N147Q, N147R, N147S, N147T, N147V, N147W, N147Y, L148A, L148C, L148D, L148E, L148F, L148G, L148H, L148I, L148M, L148N, L148Q, L148R, L148S, L148T, L148W, L148Y, A149E, A149H, A149K, A149L, A149M, A149Q, A149R, A149S, A149T, A149W, A149Y, P150M, P150N, P150R, P150S, P150T, P150V, P150W, P150Y, G151A, G151C, G151D, G151L, G151N, G151R, G151T, N152A, N152C, N152D, N152I, N152L, N152M, N152R, N152T, N152V, N152W, Y153A, Y153C, Y153D, Y153E, Y153G, Y153H, Y153I, Y153N, Y153T, Y153W, V154F, V154I, V154L, V154M, V154S, V154W, V154Y, L155A, L155D, L155E, L155G, L155H, L155I, L155P, L155Q, L155R, L155S, L155T, L155V, L155W, L155Y, R156G, R156N, R156T, R156V, R156W, R156Y, H157A, H157C, H157E, H157F, H157G, H157I, H157K, H157L, H157M, H157N, H157P, H157Q, H157R, H157S, H157T, H157V, H157Y, E158G, E158K, E158R, E158V, I159A, I159C, I159D, I159E, I159F, I159G, I159H, I159K, I159L, I159M, I159N, I159P, I159R, I159S, I159T, I159V, I159W, I159Y, I160A, I160C, I160E, I160G, I160H, I160K, I160L, I160M, I160N, I160P, I160Q, I160R, I160S, I160T, I160V, I160W, I160Y, A161D, A161F, A161G, A161H, A161I, A161K, A161M, A161N, A161P, A161Q, A161R, A161S, A161T, A161V, A161W, L162C, L162D, L162E, L162G, L162H, L162K, L162M, L162P, L162Q, L162R, L162S, L162T, L162V, L162W, L162Y, H163Q, H163S, and combinations thereof.

In certain embodiments, the parent GH61 is a fungal glycosyl hydrolase 61 (GH61), e.g., GH61A from *Hypocrea jecorina*, *Hypocrea atroviridis*, *Hypocrea virens*, *Thielavia terrestris*, or *Thielavia heterothallica* (or their respective anamorph, teleomorph or holomorph counterpart forms), e.g., GH61A selected from any one of SEQ ID NOs: 3, 72, 73, 74, and 77.

Aspects of the invention include variants in the catalytic and/or the carbohydrate binding domain of enzymes having homology to the catalytic domain of *H. jecorina* GH61A (SEQ ID NO:34) and/or the carbohydrate binding domain of *H. jecorina* GH61A (SEQ ID NO:51). Thus, any one or any combination of the variants described above that fall within the catalytic domain of *H. jecorina* GH61A can be applied to a catalytic domain that is homologous to the catalytic domain of the *H. jecorina* GH61A enzyme. Likewise, any one or any combination of the variants described above that fall within the carbohydrate binding domain of *H. jecorina* GH61A can be applied to a carbohydrate binding domain that is homologous to the carbohydrate binding domain of the *H. jecorina* GH61A enzyme. As described above, these catalytic domain and/or carbohydrate binding domain variants have at least one improved property over their respective parent enzyme. Examples of catalytic domains homologous to *H. jecorina* GH61A (SEQ ID NO:34) are shown in FIGS. 2A to 2C. Examples of carbohydrate binding domains homologous to *H. jecorina* GH61A (SEQ ID NO:51) are shown in FIG. 3. Moreover, chimeric enzymes comprising either (1) a catalytic domain from a GH61 variant and a carbohydrate binding domain of a second enzyme or (2) a carbohydrate binding domain from a GH61 variant and a catalytic domain of a second enzyme are contemplated, where the GH61 domain of the chimeric enzyme contains one or more variant amino acids as described herein.

Aspects of the subject invention include an isolated polynucleotide comprising a polynucleotide sequence encoding a variant of a parent GH61 as described herein. The isolated polynucleotide may be present in a vector, e.g., an expression vector or a vector for propagation of the polynucleotide. The vector may be present in a host cell to propagate the vector and/or that expresses the encoded GH61 variant as described herein. The host cell can be any cell that finds use in propagation of the GH61 variant polynucleotide and/or expression of the encoded GH61 variant, e.g., a bacterial cell, a fungal cell, etc. Examples of suitable fungal cell types that can be employed include filamentous fungal cells, e.g., cells of *Trichoderma reesei, Trichoderma longibrachiatum, Trichoderma viride, Trichoderma koningii, Trichoderma harzianum, Penicillium, Humicola, Humicola insolens, Humicola grisea, Chrysosporium, Chrysosporium lucknowense, Myceliophthora thermophila, Gliocladium, Aspergillus, Fusarium, Neurospora, Hypocrea, Emericella, Aspergillus niger, Aspergillus awamori, Aspergillus aculeatus*, and *Aspergillus nidulans*. Alternatively, the fungal host cell can be a yeast cell, e.g., *Saccharomyces cervisiae, Schizzosaccharomyces pombe, Schwanniomyces occidentalis, Kluveromyces lactus, Candida utilis, Candida albicans, Pichia stipitis, Pichia pastoris, Yarrowia lipolytica, Hansenula polymorpha, Phaffia rhodozyma, Arxula adeninivorans, Debaryomyces hansenii*, or *Debaryomyces polymorphus*.

Aspects of the present invention include methods of producing a variant GH61 that includes culturing a host cell that contains a polynucleotide encoding the GH61 variant in a suitable culture medium under suitable conditions to express (or produce) the GH61 variant from the polynucleotide, e.g., where the polynucleotide encoding the GH61 variant is present in an expression vector (i.e., where the GH61 variant-encoding polynucleotide is operably linked to a promoter that drives expression of the GH61 variant in the host cell). In certain embodiments, the method further includes isolating the produced GH61 variant.

Aspects of the present invention also include compositions containing a GH61 variant as described herein. Examples of suitable compositions include, but are not limited to detergent compositions, feed additives, and compositions for treating (or hydrolyzing) a cellulosic substrate (e.g., a cellulose containing textile, e.g., denim; a cellulose containing biomass material, e.g., a mixture of lignocellulosic biomass material which has optionally been subject to pre-treatment of pre-hydrolysis processing, etc.). Compositions that include a GH61 variant as described herein and a cellulosic substrate represent further aspects of the present invention. GH61 variant-containing detergent compositions include laundry detergents and dish detergents, where such detergents may further include additional components, e.g., surfactants. Examples of suitable cellulosic substrates include, but are not limited to: grass, switch grass, cord grass, rye grass, reed canary grass, *miscanthus*, sugar-processing residues, sugarcane bagasse, agricultural wastes, rice straw, rice hulls, barley straw, corn cobs, cereal straw, wheat straw, canola straw, oat straw, oat hulls, corn fiber, stover, soybean stover, corn stover, forestry wastes, wood pulp, recycled wood pulp fiber, paper sludge, sawdust, hardwood, softwood, and combinations thereof.

Aspects of the present invention include methods for hydrolyzing a cellulosic substrate comprising contacting the substrate with a variant GH61 as described herein. In certain embodiments, the GH61 variant is provided as a cell-free composition, whereas in other embodiments, the GH61 variant is provided as a host cell composition in which the host cell expresses the GH61 variant. Thus, certain embodiments of the methods for hydrolyzing a cellulosic substrate contacting the substrate with a host cell containing a GH61 variant expression vector. In certain embodiments, the method is for converting a lignocellulosic biomass to glucose, where in some of these embodiments, the lignocellulosic biomass is selected, without limitation, from: grass, switch grass, cord grass, rye grass, reed canary grass, *miscanthus*, sugar-processing residues, sugarcane bagasse, agricultural wastes, rice straw, rice hulls, barley straw, corn cobs, cereal straw, wheat straw, canola straw, oat straw, oat hulls, corn fiber, stover, soybean stover, corn stover, forestry wastes, wood pulp, recycled wood pulp fiber, paper sludge, sawdust, hardwood, softwood, and combinations thereof. In certain other embodiments, the cellulosic substrate is a cellulosic-containing textile, e.g., denim, where in some of these embodiments the method is for treating indigo dyed denim (e.g., in a stonewashing process).

Aspects of the present invention include cell culture supernatant compositions that contain a GH61 variant as described herein. For example, a cell culture supernatant obtained by culturing a host cell that contains a polynucleotide encoding the GH61 variant in a suitable culture medium under suitable conditions to express the GH61 variant from the polynucleotide and secrete the GH61 variant into the cell culture supernatant. Such a cell culture supernatant can include other proteins and/or enzymes produced by the host cell, including endogenously- and/or exogenously-expressed proteins and/or enzymes. Such supernatant of the culture medium can be used as is, with minimum or no post-production processing, which may typically include filtration to remove cell debris, cell-kill procedures, and/or ultrafiltration or other steps to enrich or concentrate the enzymes therein. Such supernatants are referred to herein as "whole broths" or "whole cellulase broths".

The GH61 variants can be produced by co-expression with one or more cellulases, and/or one or more hemicellulases. Alternatively, the GH61 variants can be produced without cellulases or hemicellulases. In the latter case, the GH61 variant optionally can be physically mixed with one or more cellulases and/or one or more hemicellulases to form an enzyme composition that is useful for a particular application, e.g., in hydrolyzing lignocellulosic biomass substrates. In a further embodiment the GH61 variants can be further co-expressed or physically mixed with one or more accessory enzymes. Known accessory enzymes include, for example, certain mannanases, which can sometimes be characterized as hemicellulases but more often are deemed accessory enzymes, galactanases, arabinases, ligninases, amylases, glucuronidases, proteases, esterases (e.g., ferulic acid esterases, acetyl xylan esterases, coumaric acid esterases, pectin methyl esterases), lipases, certain other GH61 family enzymes, xyloglucanases, CIP1, CIP1-like proteins, CIP2, CIP2-like proteins, swollenin, expansions, cellobiose hydrogenases, manganese peroxidases, and cellulose disrupting proteins, which may be, for example, cellulose binding modules.

BRIEF DESCRIPTION OF THE DRAWINGS

FIG. 1 shows the nucleic acid sequence (top line) (SEQ ID NO:1) and the amino acid sequence (bottom line) (SEQ ID NO:2) of the wild type GH61A (GH61A) from *H. jecorina*. The signal sequence in SEQ ID NO:2 is underlined.

FIGS. 2A, 2B, and 2C show an amino acid sequence alignment (Uniprot) of the catalytic domains of glycosyl hydrolase homologous to *H. jecorina* GH61A. The catalytic domains of the following enzymes are aligned (SEQ ID NOs represent the sequence of the catalytic domains of each enzyme): *Hypocrea jecorina* GH61A (SEQ ID NO:34), *Hypocrea rufa* EGIV (SEQ ID NO:35), *Trichoderma saturnisporum* EGIV (SEQ ID NO:36), *Hypocrea orientalis* EGIV (SEQ ID NO:37), *Trichoderma* sp. EGIV (SEQ ID NO:38), *Hypocrea atroviridis* GH61 (SEQ ID NO:39), *Hypocrea virens* GH61 (SEQ ID NO:40), *Thielavia terrestris* GH61 (SEQ ID NO:41), *Neurospora tetrasperma* EGIV (SEQ ID NO:42), *Neurospora tetrasperma* putative protein (SEQ ID NO:43), *Thielavia heterothallica* GH61 (SEQ ID NO:44), *Neurospora crassa* EGIV (SEQ ID NO:45), *Sordaria macrospora* putative protein (SEQ ID NO:46), *Gaeumannomyces graminis* EGIV (SEQ ID NO:47), *Nectria haematococca* putative protein (SEQ ID NO:48), *Fusarium pseudograminearum* putative protein (SEQ ID NO:49), and *Gibberella zeae* putative protein (SEQ ID NO:50).

FIG. 3 shows an amino acid sequence alignment (Uniprot) of the following carbohydrate binding domains of the indicated glycosyl hydrolase enzymes: GH61A from *Hypocrea jecorina* (SEQ ID NO:51), GH61 enzyme from *Hypocrea virens* (SEQ ID NO:52), Glycosyl hydrolase family 28 enzyme from *Thielavia terrestris* (SEQ ID NO:53), Glycosyl hydrolase family 45 enzyme from *Hypocrea atroviridis* (SEQ ID NO:54), putative Endoglucanase from *Neosartorya fumigata* (SEQ ID NO:55), putative enzyme from *Aspergillus terreus* (SEQ ID NO:56), Cip1 from *Hypocrea jecorina* (SEQ ID NO:57), Exoglucanase 1 from *Hypocrea rufa* (SEQ ID NO:58), Glycosyl hydrolase family 7 enzyme from *Hypocrea virens* (SEQ ID NO:59), Glycosyl hydrolase family 5 enzyme from *Hypocrea atroviridis* (SEQ ID NO:60), Glycosyl hydrolase family 45 enzyme from *Neosartorya fischeri* (SEQ ID NO:61), Exoglucanase 1 from *Trichoderma koningii* (SEQ ID NO:62), Glycosyl hydrolase family 61 from *Colletotrichum graminicola* (SEQ ID NO:63), Glycosyl hydrolase family 61 from *Colletotrichum graminicola* (SEQ ID NO:64), putative enzyme from *Arthrobotrys oligospora* (SEQ ID NO:65), Cellobiohydrolase from *Trichoderma harzianum* (SEQ ID NO:66), and Endoglucanase from *Penicillium* sp. (SEQ ID NO:67).

DETAILED DESCRIPTION

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 3RD ED., John Wiley and Sons, Ltd., New York (2007), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation. Practitioners are particularly directed to Green and Sambrook *Molecular Cloning: A Laboratory Manual* (Fourth Edition), Cold Spring Harbor Laboratory Press 2012, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

All publications cited herein are expressly incorporated herein by reference for the purpose of describing and disclosing compositions and methodologies which might be used in connection with the invention.

I. Definitions

The term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may have chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. As such, the present invention contemplates every possible variant nucleotide sequence encoding GH61 or a variant thereof, all of which are possible given the degeneracy of the genetic code. Unless otherwise indicated, nucleic acid sequences are presented in 5'-to-3' orientation.

"Cellulase" or "cellulase enzyme" means bacterial or fungal exoglucanases or exocellobiohydrolases, and/or endoglucanases, and/or β-glucosidases. These three different types of cellulase enzymes are known to act synergistically to convert cellulose and its derivatives to glucose.

"Endoglucanase" or "EG" or "EG enzyme" or "EG polypeptide," as used herein is defined as an endo-1,4-β-D-glucanase which catalyzes the endohydrolysis of 1,4β-D-glucosidic linkages in cellulose, lichenin and cereal β-D-glucans. In cellulose hydrolysis, this activity generates new chain ends that are substrates for CBH action. EGs will also hydrolyze 1,4-linkages in β-D-glucans that also contain 1,3-linkages. Certain EGs have been shown to act "processively" on crystalline cellulose [see, e.g., Wilson, D. B.

Three microbial strategies for plant cell wall degradation. Ann. N. Y. Acad. Sci. 2008, 1125, 289-297; and Li, Y, et al. *Increased crystalline cellulose activity via combinations of amino acid changes in the family 9 catalytic domain and family 3c cellulose binding module of Thermobifida fusca Cel9A*. Appl. Environ. Microbiol. 2010, 76, 2582-2588].

By "GH61" or "GH61 enzyme" and the like is meant an enzyme that belongs to the glycosyl hydrolase 61 family, e.g., the glycosyl hydrolase 61a (GH61A) family. The GH61 enzyme can be from a fungal cell, including filamentous fungus of the subdivision Eumycota or Oomycota. The filamentous fungi are characterized by vegetative mycelium having a cell wall composed of chitin, glucan, chitosan, mannan, and other complex polysaccharides, with vegetative growth by hyphal elongation and carbon catabolism that is obligately aerobic. A filamentous fungal parent cell may be a cell of a species of, but not limited to, *Trichoderma*, e.g., *Trichoderma longibrachiatum, Trichoderma viride, Trichoderma koningii, Trichoderma harzianum; Penicillium* sp.; *Humicola* sp., including *Humicola insolens* and *Humicola grisea; Chrysosporium* sp., including *C. lucknowense; Myceliophthora* sp.; *Gliocladium* sp.; *Aspergillus* sp.; *Fusarium* sp., *Neurospora* sp., *Hypocrea* sp., e.g., *Hypocrea jecorina*, and *Emericella* sp. As used herein, the term "*Trichoderma*" or "*Trichoderma* sp." refers to any fungal strains which have previously been classified as *Trichoderma* or are currently classified as *Trichoderma*. In certain embodiments, a GH61 enzyme can be from a non-filamentous fungal cell. Examples of GH61A enzymes include those found in *Hypocrea jecorina* (*Trichoderma reesei*), *Hypocrea rufa, Hypocrea orientalis, Hypocrea atroviridis, Hypocrea virens, Emericella nidulans, Aspergillus terreus, Aspergillus oryzae, Aspergillus niger, Aspergillus kawachii, Aspergillus flavus, Aspergillus clavatus, Gaeumannomyces graminis, Trichoderma saturnisporum, Neurospora tetrasperma, Neurospora crassa, Neosartorya fumigate, Neosartorya fumigate, Neosartorya fischeri, Thielavia terrestris*, and *Thielavia heterothallica*. In certain aspects, a GH61 enzyme comprises the amino acid sequence of any one of the mature GH61 enzyme sequences shown in SEQ ID NOs: 3, 72, 73, 74, 77, an amino acid sequence having at least 60%, 70%, 80%, 81%, 82%, 83%, 84%, 85%, 86,%, 87%, 88%, 89%, 90%, 91%, 92%, 93%, 94%, 95%, 96%, 97%, 98%, or 99% identity thereto, an allelic variant thereof, or a fragment thereof that has cellulase augmenting activity. In certain embodiments, a GH61A enzyme has cellulase augmenting activity and contains an amino acid sequence that is at least 60%, 70%, 80%, 81%, 82%, 83%, 84%, 85%, 86,%, 87%, 88%, 89%, 90%, 91%, 92%, 93%, 94%, 95%, 96%, 97%, 98%, 99% identical to SEQ ID NO:3, or a fragment or derivative thereof having cellulase augmenting activity.

By "GH61 activity" or "GH61A activity" or "activity" when in reference to a GH61 enzyme is meant the cellulase augmenting activity that is characteristic of a GH61 family member. Specifically, GH61 enzymes demonstrate an improved capacity, when combined with certain cellulases, to augment the efficacy and efficiency of hydrolyzing lignocellulosic biomass substrates, e.g., to generate monosaccharides, disaccharides, and polysaccharides.

A "variant" of an enzyme, protein, polypeptide, nucleic acid, or polynucleotide as used herein means that the variant is derived from a parent polypeptide or parent nucleic acid (e.g., native, wildtype or other defined parent polypeptide or nucleic acid) that includes at least one modification or alteration as compared to that parent, where such modification or alteration is produced by human intervention. Thus, a variant may have a few mutations as compared to a parent, where by "a few" is meant from 1 to 10 mutations. For example, a variant having from 1 to 10 amino acid substitutions as compared to SEQ ID NO:3 can be referred to as a GH61 variant having a few substitutions. Alterations/modifications can include a substitution of an amino acid/nucleic acid residue in the parent for a different amino acid/nucleic acid residue at one or more sites, deletion of an amino acid/nucleic acid residue (or a series of amino acid/nucleic acid residues) in the parent at one or more sites, insertion of an amino acid/nucleic acid residue (or a series of amino acid/nucleic acid residues) in the parent at one or more sites, truncation of amino- and/or carboxy-terminal amino acid sequences or 5' and or 3' nucleic acid sequences, and any combination thereof. A variant GH61 enzyme (sometimes referred to as a "GH61 variant" or a "GH61A variant") according to aspects of the invention retains cellulase augmenting activity but may have an altered property in some specific aspect, e.g., an improved property. For example, a variant GH61 enzyme may have an altered pH optimum, improved thermostability or oxidative stability, or a combination thereof, but will retain its characteristic cellulase augmenting activity. In certain embodiments, the variant GH61 enzyme is a variant of a GH61A enzyme as defined above and which has cellulase augmenting activity. In some aspects of the invention, a variant GH61A enzyme contains an amino acid sequence that is at least 60%, 70%, 80%, 81%, 82%, 83%, 84%, 85%, 86%, 87%, 88%, 89%, 90%, 91%, 92%, 93%, 94%, 95%, 96%, 97%, 98%, 99% identical to SEQ ID NO:3, or an enzymatically active fragment thereof.

"Combinatorial variants" are variants comprising two or more mutations, e.g., 2, 3, 4, 5, 6, 7, 8, 9, 10, 11, 12, 13, 14, 15, 16, 17, 18, 19, 20 or more, substitutions, deletions, and/or insertions.

A "parent" or "parental" polynucleotide, polypeptide, or enzyme sequence (e.g., a "parent GH61 enzyme"), or equivalents thereto, as used herein refers to a polynucleotide, polypeptide, or enzyme sequence that was used as a starting point or template for designing a variant polynucleotide, polypeptide, or enzyme. In certain embodiments, the parent enzyme is a GH61A enzyme as described above (e.g., SEQ ID NO:3). It is further noted that the words "parent" and "parental" are used interchangeably in this context.

The term "wild-type" refers to a naturally-occurring polypeptide or polynucleotide sequence, i.e., one that does not include a man-made variation. In some cases, a wild-type sequence is used as the parental sequence.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous polypeptide will often refer to two or more subsequences that are not found in the same relationship to each other in nature (e.g., a fusion polypeptide).

The term "recombinant" when used with reference, e.g., to a cell, or nucleic acid, polypeptide, or vector, indicates that the cell, nucleic acid, polypeptide or vector, has been modified by the introduction of a heterologous nucleic acid or polypeptide or the alteration of a native nucleic acid or polypeptide, or that the cell is derived from a cell so modified. Thus, for example, recombinant cells express genes that are not found within the native (non-recombinant) form of the cell or express native genes that are otherwise abnormally expressed, under expressed or not expressed at all.

The terms "isolated" or "purified" as used herein refer to a component that is removed from the environment in which it is naturally produced. In general, in an isolated or purified nucleic acid or polypeptide sample, the nucleic acid(s) or polypeptide(s) of interest are present at an increased absolute or relative concentration as compared to the environment in which they are naturally produced.

The term "enriched" when describing a component or material in a composition (e.g., a polypeptide or polynucleotide) means that the component or material is present at a relatively increased concentration in that composition as compared to the starting composition from which the enriched composition was generated. For example, an enriched GH61 composition (or sample) is one in which the relative or absolute concentration of GH61 is increased as compared to the initial fermentation product from the host organism.

As used herein, the terms "promoter" refers to a nucleic acid sequence that functions to direct transcription of a downstream gene. The promoter will generally be appropriate to the host cell in which the target gene is being expressed. The promoter, together with other transcriptional and translational regulatory nucleic acid sequences (also termed "control sequences"), are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences. A "constitutive" promoter is a promoter that is active under most environmental and developmental conditions. An "inducible" promoter is a promoter that is active under environmental or developmental regulation. An example of an inducible promoter useful in the present invention is the *T. reesei* (*H. jecorina*) cbh1 promoter which is deposited in GenBank under Accession Number D86235. In another aspect the promoter is a cbh II or xylanase promoter from *H. jecorina*. Examples of suitable promoters include the promoter from the *A. awamori* or *A. niger* glucoamylase genes (Nunberg, J. H. et al. (1984) Mol. Cell. Biol. 4, 2306-2315; Boel, E. et al. (1984) EMBO J. 3, 1581-1585), the *Mucor miehei* carboxyl protease gene, the *H. jecorina* cellobiohydrolase I gene (Shoemaker, S. P. et al. (1984) European Patent Application No. EP0137280A1), the *A. nidulans* trpC gene (Yelton, M. et al. (1984) Proc. Natl. Acad. Sci. USA 81, 1470-1474; Mullaney, E. J. et al. (1985) Mol. Gen. Genet. 199, 37-45) the *A. nidulans* alcA gene (Lockington, R. A. et al. (1986) Gene 33, 137-149), the *A. nidulans* tpiA gene (McKnight, G. L. et al. (1986) Cell 46, 143-147), the *A. nidulans* amdS gene (Hynes, M. J. et al. (1983) Mol. Cell Biol. 3, 1430-1439), the *H. jecorina* xln1 gene, the *H. jecorina* cbh2 gene, the *H. jecorina* eg1 gene, the *H. jecorina* eg2 gene, the *H. jecorina* eg3 gene, and higher eukaryotic promoters such as the SV40 early promoter (Barclay, S. L. and E. Meller (1983) Molecular and Cellular Biology 3, 2117-2130).

A nucleic acid is "operably linked" when it is placed into a functional relationship with another nucleic acid sequence. For example, DNA encoding a secretory leader, i.e., a signal peptide, is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. Thus, the term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "signal sequence", "signal peptide", "secretory sequence", "secretory peptide", "secretory signal sequence", "secretory signal peptide" and the like denotes a peptide sequence that, as a component of a larger polypeptide, directs the larger polypeptide through a secretory pathway of a cell in which it is synthesized, as well as nucleic acids encoding such peptides. In general, the larger polypeptide (or protein) is commonly cleaved to remove the secretory/signal peptide during transit through the secretory pathway, where the cleaved form of the polypeptide (i.e., the form without the signal/secretory peptide) is often referred to herein as the "mature form" of the polypeptide. For example, SEQ ID NO:2 provides the amino acid sequence of GH61A from *H. jecorina* with the signal peptide while SEQ ID NO:3 provides the amino acid sequence of the mature form of GH61A from *H. jecorina*, i.e., without the signal peptide.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct that forms an extrachromosomal self-replicating genetic element when present in many bacteria and some eukaryotes. Plasmids may be employed for any of a number of different purposes, e.g., as cloning vectors, propagation vectors, expression vectors, etc.

As used herein, the term "selectable marker" refers to a nucleotide sequence or polypeptide encoded thereby which is capable of expression in cells and where expression of the selectable marker in cells confers the ability to be differentiated from cells that do not express the selectable marker. In certain embodiments, a selectable marker allows a cell expressing it to grow in the presence of a corresponding selective agent, or under corresponding selective growth conditions. In other embodiments, a selectable marker allows a cell expressing it to be identified and/or isolated from cells that do not express it by virtue of a physical characteristic, e.g., by differences in fluorescence, immunoreactivity, etc.

In general, nucleic acid molecules which encode the variant GH61A will hybridize, under moderate to high stringency conditions to the wild type sequence (or its complement) provided herein as SEQ ID NO:1 (native *H. jecorina* GH61A). However, in some cases a GH61A-encoding nucleotide sequence is employed that possesses a substantially different codon usage, while the enzyme encoded by the GH61A-encoding nucleotide sequence has the same or substantially the same amino acid sequence as the native enzyme. For example, the coding sequence may be modified to facilitate faster expression of GH61A in a particular prokaryotic or eukaryotic expression system, in accordance with the frequency with which a particular codon is utilized by the host (commonly referred to as "codon optimization"). Te'o, et al. (FEMS Microbiology Letters 190:13-19, 2000), for example, describes the optimization of genes for expression in filamentous fungi. Such nucleic acid sequences are sometimes referred to as "degenerate" or "degenerated sequences".

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "moderate" or "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process generally includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

It follows that the term "desired glycosyl hydrolase expression" or equivalents refers to transcription and translation of the desired glycosyl hydrolase gene, the products of which include precursor RNA, mRNA, polypeptide, post-translationally processed polypeptides. By way of example, assays for GH61A expression include Western blot for GH61A enzyme, Northern blot analysis and reverse transcriptase polymerase chain reaction (RT-PCR) assays for GH61A mRNA, and cellulase augmenting activity assays, for example augmentation of assays as described in Shoemaker S. P. and Brown R. D. Jr. (Biochim. Biophys. Acta, 1978, 523:133-146) and Schulein (1988).

By the term "host cell" is meant a cell that contains a vector and supports the replication, and/or transcription and/or transcription and translation (expression) of the expression construct. Host cells for use in the present invention can be prokaryotic cells, such as *E. coli*, or eukaryotic cells such as yeast, plant, insect, amphibian, or mammalian cells. In certain embodiments, host cells are filamentous fungi.

As used herein, the term "detergent composition" refers to a mixture which is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers.

As used herein, the term "surfactant" refers to any compound generally recognized in the art as having surface active qualities. Thus, for example, surfactants comprise anionic, cationic and nonionic surfactants such as those commonly found in detergents. Anionic surfactants include linear or branched alkylbenzenesulfonates; alkyl or alkenyl ether sulfates having linear or branched alkyl groups or alkenyl groups; alkyl or alkenyl sulfates; olefinsulfonates; and alkanesulfonates. Ampholytic surfactants include quaternary ammonium salt sulfonates, and betaine-type ampholytic surfactants. Such ampholytic surfactants have both the positive and negative charged groups in the same molecule. Nonionic surfactants may comprise polyoxyalkylene ethers, as well as higher fatty acid alkanolamides or alkylene oxide adduct thereof, fatty acid glycerine monoesters, and the like.

As used herein, the term "cellulose containing fabric" refers to any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell).

As used herein, the term "cotton-containing fabric" refers to sewn or unsewn fabrics, yarns or fibers made of pure cotton or cotton blends including cotton woven fabrics, cotton knits, cotton denims, cotton yarns, raw cotton and the like.

As used herein, the term "stonewashing composition" refers to a formulation for use in stonewashing cellulose containing fabrics. Stonewashing compositions are used to modify cellulose containing fabrics prior to sale, i.e., during the manufacturing process. In contrast, detergent compositions are intended for the cleaning of soiled garments and are not used during the manufacturing process.

When an amino acid position (or residue) in a first polypeptide is noted as being "equivalent" to an amino acid position in a second, related polypeptide, it means that the amino acid position of the first polypeptide corresponds to the position noted in the second, related polypeptide by one or more of (i) primary sequence alignment (see description of sequence alignment and sequence identity below); (ii) structural sequence homology; or (iii) analogous functional property. Thus, an amino acid position in a first GH61 enzyme (or a variant thereof) can be identified as "equivalent" (or "homologous") to an amino acid position in a second GH61 enzyme (or even multiple different GH61 enzymes).

Primary Sequence Alignment:

Equivalent amino acid positions can be determined using primary amino acid sequence alignment methodologies, many of which are known in the art.

For example, by aligning the primary amino acid sequences of two or more different GH61 enzymes, it is possible to designate an amino acid position number from one GH61 enzyme as equivalent to the position number of another one of the aligned GH61 enzymes. In this manner, the numbering system originating from the amino acid sequence of one GH61 enzyme (e.g., the GH61A enzyme denoted in SEQ ID NO: 3) can be used to identify equivalent (or homologous) amino acid residues in other GH61 enzymes. See, e.g., the alignments shown in FIGS. 2 and 3.

Structural Sequence Homology:

In addition to determining "equivalent" amino acid positions using primary sequence alignment methodologies, "equivalent" amino acid positions may also be defined by determining homology at the level of secondary and/or tertiary structure. For example, for a glycosyl hydrolase whose tertiary structure has been determined by x-ray crystallography, equivalent residues can be defined as those for which the atomic coordinates of two or more of the main chain atoms of a particular amino acid residue of the glycosyl hydrolase are within 0.13 nm and preferably 0.1 nm after alignment with H. jecorina GH61A (N on N, CA on CA, C on C, and O on O). Alignment is achieved after the best model has been oriented and positioned to give the maximum overlap of atomic coordinates of non-hydrogen protein atoms of the glycosyl hydrolase in question to the H. jecorina GH61A. The best model is the crystallographic model that gives the highest resolution available. Where two or more different models have equal resolution, the model with the lowest R factor for experimental diffraction data, using the equation below, is used.

$$Rfactor = \frac{\Sigma_h |Fo(h)| - |Fc(h)|}{\Sigma_h |Fo(h)|}$$

Analogous Functional Property:

Equivalent amino acid residues in a first polypeptide which are functionally analogous to a specific residue of a second related polypeptide (e.g., a first glycosyl hydrolase and H. jecorina GH61A) are defined as those amino acids in the first polypeptide that adopt a conformation such that they alter, modify, or contribute to polypeptide structure, substrate binding, or catalysis in a manner defined and attributed to a specific residue of the second related polypeptide (e.g., H. jecorina GH61A). When a tertiary structure has been obtained by x-ray crystallography for the first polypeptide, amino acid residues of the first polypeptide that are functionally analogous to the second polypeptide occupy an analogous position to the extent that, although the main chain atoms of the given residue may not satisfy the criteria of equivalence on the basis of occupying a homologous position, the atomic coordinates of at least two of the side chain atoms of the residue lie within 0.13 nm of the corresponding side chain atoms of the second polypeptide (e.g., H. jecorina GH61A).

The term "improved" or "improved property" or "improved performance" and the like with respect to a variant enzyme (e.g., a GH61 variant) is defined herein as a characteristic or activity associated with a variant enzyme which is improved as compared to its respective parent enzyme. Improved properties include, but are not limited to, improved production from or expression in a host cell (sometimes referred to as yield), improved thermostability or altered temperature-dependent activity profile, improved activity or stability at a desired pH or pH range, improved substrate specificity, improved product specificity, and improved stability in the presence of a chemical or other component in a cellulosic hydrolysis process step, etc. Improved performance may be determined using a particular assay(s) including, but not limited to: (a) expression (Protein Content Determination, or yield), (b) Thermostability and/or melting temperature (Tm), (c) Whole Hydrolysate Dilute Acid Pretreated Corn Stover (whPCS) Hydrolysis Assay, and (d) Dilute Ammonia Pretreated Corn Stover (daCS) Hydrolysis Assay.

The term "improved thermostability" with respect to a variant polypeptide (e.g., a GH61 variant) is defined herein as a variant enzyme displaying retention of enzymatic activity (or in the specific case of a GH61 enzyme, the retention of an enzyme's capability to augment cellulase activities) after a period of incubation at an elevated temperature relative to the parent enzyme. Such a variant may or may not display an altered thermal activity profile relative to the parent. For example, a variant may have an improved ability to refold following incubation at elevated temperature relative to the parent.

By "improved product specificity" is meant a variant enzyme displaying an altered product profile as compared to the parent enzyme, where the altered product profile of the variant is improved in a given application as compared to the parent. A "product profile" is defined herein as the chemical composition of the reaction products produced by the enzyme of interest.

By "improved chemical stability" is meant that a variant enzyme displays retention of enzymatic activity after a period of incubation in the presence of a chemical or chemicals that reduce the enzymatic activity of the parent enzyme under the same conditions. Variants with improved chemical stability are better able to catalyze a reaction in the presence of such chemicals as compared to the parent enzyme.

A "pH range," with reference to an enzyme, refers to the range of pH values under which the enzyme exhibits catalytic activity.

The terms "pH stable" and "pH stability," with reference to an enzyme, relate to the ability of the enzyme to retain activity over a wide range of pH values for a predetermined period of time (e.g., 15 min., 30 min., 1 hr.).

"Percent sequence identity" or grammatical equivalents means that a particular sequence has at least a certain percentage of amino acid residues identical to those in a specified reference sequence using an alignment algorithm. An example of an algorithm that is suitable for determining sequence similarity is the BLAST algorithm, which is described in Altschul, et al., J. Mol. Biol. 215:403-410 (1990). Software for performing BLAST analyses is publicly available through the National Center for Biotechnology Information (<www.ncbi.nlm.nih.gov>). This algorithm involves first identifying high scoring sequence pairs (HSPs)

by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, Proc. Natl. Acad. Sci. USA 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

When questions of percent sequence identity arise, alignment using the CLUSTAL W algorithm with default parameters will govern. See Thompson et al. (1994) Nucleic Acids Res. 22:4673-4680. Default parameters for the CLUSTAL W algorithm are:

Gap opening penalty: 10.0
Gap extension penalty: 0.05
Protein weight matrix: BLOSUM series
DNA weight matrix: IUB
Delay divergent sequences %: 40
Gap separation distance: 8
DNA transitions weight: 0.50
List hydrophilic residues: GPSNDQEKR
Use negative matrix: OFF
Toggle Residue specific penalties: ON
Toggle hydrophilic penalties: ON
Toggle end gap separation penalty OFF.

II. Molecular Biology

Embodiments of the subject invention provide for the expression of a desired glycosyl hydrolase enzyme (or combination of glycosyl hydrolase enzymes) from glycosyl hydrolase-encoding nucleic acids under control of a promoter functional in a host cell of interest, e.g., a filamentous fungus. Therefore, this invention relies on a number of routine techniques in the field of recombinant genetics. Basic texts disclosing examples of suitable recombinant genetics methods are noted above.

Any method known in the art that can introduce mutations into a parent nucleic acid/polypeptide is contemplated by the present invention.

The present invention relates to the expression, purification and/or isolation and use of variant GH61 enzymes, e.g., GH61A enzymes. These enzymes may be prepared by recombinant methods utilizing any of a number of gh61 genes encoding the GH61 enzymes known in the art, including the GH61A/GH61 enzymes in SEQ ID NOs:2 to 11, 13, 14, and 16, e.g., GH61A from *H. jecorina*. Any convenient method for introducing mutations may be employed, including site directed mutagenesis. As indicated above, mutations (or variations) include substitutions, additions, deletions or truncations that will correspond to one or more amino acid changes in the expressed GH61 variant. Again, site directed mutagenesis and other methods of incorporating amino acid changes in expressed proteins at the DNA level can be found in numerous references, e.g., Green and Sambrook, et al. 2012 and Ausubel, et al.

DNA encoding an amino acid sequence variant of a parent GH61 is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the parent GH61A enzyme.

Site-directed mutagenesis is one method that can be employed in preparing substitution variants. This technique is well known in the art (see, e.g., Carter et al. Nucleic Acids Res. 13:4431-4443 (1985) and Kunkel et al., Proc. Natl. Acad. Sci. USA 82:488 (1987)). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the parent GH61. See Higuchi, in PCR Protocols, pp. 177-183 (Academic Press, 1990); and Vallette et al., Nuc. Acids Res. 17:723-733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence of a desired GH61 variant can be determined, and a nucleic acid sequence encoding such GH61 variant can be generated synthetically.

The desired GH61 so prepared may be subjected to further modifications, oftentimes depending on the intended use. Such modifications may involve further alteration of the amino acid sequence, fusion to heterologous polypeptide(s) and/or covalent modifications.

III. Variant GH61 Polypeptides and Nucleic Acids Encoding Same

In one aspect, variant GH61 enzymes are provided. In certain embodiments, variant GH61 enzymes have one or more mutations, as set forth herein, with respect to a parent GH61 enzyme and further have at least 60% (i.e., 60% or greater but less than 100%) amino acid sequence identity to the mature form of *H. jecorina* GH61A (SEQ ID NO:3), including at least 70%, 75%, 80%, 81%, 82%, 83% 84% 85%, 86,%, 87%, 88%, 89%, 90%, 91%, 92%, 93%, 94%, 95%, 96%, 97%, 98%, 99%, up to and including 99.6% amino acid sequence identity to SEQ ID NO:3. In certain embodiments, the parent GH61 is a fungal GH61A (as defined above). Further, the variant GH61 enzyme has cellulase augmenting activity, where in certain embodiments, the variant GH61 has an improved property as compared to the parent GH61 (as detailed herein). The amino acid sequence for the wild type, full-length form of *H. jecorina* GH61A is shown in FIG. 1 (SEQ ID NO:2). Sequence alignments of the catalytic domains and carbohydrate binding domains of *H. jecorina* GH61A with numerous other glycosyl hydrolases are shown in FIGS. 2 and 3, respectively.

In certain embodiments, a variant GH61 enzyme comprises an amino acid mutation at one or more amino acid positions in the mature form of GH61A from *H. jecorina* (SEQ ID NO:3). Because certain parent GH61 enzymes according to aspects of the invention may not have the same amino acid as wild type GH61A from *H. jecorina*, amino acid positions corresponding to the residues noted above (e.g., amino acid position I144) may also be designated either by the position number alone (e.g., amino acid position 144) or with an "X" prefix (e.g., amino acid position X144). It is noted here that all three ways of designating the amino acid positions corresponding to a specific amino acid residue in GH61A from *H. jecorina* are interchangeable. In some instances, the word "position" may be left our (e.g., amino acid 144, amino acid K144, or amino acid X144).

The amino acid sequence of the GH61 variant differs from the parent GH61 amino acid sequence by the substitution, deletion or insertion of one or more amino acids of the parent amino acid sequence. A residue (amino acid) of a GH61 variant is equivalent to a residue of *H. jecorina* GH61A if it is either homologous (i.e., corresponding in position in either primary or tertiary structure) or is functionally analogous to a specific residue or portion of that residue in *H. jecorina* GH61A (i.e., having the same or similar functional capacity to combine, react, or interact chemically or structurally). As used herein, numbering is intended to correspond to that of the mature GH61A amino acid sequence as illustrated in FIG. 1.

Alignment of amino acid sequences to determine homology can be determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by visual inspection or MOE by Chemical Computing Group, Montreal Canada. See also the description of "percent sequence identity" provided in the Definitions section above.

In certain embodiments, the mutation(s) in a variant GH61 enzyme is an amino acid substitution shown in Cohorts (1 to 4) (see Example 3), where the sites of the substitutions correspond to the mature form of GH61A from *H. jecorina* (SEQ ID NO:3). In some embodiments, a variant GH61A variant further includes an amino acid substitution shown in the Wild-Type Cohort (see Example 3). All possible combinations of the substitutions shown in Cohorts 1 to 4 are contemplated embodiments of the invention, including but not limited to the following:

1. A variant of a parent glycoside hydrolase family 61 (GH61) enzyme, where said variant has cellulase activity, has at least 80% sequence identity to SEQ ID NO:3, and has at least one improved property over said parent GH61 enzyme selected from: (a) expression, (b) thermostability and/or Tm, (c) performance in a Whole Hydrolysate Dilute Acid Pretreated Corn Stover (whPCS) hydrolysis assay, and (d) performance in a Dilute Ammonia Pretreated Corn Stover (daCS) hydrolysis assay, wherein said variant comprises at least one amino acid substitution at one or more position corresponding to amino acids 111 to 114 and 144 to 163 of SEQ ID NO:3.

2. The variant of 1, wherein said variant has improved thermostability and/or Tm and wherein said at least one amino acid substitution is selected from the group consisting of: I144G, D146F, L148P, A149P, G151Q, G151V, N152F, N152G, N152Q, N152S, N152Y, L155M, R156S, H157W, E158W, E158Y, I159Q, I160D, I160F, A161E, A161L, A161Y, L162A, L162F, H163L, H163R, H163Y, and combinations thereof.

3. The variant of 1 or 2, wherein said variant has improved performance in a whPCS hydrolysis assay and wherein said at least one amino acid substitution is selected from the group consisting of: I144K, I144R, I144S, P145G, P145H, P145I, P145K, P145R, P145S, P145V, D146A, D146C, D146E, D146F, D146K, D146M, D146Q, D146T, D146Y, N147F, N147M, L148K, L148V, A149C, A149D, A149F, A149G, A149I, A149N, A149V, P150A, P150O, P150D, P150E, P150F, P150G, P150H, P150I, P150K, P150L, P150Q, G151E, G151F, G151H, G151I, G151K, G151M, G151P, G151Q, G151S, G151V, G151W, G151Y, N152E, N152F, N152G, N152H, N152K, N152P, Y153F, Y153K, Y153L, Y153M, Y153P, Y153Q, Y153R, Y153S, Y153V, V154A, V154C, V154D, V154E, V154G, V154H, V154K, V154N, V154P, V154Q, V154R, V154T, L155C, L155F, L155K, L155M, L155N, R156A, R156C, R156D, R156E, R156F, R156H, R156I, R156K, R156L, R156M, R156P, R156Q, H157D, E158A, E158C, E158D, E158F, E158H, E158I, E158L, E158M, E158N, E158P, E158S, E158T, E158W, A161C, L162I, L162N, H163A, H163C, H163D, H163E, H163F, H163G, H163I, H163K, H163M, H163P, H163R, H163T, H163V, H163W, H163Y, and combinations thereof.

4. The variant of 1, 2 or 3, wherein said variant has improved performance in a daCS hydrolysis assay and wherein said at least one amino acid substitution is selected from the group consisting of: F112V, K113L, K113M, K113N, K113R, K113S, I114F, I114V, I144F, I144V, P145A, Y153F, V154T, H163D, H163Y, and combinations thereof.

5. The variant of 1 to 4, wherein said variant further comprises at least one second amino acid substitution selected from the group consisting of: F112M, F112W, K113P, K113T, I114L, I114M, I114T, I144A, I144C, I144D, I144E, I144H, I144N, I144P, I144Q, I144T, I144W, I144Y, P145C, P145D, P145E, P145F, P145L, P145M, P145N, P145Q, P145T, P145W, P145Y, D146G, D146H, D146I, D146L, D146N, D146P, D146R, D146S, D146V, D146W, N147A, N147C, N147D, N147E, N147G, N147H, N147I, N147K, N147L, N147P, N147Q, N147R, N147S, N147T, N147V, N147W, N147Y, L148A, L148C, L148D, L148E, L148F, L148G, L148H, L148I, L148M, L148N, L148Q, L148R, L148S, L148T, L148W, L148Y, A149E, A149H, A149K, A149L, A149M, A149Q, A149R, A149S, A149T, A149W, A149Y, P150M, P150N, P150R, P150S, P150T, P150V, P150W, P150Y, G151A, G151C, G151D, G151L, G151N, G151R, G151T, N152A, N152C, N152D, N152I, N152L, N152M, N152R, N152T, N152V, N152W, Y153A, Y153C, Y153D, Y153E, Y153G, Y153H, Y153I, Y153N, Y153T, Y153W, V154F, V154I, V154L, V154M, V154S, V154W, V154Y, L155A, L155D, L155E, L155G, L155H, L155I, L155P, L155Q, L155R, L155S, L155T, L155V, L155W, L155Y, R156G, R156N, R156T, R156V, R156W, R156Y, H157A, H157C, H157E, H157F, H157G, H157I, H157K, H157L, H157M, H157N, H157P, H157Q, H157R, H157S, H157T, H157V, H157Y, E158G, E158K, E158R, E158V, I159A, I159C, I159D, I159E, I159F, I159G, I159H, I159K, I159L, I159M, I159N, I159P, I159R, I159S, I159T, I159V, I159W, I159Y, I160A, I160C, I160E, I160G, I160H, I160K, I160L, I160M, I160N, I160P, I160Q, I160R, I160S, I160T, I160V, I160W, I160Y, A161D, A161F, A161G, A161H, A161I, A161K, A161M, A161N, A161P, A161Q, A161R, A161S, A161T, A161V, A161W, L162C, L162D, L162E, L162G, L162H, L162K, L162M, L162P, L162Q, L162R, L162S, L162T, L162V, L162W, L162Y, H163Q, H163S, and combinations thereof.

6. The variant of 1, where the variant comprises an F112V substitution.

7. The variant of 1 or 6, where the variant comprises a K113L substitution.

8. The variant of 1 or 6, where the variant comprises a K113M substitution.

9. The variant of 1 or 6, where the variant comprises a K113N substitution.

10. The variant of 1 or 6, where the variant comprises a K113R substitution.

11. The variant of 1 or 6, where the variant comprises a K113S substitution.

12. The variant of 1 or 6 to 11, where the variant comprises an I114F substitution.

13. The variant of 1 or 6 to 11, where the variant comprises an I114V substitution.

14. The variant of 1 or 6 to 13, where the variant comprises an I144F substitution.

15. The variant of 1 or 6 to 13, where the variant comprises an I144G substitution.

16. The variant of 1 or 6 to 13, where the variant comprises an I144K substitution.

17. The variant of 1 or 6 to 13, where the variant comprises an I144R substitution.

18. The variant of 1 or 6 to 13, where the variant comprises an I144S substitution.

19. The variant of 1 or 6 to 13, where the variant comprises an I144V substitution.

20. The variant of 1 or 6 to 19, where the variant comprises a P145A substitution.

21. The variant of 1 or 6 to 19, where the variant comprises a P145G substitution.

22. The variant of 1 or 6 to 19, where the variant comprises a P145H substitution.

23. The variant of 1 or 6 to 19, where the variant comprises a P145I substitution.

24. The variant of 1 or 6 to 19, where the variant comprises a P145K substitution.

25. The variant of 1 or 6 to 19, where the variant comprises a P145R substitution.

26. The variant of 1 or 6 to 19, where the variant comprises a P145S substitution.

27. The variant of 1 or 6 to 19, where the variant comprises a P145V substitution.

28. The variant of 1 or 6 to 27, where the variant comprises a D146A substitution.

29. The variant of 1 or 6 to 27, where the variant comprises a D146C substitution.

30. The variant of 1 or 6 to 27, where the variant comprises a D146E substitution.

31. The variant of 1 or 6 to 27, where the variant comprises a D146F substitution.

32. The variant of 1 or 6 to 27, where the variant comprises a D146K substitution.

33. The variant of 1 or 6 to 27, where the variant comprises a D146M substitution.

34. The variant of 1 or 6 to 27, where the variant comprises a D146Q substitution.

35. The variant of 1 or 6 to 27, where the variant comprises a D146T substitution.

36. The variant of 1 or 6 to 27, where the variant comprises a D146Y substitution.

37. The variant of 1 or 6 to 36, where the variant comprises an N147F substitution.

38. The variant of 1 or 6 to 36, where the variant comprises an N147M substitution.

39. The variant of 1 or 6 to 38, where the variant comprises an L148K substitution.

40. The variant of 1 or 6 to 38, where the variant comprises an L148P substitution.

41. The variant of 1 or 6 to 38, where the variant comprises an L148V substitution.

42. The variant of 1 or 6 to 41, where the variant comprises an A149Q substitution.

43. The variant of 1 or 6 to 41, where the variant comprises an A149D substitution.

44. The variant of 1 or 6 to 41, where the variant comprises an A149F substitution.

45. The variant of 1 or 6 to 41, where the variant comprises an A149G substitution.

46. The variant of 1 or 6 to 41, where the variant comprises an A149I substitution.

47. The variant of 1 or 6 to 41, where the variant comprises an A149N substitution.

48. The variant of 1 or 6 to 41, where the variant comprises an A149P substitution.

49. The variant of 1 or 6 to 41, where the variant comprises an A149V substitution.

50. The variant of 1 or 6 to 49, where the variant comprises a P150A substitution.

51. The variant of 1 or 6 to 49, where the variant comprises a P150C substitution.

52. The variant of 1 or 6 to 49, where the variant comprises a P150D substitution.

53. The variant of 1 or 6 to 49, where the variant comprises a P150E substitution.
54. The variant of 1 or 6 to 49, where the variant comprises a P150F substitution.
55. The variant of 1 or 6 to 49, where the variant comprises a P150G substitution.
56. The variant of 1 or 6 to 49, where the variant comprises a P150H substitution.
57. The variant of 1 or 6 to 49, where the variant comprises a P150I substitution.
58. The variant of 1 or 6 to 49, where the variant comprises a P150K substitution.
59. The variant of 1 or 6 to 49, where the variant comprises a P150L substitution.
60. The variant of 1 or 6 to 49, where the variant comprises a P150Q substitution.
61. The variant of 1 or 6 to 60, where the variant comprises a G151E substitution.
62. The variant of 1 or 6 to 60, where the variant comprises a G151F substitution.
63. The variant of 1 or 6 to 60, where the variant comprises a G151H substitution.
64. The variant of 1 or 6 to 60, where the variant comprises a G151I substitution.
65. The variant of 1 or 6 to 60, where the variant comprises a G151K substitution.
66. The variant of 1 or 6 to 60, where the variant comprises a G151M substitution.
67. The variant of 1 or 6 to 60, where the variant comprises a G151P substitution.
68. The variant of 1 or 6 to 60, where the variant comprises a G151Q substitution.
69. The variant of 1 or 6 to 60, where the variant comprises a G151S substitution.
70. The variant of 1 or 6 to 60, where the variant comprises a G151V substitution.
71. The variant of 1 or 6 to 60, where the variant comprises a G151W substitution.
72. The variant of 1 or 6 to 60, where the variant comprises a G151Y substitution.
73. The variant of 1 or 6 to 72, where the variant comprises an N152E substitution.
74. The variant of 1 or 6 to 72, where the variant comprises an N152F substitution.
75. The variant of 1 or 6 to 72, where the variant comprises an N152G substitution.
76. The variant of 1 or 6 to 72, where the variant comprises an N152H substitution.
77. The variant of 1 or 6 to 72, where the variant comprises an N152K substitution.
78. The variant of 1 or 6 to 72, where the variant comprises an N152P substitution.
79. The variant of 1 or 6 to 72, where the variant comprises an N152Q substitution.
80. The variant of 1 or 6 to 72, where the variant comprises an N152S substitution.
81. The variant of 1 or 6 to 72, where the variant comprises an N152Y substitution.
82. The variant of 1 or 6 to 81, where the variant comprises a Y153F substitution.
83. The variant of 1 or 6 to 81, where the variant comprises a Y153K substitution.
84. The variant of 1 or 6 to 81, where the variant comprises a Y153L substitution.
85. The variant of 1 or 6 to 81, where the variant comprises a Y153M substitution.
86. The variant of 1 or 6 to 81, where the variant comprises a Y153P substitution.
87. The variant of 1 or 6 to 81, where the variant comprises a Y153Q substitution.
88. The variant of 1 or 6 to 81, where the variant comprises a Y153R substitution.
89. The variant of 1 or 6 to 81, where the variant comprises a Y153S substitution.
90. The variant of 1 or 6 to 81, where the variant comprises a Y153V substitution.
91. The variant of 1 or 6 to 90, where the variant comprises a V154A substitution.
92. The variant of 1 or 6 to 90, where the variant comprises a V154C substitution.
93. The variant of 1 or 6 to 90, where the variant comprises a V154D substitution.
94. The variant of 1 or 6 to 90, where the variant comprises a V154E substitution.
95. The variant of 1 or 6 to 90, where the variant comprises a V154G substitution.
96. The variant of 1 or 6 to 90, where the variant comprises a V154H substitution.
97. The variant of 1 or 6 to 90, where the variant comprises a V154K substitution.
98. The variant of 1 or 6 to 90, where the variant comprises a V154N substitution.
99. The variant of 1 or 6 to 90, where the variant comprises a V154P substitution.
100. The variant of 1 or 6 to 90, where the variant comprises a V154Q substitution.
101. The variant of 1 or 6 to 90, where the variant comprises a V154R substitution.
102. The variant of 1 or 6 to 90, where the variant comprises a V154T substitution.
103. The variant of 1 or 6 to 102, where the variant comprises an L155C substitution.
104. The variant of 1 or 6 to 102, where the variant comprises an L155F substitution.
105. The variant of 1 or 6 to 102, where the variant comprises an L155K substitution.
106. The variant of 1 or 6 to 102, where the variant comprises an L155M substitution.
107. The variant of 1 or 6 to 102, where the variant comprises an L155N substitution.
108. The variant of 1 or 6 to 107, where the variant comprises an R156A substitution.
109. The variant of 1 or 6 to 107, where the variant comprises an R156C substitution.
110. The variant of 1 or 6 to 107, where the variant comprises an R156D substitution.
111. The variant of 1 or 6 to 107, where the variant comprises an R156E substitution.
112. The variant of 1 or 6 to 107, where the variant comprises an R156F substitution.
113. The variant of 1 or 6 to 107, where the variant comprises an R156H substitution.
114. The variant of 1 or 6 to 107, where the variant comprises an R156I substitution.
115. The variant of 1 or 6 to 107, where the variant comprises an R156K substitution.
116. The variant of 1 or 6 to 107, where the variant comprises an R156L substitution.
117. The variant of 1 or 6 to 107, where the variant comprises an R156M substitution.
118. The variant of 1 or 6 to 107, where the variant comprises an R156P substitution.

119. The variant of 1 or 6 to 107, where the variant comprises an R156Q substitution.
120. The variant of 1 or 6 to 107, where the variant comprises an R156S substitution.
121. The variant of 1 or 6 to 120, where the variant comprises an H157D substitution.
122. The variant of 1 or 6 to 120, where the variant comprises an H157W substitution.
123. The variant of 1 or 6 to 122, where the variant comprises an E158A substitution.
124. The variant of 1 or 6 to 122, where the variant comprises an E158C substitution.
125. The variant of 1 or 6 to 122, where the variant comprises an E158D substitution.
126. The variant of 1 or 6 to 122, where the variant comprises an E158F substitution.
127. The variant of 1 or 6 to 122, where the variant comprises an E158H substitution.
128. The variant of 1 or 6 to 122, where the variant comprises an E158I substitution.
129. The variant of 1 or 6 to 122, where the variant comprises an E158L substitution.
130. The variant of 1 or 6 to 122, where the variant comprises an E158M substitution.
131. The variant of 1 or 6 to 122, where the variant comprises an E158N substitution.
132. The variant of 1 or 6 to 122, where the variant comprises an E158P substitution.
133. The variant of 1 or 6 to 122, where the variant comprises an E158S substitution.
134. The variant of 1 or 6 to 122, where the variant comprises an E158T substitution.
135. The variant of 1 or 6 to 122, where the variant comprises an E158W substitution.
136. The variant of 1 or 6 to 122, where the variant comprises an E158Y substitution.
137. The variant of 1 or 6 to 136, where the variant comprises an I159Q substitution.
138. The variant of 1 or 6 to 137, where the variant comprises an I160D substitution.
139. The variant of 1 or 6 to 137, where the variant comprises an I160F substitution.
140. The variant of 1 or 6 to 139, where the variant comprises an A161C substitution.
141. The variant of 1 or 6 to 139, where the variant comprises an A161E substitution.
142. The variant of 1 or 6 to 139, where the variant comprises an A161L substitution.
143. The variant of 1 or 6 to 139, where the variant comprises an A161Y substitution.
144. The variant of 1 or 6 to 143, where the variant comprises an L162A substitution.
145. The variant of 1 or 6 to 143, where the variant comprises an L162F substitution.
146. The variant of 1 or 6 to 143, where the variant comprises an L162I substitution.
147. The variant of 1 or 6 to 143, where the variant comprises an L162N substitution.
148. The variant of 1 or 6 to 147, where the variant comprises an H163A substitution.
149. The variant of 1 or 6 to 147, where the variant comprises an H163C substitution.
150. The variant of 1 or 6 to 147, where the variant comprises an H163D substitution.
151. The variant of 1 or 6 to 147, where the variant comprises an H163E substitution.
152. The variant of 1 or 6 to 147, where the variant comprises an H163F substitution.
153. The variant of 1 or 6 to 147, where the variant comprises an H163G substitution.
154. The variant of 1 or 6 to 147, where the variant comprises an H163I substitution.
155. The variant of 1 or 6 to 147, where the variant comprises an H163K substitution.
156. The variant of 1 or 6 to 147, where the variant comprises an H163L substitution.
157. The variant of 1 or 6 to 147, where the variant comprises an H163M substitution.
158. The variant of 1 or 6 to 147, where the variant comprises an H163P substitution.
159. The variant of 1 or 6 to 147, where the variant comprises an H163R substitution.
160. The variant of 1 or 6 to 147, where the variant comprises an H163T substitution.
161. The variant of 1 or 6 to 147, where the variant comprises an H163V substitution.
162. The variant of 1 or 6 to 147, where the variant comprises an H163W substitution.
163. The variant of 1 or 6 to 147, where the variant comprises an H163Y substitution.
164. The variant of any of 1 to 163, where the parent GH61 enzyme is a fungal glycoside hydrolase family 61a (GH61A) enzyme.

In another aspect, nucleic acids encoding a variant GH61 enzyme having one or more mutations with respect to a parent GH61 enzyme (e.g., as described above) are provided. In certain embodiments, the parent GH61 enzyme encoded by the nucleic acid has at least 80% (i.e., 80% or greater but less than 100%) amino acid sequence identity to *H. jecorina* GH61A (SEQ ID NO:3). In certain embodiments, the nucleic acid encoding a variant GH61 enzyme is at least 40%, at least 50%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or even at least 99.9% homology/identity to SEQ ID NO: 1 (excluding the portion of the nucleic acid that encodes the signal sequence). It will be appreciated that due to the degeneracy of the genetic code, a plurality of nucleic acids may encode the same variant GH61 enzyme. Moreover, nucleic acids encoding a variant GH61 enzyme as described herein may be engineered to be codon optimized, e.g., to improve expression in a host cell of interest. Certain codon optimization techniques are known in the art.

In certain embodiments, the variant GH61 enzyme-encoding nucleic acid hybridizes under stringent conditions to a nucleic acid encoding (or complementary to a nucleic acid encoding) a GH61 having at least 40%, at least 50%, at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or at least 99.9% homology/identity to SEQ ID NO:1 (excluding the portion of the nucleic acid that encodes the signal sequence).

Nucleic acids may encode a "full-length" ("fl" or "FL") variant GH61 enzyme, which includes a signal sequence, only the mature form of a variant GH61 enzyme, which lacks the signal sequence, or a truncated form of a variant GH61 enzyme, which lacks portions of the N and/or C-terminus of the mature form.

A nucleic acid that encodes a variant GH61 enzyme can be operably linked to various promoters and regulators in a vector suitable for expressing the variant GH61 enzyme in a host cell(s) of interest, as described below.

IV. Expression of Recombinant GH61 Variants

Aspects of the subject invention include methods and compositions related to the generation nucleic acids encoding GH61 variants, host cells containing such nucleic acids, the production of GH61 variants by such host cells, and the isolation, purification and/or use of the GH61 variants.

As such, embodiments of the invention provide host cells that have been transduced, transformed or transfected with an expression vector comprising a desired GH61 variant-encoding nucleic acid sequence. For example, a filamentous fungal cell or yeast cell is transfected with an expression vector having a promoter or biologically active promoter fragment or one or more (e.g., a series) of enhancers which functions in the host cell line, operably linked to a DNA segment encoding a desired GH61 variant, such that desired GH61 variant is expressed in the cell line.

A. Nucleic Acid Constructs/Expression Vectors.

Natural or synthetic polynucleotide fragments encoding a desired GH61 variant may be incorporated into heterologous nucleic acid constructs or vectors, capable of introduction into, and replication in, a host cell of interest (e.g., a filamentous fungal or yeast cell). The vectors and methods disclosed herein are suitable for use in host cells for the expression of a desired GH61 variant. Any vector may be used as long as it meets the desired replication/expression characteristics in the host cell(s) into which it is introduced (such characteristics generally being defined by the user). Large numbers of suitable vectors and promoters are known to those of skill in the art, some of which are commercially available. Cloning and expression vectors are also described in Sambrook et al., 1989, Ausubel F M et al., 1989, and Strathern et al., 1981, each of which is expressly incorporated by reference herein. Appropriate expression vectors for fungi are described in van den Hondel, C. A. M. J. J. et al. (1991) In: Bennett, J. W. and Lasure, L. L. (eds.) More Gene Manipulations in Fungi. Academic Press, pp. 396-428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related subcloning procedures are deemed to be within the scope of knowledge of those skilled in the art.

Recombinant host cells comprising the coding sequence for a desired GH61 variant may be produced by introducing a heterologous nucleic acid construct comprising the desired GH61 variant coding sequence into the desired host cells (e.g., as described in further detail below). For example, a desired GH61 variant coding sequence may be inserted into a suitable vector according to well-known recombinant techniques and used to transform a filamentous fungus capable of GH61 expression. As has been noted above, due to the inherent degeneracy of the genetic code, other nucleic acid sequences which encode substantially the same or a functionally equivalent amino acid sequence may be used to clone and express a desired GH61 variant. Therefore it is appreciated that such substitutions in the coding region fall within the sequence variants covered by the present invention.

The present invention also includes recombinant nucleic acid constructs comprising one or more of the desired GH61 variant-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for a desired GH61 variant: (i) in isolation; (ii) in combination with additional coding sequences; such as fusion polypeptide or signal peptide coding sequences, where the desired GH61 variant coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the desired GH61 variant coding sequence is a heterologous gene.

In one aspect of the present invention, a heterologous nucleic acid construct is employed to transfer a desired GH61 variant-encoding nucleic acid sequence into a host cell in vitro, e.g., into established filamentous fungal and yeast lines. Long-term production of a desired GH61 variant can be achieved by generating a host cell that has stable expression of the GH61 variant. Thus, it follows that any method effective to generate stable transformants may be used in practicing the invention.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Examples of suitable promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system as described (ClonTech and BASF), the beta actin promoter and the metallothionine promoter that can upregulated by addition of certain metal salts. A promoter sequence is a DNA sequence which is recognized by the particular host cell for expression purposes. It is operably linked to DNA sequence encoding a variant GH61A polypeptide. Such linkage comprises positioning of the promoter with respect to the initiation codon of the DNA sequence encoding the variant GH61A polypeptide in the expression vector such that the promoter can drive transcription/translation of the GH61 variant-encoding sequence. The promoter sequence contains transcription and translation control sequence which mediate the expression of the variant GH61A polypeptide. Examples include the promoters from the *Aspergillus niger*, *A awamori* or *A. oryzae* glucoamylase, alpha-amylase, or alpha-glucosidase encoding genes; the *A. nidulans* gpdA or trpC Genes; the *Neurospora crassa* cbh1 or trp1 genes; the *A. niger* or *Rhizomucor miehei* aspartic proteinase encoding genes; the *H. jecorina* cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *H. jecorina*, amdS from *A. nidulans*, pyr4 from *Neurospora crassa* or *H. jecorina*, pyrG from *Aspergillus niger* or *A. nidulans*. Additional examples of suitable selectable markers include, but are not limited to trpc, trp1, oliC31, niaD or leu2, which are included in heterologous nucleic acid constructs used to transform a mutant strain such as trp-, pyr-, leu- and the like.

Such selectable markers confer to transformants the ability to utilize a metabolite that is usually not metabolized by the filamentous fungi. For example, the amdS gene from *H. jecorina* which encodes the enzyme acetamidase that allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Examples of suitable plasmids include pUC18, pBR322, pRAX and pUC100. The pRAX plasmid contains AMA1 sequences from *A. nidulans*, which make it possible to replicate in *A. niger*.

The practice of the present invention will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, 1987; Ausubel, et al., 1993; and Coligan et al., 1991.

B. Host Cells and Culture Conditions for GH61 and Variant GH61 Enzyme Production After DNA sequences that encode the GH61A variant GH61A variants have been cloned into DNA constructs, the DNA is used to transform microorganisms. The microorganism to be transformed for the purpose of expressing a variant GH61A according to the present invention can be chosen from a wide variety of host cells. The sections below are provided as examples of host cells/microorganisms and are not meant to limit the scope of host cells that can be employed in practicing aspects of the present invention.

(i) Filamentous Fungi

Aspect of the present invention include filamentous fungi which have been modified, selected and cultured in a manner effective to result in desired GH61 variant production or expression relative to the corresponding non-transformed parental filamentous fungi.

Examples of species of parental filamentous fungi that may be treated and/or modified for desired glycosyl hydrolase expression include, but are not limited to *Trichoderma, Penicillium* sp., *Humicola* sp., including *Humicola insolens; Aspergillus* sp., including *Aspergillus niger, Chrysosporium* sp., *Myceliophthora* sp., *Fusarium* sp., *Hypocrea* sp., *Talaromyces* sp., *Sporotricum* sp, and *Emericella* sp.

Cells expressing a desired GH61 variant are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71-86, 1988 and Ilmen, M. et al., Appl. Environ. Microbiol. 63:1298-1306, 1997. Standard culture conditions are known in the art, e.g., cultures are incubated at 28° C. in shaker cultures or fermenters until desired levels of desired GH61 variant expression are achieved.

Culture conditions for a given filamentous fungus can be found, for example, in the scientific literature and/or from the source of the fungi such as the American Type Culture Collection (ATCC). After fungal growth has been established, the cells are exposed to conditions effective to cause or permit the expression of a desired GH61 variant.

In cases where a desired GH61 variant coding sequence is under the control of an inducible promoter, the inducing agent, e.g., a sugar, metal salt or antibiotic, is added to the medium at a concentration effective to induce expression of the desired GH61 variant.

In one embodiment, the strain is an *Aspergillus niger* strain, which is a useful strain for obtaining overexpressed protein. For example *A. niger* var *awamori* dgr246 is known to secrete elevated amounts of secreted cellulases (Goedegebuur et al, Curr. Genet (2002) 41: 89-98). Other strains of *Aspergillus niger* var *awamori* such as GCDAP3, GCDAP4 and GAPS-4 are known Ward et al (Ward, M, Wilson, L. J. and Kodama, K. H., 1993, Appl. Microbiol. Biotechnol. 39:738-743).

In another embodiment, the strain is a *Trichoderma reesei* strain, which is a useful strain for obtaining overexpressed protein. For example, RL-P37, described by Sheir-Neiss, et al., Appl. Microbiol. Biotechnol. 20:46-53 (1984) is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in overexpressing variant GH61.

Where it is desired to obtain a GH61 variant in the absence of potentially detrimental native glycosyl hydrolase or cellulase activity, it is useful to obtain a host cell strain which has had one or more glycosyl hydrolase genes (e.g., the gh61a gene) and/or cellulase genes deleted prior to introduction of a DNA construct or plasmid containing the DNA fragment encoding the desired GH61 variant. Such strains may be prepared in any convenient manner, for example by the method disclosed in U.S. Pat. No. 5,246,853 and WO 92/06209, which disclosures are hereby incorporated by reference. By expressing a desired GH61 variant in a host microorganism that is missing one or more glycosyl hydrolase genes (e.g., the endogenous gh61a gene of a host cell), identification and subsequent purification procedures, where desired, are simplified.

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, for example from about 0.5 to about 2.0 kb may remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

In certain embodiments, more than one copy of DNA encoding a desired GH61 variant may be present in a host strain to facilitate overexpression of the GH61 variant. For example, a host cell may have multiple copies of a desired GH61 variant integrated into the genome or, alternatively, include a plasmid vector that is capable of replicating autonomously in the host organism.

(ii) Yeast

The present invention also contemplates the use of yeast as a host cell for desired GH61 production. Several other genes encoding hydrolytic enzymes have been expressed in various strains of the yeast *S. cerevisiae*. These include sequences encoding for two endoglucanases (Penttila et al., 1987), two cellobiohydrolases (Penttila et al., 1988) and one beta-glucosidase from *Trichoderma reesei* (Cummings and Fowler, 1996), a xylanase from *Aureobasidlium pullulans* (Li and Ljungdahl, 1996), an alpha-amylase from wheat (Rothstein et al., 1987), etc. In addition, a cellulase gene cassette encoding the *Butyrivibrio fibrisolvens* endo-[beta]-1,4-glucanase (END1), *Phanerochaete chrysosporium* cellobiohydrolase (CBH1), the *Ruminococcus flavefaciens* cellodextrinase (CEL1) and the *Endomyces fibrilizer* cellobiase (Bgl1) was successfully expressed in a laboratory strain of *S. cerevisiae* (Van Rensburg et al., 1998).

(iii) Other

It is further contemplated that in some embodiments, expression systems in host cells other than filamentous fungal cells or yeast cells may be employed, including insect cell or bacterial cell expression systems. Certain of the bacterial host cells can, for example, be one that is also an ethanologen, such as an engineered *Zymomonas mobilis*, which is not only capable of expressing the enzyme(s)/variant(s) of interest but also capable of metabolizing certain monomeric and other fermentable sugars, turning them into ethanol. The selection of a host cell may be determined by the desires of the user of the GH61 variants described herein, and thus no limitation in that regard is intended.

C. Introduction of a Desired GH61-Encoding Nucleic Acid Sequence into Host Cells.

The invention further provides cells and cell compositions which have been genetically modified to comprise an exogenously provided desired GH61 variant-encoding nucleic acid sequence. A parental cell or cell line may be genetically modified (e.g., transduced, transformed or transfected) with a cloning vector or an expression vector. The vector may be, for example, in the form of a plasmid, a viral particle, a phage, etc., as further described above.

The methods of transformation of the present invention may result in the stable integration of all or part of the transformation vector into the genome of the host cell. However, transformation resulting in the maintenance of a self-replicating extra-chromosomal transformation vector is also contemplated.

Any of the well-known procedures for introducing foreign nucleotide sequences into host cells may be used. These include the use of calcium phosphate transfection, polybrene, infection, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). In essence, the particular genetic engineering procedure used should be capable of successfully introducing a polynucleotide (e.g., an expression vector) into the host cell that is capable of expressing the desired GH61 variant.

Many standard transfection methods can be used to produce *Trichoderma reesei* cell lines that express large quantities of the heterologous polypeptide. Some of the published methods for the introduction of DNA constructs into cellulase-producing strains of *Trichoderma* include Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164, for *Aspergillus* Yelton, Hamer and Timberlake, 1984, Proc. Natl. Acad. Sci. USA 81: 1470-1474, for *Fusarium* Bajar, Podila and Kolattukudy, 1991, Proc. Natl. Acad. Sci. USA 88: 8202-8212, for *Streptomyces* Hopwood et al., 1985, The John Innes Foundation, Norwich, UK and for *Bacillus* Brigidi, DeRossi, Bertarini, Riccardi and Matteuzzi, 1990, FEMS Microbiol. Lett. 55: 135-138). An example of a suitable transformation process for *Aspergillus* sp. can be found in Campbell et al. Improved transformation efficiency of *A. niger* using homologous niaD gene for nitrate reductase. Curr. Genet. 16:53-56; 1989.

The invention further includes novel and useful transformants of host cells, e.g., filamentous fungi such as *H. jecorina* and *A. niger*, for use in producing fungal cellulase and glycosyl hydrolase compositions. Thus, aspects of the subject invention include transformants of filamentous fungi comprising the desired GH61 variant coding sequence, sometimes also including a deletion or an inactivating mutation of one or more endogenous glycosyl hydrolase coding sequence (e.g., deletion of gh61a coding sequence; host cells with deleted glycosyl hydrolyase and/or cellulase genes are also describe in the Examples).

In addition, heterologous nucleic acid constructs comprising a desired glycosyl hydrolase-encoding nucleic acid sequence can be transcribed in vitro, and the resulting RNA introduced into the host cell by well-known methods, e.g., by injection.

D. Analysis For GH61 Nucleic Acid Coding Sequences and/or Protein Expression.

In order to evaluate the expression of a desired GH61 variant by a cell line that has been transformed with a desired GH61 variant-encoding nucleic acid construct, assays can be carried out at the protein level, the RNA level or by use of functional bioassays particular to GH61 activity and/or production.

In general, assays employed to analyze the expression of a desired GH61 variant include, but are not limited to, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of modified GH61 may be measured in a sample directly, for example, by assays for GH61 activity (cellulase augmenting activity), expression and/or production. Assays in which GH61 cellulase augmenting activity may be assessed are described, for example, in Shoemaker, S. P. and Brown, R. D. Jr. (Biochim. Biophys. Acta, 1978, 523:133 146), Schulein (1988), and U.S. Pat. Nos. 5,246,853 and 5,475,101 each of which is expressly incorporated by reference herein. The ability of modified GH61 to augment the hydrolysis of isolated soluble and insoluble substrates can be measured using assays described in Suurnakki et al. (2000) and Ortega et al. (2001). Substrates useful for assaying augmentation by GH61 on cellobiohydrolase, endoglucanase or 6-glucosidase activities include crystalline cellulose, filter paper, phosphoric acid swollen cellulose, hydroxyethyl cellulose, carboxymethyl cellulose, cellooligosaccharides, methylumbelliferyl lactoside, methylumbelliferyl cellobioside, orthonitrophenyl lactoside, paranitrophenyl lactoside, orthonitrophenyl cellobioside, paranitrophenyl cellobioside, orthonitrophenyl glucoside, paranitrophenyl glucoside, methylumbelliferyl glycoside.

In addition, protein expression may be evaluated by immunological methods, such as ELISA, competitive immunoassays, radioimmunoassays, Western blot, indirect immunofluorescent assays, and the like. Certain of these assays can be performed using commercially available reagents and/or kits designed for detecting GH61 enzymes. Such immunoassays can be used to qualitatively and/or quantitatively evaluate expression of a desired GH61 variant. The details of such methods are known to those of skill in the art and many reagents for practicing such methods are commercially available. In certain embodiments, an immunological reagent that is specific for a desired variant GH61 enzyme but not its parent GH61 may be employed, e.g., an antibody that is specific for a GH61 substitution or a fusion partner of the GH61 variant (e.g., an N or C terminal tag sequence, e.g., a hexa-Histidine tag or a FLAG tag). Thus, aspects of the present invention include using a purified form of a desired GH61 variant to produce either monoclonal or polyclonal antibodies specific to the expressed polypeptide for use in various immunoassays. (See, e.g., Hu et al., 1991).

V. Methods for Enrichment, Isolation and/or Purification of GH61 Variant Polypeptide In general, a desired GH61 variant polypeptide produced in a host cell culture is secreted into the medium (producing a culture supernatant containing the GH61 variant) and may be enriched, purified or isolated, e.g., by removing unwanted components from the cell culture medium. However, in some cases, a desired GH61 variant polypeptide may be produced in a cellular form necessitating recovery from a cell lysate. The desired GH61 variant polypeptide is harvested from the cells or cell supernatants in which it was produced using techniques routinely employed by those of skill in the art. Examples include, but are not limited to, filtration (e.g., ultra- or micro-filtration), centrifugation, density gradient fractionation (e.g., density gradient ultracentrifugation), affinity chromatography (Tilbeurgh et al., 1984), ion-exchange chromatographic methods (Goyal et al., 1991; Fliess et al., 1983; Bhikhabhai et al., 1984; Ellouz et al., 1987), including ion-exchange using materials with high resolution power (Medve et al., 1998), hydrophobic interaction chromatography (Tomaz and Queiroz, 1999), and two-phase partitioning (Brumbauer, et al., 1999).

While enriched, isolated, or purified GH61 variant polypeptide is sometimes desired, in other embodiments a host cell expressing a GH61 variant polypeptide is employed directly in an assay that requires GH61-mediated cellulase augmenting activity. Thus, enrichment, isolation or purification of the desired GH61 variant polypeptide is not always required to obtain a GH61 variant polypeptide composition that finds use in a cellulosic biomass hydrolysis assay or process. For example, a cellulase- and glycosyl hydrolase-comprising system according to aspects of the present invention might be designed to allow a host cell that expresses a variant GH61A as described herein to be used directly in a cellulosic hydrolysis process, i.e., without isolation of the GH61A away from the host cell prior to its use in an assay of interest.

VI. Utility of GH61 Variants

It can be appreciated that the desired GH61 variant-encoding nucleic acids, the desired GH61 variant polypeptide and compositions comprising the same find utility in a wide variety applications, some of which are described below. The improved property or properties of the GH61 variants described herein can be exploited in many ways. For example, GH61 variants with improved performance under conditions of thermal stress can be used to increase cellulase augmenting activity in assays carried out at high temperatures (e.g., temperatures at which the parent GH61 would perform poorly), allowing a user to reduce the total amount of GH61 employed (as compared to using the parent GH61). Other improved properties of GH61 variant polypeptides can be exploited in assays suitable for determining cellulosic hydrolysis activities of cellulase compositions, including GH61 variants having altered pH optima, increased stability or activity in the presence of surfactants, increased specific activity for a substrate, altered substrate cleavage pattern, and/or high level expression in a host cell of interest.

GH61 variants as described herein can be used for augmenting the treatment of virtually any cellulosic material, for example for augmenting processes in the textile industry (e.g. in biofinishing or biostoning), in detergents, in animal feed, in the pulp and paper industry and/or bioethanol production.

Thus, GH61 variant polypeptides as describe herein find use in detergent compositions that exhibit enhanced cleaning ability, function as a softening agent and/or improve the feel of cotton fabrics (e.g., "stone washing" or "biopolishing"), in compositions for degrading wood pulp into sugars (e.g., for bio-ethanol production), and/or in feed compositions. The isolation and characterization of GH61 variants provides the ability to control characteristics and activity of such compositions.

An enzyme mixture composition containing a desired GH61 variant as described herein finds use in ethanol production. Ethanol from this process can be further used as an octane enhancer or directly as a fuel in lieu of gasoline which is advantageous because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

Separate saccharification and fermentation is a process whereby cellulose present in biomass, e.g., corn stover, is converted to glucose and subsequently yeast strains convert the glucose into ethanol. Simultaneous saccharification and fermentation is a process whereby cellulose present in biomass is converted to glucose and, at the same time and in the same reactor, yeast strains convert glucose into ethanol. Thus, the GH61 variants of the invention find use in the both of these processes for the degradation of biomass to ethanol. Ethanol production from readily available sources of cellulose provides a stable, renewable fuel source. It is further noted that in some processes, biomass is not fully broken down to glucose (containing, e.g., disaccharides), as such products find uses apart from ethanol production.

Cellulose-based feedstocks can take a variety of forms and can contain agricultural wastes, grasses and woods and other low-value biomass such as municipal waste (e.g., recycled paper, yard clippings, etc.). Ethanol may be produced from the fermentation of any of these cellulosic feedstocks. As such, a large variety of feedstocks may be used with the inventive desired glycosyl hydrolase(s) and the one selected for use may depend on the region where the conversion is being done. For example, in the Midwestern United States agricultural wastes such as wheat straw, corn stover and bagasse may predominate while in California rice straw may predominate. However, it should be understood that any available cellulosic biomass may be used in any region.

In another embodiment the cellulosic feedstock may be pretreated. Pretreatment may be by elevated temperature and the addition of dilute acid, concentrated acid or dilute alkali solution. The pretreatment solution is added for a time sufficient to at least partially hydrolyze the hemicellulose components and then neutralized.

In addition to biomass conversion, GH61 variant polypeptides as described herein can be present in detergent compositions which can include any one or more detergent components, e.g., a surfactant (including anionic, non-ionic and ampholytic surfactants), a hydrolase, building agents, bleaching agents, bluing agents and fluorescent dyes, caking inhibitors, solubilizers, cationic surfactants and the like. All of these components are known in the detergent art. The GH61 variant polypeptide-containing detergent composition can be in any convenient form, including liquid, granule, emulsion, gel, paste, and the like. In certain forms (e.g., granules) the detergent composition can be formulated so as to contain a cellulase protecting agent. (see, e.g., WO1997020025 entitled "Enzymatic detergent compositions", incorporated herein by reference). In certain embodiments, the GH61 variant polypeptide is present in the detergent compositions from 0.00005 weight percent to 5 weight percent relative to the total detergent composition, e.g., from about 0.0002 weight percent to about 2 weight percent relative to the total detergent composition.

As seen from above, GH61 variant polypeptides (and the nucleic acids encoding them) with improved properties as compared to their parent GH61 enzymes find use in improving any of a number of assays and processes that employ glycosyl hydrolases, typically in the presence of at least one cellulase.

EXAMPLES

The present invention is described in further detain in the following examples, which are not in any way intended to limit the scope of the invention as claimed. The attached Figures are meant to be considered as integral parts of the specification and description of the disclosure. All references cited are herein specifically incorporated by reference for all that is described therein.

In the experimental disclosure which follows, the following abbreviations apply: M (molar); mM (millimolar); µM (micromolar); nM (nanomolar); mol (moles); mmol (millimoles); µmol (micromoles); nmol (nanomoles); g and gm (grams); mg (milligrams); µg (micrograms); pg (picograms); L (liters); ml and mL (milliliters); µl and µL (microliters); cm (centimeters); mm (millimeters); µm (micrometers); nm (nanometers); U (units); V (volts); MW (molecular weight); sec (seconds); min(s) (minute/minutes); h(s) and hr(s) (hour/hours); ° C. (degrees Centigrade); QS (quantity sufficient); ND (not done); NA (not applicable); rpm (revolutions per minute); $H_2O$ (water); $dH_2O$ (deionized water); HCl (hydrochloric acid); aa (amino acid); bp (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); ABTS (2,2'-azino-bis(3-ethylbenzo-thiazoline-6-sulfonic acid) diammonium salt; HPLC (high pressure liquid chromatography); PAGE (polyacrylamide gel electrophoresis); PCR (polymerase chain reaction); whPCS (whole hydrolysate dilute acid-pretreated corn stover); daCS (diluta ammonia pre-treated corn stover); Pi or PI (performance index); RT-PCR (reverse transcription PCR); TFA (Trifluoroacetic acid); FAB (a certain hybrid beta-glucosidase, described in PCT Publication WO2012/125951); SEC (size exclusion chromatography); and RPC (reversed phase chromatography)

Example 1

Assays

The following assays were used in the examples described below. Any deviations from the protocols provided below are indicated in the examples. In these experiments, a spectrophotometer was used to measure the absorbance of the products formed after the completion of the reactions.

I. Measurement of Soluble Sugars

A. Hexokinase Assay for Measurement of Residual Glucose

Glucose produced from whPCS was measured using a hexokinase assay. Ten (10) µL of 10× diluted supernatant was added to 190 µL of a glucose hexokinase assay mixture (Instrumentation Laboratory, Breda, Netherlands) in a 96-well microtiter plate (Costar Flat Bottom PS). The plates were incubated at room temperature for 15 min. Following incubation, absorbance of the supernatant was measured at 340 nm. Supernatants of cultures containing residual glucose were excluded from pooling for further studies.

B. ABTS Assay for Measurement of Glucose

Monomeric glucose generated in the GH61A Avicel activity assays was detected using the ABTS assay. The assay buffer contained 5.48 g/L 2,2'-azino-bis(3-ethylbenzo-thiazoline-6-sulfonic acid) diammonium salt (ABTS, Sigma, catalog no. A1888), 0.2 U/mL horseradish peroxidase Type VI-A (Sigma, catalog no. P8375), and 2 U/mL food grade glucose oxidase (GENENCOR® 5989 U/mL) in 50 mM sodium acetate buffer pH 5.0. Fifty (50)µL GH61A activity assay mix (from the Avicel assay described in VIII below) was added to 50 µL ABTS assay solution. After adding the activity assay mix, the reaction was followed kinetically for 5 min at $OD_{420}$, at ambient temperature of 22° C. An appropriate calibration curve of glucose for each assay condition was always included.

C. HPLC Assay for Soluble Sugar Concentration Determination

Glucose concentrations were determined using an Agilent 1200 (Agilent Technologies) HPLC Equipped with an REZEX RFQ-Fast Fruit H+ (8%) 100×7.8 mm (Phenomenex). The column was operating at 80° C. and a flow rate of 0.9 ml/min with 0.01 N $H_2SO_4$ as eluent. Thirty (30) µL of sample was mixed with 90 µL of milliQ and filtered under vacuum over a 0.22 µm Millipore Multiscreen HTS 96 well filtration system. Ten (10 µL) of 4× diluted sample was injected. Appropriate calibration sets were used to determine exact concentrations of desired soluble sugar(s) (e.g., glucose, cellobiose, xylose, and/or arabinose).

II. Protein Purification and Dialysis

Supernatants from *H. jecorina* (Δeg1, Δeg2, Δeg3, Δeg5, Δeg6, Δgh61a, Δcbh1, Δcbh2, Δman1) expressing wild type or variant GH61A were diluted 4× in 1M HEPES pH 8.0 to yield a final volume of 500 µL. The mixture was incubated for 30 minutes, with intermediate mixing (5 times), with 200 µL Biokal Workbead 40 IDA High, charged with 100 mM $CuSO_4$. Purified protein sample, present in the flow through, was obtained by centrifuging for 2 min at 1,000 rpm. Purified samples were dialyzed (40×) overnight at 4° C. to 50 mM sodium acetate, pH 5.0 using "Harvard apparatus 96 well dispo dialyzer" 10 kD MWCO (#74-0903) plates.

III. Protein Determination by Bradford, Normalization and endoH Treatment

Protein concentrations were determined using the BioRad Bradford assay with BSA as standards. For selected samples the protein concentrations obtained by Bradford were compared with protein data obtained by SEC HPLC and/or RP HPLC with purified GH61A as a reference. Normalization of the GH61A samples to 100 ppm by diluting appropriately with 50 mM NaAC pH 5.0 was done by taking (if needed) a correction factor between the Bradford and HPLC measurement into account, were the HPLC values were directive. Protein samples were treated with 10 ppm endoH glycosidase from *S. plicatus* (e.g., NEB P0702L) and incubated for 4-20 h at 3° C. and 800 rpm.

IV. HPLC Assay for Protein Content Determination after Normalization

A. Size Exclusion Chromatography (SEC) for Protein Determination

The concentration of endoH treated and normalized GH61A variant was determined by an Agilent 1200 (Agilent Technologies) HPLC equipped with a Waters Acquity BEH125 SEC 1.7 µm (4.6×150 mm) column. Twenty five (25)µL of sample was mixed with 75 µL of milliQ. Ten (10)µL of the sample was injected on the column. Compounds were eluted using $NaH_2PO_4$ pH 6.75 running isocratic for 4.5 min at a flow of 0.35 mL/min. Proteins were detected at a wavelength of 220 nm. Protein concentrations of GH61A variants were determined from a calibration curve generated using purified wild-type GH61A (3.125, 6.25, 12.5, 25, 50, 100, 200, 400 µg/mL). To calculate performance index (PI), the concentration of a GH61A variant was divided by that of the average wild-type GH61A (e.g., a reference enzyme) in the same plate.

B. Reversed Phase Chromatography (RPC) for Protein Determination

The concentration of GH61A variant proteins from purified culture supernatants was determined by an Agilent 1200 (Agilent Technologies) HPLC equipped with a Phenomenex Aeris Widepore 3.6 u XB-C8 (50×2.1 mm) column generally as described below (with small variations for some samples). Ninety (90)µL of sample was mixed with 10 µL of 50% acetonitrile. Ten (10)µL of the sample was injected on the column. Compounds were eluted using the following gradient: Eluent A (0 min, 90%); (1.5 min 70%); (3.5 min 55%); (3.6 min 5%); (4.1 min 5%); (4.2 min 90%); (4.5 min 90%). Eluent A was MilliQ+0.1% TFA and Eluent B was acetonitrile+0.07% TFA. Proteins were detected at a wavelength of 220 nm. Protein concentrations of GH61A variants were determined from a calibration curve generated using purified wild-type GH61A (15.625, 31.25, 62.5, 125, 250, 500 µg/mL). In some incases, the samples were treated with EndoH prior to analysis (as described above). For the assays described below, the samples were normalized based on this protein determination. To calculate performance index (PI), the concentration of a GH61A variant was divided by that of the average wild-type GH61A (e.g., a reference enzyme) in the same plate.

V. Thermostability Assays

A. Avicel Assay to Measure Thermostability (Also Called "Avicel after")

Residual activity of GH61A polypeptides (including wild type and variants) after heat incubation was determined using the Avicel assay. Twenty five (25)µL aliquots were incubated in quadruplicate in a 96-well PCR plate in a PCR machine at 66° C. for 1 hr. After incubation the residual specific activity of GH61A polypeptides was determined as described below (in section VIII). The relative residual activity of the variants to that of the wild-type enzyme was determined by comparing the averaged specific activity after incubation and the averaged specific activity before incubation.

B. Protein Thermal Shift Assay Using SYPRO® Orange and RT-PCR Machine (Also Called "Tm")

Unfolding of GH61A polypeptide (including wild type and variants) was measured as follows. Twenty five (25)µL GH61A wild type and variant protein sample (non EndoH treated) and 8 µL (1000× diluted in 50 mM NaAC pH 5.0) SYPRO® orange were mixed in a 96 well Hard Shell Plate (HSP9645 BioRad). The sample was incubated in a BioRad CFX connect RT-PCR machine. Samples were incubated for 1 min at 30° C. followed by a gradient from 30° C. to 90° C. incrementing every 5 seconds with 0.2° C. Every 5 seconds fluorescence data was collected, data was analyzed using the BioRad CFX manager software. The melting temperature Tm of each GH61A variant was determined and compared to the average (median) Tm of the wild type GH61A (measured in multiples) as per the method described above. The extent of improvements seen in Tm was recorded.

VI. Whole Hydrolysate Dilute Acid Pretreated Corn Stover (whPCS) Hydrolysis Assay Corn stover was pretreated with 2% w/w $H_2SO_4$ as described (see, Schell et al., *J. Appl. Biochem. Biotechnol.*, 105:69-86, 2003) and titrated to a pH of 5.0 with 3M ammonium hydroxide, a final concentration 0.01% of sodium azide was added for preservation. A sodium acetate buffer (pH 5.0) was then added to get a final concentration of 10% solids. The cellulose concentration in the reaction mixture was about 3% Seventy (70)µL of this cellulose suspension was added per well in a 96-well microtiter plate (Corning Flat bottom non binding PS). Two different methods were employed to measure performance on whPCS: A) Forty seven (47)µL of a 2 g/L enzyme background mixture was added to the whPCS. This enzyme mixture provided CBH:BG:EG enzymes at approximately an 8:1:1 ratio, respectively. Then 22, 11, 5 and 3 µL of a 100 ug/mL purified supernatants from *H. jecorina* cells expressing either wild-type GH61A or a GH61A variant were added to the whPCS/background enzyme mixture. Compensating volumes of sodium acetate buffer were added to make up for the differences in total volume. B) Twenty five (25)µL of a 0.225 g/L enzyme background mixture was added to the whPCS. The enzyme background mixture provided CBH:BG:EG enzymes at approximately a 4:1.5:1 ratio, respectively, as well as accessory xylanase and hemicellulase enzymes (representing approximately 5% and 20% of the enzymes in the mixture). Then 25 µL of a 50 ug/mL purified supernatant from *H. jecorina* cells expressing either wild-type GH61A or a GH61A variant were added to the whPCS/background enzyme mixture. Compensating volumes of sodium acetate buffer were added to make up for the differences in total volume.

After sealing, the plates were placed in a thermostatted incubator at 50° C. with continuous shaking at 900 rpm. After 72 hr the plates were put on ice for 5 min and the hydrolysis reaction was stopped by the addition of 100 µL of 100 mM glycine buffer, pH 10, to each well. The plates were sealed and centrifuged at 3,000 rpm at room temperature for 2 min. The glucose released hydrolysis reaction products in the supernatant were analyzed by Hexokinase and/or HPLC glucose concentration determination method. A dose response curve was generated for wild-type GH61A enzyme. To calculate performance index (PI), the (average) total sugar produced by a variant GH61A was divided by the (average) total sugar produced by the wild-type GH61A (e.g., a reference enzyme) at the same dose.

VII. Dilute Ammonia Pretreated Corn Stover (daCS) Hydrolysis Assay daCS substrate: Corn stover was ground to pass a 0.9 mm screen then pretreated with dilute ammonia in accordance with the description of PCT Publication WO06110901, or the published US Patent Applications 20070031918, 20070031919, 2007-0031953, or 20070037259, and titrated to a pH of 5.0 with 1M $H_2SO_4$, a final concentration 0.01% of sodium azide was added for preservation. A sodium acetate buffer (pH 5.0) was then added to get a final concentration of 10% solids. The cellulose concentration in the reaction mixture was about 3%.

A. Microtiter assay 1: Twenty five (25)µL of a 0.225 g/L enzyme background mixture was added to (70)µL of the daCS substrate described above in the wells of a 96-well microtiter plate (Corning, Flat bottom, non-binding). The enzyme background mixture provided CBH:BG:EG enzymes (at approximately 4:1.5:1 ratio, respectively) as well as accessory xylanase and hemicellulase enzymes (representing approximately 5% and 20% of the enzymes in the mixture). Then 25 µL of a 25 ug/mL purified supernatants from *H. jecorina* cells expressing either wild-type GH61A or a GH61A variant were added to the daCS/background enzyme mixture. Compensating volumes of sodium acetate buffer were added to make up for the differences in total volume. After sealing, the plates were placed in a thermostatted incubator at 50° C. with continuous shaking at 900 rpm. After 72 hr the plates were put on ice for 5 min and the hydrolysis reaction was stopped by the addition of 100 µL of 100 mM glycine buffer, pH 10, to each well. The plates were sealed and centrifuged at 3,000 rpm at room temperature for 2 min. Soluble sugars in the supernatant were analyzed by HPLC (as in I.C. above). A dose response curve was generated for wild-type GH61A enzyme. To calculate performance index (PI), the (average) total glucose produced by a variant GH61A was divided by the (average) total glucose produced by the wild-type GH61A (e.g., a reference enzyme) at the same dose.

B. Microtiter Assay 2: Supernatants containing each GH61A enzyme were normalized to 500 ppm with 15 mM NaOAc, pH 5.0. The normalized GH61A supernatants were combined with a background mixture at a ratio of 15:85 (respectively, wt:wt), with the background mixture providing CBH:BG:EG enzymes (at a wt ratio of approximately 6:1:4.4 ratio, respectively) as well as accessory xylanase and hemicellulase enzymes (representing approximately 5% and 23% of the enzymes in the mixture) and dosed onto the daCS at a final total concentration of 10 mg enzymes/(g G+X) at 9.7% solids. The reactions (120 µL final volume) were incubated at 50° C. for 24 hours prior to quenching using 100 mM Na-glycine pH 10.0. The concentration of produced soluble sugars was determined by HPLC (as in I.C. above) and a PI was calculated for glucose production and xylose production (using WT as the reference). Each reaction was performed in triplicate.

C. Vial assay: 4 g of daCS substrate were added per vial followed by 1 mL of enzymatic background mixture of CBH:EG:BG (at a wt ratio of approximately 2.9:1:1.6, respectively) as well as accessory xylanase and hemicellulase enzymes (representing approximately 15% and 12.6% of the enzymes in the mixture). The above mixture was added in every vial at a dosing of 5.78 mg/(g G+X). Each GH61A variant was assayed at 1.2 and 0.6 mg/(g G+X); WT GH61A was assayed at 1.44 and 0.36 mg/(g G+X). 50 uL of $CuSO_4$ (10 mM) was added to reach final concentration of 100 uM. Samples were tested in triplicates. Samples were incubated at 50° C. for 4 days. 50 uL of the saccharification broth were sampled, added to 450 uL of 100 mM glycine (pH 10) and filtered. The concentration of glucose produced and xylose produced was determined by HPLC (as in I.C. above). The PI was calculated for glucose production and xylose production (using WT as the reference).

VIII. Avicel Activity Assay

Avicel was diluted with sodium acetate 50 mM (pH 5.0) to achieve a 3.33% w/v mixture. Seventy five (75) µL of a this suspension was dispensed into a 96-well microtiterplate (Corning Flat bottom non binding PS). Subsequently, 15 µL of 10 mM ascorbic acid, 15 µL 1 mM $CuCl_2$ and thirty five (35) µL of a 714 µg/mL culture supernatant from a (Δeg1, Δeg2, Δeg3, Δeg5, Δeg6, Δgh61a, Δcbh1, Δcbh2, ΔMan1) strain expressing FAB (see, PCT publication WO2012/125951) was added to the Avicel solution. Then 10 µL of a 100 µg/mL purified GH61A wild-type or GH61A variant were added to the Avicel/FAB mixture. Each wild type and variant was assayed in quadruplicate. The microtiter plate was sealed and incubated in a thermostatted incubator at 50° C. with continuous shaking at 900 rpm. After 20 hr, the hydrolysis reaction was stopped by the addition of 100 µL 100 mM glycine buffer, pH 10 to each well. The plates were sealed and centrifuged at 3,000 rpm at room temperature for 2 min. The hydrolysis reaction products in the supernatant (also called the GH61A activity assay mix in I.B above) were analyzed by the ABTS assay (see I.B, above). A dose response curve was generated for the wild-type GH61A. To calculate performance index (PI), the (average) total sugar produced by a variant GH61A was divided by the (average) total sugar produced by the wild-type GH61A (e.g., a reference enzyme) at the same dose.

Example 2

I. Generation of *Hypocrea jecorina* GH61A Variants

*H. jecorina* GH61A enzyme-encoding sequence (SEQ ID NO:1) was cloned into the pTTTpyr2 vector to produce the pTTTpyr2-GH61A plasmid (the pTTTpyr2 vector is similar to the pTTTpyrG vector described in PCT publication WO 2011/063308, incorporated herein by reference, except that the pyrG gene is replaced with the pyr2 gene). The amino acid sequence of the full length GH61A enzyme is shown in SEQ ID NO: 2. Using the pTTTpyr2-GH61A plasmid or PTTTpyrG, amino acid substitutions that fall within two stretches of amino acid residues spanning amino acids 111-114 and 144-163 in the GH61A mature enzyme (SEQ ID NO: 3) were generated and tested in one or more of the assays described in Example 1.

SEQ ID NO:1 below sets forth the reference *H. jecorina* GH61A coding DNA sequence:

ATGATCCAGAAGCTTTCCAACCTCCTTGTCACCGCACTGGCGGTGGCTAC

TGGCGTTGTCGGACATGGACATATTAATGACATTGTCATCAACGGGGTGT

GGTATCAGGCCTATGATCCTACAACGTTTCCATACGAGTCAAACCCCCCC

ATAGTAGTGGGCTGGACGGCTGCCGACCTTGACAACGGCTTCGTTTCACC

CGACGCATACCAAAACCCTGACATCATCTGCCACAAGAATGCTACGAATG

CCAAGGGGCACGCGTCTGTCAAGGCCGGAGACACTATTCTCTTCCAGTGG

-continued
```
GTGCCAGTTCCATGGCCGCCACCCTGGTCCCATTGTCGACTACCTGGCCAA

CTGCAATGGTGACTGCGAGACCGTTGACAAGACGACGCTTGAGTTCTTCA

AGATCGATGGCGTTGGTCTCCTCAGCGGCGGGGATCCGGGCACCTGGGCC

TCAGACGTGCTGATCTCCAACAACAACACCTGGGTCGTCAAGATCCCCGA

CAATCTTGCGCCAGGCAATTACGTGCTCCGCCACGAGATCATCGCGTTAC

ACAGCGCCGGGCAGGCAAACGGCGCTCAGAACTACCCCCAGTGCTTCAAC

ATTGCCGTCTCAGGCTCGGGTTCTCTGCAGCCCAGCGGCGTTCTAGGGAC

CGACCTCTATCACGCGACGGACCCTGGTGTTCTCATCAACATCTACACCA

GCCCGCTCAACTACATCATCCCTGGACCTACCGTGGTATCAGGCCTGCCA

ACGAGTGTTGCCCAGGGGAGCTCCGCCGCGACGGCCACCGCCAGCGCCAC

TGTTCCTGGAGGCGGTAGCGGCCCGACCAGCAGAACCACGACAACGGCGA

GGACGACGCAGGCCTCAAGCAGGCCCAGCTCTACGCCTCCCGCAACCACG

TCGGCACCTGCTGGCGGCCCAACCCAGACTCTGTACGGCCAGTGTGGTGG

CAGCGGTTACAGCGGGCCTACTCGATGCGCGCCGCCAGCCACTTGCTCTA

CCTTGAACCCCTACTACGCCCAGTGCCTTAAC
```

SEQ ID NO:2 below sets forth the sequence of the H. jecorina GH61A full length enzyme:

```
MIQKLSNLLVTALAVATGVVGHGHINDIVINGVWYQAYDPTTFPYESNPP

IVVGWTAADLDNGFVSPDAYQNPDIICHKNATNAKGHASVKAGDTILFQW

VPVPWPHPGPIVDYLANCNGDCETVDKTTLEFFKIDGVGLLSGGDPGTWA

SDVLISNNNTWVVKIPDNLAPGNYVLRHEIIALHSAGQANGAQNYPQCFN

IAVSGSGSLQPSGVLGTDLYHATDPGVLINIYTSPLNYIIPGPTVVSGLP

TSVAQGSSAATATASATVPGGGSGPTSRTTTTARTTQASSRPSSTPPATT

SAPAGGPTQTLYGQCGGSGYSGPTRCAPPATCSTLNPYYAQCLN
```

SEQ ID NO:3 below sets forth the sequence of the H. jecorina GH61A mature enzyme:

```
HGHINDIVINGVWYQAYDPTTFPYESNPPIVVGWTAADLDNGFVSPDAYQ

NPDIICHKNATNAKGHASVKAGDTILFQWVPVPWPHPGPIVDYLANCNGD

CETVDKTTLEFFKIDGVGLLSGGDPGTWASDVLISNNNTWVVKIPDNLAP

GNYVLRHEIIALHSAGQANGAQNYPQCFNIAVSGSGSLQPSGVLGTDLYH

ATDPGVLINIYTSPLNYIIPGPTVVSGLPTSVAQGSSAATATASATVPGG

GSGPTSRTTTTARTTQASSRPSSTPPATTSAPAGGPTQTLYGQCGGSGYS

GPTRCAPPATCSTLNPYYAQCLN
```

For each of the sites selected for variant production (i.e., amino acids in the stretches of amino acid residues spanning positions 111 to 114 and 144 to 163 of SEQ ID NO:3), typically 14-16 substitution variants were obtained. The variants were received as individually purified plasmids each encoding a GH61A variant sequence substituted at the indicated position.

II. Production of GH61A Variants

Protoplasts of H. jecorina strain (Δeg1, Δeg2, Δeg3, Δeg5, Δeg6, Δgh61a, Δcbh1, Δcbh2, Δman1) were transformed with the individual pTTTpyr2-GH61A or pTTTpyrG-GH61A constructs (a single GH61A variant per transformation) and grown on selective agar containing acetamide at 28° C. for 7 d as previously described in, for example, PCT Patent Application Publication WO 2009/048488 (incorporated herein by reference). Protoplasts of H. jecorina were generated, harvested, replated on acetamide agar, and incubated at 28° C. for 7 d. Spores were harvested in 15% glycerol and stored at −20° C.

For GH61A variant production in microtiter plates, a volume of 10 μL of the desired H. jecorina spore suspension was added to 200 μL of a glycine minimal medium supplemented with 2% glucose/sophorose mixture in a PVDF filter plate. Each GH61A variant was grown in quadruplicate. After sealing the plate with an oxygen permeable membrane, the plates were incubated at 28° C. for 6 d, with shaking at 220 rpm. Supernatants were harvested by transferring the culture medium to a microtiter plate under low pressure.

For GH61A production in shake flasks, a pre-culture (YEG medium) was inoculated with 10 μL of the desired H. jecorina spore suspension and grown for 2 days at 28° C., 200 rpm. One (1) mL of the pre-culture was used to inoculate 25 mL minimal media. Shake flask fermentations were performed for 5 days at 28° C., 200 rpm. At the end of the fermentation, the cultures were filtered prior to concentration and quantification.

Example 3

Characterization of GH61A Variants

H. jecorina GH61A variant enzymes were tested for various properties of interest. In particular, the GH61A variants having amino acid substitution in the stretches of amino acid residues spanning positions 111 to 114, and 144 to 163 of SEQ ID NO:3 were tested for protein expression as set forth in Example 1, section IV.A, thermostability as set forth in Example 1, section V.B (Tm), hydrolysis of whPCS as set forth in Example 1, section VI.A, using the Hexokinase Assay for Measurement of Residual Glucose (whPCS HK), and hydrolysis of whPCS as set forth in Example 1, section VI.B, using the HPLC assay for glucose concentration determination (whPCS HPLC).

The performance indices (PI) for each of the GH61A variants tested were determined for both of the whPCS assays noted above, and at above a certain level of protein production. PI is the ratio of performance of the GH61A variant tested to a reference GH61A (i.e., a GH61A having the wild type amino acid at that site). PIs that were less than or equal to 0.05 were generally fixed to 0.05. However, HPLC protein expression values of 0.0 were fixed to 0.04. PI values for GH61A enzymes with wild type residues were set at 1.00. Improvements in Tm were demonstrated by comparison of the Tm measurements of the variants with the average Tm measurement of the wild type parent GH61A.

Below is a listing of GH61A substitution variants having an improved property over wild type GH61A (for example, improved thermostability, protein production, or performance as manifested in PI>1.0) in at least one of the assays described above. The GH61A variants fall into the following Cohorts.

Cohort 1—

GH61A variants having improved PI in whPCS (HPLC): P145G, D146K, D146Q, D146Y, N147F, Y153K, V154A, V154C, V154D, V154E, V154G, V154H, V154P, V154Q, V154T, R156A, R156C, R156D, R156E, R156F, R156H, R156I, R156K, R156L, R156M, R156P, R156Q, E158A, E158C, E158D, E158F, E158H, E158I, E158M, E158N, E158P, E158T, H163A, H163C, H163D, H163E, H163F, H163G, H163I, H163K, H163M, H163P, H163T, and H163W.

Cohort 2—

GH61A variants having improved PI in whPCS (HK): I144K, I144R, I144S, P145G, P145H, P145I, P145K, P145R, P145S, P145V, D146A, D146C, D146E, D146F, D146K, D146M, D146T, N147F, N147M, L148K, L148V, A149C, A149D, A149F, A149G, A149I, A149N, A149V, P150A, P150C, P150D, P150E, P150F, P150G, P150H, P150I, P150K, P150L, P150Q, G151E, G151F, G151H, G151I, G151K, G151M, G151P, G151Q, G151S, G151V, G151W, G151Y, N152E, N152F, N152G, N152H, N152K, N152P, Y153F, Y153K, Y153L, Y153M, Y153P, Y153Q, Y153R, Y153S, Y153V, V154A, V154K, V154N, V154R, L155C, L155F, L155K, L155M, L155N, R156C, R156D, R156H, R156I, R156K, R156Q, H157D, E158A, E158D, E158F, E158L, E158N, E158S, E158W, A161C, L162I, L162N, H163C, H163D, H163F, H163P, H163R, H163T, H163V, H163W, and H163Y.

Cohort 3—

GH61A variants having improved thermostability and/or Tm: I144G, D146F, L148P, A149P, G151Q, G151V, N152F, N152G, N152Q, N152S, N152Y, L155M, R156S, H157W, E158W, E158Y, I159Q, I160D, I160F, A161E, A161L, A161Y, L162A, L162F, H163L, H163R, and H163Y.

Cohort 4—

GH61A variants having improved activity on daCS (in any of the assays described in VII above): F112V, K113L, K113M, K113N, K113R, K113S, I114F, I114V, I144F, I144V, P145A, Y153F, V154T, H163D, and H163Y. Any one of the GH61A variants from Cohorts 1, 2, 3 or 4 find use in the subject invention. Certain GH61A variants are present in more than one Cohort, and are of particular interest as GH61A variants according to aspects of the subject invention, e.g., GH61A variants that are present in Cohorts 1 and 2, Cohorts 1 and 3, Cohorts 1 and 4, Cohorts 2 and 3, Cohorts 2 and 4, or Cohorts 3 and 4. Variants present in three Cohorts are also of particular interest, for example, variants H163D (present in Cohorts 1, 2 and 4) and H163Y (present in Cohorts 2, 3 and 4). Further, any combination of substitutions from the GH61A variants in Cohorts 1, 2, 3 and/or 4 can be used to generate a combinatorial GH61A variant (i.e., a GH61A variant having more than one substitution). Combinatorial GH61A variants are described in further detail below.

In addition to the GH61A variants in Cohorts 1, 2, 3 and 4 above, GH61A substitution variants were identified that, while not having an improved property as compared to wild-type GH61A, displayed wild-type levels of activity in one or more of the whPCS (HPLC) assay, the whPCS (HK) assay, or any of the daCS assays. Because amino acids 111 to 114 and 144 to 163 of SEQ ID NO:3 can be understood as important to the structural integrity or stability of GH61A, as well as to its function, it is surprising that certain mutants at those residues resulted in a variant that had properties that were similar to the wild-type GH61 enzyme. These GH61A variants are as follows, forming what is referred to herein as the Wild-Type Cohort: F112M, F112W, K113P, K113T, I114L, I114M, I114T, I144A, I144C, I144D, I144E, I144H, I144N, I144P, I144Q, I144T, I144W, I144Y, P145C, P145D, P145E, P145F, P145L, P145M, P145N, P145Q, P145T, P145W, P145Y, D146G, D146H, D146I, D146L, D146N, D146P, D146R, D146S, D146V, D146W, N147A, N147C, N147D, N147E, N147G, N147H, N147I, N147K, N147L, N147P, N147Q, N147R, N147S, N147T, N147V, N147W, N147Y, L148A, L148C, L148D, L148E, L148F, L148G, L148H, L148I, L148M, L148N, L148Q, L148R, L148S, L148T, L148W, L148Y, A149E, A149H, A149K, A149L, A149M, A149Q, A149R, A149S, A149T, A149W, A149Y, P150M, P150N, P150R, P150S, P150T, P150V, P150W, P150Y, G151A, G151C, G151D, G151L, G151N, G151R, G151T, N152A, N152C, N152D, N152I, N152L, N152M, N152R, N152T, N152V, N152W, Y153A, Y153C, Y153D, Y153E, Y153G, Y153H, Y153I, Y153N, Y153T, Y153W, V154F, V154I, V154L, V154M, V154S, V154W, V154Y, L155A, L155D, L155E, L155G, L155H, L155I, L155P, L155Q, L155R, L155S, L155T, L155V, L155W, L155Y, R156G, R156N, R156T, R156V, R156W, R156Y, H157A, H157C, H157E, H157F, H157G, H157I, H157K, H157L, H157M, H157N, H157P, H157Q, H157R, H157S, H157T, H157V, H157Y, E158G, E158K, E158R, E158V, I159A, I159Q, I159D, I159E, I159F, I159G, I159H, I159K, I159L, I159M, I159N, I159P, I159R, I159S, I159T, I159V, I159W, I159Y, I160A, I160Q, I160E, I160G, I160H, I160K, I160L, I160M, I160N, I160P, I160Q, I160R, I160S, I160T, I160V, I160W, I160Y, A161 D, A161F, A161G, A161H, A161I, A161K, A161M, A161N, A161P, A161Q, A161R, A161S, A161T, A161V, A161W, L162C, L162D, L162E, L162G, L162H, L162K, L162M, L162P, L162Q, L162R, L162S, L162T, L162V, L162W, L162Y, H163Q, and H163S.

In certain embodiments of the subject invention, one or a combination of substitutions in this Wild-Type Cohort find use in generating variants of GH61. In addition, one or a combination of substitutions in this Wild-Type Cohort find use in generating combinatorial GH61A variants with one or more of the substitutions identified in Cohorts 1, 2, 3 and/or 4 above. Wild-Type Cohort substitutions also find use in combination with substitutions (or other mutations) at positions outside of the stretches of amino acid residues spanning positions 111 to 114 and 144 to 163 in GH61A, e.g., substitutions that lead to one or more improved property.

Example 4

Compensating Substitutions in GH61A

Substitutions at position F112 in GH61A show a reduced level of expression as compared to the wild-type parent enzyme, including F112A and F112V. Both of these variants were expressed at less than 500 parts per million (ppm) (as determined in Example 1, section IV.B. above) as compared to approximately 2700 ppm for the wild-type enzyme produced under the same conditions. Based on the known 3D crystal structure of GH61B of *Trichoderma reesei* (see, Karkehabadi, S. et al. *The first structure of a glycoside hydrolase family 61 member, Cel61B from Hypocrea jecorina*, at 1.6 A resolution. J. Mol. Biol. 2008, 383, 144-154), in silico analysis of amino acid side chains in GH61A was conducted to identify potentially compensating substitutions (using publicly available analysis software), i.e., substitutions that would improve the stability of GH61 variants with amino acid substitutions at position F112, and thus potentially rescue the reduced expression level of these variants. A series of combinatorial GH61A variants based on this in silico analysis were generated and expressed (as described above) and the expression level determined (as in Example 1, section IV.B. above).

The following four combinatorial variants of GH61A demonstrated expression levels that were improved over the expression level of either F112A or F112V single amino acid substitution variants:

1. L94I-F112A
2. L94V-F112I

3. F112I-L148I
4. L94I-F112V

The F112A and F112V single amino acid variants were expressed at approximately 12-15% the level of the wild-type GH61A enzyme while the four combinatorial variants above were expressed at approximately 25-60% the level of the wild-type GH61A enzyme.

In addition, these combinatorial variants were tested in the whPCS assay as described in Example 1, section VI.B above. When normalized for protein level, each of these combinatorial variants performed equivalently to the wild-type GH61A enzyme in the whPCS assay.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCES

Altschul, S. F., et al., J. Mol. Biol. 215:403-410, 1990.
Altschul, S. F., et al., Nucleic Acids Res. 25:3389-3402, 1997.
Aro, N., et al., J. Biol. Chem., 10.1074/M003624200, Apr. 13, 2001.
Aubert, et al., Ed., p11 et seq., Academic Press, 1988.
Ausubel G. M., et al. CURRENT PROTOCOLS IN MOLECULAR BIOLOGY, John Wiley & Sons, New York, N.Y., 1993.
Baldwin, D., et al., Curr. Opin. Plant Biol. 2(2):96-103, 1999.
Baulcombe, D., Arch. Virol. Suppl. 15:189-201, 1999.
Bhikhabhai, R. et al., J. Appl. Biochem. 6:336, 1984.
Boer and Koivula, 2003, Eur. J. Biochem. 270: 841-848
Brumbauer, A. et al., Bioseparation 7:287-295, 1999.
Busk et al., App. Env. Microbiol., 79(11):3380-3391, 2013.
Carter et al., Nucl. Acids Res. 13:4331, 1986.
Chen et al., Biochem. Biophys. Acta. 1121:54-60, 1992.
Coligan, J. E. et al., eds., CURRENT PROTOCOLS IN IMMUNOLOGY, 1991.
Collen, A., et al., Journal of Chromatography A 910:275-284, 2001.
Coughlan, et al., BIOCHEMISTRY AND GENETICS OF CELLULOSE DEGRADATION.
Cummings and Fowler, Curr. Genet. 29:227-233, 1996.
Dayhoff et al. in Atlas of Protein Sequence and Structure, Volume 5, Supplement 3, Chapter 22, pp. 345-352, 1978.
Deutscher, M. P., Methods Enzymol. 182:779-80, 1990.
Doolittle, R. F., OF URFS AND ORFs, University Science Books, C A, 1986.
Ellouz, S. et al., J. Chromatography 396:307, 1987.
Fields and Song, Nature 340:245-246, 1989.
Filho, et al. Can. J. Microbiol. 42:1-5, 1996.
Fliess, A., et al., Eur. J. Appl. Microbiol. Biotechnol. 17:314, 1983.
Freer, et al. J. Biol. Chem. 268:9337-9342, 1993.
Freshney, R. I., ed., ANIMAL CELL CULTURE, 1987.
Goyal, A. et al. Bioresource Technol. 36:37, 1991.
Halldorsdottir, S et al., Appl Microbiol Biotechnol. 49(3): 277-84, 1998.
Hakkinen et al., Microb. Cell Fact. October 4; 11:134. Doi:10.1186/1475-2859-11-134, 2012 Harris et al., Biochemistry, 49:3305-16, 2010.
Hu et al., Mol Cell Biol. 11:5792-9, 1991.
Hemmpel, W. H. ITB Dyeing/Printing/Finishing 3:5-14, 1991.
Herr et al., Appl. Microbiol. Biotechnol. 5:29-36, 1978.
Ihaka et al., J. Comput. Graphical Statistics 5(3): 299-314, 1996.
Jakobovits, A, et al., Ann N Y Acad Sci 764:525-35, 1995.
Jakobovits, A, Curr Opin Biotechnol 6(5):561-6, 1995.
Jones et al., Nature 321:522-525, 1986.
Karkehabadi et al., J. Mol Biol. vol. 383 issue 1: pp 144-154, 2008
Karlsson et al., Eur. J. Biochem. vol. 268, pp. 6498-6507, 2001
Kawaguchi, T et al., Gene 173(2):287-8, 1996.
Knowles, J. et al., TIBTECH 5, 255-261, 1987.
Kohler and Milstein, Nature 256:495, 1975.
Krishna, S. et al., Bioresource Tech. 77:193-196, 2001.
Kumar, A., et al., Textile Chemist and Colorist 29:37-42, 1997.
Levasseur A. et al, Biotechnol Biofuels vol 6, issue 1, pp. 41, 2013
Lehtio, J. et al., FEMS Microbiology Letters 195:197-204, 2001.
Li and Ljungdahl Appl. Environ. Microbiol. 62:209-213, 1996.
Linder, M. and Teeri, T. T., Biotechnol. 57:15-28, 1997.
Martinez et al., Nature Biotechnology vol. 26, pp. 553-560, 2008
Medve, J. et al., J. Chromatography A 808:153, 1998.
Ohmiya et al., Biotechnol. Gen. Engineer. Rev. 14:365-414, 1997.
Ooi et al., Nucleic Acids Res. 18(19):5884, 1990.
Ortega et al., International Biodeterioration and Biodegradation 47:7-14, 2001. Penttila et al., Yeast 3:175-185, 1987.
Penttila et al., Gene 63: 103-112, 1988.
Pere, J., et al., In Proc. Tappi Pulping Conf., Nashville, Tenn., 27-31, pp. 693-696, 1996.
Riechmann et al., Nature 332:323-327, 1988.
Rothstein et al., Gene 55:353-356, 1987.
Saarilahti et al., Gene 90:9-14, 1990.
Sakamoto et al., Curr. Genet. 27:435-439, 1995.
Saloheimo M, et al., Gene 63:11-22, 1988.
Saloheimo M., Eur J Biochem. vol. 249, issue 2: pp. 584-91, 1997
Sambrook et al., MOLECULAR CLONING: A LABORATORY MANUAL (Second Edition), Cold Spring Harbor Press, Plainview, N.Y., 1989.
Schulein, Methods Enzymol., 160, 25, pages 234 et seq, 1988.
Scopes, Methods Enzymol. 90 Pt E:479-90, 1982.
Spilliaert R, et al., Eur J Biochem. 224(3):923-30, 1994.
Stahlberg, J. et al., Bio/Technol. 9:286-290, 1991.
Stahlberg et al., 1996, J. Mol. Biol. 264: 337-349 Strathern et al., eds. (1981) The Molecular Biology of the Yeast *Saccharomyces*.
Suurnakki, A. et al., Cellulose 7:189-209, 2000.
Te'o, J. et al., FEMS Microbiology Letters 190:13-19, 2000.
Tilbeurgh, H. et al., FEBS Lett. 16:215, 1984.
Timberlake et al., *Cell* 1:29-37, 1981.
Tomaz, C. and Queiroz, J., J. Chromatography A 865:123-128, 1999.
Tomme, P. et al., Eur. J. Biochem. 170:575-581, 1988.
Tormo, J. et al., EMBO J. 15:5739-5751, 1996.
Tyndall, R. M., Textile Chemist and Colorist 24:23-26, 1992.
Van Rensburg et al., Yeast 14:67-76, 1998.
Van Tilbeurgh, H. et al., FEBS Lett. 204:223-227, 1986.

Verhoeyen et al., Science 239:1534-1536, 1988.
Warrington, et al., *Genomics* 13:803-808, 1992.
Wells et al., Gene 34:315, 1985.
Wells et al., Philos. Trans. R. Soc. London SerA 317:415, 1986.

Wood, Biochem. Soc. Trans., 13, pp. 407-410, 1985.
Wood et al., METHODS IN ENZYMOLOGY, 160, 25, p. 87 et seq., Academic Press, New York, 1988.
Zoller et al., Nucl. Acids Res. 10:6487, 1987.

Sequences

| SEQ ID NO | Description | Sequence |
|---|---|---|
| 1 | H. jecorina GH61A coding DNA sequence | ATGATCCAGAAGCTTTCCAACCTCCTTGTCACCGCACTGG CGGTGGCTACTGGCGTTGTCGGACATGGACATATTAATGA CATTGTCATCAACGGGGTGTGGTATCAGGCCTATGATCCT ACAACGTTTCCATACGAGTCAAACCCCCCCATAGTAGTGG GCTGGACGGCTGCCGACCTTGACAACGGCTTCGTTTCACC CGACGCATACCAAAACCCTGACATCATCTGCCACAAGAAT GCTACGAATGCCAAGGGGCACGCGTCTGTCAAGGCCGGAG ACACTATTCTCTTCCAGTGGGTGCCAGTTCCATGGCCGCA CCCTGGTCCCATTGTCGACTACCTGGCCAACTGCAATGGT GACTGCGAGACCGTTGACAAGACGACGCTTGAGTTCTTCA AGATCGATGGCGTTGGTCTCCTCAGCGGCGGGGATCCGGG CACCTGGGCCTCAGACGTGCTGATCTCCAACAACAACACC TGGGTCGTCAAGATCCCCGACAATCTTGCGCCAGGCAATT ACGTGCTCCGCCACGAGATCATCGCGTTACACAGCGCCGG GCAGGCAAACGGCGCTCAGAACTACCCCCAGTGCTTCAAC ATTGCCGTCTCAGGCTCGGGTTCTCTGCAGCCCAGCGGCG TTCTAGGGACCGACCTCTATCACGCGACGGACCCTGGTGT TCTCATCAACATCTACACCAGCCCGCTCAACTACATCATC CCTGGACCTACCGTGGTATCAGGCCTGCCAACGAGTGTTG CCCAGGGGAGCTCCGCCGCGACGGCCACCGCCAGCGCCAC TGTTCCTGGAGGCGGTAGCGGCCCGACCAGCAGAACCACG ACAACGGCGAGGACGACGCAGGCCTCAAGCAGGCCCAGCT CTACGCCTCCCGCAACCACGTCGGCACCTGCTGGCGGCCC AACCCAGACTCTGTACGGCCAGTGTGGTGGCAGCGGTTAC AGCGGGCCTACTCGATGCGCGCCGCCAGCCACTTGCTCTA CCTTGAACCCCTACTACGCCCAGTGCCTTAAC |
| 2 | H. jecorina GH61A full length protein | MIQKLSNLLVTALAVATGVVGHGHINDIVINGVWYQAYDP TTFPYESNPPIVVGWTAADLDNGFVSPDAYQNPDIICHKN ATNAKGHASVKAGDTILFQWVPVPWPHPGPIVDYLANCNG DCETVDKTTLEFFKIDGVGLLSGGDPGTWASDVLISNNNT WVVKIPDNLAPGNYVLRHEIIALHSAGQANGAQNYPQCFN IAVSGSGSLQPSGVLGTDLYHATDPGVLINIYTSPLNYII PGPTVVSGLPTSVAQGSSAATATASATVPGGGSGPTSRTT TTARTTQASSRPSSTPPATTSAPAGGPTQTLYGQCGGSGY SGPTRCAPPATCSTLNPYYAQCLN |
| 3 | H. jecorina GH61A mature protein | HGHINDIVINGVWYQAYDPTTFPYESNPPIVVGWTAADLD NGFVSPDAYQNPDIICHKNATNAKGHASVKAGDTILFQWV PVPWPHPGPIVDYLANCNGDCETVDKTTLEFFKIDGVGLL SGGDPGTWASDVLISNNNTWVVKIPDNLAPGNYVLRHEII ALHSAGQANGAQNYPQCFNIAVSGSGSLQPSGVLGTDLYH ATDPGVLINIYTSPLNYIIPGPTVVSGLPTSVAQGSSAAT ATASATVPGGGSGPTSRTTTTARTTQASSRPSSTPPATTS APAGGPTQTLYGQCGGSGYSGPTRCAPPATCSTLNPYYAQ CLN |
| 4 | Endoglucanase IV Hypocrea rufa full length protein | MIQKLSNLLVTALAVATGVVGHGHINDIVINGVWYQAYDP TTFPYESNPPIVVGWTAADLDNGFVSPDAYQNPDIICHKN ATNAKGHASVKARDTILFQWVPVPWPHPGPIVDYLANCNG DCETVDKTTLEFFKIDGVGLLSGGDPGTWASDVLISNNNT WVVKIPDNLAPGNYVLRHEIIALHSAGQANGAQNYPQCFN IAVSGSGSLQPSGVLGTDLYHATDPGVPINIYTSPLNYII PGPTVVSGLPTSVAQGSSAATATASATAPGGGSGPTSRTT TTARTTQASSRPSSTPPATTSAPAGGPTQTLYGQCGGSGY SGPTRCAPPATCSTLNPYYAQCLN |
| 5 | Type IV endoglucanase Trichoderma saturnisporum full length protein | MIQKLSNLLVAALTVATGVVGHGHINNIVINGVYYQAYDP TSFPYESNPPIVVGWTAADLDNGFVSPDAYGSPDIICHKN ATNAKGHASVRAGDTVLFQWVPLPWPHPGPIVDYLANCNG DCETVDKTSLEFFKIDGVGLISGGDPGNWASDVLIANNNT WVVKIPDDLAPGNYVLRHEIIALHSAGQANGAQNYPQCFN LAVSGSGSLKPSGVKGTALYHATDPGVLINIYTSPLNYII PGPTVVSGLPTSVAQRSSAATATASATLPGGGSPPGGPT SRPTTTARSTSQASSRPSPPATTSAPAGGPTQTLYGQCGG SGYSGPTRCAPPATVSTLNPYYARLN |

-continued

| SEQ ID NO | Description | Sequence |
|---|---|---|
| 6 | Endoglucanase IV *Hypocrea orientalis* full length protein | MIQKLSNLLLTALAVATGVVGHGHINNIVVNGVYYQGYDP TSFPYESDPPIVVGWTAADLDNGFVSPDAYQSPDIICHKN ATNAKGHASVKAGDTILFQWVPVPWPHPGPIVDYLANCNG DCETVDKTSLEFFKIDGVGLISGGDPGNWASDVLIANNNT WVVKIPEDLAPGNYVLRHEIIALHSAGQADGAQNYPQCFN LAVSGSGSLQPSGVKGTALYHSDDPGVLINIYTSPLAYTI PGPSVVSGLPTSVAQGSSAATATASATVPGGSGPGNPTSK TTTTARTTQASSSRASSTPPATTSAPGGGPTQTLYGQCGG SGYSGPTRCAPPATCSTLNPYYAQCLN |
| 7 | Endoglucanase IV *Trichoderma sp.* full length protein | MIQKLSNLLLTALAVATGVVGHGHINNIVVNGVYYQGYDP TSFPYESDPPIVVGWTAADLDNGFVSPDAYQSPDIICHKN ATNAKGHASVKAGDTIPLQWVPVPWPHPGPIVDYLANCNG DCETVDKTSLEFFKIDGVGLISGGDPGNWASDVLIANNNT WVVKIPEDLAPGNYVLRHEIIALHSAGQADGAQNYPQCFN LAVPGSGSLQPSGVKGTALYHSDDPGVLINIYTSPLAYTI PGPSVVSGLPTSVAQGSSAATATASATVPGGSGPGNPTSK TTTTARTTQASSSRASSTPPATTSAPGGGPTQTLYGQCGG SGYSGPTRCAPPATCSTLNPYYAQCLN |
| 8 | Glycoside hydrolase family 61 protein *Hypocrea atroviridis* full length protein | MAQKLSNLFAIALTVATGVVGHGHVNNIVVNGVYYQGYDP TSFPYMPDPPIVVGWTAADTDNGFVSPDAYQTPDIVCHKN GTNAKGHASVKAGDSVLFQWVPVPWPHKSTVVDYLANCNG PCETVDKTTLEFFKIDGIGLLSGGNPGTWGSDVLIGNNNT WVIQIPEDLQTGNYVLRHELIALHSAEQADGAQNYPQCFN LAVTGTGSLQPSGVLATDLYHETDPGILFNIYTSPLTYII PGPTVVSGLPSSVAQASSAATATSSATVSGGGGGSSTGGS TSKTTTVVRSTTSVTSKASSSTAVTTPPPAGGTQTLYGQC GGSGYSGPTKCASPAVCTTLNPYYAQCLN |
| 9 | Glycoside hydrolase family 61 protein *Hypocrea virens* full length protein | MTQKLTSLLVTALTVATGVIGHGHVNNIVINGAYYQGYDP TLFPYEPNPPIVVGWTASDTDNGFVAPDAYQSPDIICHRN ATNARGHASVMAGSSVLIQWVPIPWPHPGPVLDYLANCNG DCETVDKTTLEFFKIDGIGLISGGNPGRWASDVLIGNNGT WVVQIPADLETGNYVLRHELIALHSAGSVDGAQNYPQCFN LAVTGTGSLQPTGVLGTKLYQESDPGILFNIYTSPLTYTI PGPTVVSGLPSSVTQRSSTATATSIATVPGSVSTGGTSSK TTTVPRSTSSATTRRSSSSAITTSAPAGPSQTLYGQCGGS GYSGPTICASPAVCSTLNPYYAQCLTR |
| 10 | Glycoside hydrolase family 61 protein *Thielavia terrestris* full length protein | MPSFASKTLLSTLAGAASVAAHGHVSNIVINGVSYQGYDP TSFPYMQNPPIVVGWTAADTDNGFVAPDAFASGDIICHKN ATNAKGHAVVAAGDKIFIQWNTWPESHHGPVIDYLASCGS ASCETVDKTKLEFFKIDEVGLVDGSSAPGVWGSDQLIANN NSWLVEIPPTIAPGNYVLRHEIIALHSAENADGAQNYPQC FNLQITGTGTATPSGVPGTSLYTPTDPGILVNIYSAPITY TVPGPALISGAVSIAQSSSAITASGTALTGSATAPAAAAA TTTSTTNAAAATSAAAAAGTSTTTTSAAAVVQTSSSSSS APSSAAAATTTAAASARPTGCSSGRSRKQPRRHARDMVV ARGAEEAN |
| 11 | Endoglucanase IV *Neurospora tetrasperma* full length protein | MARKSILTALAGASLVAAHGHVSKVIVNGVEYQNYDPTSF PYNSNPPTVIGWTIDQKDNGFVSPDAFDSGDIICHKSATP AGGHATVKAGDKISLQWDQWPESHKGPVIDYLAACDGDCE SVDKTALKFFKIDGAGYDATNGWASDVLIKDGNSWVVEIP ENIKPGNYVLRHEIIALHSAGQANGAQNYPQCFNLKVEGS GSTVPAGVAGTELYKATDAGILFDIYKNDISYPVPGPSLI AGASSSIAQSKMAATATASATLPGATGGSNSPATSAAAAA PAPSTTLVTSTKAAAPATSAAPAAPATSAAAGSGVQAKQ TKWGQCGGNGYTGATECESGSTCTKYNDWYSQCV |
| 12 | uncharacterized protein *Neurospora tetrasperma* full length protein | MARKSILTALAGASLVAAHGHVSKVIVNGVEYQNYDPTSF PYNSNPPTVIGWTIDQKDNGFVSPDAFDSGDIICHKSATP AGGHATVKAGDKISLQWDQWPESHKGPVIDYLAACDGDCE SVDKTALKFFKIDGAGYDATNGWASDVLIKDGNSWVVEIP ENIKPGNYVLRHEIIALHSAGQANGAQNYPQCFNLKVEGS GSTVPAGVAGTELYKATDAGILFDIYKNDISYPVPGPSLI AGASSSIAQSKMAATATASATLPGATGGSNSPATSAAAAA PAPSTTLVTSTKAAAPATSAAPAAPATSAAAGSGVQAKQ TKWGQCGGNGYTGATECESGSTCTKYNDWYSQCV |
| 13 | Glycoside hydrolase family 61 protein | MSSFTSKGLLSALMGAATVAAHGHVTNIVINGVSYQNFDP FTHPYMQNPPTVVGWTASNTDNGFVGPESFSSPDIICHKS |

-continued

| SEQ ID NO | Description | Sequence |
|---|---|---|
| | *Thielavia heterothallica* full length protein | ATNAGGHAVVAAGDKVFIQWDTWPESHHGPVIDYLADCGD AGCEKVDKTTLKFFKISESGLLDGTNAPGKWASDTLIANN NSWLVQIPPNIAPGNYVLRHEIIALHSAGQQNGAQNYPQC FNLQVTGSGTQKPSGVLGTELYKATDAGILANIYTSPVTY QIPGPAIISGASAVQQTTSAITASASAITGSATAAPTAAT TTAAAAATTTTTAGSRCYRHALDRRLSFFRPACSYHRCRY LQPCSPDPLRWSEEAPSPRP |
| 14 | Endoglucanase IV *Neurospora crassa* full length protein | MARMSILTALAGASLVAAHGHVSKVIVNGVEYQNYDPTSF PYNSNPPTVIGWTIDQKDNGFVSPDAFDSGDIICHKSAKP AGGHATVKAGDKISLQWDQWPESHKGPVIDYLAACDGDCE SVDKTALKFFKIDGAGYDATNGWASDTLIKDGNSWVVEIP ESIKPGNYVLRHEIIALHSAGQANGAQNYPQCFNLKVEGS GSTVPAGVAGTELYKATDAGILFDIYKNDISYPVPGPSLI AGASSSIAQSKMAATATASATLPGATGGSNSPATSAAAAA PATSAAAATSQVQAAPATTLVTSTKAAAPATSAAAPAAPA TSAAAGGAGQVQAKQTKWGQCGGNGFTGPTECESGSTCTK YNDWYSQCV |
| 15 | Uncharacterized protein *Sordaria macrospora* full length protein | MARKSIITALAGASLVAAHGHVSKVIVNGVEYQNYDPAVF PYLSNPPTVIGWTADQKDNGFVSPDAFGTPDIICHRSATP AGGHATVKAGDKISLKWDPVWPDSHKGPVIDYLAACNGDC ETVDKTSLRFFKIDGAGYNNGVWAADALVNNGNSWLVQIP ADLKPGNYVLRHEIIALHGAGSANGAQAYPQCFNLKVEGS GNNLPSGVPLYKATDAGILFNMYQNDFTYPVPGPALIAGA VSSIPQSSSAATATASATVPGGGGSGGSPVTTTAAGATTT KATTTLVTSTKATTSDAQVTTTAPPATGGGGGAAQKYGQC GGNGWTGPTTCVSGSVCTKVNDWYSQCL |
| 16 | Endoglucanase IV *Gaeumannomyces graminis* var. tritici full length protein | MGFKSRALVSALGSAATVLAHGHVSNIVVNGVFYPGYDVT KYPWQPNAPTVVGWSATNTDNGFVEPNNFGHPDIICHRGA QPAKGHARVRAGDKILLQWDTWPESHKGPVLDYLARCPGD CETVDKTALRFFKIGEGSYISGAAPGHWAADVLLGNGFSW VVQIPEDVAPGNYVLRHEIIALHGSPNPNGAQAYPQCFNL EISGSGSRQPAGVAGTSLYRAGDPGIHFPLYNSPIVYPVP GPALIPGVPSTVAQVSTRATATSSPFLPGGGGGGGGGGGG GNPGPTSAPGGNGGGGGGQQPPQTTTAPGNGGGGGGGGG GGGGGQTRWGQCGGSGWNGPTACAQGACSTLNPYYAQCV |
| 17 | uncharacterized protein *Nectria haematococca* full length protein | MTFFTAMSTLCASAWLYLLFSAVSVSAHGHVTQVIINGVA YGGYLSTSFPLQRKPPVVLGWTIEQRDNGFVSPDKYDHPD IICHRDATPAQGHVQVAAGDTITIKWSSWPENHRGPVMDY LANCNGPCETVDKTKLEFFKIDGMGLISQDRPGKYADGAL RENGYTWSVRIPSNIAPGNYVLRHEIIALHSGLERNGAQN YPQCFNLKITGSGSDNPPGYLGTELYDANDPGILVNIYGN LPNYQVPGPTIVSGGVSSVRQSPSRATTTAKCTTRS |
| 18 | Uncharacterized protein *Fusarium pseudograminearum* full length protein | MTFQSVHSSKASFWLTLFLPALGISAHGHVDEIIVNGVSY QGYGSTDFPYMQDPPVVAGWTIEQADNGFVSPDKYDDPDI ICHRDATPAKGHIELAAGDTLTLRWSGWPENHSGPILNYL ANCNGPCERVDKTKLEFFKIDGLGLLEQGTPGRYADKVLQ DNGDRWNVRIPKNIAPGNYVLRHEIIALHNALDKGGAQNY PQCFNLKITGDSDSPSGYLGTELYDAADPGILVNVYSSS VDYEVPGPTICEGGVSSVEQKPSEATTTAKCTTRY |
| 19 | Uncharacterized protein *Gibberella zeae* full length protein | MAFQSINSSKASFWLTLLLPALGISAHGHVDEIIVNGVSY QGYGSTDFPYMQDPPVVAGWTIEQADNGFVSPDKYDDPDI ICHRDATPAKGHIELAAGDTLTLRWSGWPENHSGPILNYL ANCNGPCERVDKTKLEFFKIDGLGLLEQGTPGRYADKVLQ DNGDRWNVRIPKNIAPGNYVLRHEIIALHNALDKGGAQNY PQCFNLKITGDSDSPSGYLGTELYDAADPGILVNVYSSS VDYEVPGPTICEGGVSSVEQKPSEATTTAKCTTRY |
| 20 | Glycoside hydrolase family 28 protein *Thielavia terrestris* full length protein | MKYRPSLSLAAAALFLLEPWVQAQLSGSVGPTTSRAAKAA KKVCNIMNYGGVASATTDNSAAITAAWNACKGGGEVYIPS GSYGLSSWVTLSGGSGVSINLEGVIYRITSATAGGTMISV SSTTDFEFYSGNSKGAIQGYGYLLNASDPRLVRLTQVTNF SFHDIALVDAPEFSLVMDTCSNGEVYNSIVRAGSEGGLDG VDVWGQNIWIHDIEVTNKDECVTVKSPASNILVESIFCNW SGGSAMGSLGANTDISNIYYRNVYSQNCNQMYMIKSWGGS GTVKNVKLENFWGHSNAYTLDLNAYWTSMQAPGDGVSYQ NITFTGWKGTNSNGAQRGSIQVLCPSAVPCTGITISDVNI WTESGSTEKEICENAYGTGGCLRAGSGGTYTTTVTRTTAS NYAIQTMPNEIKAWGLGTEIPIPAIPTSFFPGLRPISALM |

| SEQ ID NO | Description | Sequence |
|---|---|---|
| | | AASSNGGGATPTTAGPTPTTTSAGTGGGVQSEYGQCGGSG YSGPTACAAPYACSTLNPYYAQCL |
| 21 | Glycoside hydrolase family 45 protein *Hypocrea atroviridis* full length protein | MKASLFVGSLIASSAAAYKATTTRYYDGQEGACGCGGANG GAAFSWQLGISSGVYTAAGSQALYDTAGASWCGAGCGKCY NLTSTGEPPCTSCGTGGVAGQSIIVMVTNLCPNNGNAQWC PTVGGTNQYGYSYHFDIMAQNEIFGDNVVVDFEPVACPGQ ATSDWQQCLCVGMQETDTTPVLGGGSSPPPGSSSSRPPAS ATSSAPTGSGTQSLYGQCGGTGWAGPTACAPPATCKVLNQ YYSQCLD |
| 22 | putative Endoglucanase *Neosartorya fumigata* full length protein | MLYFTLLHSMTDQRGSDTMTDRKELVAVEHRLLGISNGVY TAAGSQALFDTAGASWCGAGCGKCYNLTSTGSAPCTGCGT GGAAGESIIVMVTNLCPYNGNQQWCPQVGATNNYGYSYHF DIMAQSEVFGDNVVVNFEPVACPGQATSDWETCVCYGQTE TDETPVGMTPGGSNPSPLTSTTTTKTTTTETTITTTTGGA TQTLYGQCGGSGWTGPTACASGATCKVLNPYYSQCLS |
| 23 | Putative uncharacterized protein *Aspergillus terreus* full length protein | MHTLQSAILLGGLLATQVAAHGHVTNIVINGVYYRGWNID SDPYNSNPPLVAAWRTPNTANGFIAPDAFGTSDIICHLNA LNGQGHIQVAAGDRISLQWNTWPESHHGPVLDYLADCGGS CETVDKTTLKFFKIDGVGLVDDTTPPGIWGDDQLIANNNT WLVEIPSSIAPGNYVLRHELIALHGAGSANGAQNYPQCFN LQITGSGTVKPSGVLGTALYSPTDPGILVNIYNSLNYIVP GPTPIPQAVSVVQSSSAIRATGTATAPGATGGTTATTTSK ATTTSSTTLVTTTSASTTSRTTTTTTAGAGGSQTVYGQCG GTGWTGPTACVASATCTTLNPYYAQCLPTST |
| 24 | Cip1 *Hypocrea jecorina* full length protein | MVRRTALLALGALSTLSMAQISDDFESGWDQTKWPISAPD CNQGGTVSLDTTVAHSGSNSMKVVGGPNGYCGHIFFGTTQ VPTGDVYVRAWIRLQTALGSNHVTFIIMPDTAQGGKHLRI GGQSQVLDYNRESDDATLPDLSPNGIASTVTLPTGAFQCF EYHLGTDGTIETWLNGSLIPGMTVGPGVDNPNDAGWTRAS YIPEITGVNFGWEAYSGDVNTVWFDDISIASTRVGCGPGS PGGPGSSTTGRSSTSGPTSTSRPSTTIPPPTSRTTTATGP TQTHYGQCGGIGYSGPTVCASGTTCQVLNPYYSQCL |
| 25 | Exoglucanase 1 *Hypocrea rufa* full length protein | MYQKLALISAFLATARAQSACTLQAETHPPLTWQKCSSGG TCTQQTGSVVIDANWRWTHATNSSTNCYDGNTWSSTLCPD NETCAKNCCLDGAAYASTYGVTTSADSLSIGFVTQSAQKN VGARLYLMASDTTYQEFTLLGNEFSFDVDVSQLPCGLNGA LYFVSMDADGGVSKYPTNTAGAKYGTGYCDSQCPRDLKFI NGGQANVEGWEPSSNNANTGIGGHGSCCSEMDIWEANSIE ALTPHPCTTVGQEICDGDSCGGTYSGDRYGGTCDPDGCDW NPYRLGNTSFYGPGSSFTLDTTKKLTVVTQFETSGAINRY YVQNGVTFQQPNAELGDYSGNSLDDDYCAAEEEAEFGGSSF SDKGGLTQFKKATSGGMVLVMSLWDDYYANMLWLDSTYPT NETSSTPGAVRGSCSTSSGVPAQLESNSPNAKVVYSNIKF GPIGSTGNSSGGNPPGGNPPGTTTTRRPATSTGSSPGPTQ THYGQCGGIGYSGPTVCASGSTCQVLNPYYSQCL |
| 26 | Glycoside hydrolase family 7 protein *Hypocrea virens* full length protein | MYQKLAAISAFLAAARAQQVCTQQAETHPPLTWQKCSSSG CTAQSGSVVLDANWRWTHDVKSTTNCYDGNTWSKTLCPDD ATCAKNCCLDGAAYSSTYGITTSSDSLTINFVTQSNVGAR LYLMATDTSYQEFTLSGNEFSFDVDVSQLPCGLNGALYFV SMDADGGQSKYPTNAAGAKYGTGYCDSQCPRDLKFINGQA NVDGWQPSSNNANTGIGGHGSCCSEMDIWEANSISQAVTP HPCETVGQTMCSGDGCGGTYSSDRYGGTCDPDGCDWNPYR LGNTTFYGPGSGFTLDTTKKMTVVTQFATSGAISRYYVQN GVKFQQPNAQLSGYSGNTLNSDYCAAEQAAFGGTSFTDKG GLAQFNKALSGGMVLVMSLWDDYYANMLWLDSTYPTNATA STPGAKRGSCSTSSGVPSQIESQSPNAKVVFSNIRFGPIG STGGSTGNPPPGTSTTRLPPSSTGSSPGPTQTHYGQCGGI GYSGPTQCVSGTTCQVLNPYYSQCL |
| 27 | Glycoside hydrolase family 5 protein *Hypocrea atroviridis* full length protein | MNKPMGPLLLAATLMASGAIAQTQTVWGQCGGQGYSGPTN CASGSACSTLNPYYAQCIPGATSFTTSTTSTKSPGSGSST TSSASQPTGSGQTRFAGINIAGFDFGCTTDGTCVTSQIYP PLKNFGGTNNHPDGVGQMQHFVNDDKLNIFRLPVGWQYLV NNNLGGTLDSTAISNYDQLVQGCLATGAYCIVDIHNYARW NGAIIGQGGPTNAQFVSLWTQLATKYASQSKIWFGIMNEP HDVDINTWGTTVQAVVTAIRNAGATTQFISLPGTDYQSAG NFLTDGSSTALSQVKNPDGSTTNLIFDLHKYLDSDNSGTH TECVTNNIATAFQPVATWLRQNKRQGILTETGGGNTQSCI |

-continued

Sequences

| SEQ ID NO | Description | Sequence |
|---|---|---|
| | | QDVCQQNQFLNQNSDVFLGYVGWGAGSFDSTYQLTLTPTQ NGNTWTDTALAAACFSRA |
| 28 | Glycosyl hydrolase family 45 protein *Neosartorya fischeri* full length protein | MTDRKELVAVEHHLVPTLGSNGVYTAAGSQALFDTAGASW CGAGCGKCYNLTSTGNPPCTGCGTGGAAGESIIVMVTNLC PYNGNQQWCPQVGATNNYGYSYHFDIMAQSEVFGDNVVVN FEPIACPGQATSDWETCVCYGKTATDETPVGMTPGGSNPS PPTSTTTTETTTTITTSGATQTLYGQCGGSWTGPTACAS GATCKVLNSYYSQCLS |
| 29 | Exoglucanase 1 *Trichoderma koningii* full length protein | MYRKLAVISAFLATARAQSACTLQSETHPPLTWQKCSSGG TCTQQTGSVVIDANWRWTHATNSSTNCYDGNTWSSTLCPD NETCAKNCCLDGAAYASTYGVTTSGNSLSIGFVTQSAQKN VGARLYLMASDTTYQEFTLLGNEFSFDVDVSQLPCGLNGA LYFVSMDADGGVSKYPTNTAGAKYGTGYCDSQCPRDLKFI NGQANVEGWEPSSNNANTGIGGHGSCCSEMDIWEANSISE ALTPHPCTTVGQEICEGDGCGGTYSDNRYGGTCDPDGCDW NPYRLGNTSFYGPGSSFTLDTTKKLTVVTQFETSGAINRY YVQNGVTFQQPNAELGSYSGNELNDDYCTAEEAEFGGSSF SDKGGLTQFKKATSGGMVLVMSLWDDYYANMLWLDSTYPT NETSSTPGAVRGSCSTSSGVPAQVESQSPNAKVTFSNIKF GPIGSTGNPSGGNPPGGNRGTTTTRRPATTTGSSPGPTQS HYGQCGGIGYSGPTVCASGTTCQVLNPYYSQCL |
| 30 | Glycosyl hydrolase family 61 *Colletotrichum graminicola* full length protein | MSYRSKTASFVAILASAATVAAHGHVTNIVINGVSYRNYI PVQDPYTNNPPLVAGWTTDQRDNGFVAPDAYNAPDIICHR QAVAGKGRITVAAGDTVQLQWTEWPDSHKGPVIDWLANCN GPCNLVDKTDLRFFKIDGAGLIDPPQRTNRWAATALIENG NAWLVRIPANVAPGHYVLRHDIIALHSAGQQNGAQSYPQC INLEITGEGTDNPPGVLGTALYRANDAGILYNIYRDNLND YVVPGDAIIPGGVSMLPQSRIQITASGSATPYGTTSVGSS SSTRIAPSSVTSAATSSSSRESASSVEAEASTISTTIRLT RTITATHTNSTSNNIPPSSTAAPTRTLAPTTLQTQTTTAP PSGEPTQKMYGQCGGVAYMGPTQCPAYATCSTVNPYYAQC TPLPVPPGVQPLYGQCGGLNWPPESPTECVPGARCSTINP YYAQCTPA |
| 31 | Putative uncharacterized protein *Arthrobotrys oligospora* full length protein | MLSSTLLLTALAVPAAFAQSNLDWDAAYTKATTMLGKLTL QQKINMVTGVGWQKGPCVGNIAAISSAGFPGLCLQDGPVG VRYASGVTAFPAAIHLGATWDKDLMRAQGVAMGEEFRGKG VNIALAPVSGALGKIPQAGRNWEGYSNDPYHAGVGMTEVI TGVQSVGVQACAKHYIGNEQERNRETMSSNIDDRTMHELY LWPFADAAKANVATFMCSYNKLNSSWACDNDYALNKLLKG ELGFRGQVLSDWNAKTTTGGATRGLDMTMPGDNFGDNNFV WGQNLLNAVNQGSVSTSRLDDMVKRIFASWYLVGQDQNYP SVSFNSWNNNGGGDVSGNHKELARTVAGDGIILLKNVNNA LPLKKPASLAIIGRDAINNPAGINSCTDRACNDGTLAMGW GSGTTNFPYLIDPLTAIRAQAQVDGTTVVTSTTDNASQGA SAAQSASTAIVFINANSGEGYLTVQGNSGDRNNLDPWNNG NDLVKAVAAVNSKTIVVIHSVGPIILEQFVDLPNVIAVVW AGLPGQESGNGLVDVLYGSKAPGGKLPFTIAKSPSDYGTS IINGDDNFSEGLFIDYRRFDAQGITPRYEFGFGLSYTTFS FSNLVISYTSTTTGPISSTQNAPGGYPALYEPVATITARV TNTGGVAGSEVAQLYIGLPAGSPSTPPKQLRGFQKLKLAS GASGTATFVLKRKDLAYWNTASQRWVVPTGNFNIFIGASS RDIRLQGTMGPSGSTTTTIGGSTSSTTTAQTTTRVTTTPS TTVTTTRTTTAPTTTRTTTVATTTRATTTAVITTTAAPTG GPLQSKWGQCGGVGYTGASVCSPTATCSTLNPYYAQCL |
| 32 | Cellobiohydrolase *Trichoderma harzianum* full length protein | MYRKLAAISAFLAAARAQQVCTQQAETHPPLTWQKCTASG CTAQSGSVVLDANWRWTHDTKSTTNCYDGNTWSSTLCPDD ATCAKNCCLDGANYSGTYGVTTSGDALTLQFVTASNVGSR LYLMANDSTYQEFTLSGNEFSFDVDVSQLPCGLNGALYFV SMDADGGQSKYPGNAAGAKYGTGYCDSQCPRDLKFINGQA NVEGWEPSSNNANTGVGGHGSCCSEMDIWEANSISEALTP HPCETVGQTMCSGDACGGTYSNDRYGGTCDPDGCDWNPYR LGNTSFYGPGSSFALDTTKKLTVVTQFATDGSISRYYVQN GVKFQQPSASVGSYTGNTINTAYCAAEQTAFGGTSFTDKG GLAQINKAFQGGMVLVMSLWDDYAVNMLWLDSTYPTNATA STPGAKRGSCSTSSGVPAQVEAQSPNSKVIYSNIRFGPIG STGGNTGSNPPGTSTTRAPPSSTGSSPTATQTHYGQCGGT GWTGPTRCASGFTCQVLNPFYSQCL |

| SEQ ID NO | Description | Sequence |
|---|---|---|
| 33 | Endoglucanase *Penicillium sp.* full length protein | MATRPLAFAAIAALIHQAASQQAPTPDNLASLPTWKCTTS GGCVQQSTSIVVDWVYHWIHTVNGSTSCTTSSGLDSTLCG TEEECYTNCEISPATYDGLGIKTSGNALTLNQYVTSNGTT SNASPRVYLLDPAGKNYEMLQLLGQEISFDVDASNLPCGE NGALYLSEMDATGGRSQYNPAGASYGSGYCDAQCGSSSWF NGSINSAGLGSCCNEMDLWEANGEATALTPHPCSVDGPYG CSGSGACGSTGVCDKNGCGFNPYALGDQSYYGPGLTVDTSK PFTVTTQFVTNDGTKTGTLTEIRRSYTQNGKVIANAVASA SSGFSGQSSITESFCTAMDSEAGTLGGLTTMGEALGRGMV LIFSIWNDAGGYMNWLDSGSSGPCSSTAGIPSTIQANDPG TSVTFSNIKWGDIGSTGSGTGGSSSSSSSTSTSPKTTSTT TTSATTKTSATTTTTSTGATQTHYGQCGGMSYTGPTVCAS PYTCQVQNPYYSQCL |
| 34 | *H. jecorina* GH61A Cat Domain | HGHINDIVINGVWYQAYDPTTFPYESNPPIVVGWTAADLD NGFVSPDAYQNPDIICHKNATNAKGHASVKAGDTILFQWV PVPWPHPGPIVDYLANCNGDCETVDKTTLEFFKIDGVGLL SGGDPGTWASDVLISNNNTWVVKIPDNLAPGNYVLRHEII ALHSAGQANGAQNYPQCFNIAVSGSGSLQPSGVLGTDLYH ATDPGVLINIYTSPLNYIIPGPTVVSGLPTSVAQGSSAAT ATASATVPG |
| 35 | Endoglucanase IV *Hypocrea rufa* Cat Domain | HGHINDIVINGVWYQAYDPTTFPYESNPPIVVGWTAADLD NGFVSPDAYQNPDIICHKNATNAKGHASVKARDTILFQWV PVPWPHPGPIVDYLANCNGDCETVDKTTLEFFKIDGVGLL SGGDPGTWASDVLISNNNTWVVKIPDNLAPGNYVLRHEII ALHSAGQANGAQNYPQCFNIAVSGSGSLQPSGVLGTDLYH ATDPGVPINIYTSPLNYIIPGPTVVSGLPTSVAQGSSAAT ATASATAPG |
| 36 | Type IV endoglucanase *Trichoderma saturnisporum* Cat Domain | HGHINNIVINGVYYQAYDPTSFPYESNPPIVVGWTAADLD NGFVSPDAYGSPDIICHKNATNAKGHASVRAGDTVLFQWV PLPWPHPGPIVDYLANCNGDCETVDKTSLEFFKIDGVGLI SGGDPGNWASDVLIANNNTWVVKIPDDLAPGNYVLRHEII ALHSAGQANGAQNYPQCFNLAVSGSGSLKPSGVKGTALYH ATDPGVLINIYTSPLNYIIPGPTVVSGLPTSVAQRSSAAT ATASATLPG |
| 37 | Endoglucanase IV *Hypocrea orientalis* Cat Domain | HGHINNIVVNGVYYQGYDPTSFPYESDPPIVVGWTAADLD NGFVSPDAYQSPDIICHKNATNAKGHASVKAGDTILFQWV PVPWPHPGPIVDYLANCNGDCETVDKTSLEFFKIDGVGLI SGGDPGNWASDVLIANNNTWVVKIPEDLAPGNYVLRHEII ALHSAGQADGAQNYPQCFNLAVSGSGSLQPSGVKGTALYH SDDPGVLINIYTSPLAYTIPGPSVVSGLPTSVAQGSSAAT ATASATVPG |
| 38 | Endoglucanase IV *Trichoderma sp.* Cat Domain | HGHINNIVVNGVYYQGYDPTSFPYESDPPIVVGWTAADLD NGFVSPDAYQSPDIICHKNATNAKGHASVKAGDTIPLQWV PVPWPHPGPIVDYLANCNGDCETVDKTSLEFFKIDGVGLI SGGDPGNWASDVLIANNNTWVVKIPEDLAPGNYVLRHEII ALHSAGQADGAQNYPQCFNLAVPGSGSLQPSGVKGTALYH SDDPGVLINIYTSPLAYTIPGPSVVSGLPTSVAQGSSAAT ATASATVPG |
| 39 | Glycoside hydrolase family 61 protein *Hypocrea atroviridis* Cat Domain | HGHVNNIVVNGVYYQGYDPTSFPYMPDPPIVVGWTAADTD NGFVSPDAYQTPDIVCHKNGTNAKGHASVKAGDSVLFQWV PVPWPHKSTVVDYLANCNGPCETVDKTTLEFFKIDGIGLL SGGNPGTWGSDVLIGNNNTWVIQIPEDLQTGNYVLRHELI ALHSAEQADGAQNYPQCFNLAVTGTGSLQPSGVLATDLYH ETDPGILFNIYTSPLTYIIPGPTVVSGLPSSVAQASSAAT ATSSATVSG |
| 40 | Glycoside hydrolase family 61 protein *Hypocrea virens* Cat Domain | HGHVNNIVINGAYYQGYDPTLFPYEPNPPIVVGWTASDTD NGFVAPDAYQSPDIICHRNATNARGHASVMAGSSVLIQWV PIPWPHPGPVLDYLANCNGDCETVDKTTLEFFKIDGIGLI SGGNPGRWASDVLIGNNGTWVVQIPADLETGNYVLRHELI ALHSAGSVDGAQNYPQCFNLAVTGTGSLQPTGVLGTKLYQ ESDPGILFNIYTSPLTYTIPGPTVVSGLPSSVQRSSTAT ATSIATVPG |

Sequences

| SEQ ID NO | Description | Sequence |
|---|---|---|
| 41 | Glycoside hydrolase family 61 protein *Thielavia terrestris* Cat Domain | HGHVSNIVINGVSYQGYDPTSFPYMQNPPIVVGWTAADTD NGFVAPDAFASGDIICHKNATNAKGHAVVAAGDKIFIQWN TWPESHHGPVIDYLASCGSASCETVDKTKLEFFKIDEVGL VDGSSAPGVWGSDQLIANNNSWLVEIPPTIAPGNYVLRHE IIALHSAENADGAQNYPQCFNLQITGTGTATPSGVPGTSL YTPTDPGILVNIYSAPITYTVPGPALISGAVSIAQSSSAI TASGTALTGS |
| 42 | Endoglucanase IV *Neurospora tetrasperma* Cat Domain | HGHVSKVIVNGVEYQNYDPTSFPYNSNPPTVIGWTIDQKD NGFVSPDAFDSGDIICHKSATPAGGHATVKAGDKISLQWD QWPESHKGPVIDYLAACDGDCESVDKTALKFFKIDGAGYD ATNGWASDVLIKDGNSWVVEIPENIKPGNYVLRHEIIALH SAGQANGAQNYPQCFNLKVEGSGSTVPAGVAGTELYKATD AGILFDIYKNDISYPVPGPSLIAGASSSIAQSKMAATATA SATLPG |
| 43 | Putative uncharacterized protein *Neurospora tetrasperma* Cat Domain | HGHVSKVIVNGVEYQNYDPTSFPYNSNPPTVIGWTIDQKD NGFVSPDAFDSGDIICHKSATPAGGHATVKAGDKISLQWD QWPESHKGPVIDYLAACDGDCESVDKTALKFFKIDGAGYD ATNGWASDVLIKDGNSWVVEIPENIKPGNYVLRHEIIALH SAGQANGAQNYPQCFNLKVEGSGSTVPAGVAGTELYKATD AGILFDIYKNDISYPVPGPSLIAGASSSIAQSKMAATATA SATLPG |
| 44 | Glycoside hydrolase family 61 protein *Thielavia heterothallica* Cat Domain | HGHVTNIVINGVSYQNFDPFTHPYMQNPPTVVGWTASNTD NGFVGPESFSSPDIICHKSATNAGGHAVVAAGDKVFIQWD TWPESHHGPVIDYLADCGDAGCEKVDKTTLKFFKISESGL LDGTNAPGKWASDTLIANNNSWLVQIPPNIAPGNYVLRHE IIALHSAGQQNGAQNYPQCFNLQVTGSGTQKPSGVLGTEL YKATDAGILANIYTSPVTYQIPGPAIISGASAVQQTTSAI TASASAITGS |
| 45 | Endoglucanase IV *Neurospora crassa* Cat Domain | HGHVSKVIVNGVEYQNYDPTSFPYNSNPPTVIGWTIDQKD NGFVSPDAFDSGDIICHKSAKPAGGHATVKAGDKISLQWD QWPESHKGPVIDYLAACDGDCESVDKTALKFFKIDGAGYD ATNGWASDTLIKDGNSWVVEIPESIKPGNYVLRHEIIALH SAGQANGAQNYPQCFNLKVEGSGSTVPAGVAGTELYKATD AGILFDIYKNDISYPVPGPSLIAGASSSIAQSKMAATATA SATLPG |
| 46 | Uncharacterized protein *Sordaria macrospora* Cat Domain | HGHVSKVIVNGVEYQNYDPAVFPYLSNPPTVIGWTADQKD NGFVSPDAFGTPDIICHRSATPAGGHATVKAGDKISLKWD PVVWPDSHKGPVIDYLAACNGDCETVDKTSLRFFKIDGAGY NNGVWAADALVNNGNSWLVQIPADLKPGNYVLRHEIIALH GAGSANGAQAYPQCFNLKVEGSGNNLPSGVPLYKATDAGI LFNMYQNDFTYPVPGPALIAGAVSSIPQSSSAATATASAT VPG |
| 47 | Endoglucanase IV *Gaeumannomyces graminis* var. *tritici* Cat Domain | HGHVSNIVVNGVFYPGYDVTKYPWQPNAPTVVGWSATNTD NGFVEPNNFGHPDIICHRGAQPAKGHARVRAGDKILLQWD TWPESHKGPVLDYLARCPGDCETVDKTALRFFKIGEGSYI SGAAPGHWAADVLLGNGFSWVVQIPEDVAPGNYVLRHEII ALHGSPNPNGAQAYPQCFNLEISGSGSRQPAGVAGTSLYR AGDPGIHFPLYNSPIVYPVPGPALIPGVPSTVAQVSTRAT ATSSPFLPG |
| 48 | Putative uncharacterized protein *Nectria haematococca* Cat Domain | HGHVTQVIINGVAYGGYLSTSFPLQRKPPVVLGWTIEQRD NGFVSPDKYDHPDIICHRDATPAQGHVQVAAGDTITIKWS SWPENHRGPVMDYLANCNGPCETVDKTKLEFFKIDGMGLI SQDRPGKYADGALRENGYTWSVRIPSNIAPGNYVLRHEII ALHSGLERNGAQNYPQCFNLKITGSGSDNPPGYLGTELYD ANDPGILVNIYGNLPNYQVPGPTIVSGGVSSVRQSPSRAT TTAKCTTRS |
| 49 | Uncharacterized protein *Fusarium pseudograminearum* Cat Domain | HGHVDEIIVNGVSYQGYGSTDFPYMQDPPVVAGWTIEQAD NGFVSPDKYDDPDIICHRDATPAKGHIELAAGDTLTLRWS GWPENHSGPILNYLANCNGPCERVDKTKLEFFKIDGLGLL EQGTPGRYADKVLQDNGDRWNVRIPKNIAPGNYVLRHEII ALHNALDKGGAQNYPQCFNLKITGDGSDSPSGYLGTELYD AADPGILVNVYSSSVDYEVPGPTICEGGVSSVEQKPSEAT TTAKCTTRY |

-continued

Sequences

| SEQ ID NO | Description | Sequence |
|---|---|---|
| 50 | Uncharacterized protein *Gibberella zeae* Cat Domain | HGHVDEIIVNGVSYQGYGSTDFPYMQDPPVVAGWTIEQAD NGFVSPDKYDDPDIICHRDATPAKGHIELAAGDTLTLRWS GWPENHSGPILNYLANCNGPCERVDKTKLEFFKIDGLGLL EQGTPGRYADKVLQDNGDRWNVRIPKNIAPGNYVLRHEII ALHNALDKGGAQNYPQCFNLKITGDGSDSPSGYLGTELYD AADPGILVNVYSSSVDYEVPGPTICEGGVSSVEQKPSEAT TTAKCTTRY |
| 51 | *H. jecorina* GH61A Carb bind domain | PTQTLYGQCGGSGYSGPTRCAPPATCSTLNPYYAQCL |
| 52 | Glycoside hydrolase family 61 protein *Hypocrea virens* Carb bind domain | PSQTLYGQCGGSGYSGPTICASPAVCSTLNPYYAQCL |
| 53 | Glycoside hydrolase family 28 protein *Thielavia terrestris* Carb bind domain | GVQSEYGQCGGSGYSGPTACAAPYACSTLNPYYAQCL |
| 54 | Glycoside hydrolase family 45 protein *Hypocrea atroviridis* Carb bind domain | GTQSLYGQCGGTGWAGPTACAPPATCKVLNQYYSQCL |
| 55 | Endoglucanase, putative *Neosartorya fumigata* Carb bind domain | ATQTLYGQCGGSGWTGPTACASGATCKVLNPYYSQCL |
| 56 | Putative uncharacterized protein *Aspergillus terreus* Carb bind domain | GSQTVYGQCGGTGWTGPTACVASATCTTLNPYYAQCL |
| 57 | Cip1 *Hypocrea jecorina* Carb bind domain | PTQTHYGQCGGIGYSGPTVCASGTTCQVLNPYYSQCL |
| 58 | Exoglucanase 1 *Hypocrea rufa* Carb bind domain | PTQTHYGQCGGIGYSGPTVCASGSTCQVLNPYYSQCL |
| 59 | Glycoside hydrolase family 7 protein *Hypocrea virens* Carb bind domain | PTQTHYGQCGGIGYSGPTQCVSGTTCQVLNPYYSQCL |
| 60 | Glycoside hydrolase family 5 protein *Hypocrea atroviridis* Carb bind domain | QTQTVWGQCGGQGYSGPTNCASGSACSTLNPYYAQCI |
| 61 | Glycosyl hydrolase family 45 protein *Neosartorya fischeri* Carb bind domain | ATQTLYGQCGGSGWTGPTACASGATCKVLNSYYSQCL |
| 62 | Exoglucanase 1 *Trichoderma koningii* Carb bind domain | PTQSHYGQCGGIGYSGPTVCASGTTCQVLNPYYSQCL |
| 63 | Glycosyl hydrolase family 61 *Colletotrichum graminicola* Carb bind domain | PTQKMYGQCGGVAYMGPTQCPAYATCSTVNPYYAQC |

| SEQ ID NO | Description | Sequence |
|---|---|---|
| 64 | Glycosyl hydrolase family 61 *Colletotrichum graminicola* Carb bind domain | QPLYGQCGGLNWPPESPTECVPGARCSTINPYYAQC |
| 65 | Putative uncharacterized protein *Arthrobotrys oligospora* Carb bind domain | PLQSKWGQCGGVGYTGASVCSPTATCSTLNPYYAQCL |
| 66 | Cellobiohydrolase *Trichoderma harzianum* Carb bind domain | ATQTHYGQCGGTGWTGPTRCASGFTCQVLNPFYSQCL |
| 67 | Endoglucanase *Penicillium sp.* Carb bind domain | ATQTHYGQCGGMSYTGPTVCASPYTCQVQNPYYSQCL |
| 68 | Endoglucanase IV *Hypocrea rufa* MATURE | HGHINDIVINGVWYQAYDPTTFPYESNPPIVVGWTAADLD NGFVSPDAYQNPDIICHKNATNAKGHASVKARDTILFQWV PVPWPHPGPIVDYLANCNGDCETVDKTTLEFFKIDGVGLL SGGDPGTWASDVLISNNNTWVVKIPDNLAPGNYVLRHEII ALHSAGQANGAQNYPQCFNIAVSGSGSLQPSGVLGTDLYH ATDPGVPINIYTSPLNYIIPGPTVVSGLPTSVAQGSSAAT ATASATAPGGGSGPTSRTTTTARTTQASSRPSSTPPATTS APAGGPTQTLYGQCGGSGYSGPTRCAPPATCSTLNPYYAQ CLN |
| 69 | Type IV endoglucanase *Trichoderma saturnisporum* MATURE | HGHINNIVINGVYYQAYDPTSFPYESNPPIVVGWTAADLD NGFVSPDAYGSPDIICHKNATNAKGHASVRAGDTVLFQWV PLPWPHPGPIVDYLANCNGDCETVDKTSLEFFKIDGVGLI SGGDPGNWASDVLIANNNTWVVKIPDDLAPGNYVLRHEII ALHSAGQANGAQNYPQCFNLAVSGSGSLKPSGVKGTALYH ATDPGVLINIYTSPLNYIIPGPTVVSGLPTSVAQRSSAAT ATASATLPGGGGSPPGGPTSRPTTTARSTSQASSRPSPPA TTSAPAGGGPTQTLYGQCGGSGYSGPTRCAPPATVSTLNPY YARLN |
| 70 | Endoglucanase IV *Hypocrea orientalis* MATURE | HGHINNIVVNGVYYQGYDPTSFPYESDPPIVVGWTAADLD NGFVSPDAYQSPDIICHKNATNAKGHASVKAGDTILFQWV PVPWPHPGPIVDYLANCNGDCETVDKTSLEFFKIDGVGLI SGGDPGNWASDVLIANNNTWVVKIPEDLAPGNYVLRHEII ALHSAGQADGAQNYPQCFNLAVSGSGSLQPSGVKGTALYH SDDPGVLINIYTSPLAYTIPGPSVVSGLPTSVAQGSSAAT ATASATVPGGSGPGNPTSKTTTTARTTQASSSRASSTPPA TTSAPGGGPTQTLYGQCGGSGYSGPTRCAPPATCSTLNPY YAQCLN |
| 71 | Endoglucanase IV *Trichoderma sp.* MATURE | HGHINNIVVNGVYYQGYDPTSFPYESDPPIVVGWTAADLD NGFVSPDAYQSPDIICHKNATNAKGHASVKAGDTIPLQWV PVPWPHPGPIVDYLANCNGDCETVDKTSLEFFKIDGVGLI SGGDPGNWASDVLIANNNTWVVKIPEDLAPGNYVLRHEII ALHSAGQADGAQNYPQCFNLAVPGSGSLQPSGVKGTALYH SDDPGVLINIYTSPLAYTIPGPSVVSGLPTSVAQGSSAAT ATASATVPGGSGPGNPTSKTTTTARTTQASSSRASSTPPA TTSAPGGGPTQTLYGQCGGSGYSGPTRCAPPATCSTLNPY YAQCLN |
| 72 | Glycoside hydrolase family 61 protein *Hypocrea atroviridis* MATURE | HGHVNNIVVNGVYYQGYDPTSFPYMPDPPIVVGWTAADTD NGFVSPDAYQTPDIVCHKNGTNAKGHASVKAGDSVLFQWV PVPWPHKSTVVDYLANCNGPCETVDKTTLEFFKIDGIGLL SGGNPGTWGSDVLIGNNNTWVIQIPEDLQTGNYVLRHELI ALHSAEQADGAQNYPQCFNLAVTGTGSLQPSGVLATDLYH ETDPGILFNIYTSPLTYIIPGPTVVSGLPSSVAQASSAAT ATSSATVSGGGGGSSTGGSTSKTTTVVRSTTSVTSKASSS TAVTTPPPAGGTQTLYGQCGGSGYSGPTKCASPAVCTTLN PYYAQCLN |

| SEQ ID NO | Description | Sequence |
|---|---|---|
| 73 | Glycoside hydrolase family 61 protein *Hypocrea virens* MATURE | HGHVNNIVINGAYYQGYDPTLFPYEPNPPIVVGWTASDTD NGFVAPDAYQSPDIICHRNATNARGHASVMAGSSVLIQWV PIPWPHPGPVLDYLANCNGDCETVDKTTLEFFKIDGIGLI SGGNPGRWASDVLIGNNGTWVVQIPADLETGNYVLRHELI ALHSAGSVDGAQNYPQCFNLAVTGTGSLQPTGVLGTKLYQ ESDPGILFNIYTSPLTYTIPGPTVVSGLPSSVTQRSSTAT ATSIATVPGSVSTGGTSSKTTTVPRSTSSATTRRSSSSAI TTSAPAGPSQTLYGQCGGSGYSGPTICASPAVCSTLNPYY AQCLTR |
| 74 | Glycoside hydrolase family 61 protein *Thielavia terrestris* MATURE | HGHVSNIVINGVSYQGYDPTSFPYMQNPPIVVGWTAADTD NGFVAPDAFASGDIICHKNATNAKGHAVVAAGDKIFIQWN TWPESHHGPVIDYLASCGSASCETVDKTKLEFFKIDEVGL VDGSSAPGVWGSDQLIANNNSWLVEIPPTIAPGNYVLRHE IIALHSAENADGAQNYPQCFNLQITGTGTATPSGVPGTSL YTPTDPGILVNIYSAPITYTVPGPALISGAVSIAQSSSAI TASGTALTGSATAPAAAATTTSTTNAAAAATSAAAAAGT STTTTSAAAVVQTSSSSSSAPSSAAAAATTTAAASARPTG CSSGRSRKQPRRHARDMVVARGAEEAN |
| 75 | Endoglucanase IV *Neurospora tetrasperma* MATURE | HGHVSKVIVNGVEYQNYDPTSFPYNSNPPTVIGWTIDQKD NGFVSPDAFDSGDIICHKSATPAGGHATVKAGDKISLQWD QWPESHKGPVIDYLAACDGDCESVDKTALKFFKIDGAGYD ATNGWASDVLIKDGNSWVVEIPENIKPGNYVLRHEIIALH SAGQANGAQNYPQCFNLKVEGSGSTVPAGVAGTELYKATD AGILFDIYKNDISYPVPGPSLIAGASSSIAQSKMAATATA SATLPGATGGSNSPATSAAAAAPAPSTTLVTSTKAAAPAT SAAPAAPATSAAAGSGQVQAKQTKWGQCGGNGYTGATECE SGSTCTKYNDWYSQCV |
| 76 | Putative uncharacterized protein *Neurospora tetrasperma* MATURE | HGHVSKVIVNGVEYQNYDPTSFPYNSNPPTVIGWTIDQKD NGFVSPDAFDSGDIICHKSATPAGGHATVKAGDKISLQWD QWPESHKGPVIDYLAACDGDCESVDKTALKFFKIDGAGYD ATNGWASDVLIKDGNSWVVEIPENIKPGNYVLRHEIIALH SAGQANGAQNYPQCFNLKVEGSGSTVPAGVAGTELYKATD AGILFDIYKNDISYPVPGPSLIAGASSSIAQSKMAATATA SATLPGATGGSNSPATSAAAAAPAPSTTLVTSTKAAAPAT SAAPAAPATSAAAGSGQVQAKQTKWGQCGGNGYTGATECE SGSTCTKYNDWYSQCV |
| 77 | Glycoside hydrolase family 61 protein *Thielavia heterothallica* MATURE | HGHVTNIVINGVSYQNFDPFTHPYMQNPPTVVGWTASNTD NGFVGPESFSSPDIICHKSATNAGGHAVVAAGDKVFIQWD TWPESHHGPVIDYLADCGDAGCEKVDKTTLKFFKISESGL LDGTNAPGKWASDTLIANNNSWLVQIPPNIAPGNYVLRHE IIALHSAGQQNGAQNYPQCFNLQVTGSGTQKPSGVLGTEL YKATDAGILANIYTSPVTYQIPGPAIISGASAVQQTTSAI TASASAITGSATAAPTAATTTAAAATTTTTAGSRCYRHA LDRRLSFFRPACSYHRCRYLQPCSPDPLRWSEEAPSPRP |
| 78 | Endoglucanase IV *Neurospora crassa* MATURE | HGHVSKVIVNGVEYQNYDPTSFPYNSNPPTVIGWTIDQKD NGFVSPDAFDSGDIICHKSAKPAGGHATVKAGDKISLQWD QWPESHKGPVIDYLAACDGDCESVDKTALKFFKIDGAGYD ATNGWASDTLIKDGNSWVVEIPESIKPGNYVLRHEIIALH SAGQANGAQNYPQCFNLKVEGSGSTVPAGVAGTELYKATD AGILFDIYKNDISYPVPGPSLIAGASSSIAQSKMAATATA SATLPGATGGSNSPATSAAAAAPATSAAAATSQVQAAPAT TLVTSTKAAAPATSAAAPAAPATSAAAGGAGQVQAKQTKW GQCGGNGFTGPTECESGSTCTKYNDWYSQCV |
| 79 | Endoglucanase IV *Gaeumannomyces graminis* var. *tritici* MATURE | HGHVSNIVVNGVFYPGYDVTKYPWQPNAPTVVGWSATNTD NGFVEPNNFGHPDIICHRGAQPAKGHARVRAGDKILLQWD TWPESHKGPVLDYLARCPGDCETVDKTALRFFKIGEGSYI SGAAPGHWAADVLLGNGFSWVVQIPEDVAPGNYVLRHEII ALHGSPNPNGAQAYPQCFNLEISGSGSRQPAGVAGTSLYR AGDPGIHFPLYNSPIVYPVPGPALIPGVPSTVAQVSTRAT ATSSPFLPGGGGGGGGGGGGNPGPTSAPGGNGPTSAPGGGNGGGGGGQ QPPQTTTAPGNGGGGGGGGGGGGGGQTRWGQCGGSGWNGP TACAQGACSTLNPYYAQCV |

What is claimed is:

1. A variant glycoside hydrolase family 61 (GH61) polypeptide, wherein said variant has cellulase enhancing activity, has at least 95% sequence identity to the amino acid sequence of SEQ ID NO:3 and the amino acid substitution I114L, and has at least one improved property relative to a parent GH61 polypeptide, wherein said improved property is selected from the group consisting of (a) expression based on protein level and RNA level or activity of the variant GH61 polypeptide, (b) thermostability and/or melting temperature (Tm), (c) performance in a Whole Hydrolysate Dilute Acid Pretreated Corn Stover (whPCS) hydrolysis assay.

2. The variant of claim 1, wherein said variant is a combinatorial variant.

3. The variant of claim 1, wherein said parent GH61 polypeptide is a fungal glycosyl hydrolase 61a (GH61A).

4. The variant of claim 3, wherein said fungal GH61A is from *Hypocrea jecorina*, *Hypocrea rufa*, *Hypocrea orientalis*, *Hypocrea atroviridis*, *Hypocrea virens*, *Emericella nidulans*, *Aspergillus terreus*, *Aspergillus oryzae*, *Aspergillus niger*, *Aspergillus kawachii*, *Aspergillus flavus*, *Aspergillus clavatus*, *Gaeumannomyces graminis*, *Trichoderma saturnisporum*, *Neurospora tetrasperma*, *Neurospora crassa*, *Neosartorya fumigata*, *Neosartorya fumigate*, *Neosartorya fischeri*, *Thielavia terrestris*, *Talaromyces* sp., *Sporotricum* sp, and *Thielavia heterothallica*.

* * * * *

SEQUENCE LISTING

<160> NUMBER OF SEQ ID NOS: 79

<210> SEQ ID NO 1
<211> LENGTH: 1032
<212> TYPE: DNA
<213> ORGANISM: H. jecorina GH61A
<220> FEATURE:
<221> NAME/KEY: misc_feature
<222> LOCATION: (1)..(1032)
<223> OTHER INFORMATION: coding DNA sequence

<400> SEQUENCE: 1

```
atgatccaga agctttccaa cctccttgtc accgcactgg cggtggctac tggcgttgtc      60
ggacatggac atattaatga cattgtcatc aacggggtgt ggtatcaggc ctatgatcct     120
acaacgtttc catacgagtc aaaccccccc atagtagtgg gctggacggc tgccgacctt     180
gacaacggct tcgtttcacc cgacgcatac caaaaccctg acatcatctg ccacaagaat     240
gctacgaatg ccaaggggca cgcgtctgtc aaggccggag acactattct cttccagtgg     300
gtgccagttc catggccgca ccctggtccc attgtcgact acctggccaa ctgcaatggt     360
gactgcgaga ccgttgacaa gacgacgctt gagttcttca gatcgatgg cgttggtctc      420 ctcagcggcg gggatccggg cacctgggcc tcagacgtgc tgatctccaa caacaacacc     480
tgggtcgtca agatccccga caatcttgcg ccaggcaatt acgtgctccg ccacgagatc     540
atcgcgttac acagcgccgg gcaggcaaac ggcgctcaga actaccccca gtgcttcaac     600
attgccgtct caggctcggg ttctctgcag cccagcggcg ttctagggac cgacctctat     660
cacgcgacgg accctggtgt tctcatcaac atctacacca gcccgctcaa ctacatcatc     720
cctggaccta ccgtggtatc aggcctgcca acgagtgttg cccaggggag ctccgccgcg     780
acggccaccg ccagcgccac tgttcctgga ggcggtagcg gcccgaccag cagaaccacg     840
acaacggcga ggacgacgca ggcctcaagc aggcccagct ctacgcctcc cgcaaccacg     900
tcggcacctg ctggcggccc aacccagact ctgtacggcc agtgtggtgg cagcggttac     960
agcgggccta ctcgatgcgc gccgccagcc acttgctcta ccttgaaccc ctactacgcc    1020
cagtgcctta ac                                                       1032
```

<210> SEQ ID NO 2
<211> LENGTH: 344
<212> TYPE: PRT
<213> ORGANISM: H. jecorina GH61A
<220> FEATURE:
<221> NAME/KEY: misc_feature
<222> LOCATION: (1)..(344)
<223> OTHER INFORMATION: full length protein

<400> SEQUENCE: 2

```
Met Ile Gln Lys Leu Ser Asn Leu Leu Val Thr Ala Leu Ala Val Ala
1               5                   10                  15

Thr Gly Val Val Gly His Gly His Ile Asn Asp Ile Val Ile Asn Gly
                20                  25                  30

Val Trp Tyr Gln Ala Tyr Asp Pro Thr Thr Phe Pro Tyr Glu Ser Asn
            35                  40                  45

Pro Pro Ile Val Val Gly Trp Thr Ala Ala Asp Leu Asp Asn Gly Phe
        50                  55                  60

Val Ser Pro Asp Ala Tyr Gln Asn Pro Asp Ile Ile Cys His Lys Asn
65                  70                  75                  80

Ala Thr Asn Ala Lys Gly His Ala Ser Val Lys Ala Gly Asp Thr Ile
                85                  90                  95
```

Leu Phe Gln Trp Val Pro Val Pro Trp Pro His Pro Gly Pro Ile Val
                100                 105                 110

Asp Tyr Leu Ala Asn Cys Asn Gly Asp Cys Glu Thr Val Asp Lys Thr
                115                 120                 125

Thr Leu Glu Phe Phe Lys Ile Asp Gly Val Gly Leu Leu Ser Gly Gly
130                 135                 140

Asp Pro Gly Thr Trp Ala Ser Asp Val Leu Ile Ser Asn Asn Asn Thr
145                 150                 155                 160

Trp Val Val Lys Ile Pro Asp Asn Leu Ala Pro Gly Asn Tyr Val Leu
                165                 170                 175

Arg His Glu Ile Ile Ala Leu His Ser Ala Gly Gln Ala Asn Gly Ala
                180                 185                 190

Gln Asn Tyr Pro Gln Cys Phe Asn Ile Ala Val Ser Gly Ser Gly Ser
                195                 200                 205

Leu Gln Pro Ser Gly Val Leu Gly Thr Asp Leu Tyr His Ala Thr Asp
                210                 215                 220

Pro Gly Val Leu Ile Asn Ile Tyr Thr Ser Pro Leu Asn Tyr Ile Ile
225                 230                 235                 240

Pro Gly Pro Thr Val Val Ser Gly Leu Pro Thr Ser Val Ala Gln Gly
                245                 250                 255

Ser Ser Ala Ala Thr Ala Thr Ala Ser Ala Thr Val Pro Gly Gly Gly
                260                 265                 270

Ser Gly Pro Thr Ser Arg Thr Thr Thr Ala Arg Thr Thr Gln Ala
                275                 280                 285

Ser Ser Arg Pro Ser Ser Thr Pro Pro Ala Thr Thr Ser Ala Pro Ala
                290                 295                 300

Gly Gly Pro Thr Gln Thr Leu Tyr Gly Gln Cys Gly Gly Ser Gly Tyr
305                 310                 315                 320

Ser Gly Pro Thr Arg Cys Ala Pro Pro Ala Thr Cys Ser Thr Leu Asn
                325                 330                 335

Pro Tyr Tyr Ala Gln Cys Leu Asn
                340

<210> SEQ ID NO 3
<211> LENGTH: 323
<212> TYPE: PRT
<213> ORGANISM: H. jecorina GH61A
<220> FEATURE:
<221> NAME/KEY: misc_feature
<222> LOCATION: (1)..(323)
<223> OTHER INFORMATION: mature protein

<400> SEQUENCE: 3

His Gly His Ile Asn Asp Ile Val Ile Asn Gly Val Trp Tyr Gln Ala
1               5                   10                  15

Tyr Asp Pro Thr Thr Phe Pro Tyr Glu Ser Asn Pro Pro Ile Val Val
                20                  25                  30

Gly Trp Thr Ala Ala Asp Leu Asp Asn Gly Phe Val Ser Pro Asp Ala
                35                  40                  45

Tyr Gln Asn Pro Asp Ile Ile Cys His Lys Asn Ala Thr Asn Ala Lys
                50                  55                  60

Gly His Ala Ser Val Lys Ala Gly Asp Thr Ile Leu Phe Gln Trp Val
65                  70                  75                  80

Pro Val Pro Trp Pro His Pro Gly Pro Ile Val Asp Tyr Leu Ala Asn
                85                  90                  95

```
Cys Asn Gly Asp Cys Glu Thr Val Asp Lys Thr Thr Leu Glu Phe Phe
            100                 105                 110

Lys Ile Asp Gly Val Gly Leu Leu Ser Gly Gly Asp Pro Gly Thr Trp
            115                 120                 125

Ala Ser Asp Val Leu Ile Ser Asn Asn Asn Thr Trp Val Val Lys Ile
        130                 135                 140

Pro Asp Asn Leu Ala Pro Gly Asn Tyr Val Leu Arg His Glu Ile Ile
145                 150                 155                 160

Ala Leu His Ser Ala Gly Gln Ala Asn Gly Ala Gln Asn Tyr Pro Gln
                165                 170                 175

Cys Phe Asn Ile Ala Val Ser Gly Ser Gly Ser Leu Gln Pro Ser Gly
            180                 185                 190

Val Leu Gly Thr Asp Leu Tyr His Ala Thr Asp Pro Gly Val Leu Ile
        195                 200                 205

Asn Ile Tyr Thr Ser Pro Leu Asn Tyr Ile Ile Pro Gly Pro Thr Val
210                 215                 220

Val Ser Gly Leu Pro Thr Ser Val Ala Gln Gly Ser Ser Ala Ala Thr
225                 230                 235                 240

Ala Thr Ala Ser Ala Thr Val Pro Gly Gly Gly Ser Gly Pro Thr Ser
                245                 250                 255

Arg Thr Thr Thr Thr Ala Arg Thr Thr Gln Ala Ser Ser Arg Pro Ser
            260                 265                 270

Ser Thr Pro Pro Ala Thr Thr Ser Ala Pro Ala Gly Gly Pro Thr Gln
        275                 280                 285

Thr Leu Tyr Gly Gln Cys Gly Gly Ser Gly Tyr Ser Gly Pro Thr Arg
        290                 295                 300

Cys Ala Pro Pro Ala Thr Cys Ser Thr Leu Asn Pro Tyr Tyr Ala Gln
305                 310                 315                 320

Cys Leu Asn

<210> SEQ ID NO 4
<211> LENGTH: 344
<212> TYPE: PRT
<213> ORGANISM: Hypocrea rufa
<220> FEATURE:
<221> NAME/KEY: misc_feature
<222> LOCATION: (1)..(344)
<223> OTHER INFORMATION: Endoglucanase IV Hypocrea rufa

<400> SEQUENCE: 4

Met Ile Gln Lys Leu Ser Asn Leu Leu Val Thr Ala Leu Ala Val Ala
1               5                   10                  15

Thr Gly Val Val Gly His Gly His Ile Asn Asp Ile Val Ile Asn Gly
            20                  25                  30

Val Trp Tyr Gln Ala Tyr Asp Pro Thr Thr Phe Pro Tyr Glu Ser Asn
        35                  40                  45

Pro Pro Ile Val Val Gly Trp Thr Ala Ala Asp Leu Asp Asn Gly Phe
    50                  55                  60

Val Ser Pro Asp Ala Tyr Gln Asn Pro Asp Ile Ile Cys His Lys Asn
65                  70                  75                  80

Ala Thr Asn Ala Lys Gly His Ala Ser Val Lys Ala Arg Asp Thr Ile
                85                  90                  95

Leu Phe Gln Trp Val Pro Val Pro Trp Pro His Pro Gly Pro Ile Val
            100                 105                 110

Asp Tyr Leu Ala Asn Cys Asn Gly Asp Cys Glu Thr Val Asp Lys Thr
        115                 120                 125
```

-continued

```
Thr Leu Glu Phe Phe Lys Ile Asp Gly Val Gly Leu Leu Ser Gly Gly
    130                 135                 140

Asp Pro Gly Thr Trp Ala Ser Asp Val Leu Ile Ser Asn Asn Asn Thr
145                 150                 155                 160

Trp Val Val Lys Ile Pro Asp Asn Leu Ala Pro Gly Asn Tyr Val Leu
                165                 170                 175

Arg His Glu Ile Ile Ala Leu His Ser Ala Gly Gln Ala Asn Gly Ala
                180                 185                 190

Gln Asn Tyr Pro Gln Cys Phe Asn Ile Ala Val Ser Gly Ser Gly Ser
            195                 200                 205

Leu Gln Pro Ser Gly Val Leu Gly Thr Asp Leu Tyr His Ala Thr Asp
    210                 215                 220

Pro Gly Val Pro Ile Asn Ile Tyr Thr Ser Pro Leu Asn Tyr Ile Ile
225                 230                 235                 240

Pro Gly Pro Thr Val Val Ser Gly Leu Pro Thr Ser Val Ala Gln Gly
                245                 250                 255

Ser Ser Ala Ala Thr Ala Thr Ala Ser Ala Thr Ala Pro Gly Gly Gly
                260                 265                 270

Ser Gly Pro Thr Ser Arg Thr Thr Thr Ala Arg Thr Thr Gln Ala
    275                 280                 285

Ser Ser Arg Pro Ser Ser Thr Pro Pro Ala Thr Thr Ser Ala Pro Ala
290                 295                 300

Gly Gly Pro Thr Gln Thr Leu Tyr Gly Gln Cys Gly Gly Ser Gly Tyr
305                 310                 315                 320

Ser Gly Pro Thr Arg Cys Ala Pro Pro Ala Thr Cys Ser Thr Leu Asn
                325                 330                 335

Pro Tyr Tyr Ala Gln Cys Leu Asn
            340

<210> SEQ ID NO 5
<211> LENGTH: 346
<212> TYPE: PRT
<213> ORGANISM: Trichoderma saturnisporum
<220> FEATURE:
<221> NAME/KEY: misc_feature
<222> LOCATION: (1)..(346)
<223> OTHER INFORMATION: Type IV endoglucanase Trichoderma saturnisporum

<400> SEQUENCE: 5

Met Ile Gln Lys Leu Ser Asn Leu Leu Val Ala Ala Leu Thr Val Ala
1               5                   10                  15

Thr Gly Val Val Gly His Gly His Ile Asn Asn Ile Val Ile Asn Gly
                20                  25                  30

Val Tyr Tyr Gln Ala Tyr Asp Pro Thr Ser Phe Pro Tyr Glu Ser Asn
            35                  40                  45

Pro Pro Ile Val Val Gly Trp Thr Ala Ala Asp Leu Asp Asn Gly Phe
50                  55                  60

Val Ser Pro Asp Ala Tyr Gly Ser Pro Asp Ile Ile Cys His Lys Asn
65                  70                  75                  80

Ala Thr Asn Ala Lys Gly His Ala Ser Val Arg Ala Gly Asp Thr Val
                85                  90                  95

Leu Phe Gln Trp Val Pro Leu Pro Trp Pro His Pro Gly Pro Ile Val
            100                 105                 110

Asp Tyr Leu Ala Asn Cys Asn Gly Asp Cys Glu Thr Val Asp Lys Thr
        115                 120                 125
```

```
Ser Leu Glu Phe Phe Lys Ile Asp Gly Val Gly Leu Ile Ser Gly Gly
        130                 135                 140

Asp Pro Gly Asn Trp Ala Ser Asp Val Leu Ile Ala Asn Asn Asn Thr
145                 150                 155                 160

Trp Val Val Lys Ile Pro Asp Asp Leu Ala Pro Gly Asn Tyr Val Leu
                165                 170                 175

Arg His Glu Ile Ile Ala Leu His Ser Ala Gly Gln Ala Asn Gly Ala
                180                 185                 190

Gln Asn Tyr Pro Gln Cys Phe Asn Leu Ala Val Ser Gly Ser Gly Ser
            195                 200                 205

Leu Lys Pro Ser Gly Val Lys Gly Thr Ala Leu Tyr His Ala Thr Asp
210                 215                 220

Pro Gly Val Leu Ile Asn Ile Tyr Thr Ser Pro Leu Asn Tyr Ile Ile
225                 230                 235                 240

Pro Gly Pro Thr Val Val Ser Gly Leu Pro Thr Ser Val Ala Gln Arg
                245                 250                 255

Ser Ser Ala Ala Thr Ala Thr Ala Ser Ala Thr Leu Pro Gly Gly Gly
                260                 265                 270

Gly Ser Pro Pro Gly Gly Pro Thr Ser Arg Pro Thr Thr Thr Ala Arg
            275                 280                 285

Ser Thr Ser Gln Ala Ser Ser Arg Pro Ser Pro Ala Thr Thr Ser
290                 295                 300

Ala Pro Ala Gly Gly Pro Thr Gln Thr Leu Tyr Gly Gln Cys Gly Gly
305                 310                 315                 320

Ser Gly Tyr Ser Gly Pro Thr Arg Cys Ala Pro Pro Ala Thr Val Ser
                325                 330                 335

Thr Leu Asn Pro Tyr Tyr Ala Arg Leu Asn
            340                 345

<210> SEQ ID NO 6
<211> LENGTH: 347
<212> TYPE: PRT
<213> ORGANISM: Hypocrea orientalis
<220> FEATURE:
<221> NAME/KEY: misc_feature
<222> LOCATION: (1)..(347)
<223> OTHER INFORMATION: Endoglucanase IV Hypocrea orientalis

<400> SEQUENCE: 6

Met Ile Gln Lys Leu Ser Asn Leu Leu Thr Ala Leu Ala Val Ala
1               5                   10                  15

Thr Gly Val Val Gly His Gly His Ile Asn Asn Ile Val Val Asn Gly
                20                  25                  30

Val Tyr Tyr Gln Gly Tyr Asp Pro Thr Ser Phe Pro Tyr Glu Ser Asp
            35                  40                  45

Pro Pro Ile Val Val Gly Trp Thr Ala Ala Asp Leu Asp Asn Gly Phe
50                  55                  60

Val Ser Pro Asp Ala Tyr Gln Ser Pro Asp Ile Ile Cys His Lys Asn
65                  70                  75                  80

Ala Thr Asn Ala Lys Gly His Ala Ser Val Lys Ala Gly Asp Thr Ile
                85                  90                  95

Leu Phe Gln Trp Val Pro Val Pro Trp Pro His Pro Gly Pro Ile Val
                100                 105                 110

Asp Tyr Leu Ala Asn Cys Asn Gly Asp Cys Glu Thr Val Asp Lys Thr
            115                 120                 125

Ser Leu Glu Phe Phe Lys Ile Asp Gly Val Gly Leu Ile Ser Gly Gly
```

```
                    130                 135                 140
Asp Pro Gly Asn Trp Ala Ser Asp Val Leu Ile Ala Asn Asn Asn Thr
145                 150                 155                 160

Trp Val Val Lys Ile Pro Glu Asp Leu Ala Pro Gly Asn Tyr Val Leu
                165                 170                 175

Arg His Glu Ile Ile Ala Leu His Ser Ala Gly Gln Ala Asp Gly Ala
                180                 185                 190

Gln Asn Tyr Pro Gln Cys Phe Asn Leu Ala Val Ser Gly Ser Gly Ser
            195                 200                 205

Leu Gln Pro Ser Gly Val Lys Gly Thr Ala Leu Tyr His Ser Asp Asp
        210                 215                 220

Pro Gly Val Leu Ile Asn Ile Tyr Thr Ser Pro Leu Ala Tyr Thr Ile
225                 230                 235                 240

Pro Gly Pro Ser Val Val Ser Gly Leu Pro Thr Ser Val Ala Gln Gly
                245                 250                 255

Ser Ser Ala Ala Thr Ala Thr Ala Ser Ala Thr Val Pro Gly Gly Ser
                260                 265                 270

Gly Pro Gly Asn Pro Thr Ser Lys Thr Thr Thr Thr Ala Arg Thr Thr
            275                 280                 285

Gln Ala Ser Ser Ser Arg Ala Ser Ser Thr Pro Pro Ala Thr Thr Ser
        290                 295                 300

Ala Pro Gly Gly Gly Pro Thr Gln Thr Leu Tyr Gly Gln Cys Gly Gly
305                 310                 315                 320

Ser Gly Tyr Ser Gly Pro Thr Arg Cys Ala Pro Pro Ala Thr Cys Ser
                325                 330                 335

Thr Leu Asn Pro Tyr Tyr Ala Gln Cys Leu Asn
                340                 345

<210> SEQ ID NO 7
<211> LENGTH: 347
<212> TYPE: PRT
<213> ORGANISM: Trichoderma sp.
<220> FEATURE:
<221> NAME/KEY: misc_feature
<222> LOCATION: (1)..(347)
<223> OTHER INFORMATION: Endoglucanase IV Trichoderma sp.

<400> SEQUENCE: 7

Met Ile Gln Lys Leu Ser Asn Leu Leu Leu Thr Ala Leu Ala Val Ala
1               5                   10                  15

Thr Gly Val Val Gly His Gly His Ile Asn Asn Ile Val Val Asn Gly
                20                  25                  30

Val Tyr Tyr Gln Gly Tyr Asp Pro Thr Ser Phe Pro Tyr Glu Ser Asp
            35                  40                  45

Pro Pro Ile Val Val Gly Trp Thr Ala Ala Asp Leu Asp Asn Gly Phe
        50                  55                  60

Val Ser Pro Asp Ala Tyr Gln Ser Pro Asp Ile Ile Cys His Lys Asn
65                  70                  75                  80

Ala Thr Asn Ala Lys Gly His Ala Ser Val Lys Ala Gly Asp Thr Ile
                85                  90                  95

Pro Leu Gln Trp Val Pro Val Pro Trp Pro His Pro Gly Pro Ile Val
                100                 105                 110

Asp Tyr Leu Ala Asn Cys Asn Gly Asp Cys Glu Thr Val Asp Lys Thr
            115                 120                 125

Ser Leu Glu Phe Phe Lys Ile Asp Gly Val Gly Leu Ile Ser Gly Gly
        130                 135                 140
```

-continued

Asp Pro Gly Asn Trp Ala Ser Asp Val Leu Ile Ala Asn Asn Asn Thr
145                 150                 155                 160

Trp Val Val Lys Ile Pro Glu Asp Leu Ala Pro Gly Asn Tyr Val Leu
            165                 170                 175

Arg His Glu Ile Ile Ala Leu His Ser Ala Gly Gln Ala Asp Gly Ala
        180                 185                 190

Gln Asn Tyr Pro Gln Cys Phe Asn Leu Ala Val Pro Gly Ser Gly Ser
            195                 200                 205

Leu Gln Pro Ser Gly Val Lys Gly Thr Ala Leu Tyr His Ser Asp Asp
        210                 215                 220

Pro Gly Val Leu Ile Asn Ile Tyr Thr Ser Pro Leu Ala Tyr Thr Ile
225                 230                 235                 240

Pro Gly Pro Ser Val Val Ser Gly Leu Pro Thr Ser Val Ala Gln Gly
            245                 250                 255

Ser Ser Ala Ala Thr Ala Thr Ala Ser Ala Thr Val Pro Gly Gly Ser
        260                 265                 270

Gly Pro Gly Asn Pro Thr Ser Lys Thr Thr Thr Thr Ala Arg Thr Thr
            275                 280                 285

Gln Ala Ser Ser Ser Arg Ala Ser Ser Thr Pro Pro Ala Thr Thr Ser
290                 295                 300

Ala Pro Gly Gly Gly Pro Thr Gln Thr Leu Tyr Gly Gln Cys Gly Gly
305                 310                 315                 320

Ser Gly Tyr Ser Gly Pro Thr Arg Cys Ala Pro Pro Ala Thr Cys Ser
            325                 330                 335

Thr Leu Asn Pro Tyr Tyr Ala Gln Cys Leu Asn
            340                 345

<210> SEQ ID NO 8
<211> LENGTH: 349
<212> TYPE: PRT
<213> ORGANISM: Hypocrea atroviridis
<220> FEATURE:
<221> NAME/KEY: misc_feature
<222> LOCATION: (1)..(349)
<223> OTHER INFORMATION: Glycoside hydrolase family 61 protein

<400> SEQUENCE: 8

Met Ala Gln Lys Leu Ser Asn Leu Phe Ala Ile Ala Leu Thr Val Ala
1               5                   10                  15

Thr Gly Val Val Gly His Gly His Val Asn Asn Ile Val Val Asn Gly
            20                  25                  30

Val Tyr Tyr Gln Gly Tyr Asp Pro Thr Ser Phe Pro Tyr Met Pro Asp
        35                  40                  45

Pro Pro Ile Val Val Gly Trp Thr Ala Ala Asp Thr Asp Asn Gly Phe
50                  55                  60

Val Ser Pro Asp Ala Tyr Gln Thr Pro Asp Ile Val Cys His Lys Asn
65                  70                  75                  80

Gly Thr Asn Ala Lys Gly His Ala Ser Val Lys Ala Gly Asp Ser Val
            85                  90                  95

Leu Phe Gln Trp Val Pro Val Pro Trp Pro His Lys Ser Thr Val Val
        100                 105                 110

Asp Tyr Leu Ala Asn Cys Asn Gly Pro Cys Glu Thr Val Asp Lys Thr
    115                 120                 125

Thr Leu Glu Phe Phe Lys Ile Asp Gly Ile Gly Leu Leu Ser Gly Gly
        130                 135                 140

-continued

Asn Pro Gly Thr Trp Gly Ser Asp Val Leu Ile Gly Asn Asn Asn Thr
145                 150                 155                 160

Trp Val Ile Gln Ile Pro Glu Asp Leu Gln Thr Gly Asn Tyr Val Leu
            165                 170                 175

Arg His Glu Leu Ile Ala Leu His Ser Ala Glu Gln Ala Asp Gly Ala
        180                 185                 190

Gln Asn Tyr Pro Gln Cys Phe Asn Leu Ala Val Thr Gly Thr Gly Ser
    195                 200                 205

Leu Gln Pro Ser Gly Val Leu Ala Thr Asp Leu Tyr His Glu Thr Asp
210                 215                 220

Pro Gly Ile Leu Phe Asn Ile Tyr Thr Ser Pro Leu Thr Tyr Ile Ile
225                 230                 235                 240

Pro Gly Pro Thr Val Val Ser Gly Leu Pro Ser Ser Val Ala Gln Ala
            245                 250                 255

Ser Ser Ala Ala Thr Ala Thr Ser Ser Ala Thr Val Ser Gly Gly Gly
        260                 265                 270

Gly Gly Ser Ser Thr Gly Gly Ser Thr Ser Lys Thr Thr Thr Val Val
    275                 280                 285

Arg Ser Thr Thr Ser Val Thr Ser Lys Ala Ser Ser Thr Ala Val
290                 295                 300

Thr Thr Pro Pro Pro Ala Gly Thr Gln Thr Leu Tyr Gly Gln Cys
305                 310                 315                 320

Gly Gly Ser Gly Tyr Ser Gly Pro Thr Lys Cys Ala Ser Pro Ala Val
            325                 330                 335

Cys Thr Thr Leu Asn Pro Tyr Tyr Ala Gln Cys Leu Asn
            340                 345

<210> SEQ ID NO 9
<211> LENGTH: 347
<212> TYPE: PRT
<213> ORGANISM: Hypocrea virens
<220> FEATURE:
<221> NAME/KEY: misc_feature
<222> LOCATION: (1)..(347)
<223> OTHER INFORMATION: Glycoside hydrolase family 61 protein

<400> SEQUENCE: 9

Met Thr Gln Lys Leu Thr Ser Leu Leu Val Thr Ala Leu Thr Val Ala
1               5                   10                  15

Thr Gly Val Ile Gly His Gly His Val Asn Asn Ile Val Ile Asn Gly
            20                  25                  30

Ala Tyr Tyr Gln Gly Tyr Asp Pro Thr Leu Phe Pro Tyr Glu Pro Asn
        35                  40                  45

Pro Pro Ile Val Val Gly Trp Thr Ala Ser Asp Thr Asp Asn Gly Phe
    50                  55                  60

Val Ala Pro Asp Ala Tyr Gln Ser Pro Asp Ile Ile Cys His Arg Asn
65                  70                  75                  80

Ala Thr Asn Ala Arg Gly His Ala Ser Val Met Ala Gly Ser Ser Val
            85                  90                  95

Leu Ile Gln Trp Val Pro Ile Pro Trp Pro His Pro Gly Pro Val Leu
        100                 105                 110

Asp Tyr Leu Ala Asn Cys Asn Gly Asp Cys Glu Thr Val Asp Lys Thr
    115                 120                 125

Thr Leu Glu Phe Phe Lys Ile Asp Gly Ile Gly Leu Ile Ser Gly Gly
130                 135                 140

Asn Pro Gly Arg Trp Ala Ser Asp Val Leu Ile Gly Asn Asn Gly Thr

```
                145                 150                 155                 160
Trp Val Val Gln Ile Pro Ala Asp Leu Glu Thr Gly Asn Tyr Val Leu
                165                 170                 175
Arg His Glu Leu Ile Ala Leu His Ser Ala Gly Ser Val Asp Gly Ala
                180                 185                 190
Gln Asn Tyr Pro Gln Cys Phe Asn Leu Ala Val Thr Gly Thr Gly Ser
                195                 200                 205
Leu Gln Pro Thr Gly Val Leu Gly Thr Lys Leu Tyr Gln Glu Ser Asp
        210                 215                 220
Pro Gly Ile Leu Phe Asn Ile Tyr Thr Ser Pro Leu Thr Tyr Thr Ile
225                 230                 235                 240
Pro Gly Pro Thr Val Val Ser Gly Leu Pro Ser Ser Val Thr Gln Arg
                245                 250                 255
Ser Ser Thr Ala Thr Ala Thr Ser Ile Ala Thr Val Pro Gly Ser Val
                260                 265                 270
Ser Thr Gly Gly Thr Ser Ser Lys Thr Thr Thr Val Pro Arg Ser Thr
            275                 280                 285
Ser Ser Ala Thr Thr Arg Arg Ser Ser Ser Ser Ala Ile Thr Thr Ser
        290                 295                 300
Ala Pro Ala Gly Pro Ser Gln Thr Leu Tyr Gly Gln Cys Gly Gly Ser
305                 310                 315                 320
Gly Tyr Ser Gly Pro Thr Ile Cys Ala Ser Pro Ala Val Cys Ser Thr
                325                 330                 335
Leu Asn Pro Tyr Tyr Ala Gln Cys Leu Thr Arg
                340                 345

<210> SEQ ID NO 10
<211> LENGTH: 368
<212> TYPE: PRT
<213> ORGANISM: Thielavia terrestris
<220> FEATURE:
<221> NAME/KEY: misc_feature
<222> LOCATION: (1)..(368)
<223> OTHER INFORMATION: Glycoside hydrolase family 61 protein

<400> SEQUENCE: 10

Met Pro Ser Phe Ala Ser Lys Thr Leu Leu Ser Thr Leu Ala Gly Ala
1               5                   10                  15
Ala Ser Val Ala Ala His Gly His Val Ser Asn Ile Val Ile Asn Gly
                20                  25                  30
Val Ser Tyr Gln Gly Tyr Asp Pro Thr Ser Phe Pro Tyr Met Gln Asn
            35                  40                  45
Pro Pro Ile Val Val Gly Trp Thr Ala Ala Asp Thr Asp Asn Gly Phe
        50                  55                  60
Val Ala Pro Asp Ala Phe Ala Ser Gly Asp Ile Ile Cys His Lys Asn
65                  70                  75                  80
Ala Thr Asn Ala Lys Gly His Ala Val Val Ala Gly Asp Lys Ile
                85                  90                  95
Phe Ile Gln Trp Asn Thr Trp Pro Glu Ser His His Gly Pro Val Ile
            100                 105                 110
Asp Tyr Leu Ala Ser Cys Gly Ser Ala Ser Cys Glu Thr Val Asp Lys
        115                 120                 125
Thr Lys Leu Glu Phe Phe Lys Ile Asp Glu Val Gly Leu Val Asp Gly
    130                 135                 140
Ser Ser Ala Pro Gly Val Trp Gly Ser Asp Gln Leu Ile Ala Asn Asn
145                 150                 155                 160
```

```
Asn Ser Trp Leu Val Glu Ile Pro Pro Thr Ile Ala Pro Gly Asn Tyr
            165                 170                 175

Val Leu Arg His Glu Ile Ile Ala Leu His Ser Ala Glu Asn Ala Asp
        180                 185                 190

Gly Ala Gln Asn Tyr Pro Gln Cys Phe Asn Leu Gln Ile Thr Gly Thr
    195                 200                 205

Gly Thr Ala Thr Pro Ser Gly Val Pro Gly Thr Ser Leu Tyr Thr Pro
210                 215                 220

Thr Asp Pro Gly Ile Leu Val Asn Ile Tyr Ser Ala Pro Ile Thr Tyr
225                 230                 235                 240

Thr Val Pro Gly Pro Ala Leu Ile Ser Gly Ala Val Ser Ile Ala Gln
            245                 250                 255

Ser Ser Ser Ala Ile Thr Ala Ser Gly Thr Ala Leu Thr Gly Ser Ala
            260                 265                 270

Thr Ala Pro Ala Ala Ala Ala Thr Thr Ser Thr Thr Asn Ala
            275                 280                 285

Ala Ala Ala Thr Ser Ala Ala Ala Ala Gly Thr Ser Thr Thr
    290                 295                 300

Thr Thr Ser Ala Ala Ala Val Val Gln Thr Ser Ser Ser Ser Ser Ser
305                 310                 315                 320

Ala Pro Ser Ser Ala Ala Ala Ala Thr Thr Thr Ala Ala Ala Ser
            325                 330                 335

Ala Arg Pro Thr Gly Cys Ser Ser Gly Arg Ser Arg Lys Gln Pro Arg
            340                 345                 350

Arg His Ala Arg Asp Met Val Val Ala Arg Gly Ala Glu Glu Ala Asn
    355                 360                 365

<210> SEQ ID NO 11
<211> LENGTH: 354
<212> TYPE: PRT
<213> ORGANISM: Neurospora tetrasperma
<220> FEATURE:
<221> NAME/KEY: misc_feature
<222> LOCATION: (1)..(354)
<223> OTHER INFORMATION: Endoglucanase IV

<400> SEQUENCE: 11

Met Ala Arg Lys Ser Ile Leu Thr Ala Leu Ala Gly Ala Ser Leu Val
1               5                   10                  15

Ala Ala His Gly His Val Ser Lys Val Ile Val Asn Gly Val Glu Tyr
            20                  25                  30

Gln Asn Tyr Asp Pro Thr Ser Phe Pro Tyr Asn Ser Asn Pro Pro Thr
        35                  40                  45

Val Ile Gly Trp Thr Ile Asp Gln Lys Asp Asn Gly Phe Val Ser Pro
    50                  55                  60

Asp Ala Phe Asp Ser Gly Asp Ile Ile Cys His Lys Ser Ala Thr Pro
65                  70                  75                  80

Ala Gly Gly His Ala Thr Val Lys Ala Gly Asp Lys Ile Ser Leu Gln
                85                  90                  95

Trp Asp Gln Trp Pro Glu Ser His Lys Gly Pro Val Ile Asp Tyr Leu
            100                 105                 110

Ala Ala Cys Asp Gly Asp Cys Glu Ser Val Asp Lys Thr Ala Leu Lys
        115                 120                 125

Phe Phe Lys Ile Asp Gly Ala Gly Tyr Asp Ala Thr Asn Gly Trp Ala
    130                 135                 140
```

-continued

```
Ser Asp Val Leu Ile Lys Asp Gly Asn Ser Trp Val Glu Ile Pro
145                 150                 155                 160

Glu Asn Ile Lys Pro Gly Asn Tyr Val Leu Arg His Glu Ile Ala
            165                 170                 175

Leu His Ser Ala Gly Gln Ala Asn Gly Ala Gln Asn Tyr Pro Gln Cys
                180                 185                 190

Phe Asn Leu Lys Val Glu Gly Ser Gly Ser Thr Val Pro Ala Gly Val
            195                 200                 205

Ala Gly Thr Glu Leu Tyr Lys Ala Thr Asp Ala Gly Ile Leu Phe Asp
        210                 215                 220

Ile Tyr Lys Asn Asp Ile Ser Tyr Pro Val Pro Gly Pro Ser Leu Ile
225                 230                 235                 240

Ala Gly Ala Ser Ser Ile Ala Gln Ser Lys Met Ala Ala Thr Ala
            245                 250                 255

Thr Ala Ser Ala Thr Leu Pro Gly Ala Thr Gly Ser Asn Ser Pro
            260                 265                 270

Ala Thr Ser Ala Ala Ala Ala Pro Ala Pro Ser Thr Thr Leu Val
            275                 280                 285

Thr Ser Thr Lys Ala Ala Ala Pro Ala Thr Ser Ala Ala Pro Ala Ala
290                 295                 300

Pro Ala Thr Ser Ala Ala Gly Ser Gly Gln Val Gln Ala Lys Gln
305                 310                 315                 320

Thr Lys Trp Gly Gln Cys Gly Gly Asn Gly Tyr Thr Gly Ala Thr Glu
            325                 330                 335

Cys Glu Ser Gly Ser Thr Cys Thr Lys Tyr Asn Asp Trp Tyr Ser Gln
            340                 345                 350

Cys Val

<210> SEQ ID NO 12
<211> LENGTH: 354
<212> TYPE: PRT
<213> ORGANISM: Neurospora tetrasperma
<220> FEATURE:
<221> NAME/KEY: misc_feature
<222> LOCATION: (1)..(354)
<223> OTHER INFORMATION: full length protein

<400> SEQUENCE: 12

Met Ala Arg Lys Ser Ile Leu Thr Ala Leu Ala Gly Ala Ser Leu Val
1               5                   10                  15

Ala Ala His Gly His Val Ser Lys Val Ile Val Asn Gly Val Glu Tyr
            20                  25                  30

Gln Asn Tyr Asp Pro Thr Ser Phe Pro Tyr Asn Ser Asn Pro Pro Thr
        35                  40                  45

Val Ile Gly Trp Thr Ile Asp Gln Lys Asp Asn Gly Phe Val Ser Pro
    50                  55                  60

Asp Ala Phe Asp Ser Gly Asp Ile Ile Cys His Lys Ser Ala Thr Pro
65                  70                  75                  80

Ala Gly Gly His Ala Thr Val Lys Ala Gly Asp Lys Ile Ser Leu Gln
            85                  90                  95

Trp Asp Gln Trp Pro Glu Ser His Lys Gly Pro Val Ile Asp Tyr Leu
        100                 105                 110

Ala Ala Cys Asp Gly Asp Cys Glu Ser Val Asp Lys Thr Ala Leu Lys
    115                 120                 125

Phe Phe Lys Ile Asp Gly Ala Gly Tyr Asp Ala Thr Asn Gly Trp Ala
130                 135                 140
```

Ser Asp Val Leu Ile Lys Asp Gly Asn Ser Trp Val Glu Ile Pro
145                 150                 155                 160

Glu Asn Ile Lys Pro Gly Asn Tyr Val Leu Arg His Glu Ile Ile Ala
                165                 170                 175

Leu His Ser Ala Gly Gln Ala Asn Gly Ala Gln Asn Tyr Pro Gln Cys
            180                 185                 190

Phe Asn Leu Lys Val Glu Gly Ser Gly Ser Thr Val Pro Ala Gly Val
        195                 200                 205

Ala Gly Thr Glu Leu Tyr Lys Ala Thr Asp Ala Gly Ile Leu Phe Asp
    210                 215                 220

Ile Tyr Lys Asn Asp Ile Ser Tyr Pro Val Pro Gly Pro Ser Leu Ile
225                 230                 235                 240

Ala Gly Ala Ser Ser Ile Ala Gln Ser Lys Met Ala Ala Thr Ala
                245                 250                 255

Thr Ala Ser Ala Thr Leu Pro Gly Ala Thr Gly Gly Ser Asn Ser Pro
            260                 265                 270

Ala Thr Ser Ala Ala Ala Ala Pro Ala Pro Ser Thr Thr Leu Val
        275                 280                 285

Thr Ser Thr Lys Ala Ala Ala Pro Ala Thr Ser Ala Ala Pro Ala Ala
    290                 295                 300

Pro Ala Thr Ser Ala Ala Ala Gly Ser Gly Gln Val Gln Ala Lys Gln
305                 310                 315                 320

Thr Lys Trp Gly Gln Cys Gly Gly Asn Gly Tyr Thr Gly Ala Thr Glu
                325                 330                 335

Cys Glu Ser Gly Ser Thr Cys Thr Lys Tyr Asn Asp Trp Tyr Ser Gln
            340                 345                 350

Cys Val

<210> SEQ ID NO 13
<211> LENGTH: 340
<212> TYPE: PRT
<213> ORGANISM: Thielavia heterothallica
<220> FEATURE:
<221> NAME/KEY: misc_feature
<222> LOCATION: (1)..(340)
<223> OTHER INFORMATION: Glycoside hydrolase family 61 protein

<400> SEQUENCE: 13

Met Ser Ser Phe Thr Ser Lys Gly Leu Leu Ser Ala Leu Met Gly Ala
1               5                   10                  15

Ala Thr Val Ala Ala His Gly Val Thr Asn Ile Val Ile Asn Gly
            20                  25                  30

Val Ser Tyr Gln Asn Phe Asp Pro Phe Thr His Pro Tyr Met Gln Asn
        35                  40                  45

Pro Pro Thr Val Val Gly Trp Thr Ala Ser Asn Thr Asp Asn Gly Phe
    50                  55                  60

Val Gly Pro Glu Ser Phe Ser Pro Asp Ile Ile Cys His Lys Ser
65                  70                  75                  80

Ala Thr Asn Ala Gly Gly His Ala Val Val Ala Ala Gly Asp Lys Val
                85                  90                  95

Phe Ile Gln Trp Asp Thr Trp Pro Glu Ser His His Gly Pro Val Ile
            100                 105                 110

Asp Tyr Leu Ala Asp Cys Gly Asp Ala Gly Cys Glu Lys Val Asp Lys
        115                 120                 125

Thr Thr Leu Lys Phe Phe Lys Ile Ser Glu Ser Gly Leu Leu Asp Gly

```
                130                 135                 140
Thr Asn Ala Pro Gly Lys Trp Ala Ser Asp Thr Leu Ile Ala Asn Asn
145                 150                 155                 160

Asn Ser Trp Leu Val Gln Ile Pro Asn Ile Ala Pro Gly Asn Tyr
                165                 170                 175

Val Leu Arg His Glu Ile Ile Ala Leu His Ser Ala Gly Gln Gln Asn
                180                 185                 190

Gly Ala Gln Asn Tyr Pro Gln Cys Phe Asn Leu Gln Val Thr Gly Ser
            195                 200                 205

Gly Thr Gln Lys Pro Ser Gly Val Leu Gly Thr Glu Leu Tyr Lys Ala
        210                 215                 220

Thr Asp Ala Gly Ile Leu Ala Asn Ile Tyr Thr Ser Pro Val Thr Tyr
225                 230                 235                 240

Gln Ile Pro Gly Pro Ala Ile Ile Ser Gly Ala Ser Ala Val Gln Gln
                245                 250                 255

Thr Thr Ser Ala Ile Thr Ala Ser Ala Ser Ala Ile Thr Gly Ser Ala
                260                 265                 270

Thr Ala Ala Pro Thr Ala Ala Thr Thr Thr Ala Ala Ala Ala Thr
            275                 280                 285

Thr Thr Thr Thr Ala Gly Ser Arg Cys Tyr Arg His Ala Leu Asp Arg
        290                 295                 300

Arg Leu Ser Phe Phe Arg Pro Ala Cys Ser Tyr His Arg Cys Arg Tyr
305                 310                 315                 320

Leu Gln Pro Cys Ser Pro Asp Pro Leu Arg Trp Ser Glu Glu Ala Pro
                325                 330                 335

Ser Pro Arg Pro
            340

<210> SEQ ID NO 14
<211> LENGTH: 369
<212> TYPE: PRT
<213> ORGANISM: Neurospora crassa
<220> FEATURE:
<221> NAME/KEY: misc_feature
<222> LOCATION: (1)..(369)
<223> OTHER INFORMATION: Endoglucanase IV

<400> SEQUENCE: 14

Met Ala Arg Met Ser Ile Leu Thr Ala Leu Ala Gly Ala Ser Leu Val
1               5                   10                  15

Ala Ala His Gly His Val Ser Lys Val Ile Val Asn Gly Val Glu Tyr
                20                  25                  30

Gln Asn Tyr Asp Pro Thr Ser Phe Pro Tyr Asn Ser Asn Pro Pro Thr
            35                  40                  45

Val Ile Gly Trp Thr Ile Asp Gln Lys Asp Asn Gly Phe Val Ser Pro
        50                  55                  60

Asp Ala Phe Asp Ser Gly Asp Ile Ile Cys His Lys Ser Ala Lys Pro
65                  70                  75                  80

Ala Gly Gly His Ala Thr Val Lys Ala Gly Asp Lys Ile Ser Leu Gln
                85                  90                  95

Trp Asp Gln Trp Pro Glu Ser His Lys Gly Pro Val Ile Asp Tyr Leu
            100                 105                 110

Ala Ala Cys Asp Gly Asp Cys Glu Ser Val Asp Lys Thr Ala Leu Lys
        115                 120                 125

Phe Phe Lys Ile Asp Gly Ala Gly Tyr Asp Ala Thr Asn Gly Trp Ala
    130                 135                 140
```

```
Ser Asp Thr Leu Ile Lys Asp Gly Asn Ser Trp Val Val Glu Ile Pro
145                 150                 155                 160

Glu Ser Ile Lys Pro Gly Asn Tyr Val Leu Arg His Glu Ile Ile Ala
            165                 170                 175

Leu His Ser Ala Gly Gln Ala Asn Gly Ala Gln Asn Tyr Pro Gln Cys
            180                 185                 190

Phe Asn Leu Lys Val Glu Gly Ser Gly Ser Thr Val Pro Ala Gly Val
        195                 200                 205

Ala Gly Thr Glu Leu Tyr Lys Ala Thr Asp Ala Gly Ile Leu Phe Asp
    210                 215                 220

Ile Tyr Lys Asn Asp Ile Ser Tyr Pro Val Pro Gly Pro Ser Leu Ile
225                 230                 235                 240

Ala Gly Ala Ser Ser Ile Ala Gln Ser Lys Met Ala Ala Thr Ala
            245                 250                 255

Thr Ala Ser Ala Thr Leu Pro Gly Ala Thr Gly Gly Ser Asn Ser Pro
            260                 265                 270

Ala Thr Ser Ala Ala Ala Ala Pro Ala Thr Ser Ala Ala Ala Ala
            275                 280                 285

Thr Ser Gln Val Gln Ala Ala Pro Ala Thr Thr Leu Val Thr Ser Thr
            290                 295                 300

Lys Ala Ala Ala Pro Ala Thr Ser Ala Ala Ala Pro Ala Ala Pro Ala
305                 310                 315                 320

Thr Ser Ala Ala Ala Gly Gly Ala Gly Gln Val Gln Ala Lys Gln Thr
            325                 330                 335

Lys Trp Gly Gln Cys Gly Gly Asn Gly Phe Thr Gly Pro Thr Glu Cys
            340                 345                 350

Glu Ser Gly Ser Thr Cys Thr Lys Tyr Asn Asp Trp Tyr Ser Gln Cys
            355                 360                 365

Val
```

<210> SEQ ID NO 15
<211> LENGTH: 348
<212> TYPE: PRT
<213> ORGANISM: Sordaria macrospora
<220> FEATURE:
<221> NAME/KEY: misc_feature
<222> LOCATION: (1)..(348)
<223> OTHER INFORMATION: full length protein

<400> SEQUENCE: 15

```
Met Ala Arg Lys Ser Ile Ile Thr Ala Leu Ala Gly Ala Ser Leu Val
1               5                   10                  15

Ala Ala His Gly His Val Ser Lys Val Ile Val Asn Gly Val Glu Tyr
            20                  25                  30

Gln Asn Tyr Asp Pro Ala Val Phe Pro Tyr Leu Ser Asn Pro Pro Thr
        35                  40                  45

Val Ile Gly Trp Thr Ala Asp Gln Lys Asp Asn Gly Phe Val Ser Pro
    50                  55                  60

Asp Ala Phe Gly Thr Pro Asp Ile Ile Cys His Arg Ser Ala Thr Pro
65                  70                  75                  80

Ala Gly Gly His Ala Thr Val Lys Ala Gly Asp Lys Ile Ser Leu Lys
                85                  90                  95

Trp Asp Pro Val Trp Pro Asp Ser His Lys Gly Pro Val Ile Asp Tyr
            100                 105                 110

Leu Ala Ala Cys Asn Gly Asp Cys Glu Thr Val Asp Lys Thr Ser Leu
```

```
            115                 120                 125
Arg Phe Phe Lys Ile Asp Gly Ala Gly Tyr Asn Asn Gly Val Trp Ala
        130                 135                 140

Ala Asp Ala Leu Val Asn Asn Gly Asn Ser Trp Leu Val Gln Ile Pro
145                 150                 155                 160

Ala Asp Leu Lys Pro Gly Asn Tyr Val Leu Arg His Glu Ile Ile Ala
                165                 170                 175

Leu His Gly Ala Gly Ser Ala Asn Gly Ala Gln Ala Tyr Pro Gln Cys
            180                 185                 190

Phe Asn Leu Lys Val Glu Gly Ser Gly Asn Asn Leu Pro Ser Gly Val
        195                 200                 205

Pro Leu Tyr Lys Ala Thr Asp Ala Gly Ile Leu Phe Asn Met Tyr Gln
210                 215                 220

Asn Asp Phe Thr Tyr Pro Val Pro Gly Pro Ala Leu Ile Ala Gly Ala
225                 230                 235                 240

Val Ser Ser Ile Pro Gln Ser Ser Ser Ala Ala Thr Ala Thr Ala Ser
                245                 250                 255

Ala Thr Val Pro Gly Gly Gly Ser Gly Gly Ser Pro Val Thr Thr
            260                 265                 270

Thr Ala Ala Gly Ala Thr Thr Thr Lys Ala Thr Thr Thr Leu Val Thr
            275                 280                 285

Ser Thr Lys Ala Thr Thr Ser Asp Ala Gln Val Thr Thr Thr Ala Pro
290                 295                 300

Pro Ala Thr Gly Gly Gly Gly Ala Ala Gln Lys Tyr Gly Gln Cys
305                 310                 315                 320

Gly Gly Asn Gly Trp Thr Gly Pro Thr Thr Cys Val Ser Gly Ser Val
                325                 330                 335

Cys Thr Lys Val Asn Asp Trp Tyr Ser Gln Cys Leu
                340                 345

<210> SEQ ID NO 16
<211> LENGTH: 359
<212> TYPE: PRT
<213> ORGANISM: Gaeumannomyces graminis var. tritici
<220> FEATURE:
<221> NAME/KEY: misc_feature
<222> LOCATION: (1)..(359)
<223> OTHER INFORMATION: Endoglucanase IV

<400> SEQUENCE: 16

Met Gly Phe Lys Ser Arg Ala Leu Val Ser Ala Leu Gly Ser Ala Ala
1               5                   10                  15

Thr Val Leu Ala His Gly His Val Ser Asn Ile Val Asn Gly Val
                20                  25                  30

Phe Tyr Pro Gly Tyr Asp Val Thr Lys Tyr Pro Trp Gln Pro Asn Ala
            35                  40                  45

Pro Thr Val Val Gly Trp Ser Ala Thr Asn Thr Asp Asn Gly Phe Val
        50                  55                  60

Glu Pro Asn Asn Phe Gly His Pro Asp Ile Ile Cys His Arg Gly Ala
65                  70                  75                  80

Gln Pro Ala Lys Gly His Ala Arg Val Arg Ala Gly Asp Lys Ile Leu
                85                  90                  95

Leu Gln Trp Asp Thr Trp Pro Glu Ser His Lys Gly Pro Val Leu Asp
            100                 105                 110

Tyr Leu Ala Arg Cys Pro Gly Asp Cys Glu Thr Val Asp Lys Thr Ala
        115                 120                 125
```

```
Leu Arg Phe Phe Lys Ile Gly Glu Gly Ser Tyr Ile Ser Gly Ala Ala
        130                 135                 140

Pro Gly His Trp Ala Ala Asp Val Leu Leu Gly Asn Gly Phe Ser Trp
145                 150                 155                 160

Val Val Gln Ile Pro Glu Asp Val Ala Pro Gly Asn Tyr Val Leu Arg
                165                 170                 175

His Glu Ile Ile Ala Leu His Gly Ser Pro Asn Pro Asn Gly Ala Gln
            180                 185                 190

Ala Tyr Pro Gln Cys Phe Asn Leu Glu Ile Ser Gly Ser Gly Ser Arg
        195                 200                 205

Gln Pro Ala Gly Val Ala Gly Thr Ser Leu Tyr Arg Ala Gly Asp Pro
210                 215                 220

Gly Ile His Phe Pro Leu Tyr Asn Ser Pro Ile Val Tyr Pro Val Pro
225                 230                 235                 240

Gly Pro Ala Leu Ile Pro Gly Val Pro Ser Thr Val Ala Gln Val Ser
                245                 250                 255

Thr Arg Ala Thr Ala Thr Ser Ser Pro Phe Leu Pro Gly Gly Gly Gly
            260                 265                 270

Gly Gly Gly Gly Gly Gly Gly Gly Asn Pro Gly Pro Thr Ser Ala
        275                 280                 285

Pro Gly Gly Gly Asn Gly Gly Gly Gly Gly Gln Gln Pro Pro Gln
290                 295                 300

Thr Thr Thr Ala Pro Gly Asn Gly Gly Gly Gly Gly Gly Gly Gly
305                 310                 315                 320

Gly Gly Gly Gly Gly Gln Thr Arg Trp Gly Gln Cys Gly Gly Ser Gly
                325                 330                 335

Trp Asn Gly Pro Thr Ala Cys Ala Gln Gly Ala Cys Ser Thr Leu Asn
                340                 345                 350

Pro Tyr Tyr Ala Gln Cys Val
        355

<210> SEQ ID NO 17
<211> LENGTH: 276
<212> TYPE: PRT
<213> ORGANISM: Nectria haematococca
<220> FEATURE:
<221> NAME/KEY: misc_feature
<222> LOCATION: (1)..(276)
<223> OTHER INFORMATION: full length protein

<400> SEQUENCE: 17

Met Thr Phe Phe Thr Ala Met Ser Thr Leu Cys Ala Ser Ala Trp Leu
1               5                   10                  15

Tyr Leu Leu Phe Ser Ala Val Ser Val Ser Ala His Gly His Val Thr
                20                  25                  30

Gln Val Ile Ile Asn Gly Val Ala Tyr Gly Gly Tyr Leu Ser Thr Ser
            35                  40                  45

Phe Pro Leu Gln Arg Lys Pro Pro Val Val Leu Gly Trp Thr Ile Glu
        50                  55                  60

Gln Arg Asp Asn Gly Phe Val Ser Pro Asp Lys Tyr Asp His Pro Asp
65                  70                  75                  80

Ile Ile Cys His Arg Asp Ala Thr Pro Ala Gln Gly His Val Gln Val
                85                  90                  95

Ala Ala Gly Asp Thr Ile Thr Ile Lys Trp Ser Ser Trp Pro Glu Asn
            100                 105                 110
```

His Arg Gly Pro Val Met Asp Tyr Leu Ala Asn Cys Asn Gly Pro Cys
            115                 120                 125

Glu Thr Val Asp Lys Thr Lys Leu Glu Phe Phe Lys Ile Asp Gly Met
    130                 135                 140

Gly Leu Ile Ser Gln Asp Arg Pro Gly Lys Tyr Ala Asp Gly Ala Leu
145                 150                 155                 160

Arg Glu Asn Gly Tyr Thr Trp Ser Val Arg Ile Pro Ser Asn Ile Ala
                165                 170                 175

Pro Gly Asn Tyr Val Leu Arg His Glu Ile Ile Ala Leu His Ser Gly
            180                 185                 190

Leu Glu Arg Asn Gly Ala Gln Asn Tyr Pro Gln Cys Phe Asn Leu Lys
        195                 200                 205

Ile Thr Gly Ser Gly Ser Asp Asn Pro Pro Gly Tyr Leu Gly Thr Glu
    210                 215                 220

Leu Tyr Asp Ala Asn Asp Pro Gly Ile Leu Val Asn Ile Tyr Gly Asn
225                 230                 235                 240

Leu Pro Asn Tyr Gln Val Pro Gly Pro Thr Ile Val Ser Gly Gly Val
                245                 250                 255

Ser Ser Val Arg Gln Ser Pro Ser Arg Ala Thr Thr Thr Ala Lys Cys
            260                 265                 270

Thr Thr Arg Ser
        275

<210> SEQ ID NO 18
<211> LENGTH: 275
<212> TYPE: PRT
<213> ORGANISM: Fusarium pseudograminearum
<220> FEATURE:
<221> NAME/KEY: misc_feature
<222> LOCATION: (1)..(275)
<223> OTHER INFORMATION: full length protein

<400> SEQUENCE: 18

Met Thr Phe Gln Ser Val His Ser Ser Lys Ala Ser Phe Trp Leu Thr
1               5                   10                  15

Leu Phe Leu Pro Ala Leu Gly Ile Ser Ala His Gly His Val Asp Glu
            20                  25                  30

Ile Ile Val Asn Gly Val Ser Tyr Gln Gly Tyr Gly Ser Thr Asp Phe
        35                  40                  45

Pro Tyr Met Gln Asp Pro Pro Val Val Ala Gly Trp Thr Ile Glu Gln
50                  55                  60

Ala Asp Asn Gly Phe Val Ser Pro Asp Lys Tyr Asp Pro Asp Ile
65                  70                  75                  80

Ile Cys His Arg Asp Ala Thr Pro Ala Lys Gly His Ile Glu Leu Ala
                85                  90                  95

Ala Gly Asp Thr Leu Thr Leu Arg Trp Ser Gly Trp Pro Glu Asn His
            100                 105                 110

Ser Gly Pro Ile Leu Asn Tyr Leu Ala Asn Cys Asn Gly Pro Cys Glu
        115                 120                 125

Arg Val Asp Lys Thr Lys Leu Glu Phe Phe Lys Ile Asp Gly Leu Gly
    130                 135                 140

Leu Leu Glu Gln Gly Thr Pro Gly Arg Tyr Ala Asp Lys Val Leu Gln
145                 150                 155                 160

Asp Asn Gly Asp Arg Trp Asn Val Arg Ile Pro Lys Asn Ile Ala Pro
                165                 170                 175

Gly Asn Tyr Val Leu Arg His Glu Ile Ile Ala Leu His Asn Ala Leu

```
            180                 185                 190
Asp Lys Gly Gly Ala Gln Asn Tyr Pro Gln Cys Phe Asn Leu Lys Ile
            195                 200                 205

Thr Gly Asp Gly Ser Asp Ser Pro Ser Gly Tyr Leu Gly Thr Glu Leu
            210                 215                 220

Tyr Asp Ala Ala Asp Pro Gly Ile Leu Val Asn Val Tyr Ser Ser Ser
225                 230                 235                 240

Val Asp Tyr Glu Val Pro Gly Pro Thr Ile Cys Glu Gly Gly Val Ser
                245                 250                 255

Ser Val Glu Gln Lys Pro Ser Glu Ala Thr Thr Thr Ala Lys Cys Thr
            260                 265                 270

Thr Arg Tyr
        275

<210> SEQ ID NO 19
<211> LENGTH: 275
<212> TYPE: PRT
<213> ORGANISM: Gibberella zeae
<220> FEATURE:
<221> NAME/KEY: misc_feature
<222> LOCATION: (1)..(275)
<223> OTHER INFORMATION: full length protein

<400> SEQUENCE: 19

Met Ala Phe Gln Ser Ile Asn Ser Ser Lys Ala Ser Phe Trp Leu Thr
1               5                   10                  15

Leu Leu Leu Pro Ala Leu Gly Ile Ser Ala His Gly His Val Asp Glu
            20                  25                  30

Ile Ile Val Asn Gly Val Ser Tyr Gln Gly Tyr Gly Ser Thr Asp Phe
            35                  40                  45

Pro Tyr Met Gln Asp Pro Val Val Ala Gly Trp Thr Ile Glu Gln
        50                  55                  60

Ala Asp Asn Gly Phe Val Ser Pro Asp Lys Tyr Asp Pro Asp Ile
65                  70                  75                  80

Ile Cys His Arg Asp Ala Thr Pro Ala Lys Gly His Ile Glu Leu Ala
                85                  90                  95

Ala Gly Asp Thr Leu Thr Leu Arg Trp Ser Gly Trp Pro Glu Asn His
            100                 105                 110

Ser Gly Pro Ile Leu Asn Tyr Leu Ala Asn Cys Asn Gly Pro Cys Glu
            115                 120                 125

Arg Val Asp Lys Thr Lys Leu Glu Phe Phe Lys Ile Asp Gly Leu Gly
            130                 135                 140

Leu Leu Glu Gln Gly Thr Pro Gly Arg Tyr Ala Asp Lys Val Leu Gln
145                 150                 155                 160

Asp Asn Gly Asp Arg Trp Asn Val Arg Ile Pro Lys Asn Ile Ala Pro
                165                 170                 175

Gly Asn Tyr Val Leu Arg His Glu Ile Ile Ala Leu His Asn Ala Leu
            180                 185                 190

Asp Lys Gly Gly Ala Gln Asn Tyr Pro Gln Cys Phe Asn Leu Lys Ile
            195                 200                 205

Thr Gly Asp Gly Ser Asp Ser Pro Ser Gly Tyr Leu Gly Thr Glu Leu
            210                 215                 220

Tyr Asp Ala Ala Asp Pro Gly Ile Leu Val Asn Val Tyr Ser Ser Ser
225                 230                 235                 240

Val Asp Tyr Glu Val Pro Gly Pro Thr Ile Cys Glu Gly Gly Val Ser
                245                 250                 255
```

```
Ser Val Glu Gln Lys Pro Ser Glu Ala Thr Thr Thr Ala Lys Cys Thr
            260                 265                 270

Thr Arg Tyr
        275

<210> SEQ ID NO 20
<211> LENGTH: 504
<212> TYPE: PRT
<213> ORGANISM: Thielavia terrestris
<220> FEATURE:
<221> NAME/KEY: misc_feature
<222> LOCATION: (1)..(504)
<223> OTHER INFORMATION: Glycoside hydrolase family 28 protein

<400> SEQUENCE: 20

Met Lys Tyr Arg Pro Ser Leu Ser Leu Ala Ala Ala Leu Phe Leu
1               5                   10                  15

Leu Glu Pro Trp Val Gln Ala Gln Leu Ser Gly Ser Val Gly Pro Thr
                20                  25                  30

Thr Ser Arg Ala Ala Lys Ala Ala Lys Lys Val Cys Asn Ile Met Asn
            35                  40                  45

Tyr Gly Gly Val Ala Ser Ala Thr Thr Asp Asn Ser Ala Ala Ile Thr
    50                  55                  60

Ala Ala Trp Asn Ala Cys Lys Gly Gly Gly Glu Val Tyr Ile Pro Ser
65                  70                  75                  80

Gly Ser Tyr Gly Leu Ser Ser Trp Val Thr Leu Ser Gly Ser Gly
                85                  90                  95

Val Ser Ile Asn Leu Glu Gly Val Ile Tyr Arg Ile Thr Ser Ala Thr
                100                 105                 110

Ala Gly Gly Thr Met Ile Ser Val Ser Ser Thr Thr Asp Phe Glu Phe
            115                 120                 125

Tyr Ser Gly Asn Ser Lys Gly Ala Ile Gln Gly Tyr Gly Tyr Leu Leu
    130                 135                 140

Asn Ala Ser Asp Pro Arg Leu Val Arg Leu Thr Gln Val Thr Asn Phe
145                 150                 155                 160

Ser Phe His Asp Ile Ala Leu Val Asp Ala Pro Glu Phe Ser Leu Val
                165                 170                 175

Met Asp Thr Cys Ser Asn Gly Glu Val Tyr Asn Ser Ile Val Arg Ala
            180                 185                 190

Gly Ser Glu Gly Gly Leu Asp Gly Val Asp Val Trp Gly Gln Asn Ile
    195                 200                 205

Trp Ile His Asp Ile Glu Val Thr Asn Lys Asp Glu Cys Val Thr Val
210                 215                 220

Lys Ser Pro Ala Ser Asn Ile Leu Val Glu Ser Ile Phe Cys Asn Trp
225                 230                 235                 240

Ser Gly Gly Ser Ala Met Gly Ser Leu Gly Ala Asn Thr Asp Ile Ser
                245                 250                 255

Asn Ile Tyr Tyr Arg Asn Val Tyr Ser Gln Asn Cys Asn Gln Met Tyr
            260                 265                 270

Met Ile Lys Ser Trp Gly Gly Ser Gly Thr Val Lys Asn Val Lys Leu
    275                 280                 285

Glu Asn Phe Trp Gly His Ser Asn Ala Tyr Thr Leu Asp Leu Asn Ala
    290                 295                 300

Tyr Trp Thr Ser Met Thr Gln Ala Pro Gly Asp Gly Val Ser Tyr Gln
305                 310                 315                 320
```

```
Asn Ile Thr Phe Thr Gly Trp Lys Gly Thr Asn Ser Asn Gly Ala Gln
            325                 330                 335

Arg Gly Ser Ile Gln Val Leu Cys Pro Ser Ala Val Pro Cys Thr Gly
        340                 345                 350

Ile Thr Ile Ser Asp Val Asn Ile Trp Thr Glu Ser Gly Ser Thr Glu
            355                 360                 365

Lys Glu Ile Cys Glu Asn Ala Tyr Gly Thr Gly Cys Leu Arg Ala
370                 375                 380

Gly Ser Gly Gly Thr Tyr Thr Thr Thr Val Thr Arg Thr Thr Ala Ser
385                 390                 395                 400

Asn Tyr Ala Ile Gln Thr Met Pro Asn Glu Ile Lys Ala Trp Gly Leu
            405                 410                 415

Gly Thr Glu Ile Pro Ile Pro Ala Ile Pro Thr Ser Phe Phe Pro Gly
            420                 425                 430

Leu Arg Pro Ile Ser Ala Leu Met Ala Ala Ser Ser Asn Gly Gly Gly
        435                 440                 445

Ala Thr Pro Thr Thr Ala Gly Pro Thr Pro Thr Thr Ser Ala Gly
    450                 455                 460

Thr Gly Gly Gly Val Gln Ser Glu Tyr Gly Gln Cys Gly Gly Ser Gly
465                 470                 475                 480

Tyr Ser Gly Pro Thr Ala Cys Ala Ala Pro Tyr Ala Cys Ser Thr Leu
                485                 490                 495

Asn Pro Tyr Tyr Ala Gln Cys Leu
            500

<210> SEQ ID NO 21
<211> LENGTH: 247
<212> TYPE: PRT
<213> ORGANISM: Hypocrea atroviridis
<220> FEATURE:
<221> NAME/KEY: misc_feature
<222> LOCATION: (1)..(247)
<223> OTHER INFORMATION: Glycoside hydrolase family 45 protein

<400> SEQUENCE: 21

Met Lys Ala Ser Leu Phe Val Gly Ser Leu Ile Ala Ser Ser Ala Ala
1               5                   10                  15

Ala Tyr Lys Ala Thr Thr Thr Arg Tyr Tyr Asp Gly Gln Glu Gly Ala
            20                  25                  30

Cys Gly Cys Gly Gly Ala Asn Gly Ala Ala Phe Ser Trp Gln Leu
        35                  40                  45

Gly Ile Ser Ser Gly Val Tyr Thr Ala Ala Gly Ser Gln Ala Leu Tyr
    50                  55                  60

Asp Thr Ala Gly Ala Ser Trp Cys Gly Ala Gly Cys Gly Lys Cys Tyr
65                  70                  75                  80

Asn Leu Thr Ser Thr Gly Glu Pro Pro Cys Thr Ser Cys Gly Thr Gly
                85                  90                  95

Gly Val Ala Gly Gln Ser Ile Ile Val Met Val Thr Asn Leu Cys Pro
            100                 105                 110

Asn Asn Gly Asn Ala Gln Trp Cys Pro Thr Val Gly Gly Thr Asn Gln
        115                 120                 125

Tyr Gly Tyr Ser Tyr His Phe Asp Ile Met Ala Gln Asn Glu Ile Phe
    130                 135                 140

Gly Asp Asn Val Val Val Asp Phe Glu Pro Val Ala Cys Pro Gly Gln
145                 150                 155                 160

Ala Thr Ser Asp Trp Gln Gln Cys Leu Cys Val Gly Met Gln Glu Thr
```

```
                165                 170                 175
Asp Thr Thr Pro Val Leu Gly Gly Ser Ser Pro Pro Gly Ser
            180                 185                 190

Ser Ser Ser Arg Pro Pro Ala Ser Ala Thr Ser Ser Ala Pro Thr Gly
        195                 200                 205

Ser Gly Thr Gln Ser Leu Tyr Gly Gln Cys Gly Gly Thr Gly Trp Ala
        210                 215                 220

Gly Pro Thr Ala Cys Ala Pro Pro Ala Thr Cys Lys Val Leu Asn Gln
225                 230                 235                 240

Tyr Tyr Ser Gln Cys Leu Asp
                245

<210> SEQ ID NO 22
<211> LENGTH: 237
<212> TYPE: PRT
<213> ORGANISM: Neosartorya fumigata
<220> FEATURE:
<221> NAME/KEY: misc_feature
<222> LOCATION: (1)..(237)
<223> OTHER INFORMATION: putative Endoglucanase

<400> SEQUENCE: 22

Met Leu Tyr Phe Thr Leu Leu His Ser Met Thr Asp Gln Arg Gly Ser
1               5                   10                  15

Asp Thr Met Thr Asp Arg Lys Glu Leu Val Ala Val Glu His Arg Leu
            20                  25                  30

Leu Gly Ile Ser Asn Gly Val Tyr Thr Ala Ala Gly Ser Gln Ala Leu
        35                  40                  45

Phe Asp Thr Ala Gly Ala Ser Trp Cys Gly Ala Gly Cys Gly Lys Cys
    50                  55                  60

Tyr Asn Leu Thr Ser Thr Gly Ser Ala Pro Cys Thr Gly Cys Gly Thr
65                  70                  75                  80

Gly Gly Ala Ala Gly Glu Ser Ile Ile Val Met Val Thr Asn Leu Cys
                85                  90                  95

Pro Tyr Asn Gly Asn Gln Gln Trp Cys Pro Gln Val Gly Ala Thr Asn
            100                 105                 110

Asn Tyr Gly Tyr Ser Tyr His Phe Asp Ile Met Ala Gln Ser Glu Val
        115                 120                 125

Phe Gly Asp Asn Val Val Val Asn Phe Glu Pro Val Ala Cys Pro Gly
    130                 135                 140

Gln Ala Thr Ser Asp Trp Glu Thr Cys Val Cys Tyr Gly Gln Thr Glu
145                 150                 155                 160

Thr Asp Glu Thr Pro Val Gly Met Thr Pro Gly Gly Ser Asn Pro Ser
                165                 170                 175

Pro Leu Thr Ser Thr Thr Thr Lys Thr Thr Thr Glu Thr Thr
            180                 185                 190

Ile Thr Thr Thr Thr Gly Gly Ala Thr Gln Thr Leu Tyr Gly Gln Cys
        195                 200                 205

Gly Gly Ser Gly Trp Thr Gly Pro Thr Ala Cys Ala Ser Gly Ala Thr
    210                 215                 220

Cys Lys Val Leu Asn Pro Tyr Tyr Ser Gln Cys Leu Ser
225                 230                 235

<210> SEQ ID NO 23
<211> LENGTH: 351
<212> TYPE: PRT
<213> ORGANISM: Aspergillus terreus
```

```
<220> FEATURE:
<221> NAME/KEY: misc_feature
<222> LOCATION: (1)..(351)
<223> OTHER INFORMATION: full length protein

<400> SEQUENCE: 23
```

| | | | | | | | | | | | | | | | |
|---|---|---|---|---|---|---|---|---|---|---|---|---|---|---|---|
| Met | His | Thr | Leu | Gln | Ser | Ala | Ile | Leu | Leu | Gly | Gly | Leu | Leu | Ala | Thr |
| 1 | | | | 5 | | | | | 10 | | | | | 15 | |
| Gln | Val | Ala | Ala | His | Gly | His | Val | Thr | Asn | Ile | Val | Ile | Asn | Gly | Val |
| | | | 20 | | | | | 25 | | | | | 30 | | |
| Tyr | Tyr | Arg | Gly | Trp | Asn | Ile | Asp | Ser | Asp | Pro | Tyr | Asn | Ser | Asn | Pro |
| | | | 35 | | | | | 40 | | | | | 45 | | |
| Pro | Leu | Val | Ala | Ala | Trp | Arg | Thr | Pro | Asn | Thr | Ala | Asn | Gly | Phe | Ile |
| | 50 | | | | | 55 | | | | | 60 | | | | |
| Ala | Pro | Asp | Ala | Phe | Gly | Thr | Ser | Asp | Ile | Ile | Cys | His | Leu | Asn | Ala |
| 65 | | | | | 70 | | | | | 75 | | | | | 80 |
| Leu | Asn | Gly | Gln | Gly | His | Ile | Gln | Val | Ala | Ala | Gly | Asp | Arg | Ile | Ser |
| | | | | 85 | | | | | 90 | | | | | 95 | |
| Leu | Gln | Trp | Asn | Thr | Trp | Pro | Glu | Ser | His | His | Gly | Pro | Val | Leu | Asp |
| | | | 100 | | | | | 105 | | | | | 110 | | |
| Tyr | Leu | Ala | Asp | Cys | Gly | Gly | Ser | Cys | Glu | Thr | Val | Asp | Lys | Thr | Thr |
| | | | 115 | | | | | 120 | | | | | 125 | | |
| Leu | Lys | Phe | Phe | Lys | Ile | Asp | Gly | Val | Gly | Leu | Val | Asp | Asp | Thr | Thr |
| | 130 | | | | | 135 | | | | | 140 | | | | |
| Pro | Pro | Gly | Ile | Trp | Gly | Asp | Asp | Gln | Leu | Ile | Ala | Asn | Asn | Asn | Thr |
| 145 | | | | | 150 | | | | | 155 | | | | | 160 |
| Trp | Leu | Val | Glu | Ile | Pro | Ser | Ser | Ile | Ala | Pro | Gly | Asn | Tyr | Val | Leu |
| | | | | 165 | | | | | 170 | | | | | 175 | |
| Arg | His | Glu | Leu | Ile | Ala | Leu | His | Gly | Ala | Gly | Ser | Ala | Asn | Gly | Ala |
| | | | 180 | | | | | 185 | | | | | 190 | | |
| Gln | Asn | Tyr | Pro | Gln | Cys | Phe | Asn | Leu | Gln | Ile | Thr | Gly | Ser | Gly | Thr |
| | | | 195 | | | | | 200 | | | | | 205 | | |
| Val | Lys | Pro | Ser | Gly | Val | Leu | Gly | Thr | Ala | Leu | Tyr | Ser | Pro | Thr | Asp |
| | 210 | | | | | 215 | | | | | 220 | | | | |
| Pro | Gly | Ile | Leu | Val | Asn | Ile | Tyr | Asn | Ser | Leu | Asn | Tyr | Ile | Val | Pro |
| 225 | | | | | 230 | | | | | 235 | | | | | 240 |
| Gly | Pro | Thr | Pro | Ile | Pro | Gln | Ala | Val | Ser | Val | Val | Gln | Ser | Ser | Ser |
| | | | | 245 | | | | | 250 | | | | | 255 | |
| Ala | Ile | Arg | Ala | Thr | Gly | Thr | Ala | Thr | Ala | Pro | Gly | Ala | Thr | Gly | Gly |
| | | | 260 | | | | | 265 | | | | | 270 | | |
| Thr | Thr | Ala | Thr | Thr | Thr | Ser | Lys | Ala | Thr | Thr | Thr | Ser | Ser | Thr | Thr |
| | | | 275 | | | | | 280 | | | | | 285 | | |
| Leu | Val | Thr | Thr | Thr | Ser | Ala | Ser | Thr | Thr | Ser | Arg | Thr | Thr | Thr | Thr |
| | 290 | | | | | 295 | | | | | 300 | | | | |
| Thr | Thr | Ala | Gly | Ala | Gly | Gly | Ser | Gln | Thr | Val | Tyr | Gly | Gln | Cys | Gly |
| 305 | | | | | 310 | | | | | 315 | | | | | 320 |
| Gly | Thr | Gly | Trp | Thr | Gly | Pro | Thr | Ala | Cys | Val | Ala | Ser | Ala | Thr | Cys |
| | | | | 325 | | | | | 330 | | | | | 335 | |
| Thr | Thr | Leu | Asn | Pro | Tyr | Tyr | Ala | Gln | Cys | Leu | Pro | Thr | Ser | Thr | |
| | | | 340 | | | | | 345 | | | | | 350 | | |

```
<210> SEQ ID NO 24
<211> LENGTH: 316
<212> TYPE: PRT
<213> ORGANISM: Hypocrea jecorina
<220> FEATURE:
```

```
<221> NAME/KEY: misc_feature
<222> LOCATION: (1)..(316)
<223> OTHER INFORMATION: Cip1 full length protein

<400> SEQUENCE: 24
```

| | | | | | | | | | | | | | | |
|---|---|---|---|---|---|---|---|---|---|---|---|---|---|---|
| Met | Val | Arg | Arg | Thr | Ala | Leu | Leu | Ala | Leu | Gly | Ala | Leu | Ser | Thr | Leu |
| 1 | | | | 5 | | | | | 10 | | | | | 15 | |
| Ser | Met | Ala | Gln | Ile | Ser | Asp | Asp | Phe | Glu | Ser | Gly | Trp | Asp | Gln | Thr |
| | | | 20 | | | | | 25 | | | | | 30 | | |
| Lys | Trp | Pro | Ile | Ser | Ala | Pro | Asp | Cys | Asn | Gln | Gly | Thr | Val | Ser | |
| | | | 35 | | | | | 40 | | | | | 45 | | |
| Leu | Asp | Thr | Thr | Val | Ala | His | Ser | Gly | Ser | Asn | Ser | Met | Lys | Val | Val |
| | 50 | | | | | 55 | | | | | 60 | | | | |
| Gly | Gly | Pro | Asn | Gly | Tyr | Cys | Gly | His | Ile | Phe | Phe | Gly | Thr | Thr | Gln |
| 65 | | | | | 70 | | | | | 75 | | | | | 80 |
| Val | Pro | Thr | Gly | Asp | Val | Tyr | Val | Arg | Ala | Trp | Ile | Arg | Leu | Gln | Thr |
| | | | | 85 | | | | | 90 | | | | | 95 | |
| Ala | Leu | Gly | Ser | Asn | His | Val | Thr | Phe | Ile | Ile | Met | Pro | Asp | Thr | Ala |
| | | | | 100 | | | | | 105 | | | | | 110 | |
| Gln | Gly | Gly | Lys | His | Leu | Arg | Ile | Gly | Gly | Gln | Ser | Gln | Val | Leu | Asp |
| | | | 115 | | | | | 120 | | | | | 125 | | |
| Tyr | Asn | Arg | Glu | Ser | Asp | Asp | Ala | Thr | Leu | Pro | Asp | Leu | Ser | Pro | Asn |
| | 130 | | | | | 135 | | | | | 140 | | | | |
| Gly | Ile | Ala | Ser | Thr | Val | Thr | Leu | Pro | Thr | Gly | Ala | Phe | Gln | Cys | Phe |
| 145 | | | | | 150 | | | | | 155 | | | | | 160 |
| Glu | Tyr | His | Leu | Gly | Thr | Asp | Gly | Thr | Ile | Glu | Thr | Trp | Leu | Asn | Gly |
| | | | | 165 | | | | | 170 | | | | | 175 | |
| Ser | Leu | Ile | Pro | Gly | Met | Thr | Val | Gly | Pro | Gly | Val | Asp | Asn | Pro | Asn |
| | | | | 180 | | | | | 185 | | | | | 190 | |
| Asp | Ala | Gly | Trp | Thr | Arg | Ala | Ser | Tyr | Ile | Pro | Glu | Ile | Thr | Gly | Val |
| | | | 195 | | | | | 200 | | | | | 205 | | |
| Asn | Phe | Gly | Trp | Glu | Ala | Tyr | Ser | Gly | Asp | Val | Asn | Thr | Val | Trp | Phe |
| | 210 | | | | | 215 | | | | | 220 | | | | |
| Asp | Asp | Ile | Ser | Ile | Ala | Ser | Thr | Arg | Val | Gly | Cys | Gly | Pro | Gly | Ser |
| 225 | | | | | 230 | | | | | 235 | | | | | 240 |
| Pro | Gly | Gly | Pro | Gly | Ser | Ser | Thr | Thr | Gly | Arg | Ser | Thr | Ser | Ser | Gly |
| | | | | 245 | | | | | 250 | | | | | 255 | |
| Pro | Thr | Ser | Thr | Ser | Arg | Pro | Ser | Thr | Thr | Ile | Pro | Pro | Thr | Ser | |
| | | | 260 | | | | | 265 | | | | | 270 | | |
| Arg | Thr | Thr | Thr | Ala | Thr | Gly | Pro | Thr | Gln | Thr | His | Tyr | Gly | Gln | Cys |
| | | 275 | | | | | 280 | | | | | 285 | | | |
| Gly | Gly | Ile | Gly | Tyr | Ser | Gly | Pro | Thr | Val | Cys | Ala | Ser | Gly | Thr | Thr |
| | 290 | | | | | 295 | | | | | 300 | | | | |
| Cys | Gln | Val | Leu | Asn | Pro | Tyr | Tyr | Ser | Gln | Cys | Leu | | | | |
| 305 | | | | | 310 | | | | | 315 | | | | | |

```
<210> SEQ ID NO 25
<211> LENGTH: 514
<212> TYPE: PRT
<213> ORGANISM: Hypocrea rufa
<220> FEATURE:
<221> NAME/KEY: misc_feature
<222> LOCATION: (1)..(514)
<223> OTHER INFORMATION: Exoglucanase 1

<400> SEQUENCE: 25
```

Met Tyr Gln Lys Leu Ala Leu Ile Ser Ala Phe Leu Ala Thr Ala Arg

-continued

```
1               5                   10                  15
Ala Gln Ser Ala Cys Thr Leu Gln Ala Glu Thr His Pro Pro Leu Thr
            20                  25                  30

Trp Gln Lys Cys Ser Ser Gly Gly Thr Cys Thr Gln Gln Thr Gly Ser
            35                  40                  45

Val Val Ile Asp Ala Asn Trp Arg Trp Thr His Ala Thr Asn Ser Ser
            50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Ala Asp Ser Leu Ser Ile Gly Phe
                100                 105                 110

Val Thr Gln Ser Ala Gln Lys Asn Val Gly Ala Arg Leu Tyr Leu Met
            115                 120                 125

Ala Ser Asp Thr Thr Tyr Gln Glu Phe Thr Leu Leu Gly Asn Glu Phe
130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
                180                 185                 190

Cys Pro Arg Asp Leu Lys Phe Ile Asn Gly Gln Ala Asn Val Glu Gly
            195                 200                 205

Trp Glu Pro Ser Ser Asn Asn Ala Asn Thr Gly Ile Gly Gly His Gly
            210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Asp
                245                 250                 255

Gly Asp Ser Cys Gly Gly Thr Tyr Ser Gly Asp Arg Tyr Gly Gly Thr
                260                 265                 270

Cys Asp Pro Asp Gly Cys Asp Trp Asn Pro Tyr Arg Leu Gly Asn Thr
            275                 280                 285

Ser Phe Tyr Gly Pro Gly Ser Ser Phe Thr Leu Asp Thr Thr Lys Lys
            290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Asp Tyr Ser Gly Asn Ser Leu Asp Asp Tyr Cys Ala Ala Glu Glu
                340                 345                 350

Ala Glu Phe Gly Gly Ser Ser Phe Ser Asp Lys Gly Gly Leu Thr Gln
            355                 360                 365

Phe Lys Lys Ala Thr Ser Gly Gly Met Val Leu Val Met Ser Leu Trp
370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Leu Glu Ser Asn Ser Pro Asn Ala Lys
                420                 425                 430
```

```
Val Val Tyr Ser Asn Ile Lys Phe Gly Pro Ile Gly Ser Thr Gly Asn
        435                 440                 445

Ser Ser Gly Gly Asn Pro Pro Gly Gly Asn Pro Pro Gly Thr Thr Thr
    450                 455                 460

Thr Arg Arg Pro Ala Thr Ser Thr Gly Ser Ser Pro Gly Pro Thr Gln
465                 470                 475                 480

Thr His Tyr Gly Gln Cys Gly Gly Ile Gly Tyr Ser Gly Pro Thr Val
                485                 490                 495

Cys Ala Ser Gly Ser Thr Cys Gln Val Leu Asn Pro Tyr Tyr Ser Gln
                500                 505                 510

Cys Leu
```

<210> SEQ ID NO 26
<211> LENGTH: 505
<212> TYPE: PRT
<213> ORGANISM: Hypocrea virens
<220> FEATURE:
<221> NAME/KEY: misc_feature
<222> LOCATION: (1)..(505)
<223> OTHER INFORMATION: Glycoside hydrolase family 7 protein

<400> SEQUENCE: 26

```
Met Tyr Gln Lys Leu Ala Ala Ile Ser Ala Phe Leu Ala Ala Ala Arg
1               5                   10                  15

Ala Gln Gln Val Cys Thr Gln Ala Glu Thr His Pro Pro Leu Thr
                20                  25                  30

Trp Gln Lys Cys Ser Ser Ser Gly Cys Thr Ala Gln Ser Gly Ser Val
            35                  40                  45

Val Leu Asp Ala Asn Trp Arg Trp Thr His Asp Val Lys Ser Thr Thr
    50                  55                  60

Asn Cys Tyr Asp Gly Asn Thr Trp Ser Lys Thr Leu Cys Pro Asp Asp
65                  70                  75                  80

Ala Thr Cys Ala Lys Asn Cys Cys Leu Asp Gly Ala Ala Tyr Ser Ser
                85                  90                  95

Thr Tyr Gly Ile Thr Thr Ser Ser Asp Ser Leu Thr Ile Asn Phe Val
                100                 105                 110

Thr Gln Ser Asn Val Gly Ala Arg Leu Tyr Leu Met Ala Thr Asp Thr
            115                 120                 125

Ser Tyr Gln Glu Phe Thr Leu Ser Gly Asn Glu Phe Ser Phe Asp Val
    130                 135                 140

Asp Val Ser Gln Leu Pro Cys Gly Leu Asn Gly Ala Leu Tyr Phe Val
145                 150                 155                 160

Ser Met Asp Ala Asp Gly Gly Gln Ser Lys Tyr Pro Thr Asn Ala Ala
                165                 170                 175

Gly Ala Lys Tyr Gly Thr Gly Tyr Cys Asp Ser Gln Cys Pro Arg Asp
                180                 185                 190

Leu Lys Phe Ile Asn Gly Gln Ala Asn Val Asp Gly Trp Gln Pro Ser
            195                 200                 205

Ser Asn Asn Ala Asn Thr Gly Ile Gly Gly His Gly Ser Cys Cys Ser
    210                 215                 220

Glu Met Asp Ile Trp Glu Ala Asn Ser Ile Ser Gln Ala Val Thr Pro
225                 230                 235                 240

His Pro Cys Glu Thr Val Gly Gln Thr Met Cys Ser Gly Asp Gly Cys
                245                 250                 255

Gly Gly Thr Tyr Ser Ser Asp Arg Tyr Gly Gly Thr Cys Asp Pro Asp
```

```
                    260                 265                 270
Gly Cys Asp Trp Asn Pro Tyr Arg Leu Gly Asn Thr Thr Phe Tyr Gly
            275                 280                 285

Pro Gly Ser Gly Phe Thr Leu Asp Thr Thr Lys Lys Met Thr Val Val
        290                 295                 300

Thr Gln Phe Ala Thr Ser Gly Ala Ile Ser Arg Tyr Tyr Val Gln Asn
305                 310                 315                 320

Gly Val Lys Phe Gln Gln Pro Asn Ala Gln Leu Ser Gly Tyr Ser Gly
            325                 330                 335

Asn Thr Leu Asn Ser Asp Tyr Cys Ala Ala Glu Gln Ala Ala Phe Gly
        340                 345                 350

Gly Thr Ser Phe Thr Asp Lys Gly Leu Ala Gln Phe Asn Lys Ala
        355                 360                 365

Leu Ser Gly Gly Met Val Leu Val Met Ser Leu Trp Asp Asp Tyr Tyr
        370                 375                 380

Ala Asn Met Leu Trp Leu Asp Ser Thr Tyr Pro Thr Asn Ala Thr Ala
385                 390                 395                 400

Ser Thr Pro Gly Ala Lys Arg Gly Ser Cys Ser Thr Ser Ser Gly Val
            405                 410                 415

Pro Ser Gln Ile Glu Ser Gln Ser Pro Asn Ala Lys Val Val Phe Ser
        420                 425                 430

Asn Ile Arg Phe Gly Pro Ile Gly Ser Thr Gly Gly Ser Thr Gly Asn
        435                 440                 445

Pro Pro Pro Gly Thr Ser Thr Thr Arg Leu Pro Pro Ser Ser Thr Gly
        450                 455                 460

Ser Ser Pro Gly Pro Thr Gln Thr His Tyr Gly Gln Cys Gly Gly Ile
465                 470                 475                 480

Gly Tyr Ser Gly Pro Thr Gln Cys Val Ser Gly Thr Thr Cys Gln Val
            485                 490                 495

Leu Asn Pro Tyr Tyr Ser Gln Cys Leu
            500                 505

<210> SEQ ID NO 27
<211> LENGTH: 418
<212> TYPE: PRT
<213> ORGANISM: Hypocrea atroviridis
<220> FEATURE:
<221> NAME/KEY: misc_feature
<222> LOCATION: (1)..(418)
<223> OTHER INFORMATION: Glycoside hydrolase family 5 protein

<400> SEQUENCE: 27

Met Asn Lys Pro Met Gly Pro Leu Leu Leu Ala Ala Thr Leu Met Ala
1               5                   10                  15

Ser Gly Ala Ile Ala Gln Thr Gln Thr Val Trp Gly Gln Cys Gly Gly
            20                  25                  30

Gln Gly Tyr Ser Gly Pro Thr Asn Cys Ala Ser Gly Ser Ala Cys Ser
        35                  40                  45

Thr Leu Asn Pro Tyr Tyr Ala Gln Cys Ile Pro Gly Ala Thr Ser Phe
50                  55                  60

Thr Thr Ser Thr Thr Ser Thr Lys Ser Pro Gly Ser Gly Ser Ser Thr
65                  70                  75                  80

Thr Ser Ser Ala Ser Gln Pro Thr Gly Ser Gly Gln Thr Arg Phe Ala
            85                  90                  95

Gly Ile Asn Ile Ala Gly Phe Asp Phe Gly Cys Thr Thr Asp Gly Thr
        100                 105                 110
```

```
Cys Val Thr Ser Gln Ile Tyr Pro Pro Leu Lys Asn Phe Gly Gly Thr
            115                 120                 125

Asn Asn His Pro Asp Gly Val Gly Gln Met Gln His Phe Val Asn Asp
    130                 135                 140

Asp Lys Leu Asn Ile Phe Arg Leu Pro Val Gly Trp Gln Tyr Leu Val
145                 150                 155                 160

Asn Asn Asn Leu Gly Gly Thr Leu Asp Ser Thr Ala Ile Ser Asn Tyr
                165                 170                 175

Asp Gln Leu Val Gln Gly Cys Leu Ala Thr Gly Ala Tyr Cys Ile Val
            180                 185                 190

Asp Ile His Asn Tyr Ala Arg Trp Asn Gly Ala Ile Ile Gly Gln Gly
            195                 200                 205

Gly Pro Thr Asn Ala Gln Phe Val Ser Leu Trp Thr Gln Leu Ala Thr
    210                 215                 220

Lys Tyr Ala Ser Gln Ser Lys Ile Trp Phe Gly Ile Met Asn Glu Pro
225                 230                 235                 240

His Asp Val Asp Ile Asn Thr Trp Gly Thr Thr Val Gln Ala Val Val
                245                 250                 255

Thr Ala Ile Arg Asn Ala Gly Ala Thr Thr Gln Phe Ile Ser Leu Pro
            260                 265                 270

Gly Thr Asp Tyr Gln Ser Ala Gly Asn Phe Leu Thr Asp Gly Ser Ser
    275                 280                 285

Thr Ala Leu Ser Gln Val Lys Asn Pro Asp Gly Ser Thr Thr Asn Leu
    290                 295                 300

Ile Phe Asp Leu His Lys Tyr Leu Asp Ser Asp Asn Ser Gly Thr His
305                 310                 315                 320

Thr Glu Cys Val Thr Asn Asn Ile Ala Thr Ala Phe Gln Pro Val Ala
                325                 330                 335

Thr Trp Leu Arg Gln Asn Lys Arg Gln Gly Ile Leu Thr Glu Thr Gly
            340                 345                 350

Gly Gly Asn Thr Gln Ser Cys Ile Gln Asp Val Cys Gln Gln Asn Gln
    355                 360                 365

Phe Leu Asn Gln Asn Ser Asp Val Phe Leu Gly Tyr Val Gly Trp Gly
370                 375                 380

Ala Gly Ser Phe Asp Ser Thr Tyr Gln Leu Thr Leu Thr Pro Thr Gln
385                 390                 395                 400

Asn Gly Asn Thr Trp Thr Asp Thr Ala Leu Ala Ala Ala Cys Phe Ser
                405                 410                 415

Arg Ala

<210> SEQ ID NO 28
<211> LENGTH: 216
<212> TYPE: PRT
<213> ORGANISM: Neosartorya fischeri
<220> FEATURE:
<221> NAME/KEY: misc_feature
<222> LOCATION: (1)..(216)
<223> OTHER INFORMATION: Glycosyl hydrolase family 45 protein

<400> SEQUENCE: 28

Met Thr Asp Arg Lys Glu Leu Val Ala Val Glu His His Leu Val Pro
1               5                   10                  15

Thr Leu Gly Ser Asn Gly Val Tyr Thr Ala Ala Gly Ser Gln Ala Leu
            20                  25                  30

Phe Asp Thr Ala Gly Ala Ser Trp Cys Gly Ala Gly Cys Gly Lys Cys
```

-continued

```
             35                  40                  45
Tyr Asn Leu Thr Ser Thr Gly Asn Pro Pro Cys Thr Gly Cys Gly Thr
         50                  55                  60

Gly Gly Ala Ala Gly Glu Ser Ile Ile Val Met Val Thr Asn Leu Cys
 65                  70                  75                  80

Pro Tyr Asn Gly Asn Gln Gln Trp Cys Pro Gln Val Gly Ala Thr Asn
                 85                  90                  95

Asn Tyr Gly Tyr Ser Tyr His Phe Asp Ile Met Ala Gln Ser Glu Val
            100                 105                 110

Phe Gly Asp Asn Val Val Val Asn Phe Glu Pro Ile Ala Cys Pro Gly
        115                 120                 125

Gln Ala Thr Ser Asp Trp Glu Thr Cys Val Cys Tyr Gly Lys Thr Ala
    130                 135                 140

Thr Asp Glu Thr Pro Val Gly Met Thr Pro Gly Gly Ser Asn Pro Ser
145                 150                 155                 160

Pro Pro Thr Ser Thr Thr Thr Glu Thr Thr Thr Ile Thr Thr
                165                 170                 175

Ser Gly Ala Thr Gln Thr Leu Tyr Gly Gln Cys Gly Gly Ser Gly Trp
            180                 185                 190

Thr Gly Pro Thr Ala Cys Ala Ser Gly Ala Thr Cys Lys Val Leu Asn
        195                 200                 205

Ser Tyr Tyr Ser Gln Cys Leu Ser
    210                 215

<210> SEQ ID NO 29
<211> LENGTH: 513
<212> TYPE: PRT
<213> ORGANISM: Trichoderma koningii
<220> FEATURE:
<221> NAME/KEY: misc_feature
<222> LOCATION: (1)..(513)
<223> OTHER INFORMATION: Exoglucanase 1

<400> SEQUENCE: 29

Met Tyr Arg Lys Leu Ala Val Ile Ser Ala Phe Leu Ala Thr Ala Arg
 1                5                  10                  15

Ala Gln Ser Ala Cys Thr Leu Gln Ser Glu Thr His Pro Pro Leu Thr
             20                  25                  30

Trp Gln Lys Cys Ser Ser Gly Gly Thr Cys Thr Gln Gln Thr Gly Ser
         35                  40                  45

Val Val Ile Asp Ala Asn Trp Arg Trp Thr His Ala Thr Asn Ser Ser
 50                  55                  60

Thr Asn Cys Tyr Asp Gly Asn Thr Trp Ser Ser Thr Leu Cys Pro Asp
 65                  70                  75                  80

Asn Glu Thr Cys Ala Lys Asn Cys Cys Leu Asp Gly Ala Ala Tyr Ala
             85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175
```

```
Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
            195                 200                 205

Trp Glu Pro Ser Ser Asn Asn Ala Asn Thr Gly Ile Gly Gly His Gly
            210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
            245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
            275                 280                 285

Ser Phe Tyr Gly Pro Gly Ser Ser Phe Thr Leu Asp Thr Thr Lys Lys
            290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
            325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
            355                 360                 365

Phe Lys Lys Ala Thr Ser Gly Gly Met Val Leu Val Met Ser Leu Trp
            370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
            405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Arg Gly Thr Thr Thr Thr
            450                 455                 460

Arg Arg Pro Ala Thr Thr Thr Gly Ser Ser Pro Gly Pro Thr Gln Ser
465                 470                 475                 480

His Tyr Gly Gln Cys Gly Gly Ile Gly Tyr Ser Gly Pro Thr Val Cys
            485                 490                 495

Ala Ser Gly Thr Thr Cys Gln Val Leu Asn Pro Tyr Tyr Ser Gln Cys
            500                 505                 510

Leu
```

<210> SEQ ID NO 30
<211> LENGTH: 448
<212> TYPE: PRT
<213> ORGANISM: Colletotrichum graminicola
<220> FEATURE:
<221> NAME/KEY: misc_feature
<222> LOCATION: (1)..(448)
<223> OTHER INFORMATION: Glycosyl hydrolase family 61

<400> SEQUENCE: 30

Met Ser Tyr Arg Ser Lys Thr Ala Ser Phe Val Ala Ile Leu Ala Ser

-continued

```
1               5                   10                  15
Ala Ala Thr Val Ala Ala His Gly His Val Thr Asn Ile Val Ile Asn
                20                  25                  30
Gly Val Ser Tyr Arg Asn Tyr Ile Pro Val Gln Asp Pro Tyr Thr Asn
                35                  40                  45
Asn Pro Pro Leu Val Ala Gly Trp Thr Thr Asp Gln Arg Asp Asn Gly
 50                  55                  60
Phe Val Ala Pro Asp Ala Tyr Asn Ala Pro Asp Ile Ile Cys His Arg
 65                  70                  75                  80
Gln Ala Val Ala Gly Lys Gly Arg Ile Thr Val Ala Ala Gly Asp Thr
                85                  90                  95
Val Gln Leu Gln Trp Thr Glu Trp Pro Asp Ser His Lys Gly Pro Val
                100                 105                 110
Ile Asp Trp Leu Ala Asn Cys Asn Gly Pro Cys Asn Leu Val Asp Lys
                115                 120                 125
Thr Asp Leu Arg Phe Phe Lys Ile Asp Gly Ala Gly Leu Ile Asp Pro
                130                 135                 140
Pro Gln Arg Thr Asn Arg Trp Ala Ala Thr Ala Leu Ile Glu Asn Gly
145                 150                 155                 160
Asn Ala Trp Leu Val Arg Ile Pro Ala Asn Val Ala Pro Gly His Tyr
                165                 170                 175
Val Leu Arg His Asp Ile Ile Ala Leu His Ser Ala Gly Gln Gln Asn
                180                 185                 190
Gly Ala Gln Ser Tyr Pro Gln Cys Ile Asn Leu Glu Ile Thr Gly Glu
                195                 200                 205
Gly Thr Asp Asn Pro Pro Gly Val Leu Gly Thr Ala Leu Tyr Arg Ala
                210                 215                 220
Asn Asp Ala Gly Ile Leu Tyr Asn Ile Tyr Arg Asp Asn Leu Asn Asp
225                 230                 235                 240
Tyr Val Val Pro Gly Asp Ala Ile Ile Pro Gly Gly Val Ser Met Leu
                245                 250                 255
Pro Gln Ser Arg Ile Gln Ile Thr Ala Ser Gly Ser Ala Thr Pro Tyr
                260                 265                 270
Gly Thr Thr Ser Val Gly Ser Ser Ser Thr Arg Ile Ala Pro Ser
                275                 280                 285
Ser Val Thr Ser Ala Ala Thr Ser Ser Ser Arg Glu Ser Ala Ser
                290                 295                 300
Ser Val Glu Ala Glu Ala Ser Thr Ile Ser Thr Thr Ile Arg Leu Thr
305                 310                 315                 320
Arg Thr Ile Thr Ala Thr His Thr Asn Ser Thr Ser Asn Asn Ile Pro
                325                 330                 335
Pro Ser Ser Thr Ala Ala Pro Thr Arg Thr Leu Ala Pro Thr Thr Leu
                340                 345                 350
Gln Thr Gln Thr Thr Thr Ala Pro Pro Ser Gly Glu Pro Thr Gln Lys
                355                 360                 365
Met Tyr Gly Gln Cys Gly Gly Val Ala Tyr Met Gly Pro Thr Gln Cys
                370                 375                 380
Pro Ala Tyr Ala Thr Cys Ser Thr Val Asn Pro Tyr Tyr Ala Gln Cys
385                 390                 395                 400
Thr Pro Leu Pro Val Pro Pro Gly Val Gln Pro Leu Tyr Gly Gln Cys
                405                 410                 415
Gly Gly Leu Asn Trp Pro Pro Glu Ser Pro Thr Glu Cys Val Pro Gly
                420                 425                 430
```

```
Ala Arg Cys Ser Thr Ile Asn Pro Tyr Tyr Ala Gln Cys Thr Pro Ala
        435                 440                 445
```

<210> SEQ ID NO 31
<211> LENGTH: 838
<212> TYPE: PRT
<213> ORGANISM: Arthrobotrys oligospora
<220> FEATURE:
<221> NAME/KEY: misc_feature
<222> LOCATION: (1)..(838)
<223> OTHER INFORMATION: full length protein

<400> SEQUENCE: 31

```
Met Leu Ser Ser Thr Leu Leu Leu Thr Ala Leu Ala Val Pro Ala Ala
1               5                   10                  15

Phe Ala Gln Ser Asn Leu Asp Trp Asp Ala Ala Tyr Thr Lys Ala Thr
            20                  25                  30

Thr Met Leu Gly Lys Leu Thr Leu Gln Gln Lys Ile Asn Met Val Thr
        35                  40                  45

Gly Val Gly Trp Gln Lys Gly Pro Cys Val Gly Asn Ile Ala Ala Ile
    50                  55                  60

Ser Ser Ala Gly Phe Pro Gly Leu Cys Leu Gln Asp Gly Pro Val Gly
65                  70                  75                  80

Val Arg Tyr Ala Ser Gly Val Thr Ala Phe Pro Ala Ala Ile His Leu
                85                  90                  95

Gly Ala Thr Trp Asp Lys Asp Leu Met Arg Ala Gln Gly Val Ala Met
            100                 105                 110

Gly Glu Glu Phe Arg Gly Lys Gly Val Asn Ile Ala Leu Ala Pro Val
        115                 120                 125

Ser Gly Ala Leu Gly Lys Ile Pro Gln Ala Gly Arg Asn Trp Glu Gly
    130                 135                 140

Tyr Ser Asn Asp Pro Tyr His Ala Gly Val Gly Met Thr Glu Val Ile
145                 150                 155                 160

Thr Gly Val Gln Ser Val Gly Val Gln Ala Cys Ala Lys His Tyr Ile
                165                 170                 175

Gly Asn Glu Gln Glu Arg Asn Arg Glu Thr Met Ser Ser Asn Ile Asp
            180                 185                 190

Asp Arg Thr Met His Glu Leu Tyr Leu Trp Pro Phe Ala Asp Ala Ala
        195                 200                 205

Lys Ala Asn Val Ala Thr Phe Met Cys Ser Tyr Asn Lys Leu Asn Ser
    210                 215                 220

Ser Trp Ala Cys Asp Asn Asp Tyr Ala Leu Asn Lys Leu Leu Lys Gly
225                 230                 235                 240

Glu Leu Gly Phe Arg Gly Gln Val Leu Ser Asp Trp Asn Ala Lys Thr
                245                 250                 255

Thr Thr Gly Gly Ala Thr Arg Gly Leu Asp Met Thr Met Pro Gly Asp
            260                 265                 270

Asn Phe Gly Asp Asn Asn Phe Val Trp Gly Gln Asn Leu Leu Asn Ala
        275                 280                 285

Val Asn Gln Gly Ser Val Ser Thr Ser Arg Leu Asp Asp Met Val Lys
    290                 295                 300

Arg Ile Phe Ala Ser Trp Tyr Leu Val Gly Gln Asp Gln Asn Tyr Pro
305                 310                 315                 320

Ser Val Ser Phe Asn Ser Trp Asn Asn Asn Gly Gly Gly Asp Val Ser
                325                 330                 335
```

```
Gly Asn His Lys Glu Leu Ala Arg Thr Val Ala Gly Asp Ile Ile
            340                 345                 350

Leu Leu Lys Asn Val Asn Asn Ala Leu Pro Leu Lys Lys Pro Ala Ser
        355                 360                 365

Leu Ala Ile Ile Gly Arg Asp Ala Ile Asn Asn Pro Ala Gly Ile Asn
    370                 375                 380

Ser Cys Thr Asp Arg Ala Cys Asn Asp Gly Thr Leu Ala Met Gly Trp
385                 390                 395                 400

Gly Ser Gly Thr Thr Asn Phe Pro Tyr Leu Ile Asp Pro Leu Thr Ala
                405                 410                 415

Ile Arg Ala Gln Ala Gln Val Asp Gly Thr Thr Val Val Thr Ser Thr
            420                 425                 430

Thr Asp Asn Ala Ser Gln Gly Ala Ser Ala Ala Gln Ser Ala Ser Thr
        435                 440                 445

Ala Ile Val Phe Ile Asn Ala Asn Ser Gly Glu Gly Tyr Leu Thr Val
    450                 455                 460

Gln Gly Asn Ser Gly Asp Arg Asn Asn Leu Asp Pro Trp Asn Asn Gly
465                 470                 475                 480

Asn Asp Leu Val Lys Ala Val Ala Ala Val Asn Ser Lys Thr Ile Val
                485                 490                 495

Val Ile His Ser Val Gly Pro Ile Ile Leu Glu Gln Phe Val Asp Leu
            500                 505                 510

Pro Asn Val Ile Ala Val Val Trp Ala Gly Leu Pro Gly Gln Glu Ser
        515                 520                 525

Gly Asn Gly Leu Val Asp Val Leu Tyr Gly Ser Lys Ala Pro Gly Gly
    530                 535                 540

Lys Leu Pro Phe Thr Ile Ala Lys Ser Pro Ser Asp Tyr Gly Thr Ser
545                 550                 555                 560

Ile Ile Asn Gly Asp Asp Asn Phe Ser Glu Gly Leu Phe Ile Asp Tyr
                565                 570                 575

Arg Arg Phe Asp Ala Gln Gly Ile Thr Pro Arg Tyr Glu Phe Gly Phe
            580                 585                 590

Gly Leu Ser Tyr Thr Thr Phe Ser Phe Ser Asn Leu Val Ile Ser Tyr
        595                 600                 605

Thr Ser Thr Thr Thr Gly Pro Ile Ser Ser Thr Gln Asn Ala Pro Gly
    610                 615                 620

Gly Tyr Pro Ala Leu Tyr Glu Pro Val Ala Thr Ile Thr Ala Arg Val
625                 630                 635                 640

Thr Asn Thr Gly Gly Val Ala Gly Ser Glu Val Ala Gln Leu Tyr Ile
                645                 650                 655

Gly Leu Pro Ala Gly Ser Pro Ser Thr Pro Pro Lys Gln Leu Arg Gly
            660                 665                 670

Phe Gln Lys Leu Lys Leu Ala Ser Gly Ala Ser Gly Thr Ala Thr Phe
        675                 680                 685

Val Leu Lys Arg Lys Asp Leu Ala Tyr Trp Asn Thr Ala Ser Gln Arg
    690                 695                 700

Trp Val Val Pro Thr Gly Asn Phe Asn Ile Phe Ile Gly Ala Ser Ser
705                 710                 715                 720

Arg Asp Ile Arg Leu Gln Gly Thr Met Gly Pro Ser Gly Ser Thr Thr
                725                 730                 735

Thr Thr Ile Gly Gly Ser Thr Ser Ser Thr Thr Ala Gln Thr Thr
            740                 745                 750

Thr Arg Val Thr Thr Thr Pro Ser Thr Thr Val Thr Thr Thr Arg Thr
```

```
                755                 760                 765
Thr Thr Ala Pro Thr Thr Thr Arg Thr Thr Val Ala Thr Thr Thr
770                 775                 780

Arg Ala Thr Thr Thr Ala Val Ile Thr Thr Thr Ala Ala Pro Thr Gly
785                 790                 795                 800

Gly Pro Leu Gln Ser Lys Trp Gly Gln Cys Gly Gly Val Gly Tyr Thr
                805                 810                 815

Gly Ala Ser Val Cys Ser Pro Thr Ala Thr Cys Ser Thr Leu Asn Pro
                820                 825                 830

Tyr Tyr Ala Gln Cys Leu
        835

<210> SEQ ID NO 32
<211> LENGTH: 505
<212> TYPE: PRT
<213> ORGANISM: Trichoderma harzianum
<220> FEATURE:
<221> NAME/KEY: misc_feature
<222> LOCATION: (1)..(505)
<223> OTHER INFORMATION: Cellobiohydrolase

<400> SEQUENCE: 32

Met Tyr Arg Lys Leu Ala Ala Ile Ser Ala Phe Leu Ala Ala Ala Arg
1               5                   10                  15

Ala Gln Gln Val Cys Thr Gln Ala Glu Thr His Pro Pro Leu Thr
                20                  25                  30

Trp Gln Lys Cys Thr Ala Ser Gly Cys Thr Ala Gln Ser Gly Ser Val
            35                  40                  45

Val Leu Asp Ala Asn Trp Arg Trp Thr His Asp Thr Lys Ser Thr Thr
50                  55                  60

Asn Cys Tyr Asp Gly Asn Thr Trp Ser Ser Thr Leu Cys Pro Asp Asp
65                  70                  75                  80

Ala Thr Cys Ala Lys Asn Cys Cys Leu Asp Gly Ala Asn Tyr Ser Gly
                85                  90                  95

Thr Tyr Gly Val Thr Thr Ser Gly Asp Ala Leu Thr Leu Gln Phe Val
                100                 105                 110

Thr Ala Ser Asn Val Gly Ser Arg Leu Tyr Leu Met Ala Asn Asp Ser
            115                 120                 125

Thr Tyr Gln Glu Phe Thr Leu Ser Gly Asn Glu Phe Ser Phe Asp Val
        130                 135                 140

Asp Val Ser Gln Leu Pro Cys Gly Leu Asn Gly Ala Leu Tyr Phe Val
145                 150                 155                 160

Ser Met Asp Ala Asp Gly Gly Gln Ser Lys Tyr Pro Gly Asn Ala Ala
                165                 170                 175

Gly Ala Lys Tyr Gly Thr Gly Tyr Cys Asp Ser Gln Cys Pro Arg Asp
                180                 185                 190

Leu Lys Phe Ile Asn Gly Gln Ala Asn Val Glu Gly Trp Glu Pro Ser
            195                 200                 205

Ser Asn Asn Ala Asn Thr Gly Val Gly Gly His Gly Ser Cys Cys Ser
        210                 215                 220

Glu Met Asp Ile Trp Glu Ala Asn Ser Ile Ser Glu Ala Leu Thr Pro
225                 230                 235                 240

His Pro Cys Glu Thr Val Gly Gln Thr Met Cys Ser Gly Asp Ala Cys
                245                 250                 255

Gly Gly Thr Tyr Ser Asn Asp Arg Tyr Gly Gly Thr Cys Asp Pro Asp
                260                 265                 270
```

```
Gly Cys Asp Trp Asn Pro Tyr Arg Leu Gly Asn Thr Ser Phe Tyr Gly
            275                 280                 285

Pro Gly Ser Ser Phe Ala Leu Asp Thr Thr Lys Lys Leu Thr Val Val
        290                 295                 300

Thr Gln Phe Ala Thr Asp Gly Ser Ile Ser Arg Tyr Tyr Val Gln Asn
305                 310                 315                 320

Gly Val Lys Phe Gln Gln Pro Ser Ala Ser Val Gly Ser Tyr Thr Gly
            325                 330                 335

Asn Thr Ile Asn Thr Ala Tyr Cys Ala Ala Glu Gln Thr Ala Phe Gly
            340                 345                 350

Gly Thr Ser Phe Thr Asp Lys Gly Gly Leu Ala Gln Ile Asn Lys Ala
            355                 360                 365

Phe Gln Gly Gly Met Val Leu Val Met Ser Leu Trp Asp Asp Tyr Ala
            370                 375                 380

Val Asn Met Leu Trp Leu Asp Ser Thr Tyr Pro Thr Asn Ala Thr Ala
385                 390                 395                 400

Ser Thr Pro Gly Ala Lys Arg Gly Ser Cys Ser Thr Ser Ser Gly Val
            405                 410                 415

Pro Ala Gln Val Glu Ala Gln Ser Pro Asn Ser Lys Val Ile Tyr Ser
            420                 425                 430

Asn Ile Arg Phe Gly Pro Ile Gly Ser Thr Gly Gly Asn Thr Gly Ser
            435                 440                 445

Asn Pro Pro Gly Thr Thr Thr Arg Ala Pro Pro Ser Ser Thr Gly
            450                 455                 460

Ser Ser Pro Thr Ala Thr Gln Thr His Tyr Gly Gln Cys Gly Gly Thr
465                 470                 475                 480

Gly Trp Thr Gly Pro Thr Arg Cys Ala Ser Gly Phe Thr Cys Gln Val
            485                 490                 495

Leu Asn Pro Phe Tyr Ser Gln Cys Leu
            500                 505

<210> SEQ ID NO 33
<211> LENGTH: 495
<212> TYPE: PRT
<213> ORGANISM: Penicillium sp.
<220> FEATURE:
<221> NAME/KEY: misc_feature
<222> LOCATION: (1)..(495)
<223> OTHER INFORMATION: Endoglucanase

<400> SEQUENCE: 33

Met Ala Thr Arg Pro Leu Ala Phe Ala Ala Ile Ala Ala Leu Ile His
1               5                   10                  15

Gln Ala Ala Ser Gln Gln Ala Pro Thr Pro Asp Asn Leu Ala Ser Leu
            20                  25                  30

Pro Thr Trp Lys Cys Thr Thr Ser Gly Gly Cys Val Gln Gln Ser Thr
        35                  40                  45

Ser Ile Val Val Asp Trp Val Tyr His Trp Ile His Thr Val Asn Gly
    50                  55                  60

Ser Thr Ser Cys Thr Thr Ser Ser Gly Leu Asp Ser Thr Leu Cys Gly
65                  70                  75                  80

Thr Glu Glu Glu Cys Tyr Thr Asn Cys Glu Ile Ser Pro Ala Thr Tyr
                85                  90                  95

Asp Gly Leu Gly Ile Lys Thr Ser Gly Asn Ala Leu Thr Leu Asn Gln
            100                 105                 110
```

```
Tyr Val Thr Ser Asn Gly Thr Thr Ser Asn Ala Ser Pro Arg Val Tyr
            115                 120                 125

Leu Leu Asp Pro Ala Gly Lys Asn Tyr Glu Met Leu Gln Leu Leu Gly
    130                 135                 140

Gln Glu Ile Ser Phe Asp Val Asp Ala Ser Asn Leu Pro Cys Gly Glu
145                 150                 155                 160

Asn Gly Ala Leu Tyr Leu Ser Glu Met Asp Ala Thr Gly Gly Arg Ser
                165                 170                 175

Gln Tyr Asn Pro Ala Gly Ala Ser Tyr Gly Ser Gly Tyr Cys Asp Ala
            180                 185                 190

Gln Cys Gly Ser Ser Ser Trp Phe Asn Gly Ser Ile Asn Ser Ala Gly
    195                 200                 205

Leu Gly Ser Cys Cys Asn Glu Met Asp Leu Trp Glu Ala Asn Gly Glu
210                 215                 220

Ala Thr Ala Leu Thr Pro His Pro Cys Ser Val Asp Gly Pro Tyr Gly
225                 230                 235                 240

Cys Ser Gly Ser Ala Cys Gly Ser Thr Gly Val Cys Asp Lys Asn Gly
                245                 250                 255

Cys Gly Phe Asn Pro Tyr Ala Leu Gly Asp Gln Ser Tyr Tyr Gly Pro
            260                 265                 270

Gly Leu Thr Val Asp Thr Ser Lys Pro Phe Thr Val Thr Thr Gln Phe
    275                 280                 285

Val Thr Asn Asp Gly Thr Lys Thr Gly Thr Leu Thr Glu Ile Arg Arg
290                 295                 300

Ser Tyr Thr Gln Asn Gly Lys Val Ile Ala Asn Ala Val Ala Ser Ala
305                 310                 315                 320

Ser Ser Gly Phe Ser Gly Gln Ser Ser Ile Thr Glu Ser Phe Cys Thr
                325                 330                 335

Ala Met Asp Ser Glu Ala Gly Thr Leu Gly Gly Leu Thr Thr Met Gly
            340                 345                 350

Glu Ala Leu Gly Arg Gly Met Val Leu Ile Phe Ser Ile Trp Asn Asp
    355                 360                 365

Ala Gly Gly Tyr Met Asn Trp Leu Asp Ser Gly Ser Ser Gly Pro Cys
370                 375                 380

Ser Ser Thr Ala Gly Ile Pro Ser Thr Ile Gln Ala Asn Asp Pro Gly
385                 390                 395                 400

Thr Ser Val Thr Phe Ser Asn Ile Lys Trp Gly Asp Ile Gly Ser Thr
                405                 410                 415

Gly Ser Gly Thr Gly Ser Ser Ser Ser Ser Ser Thr Ser Thr
            420                 425                 430

Ser Pro Lys Thr Thr Ser Thr Thr Thr Ser Ala Thr Thr Lys Thr
    435                 440                 445

Ser Ala Thr Thr Thr Thr Ser Thr Gly Ala Thr Gln Thr His Tyr
450                 455                 460

Gly Gln Cys Gly Gly Met Ser Tyr Thr Gly Pro Thr Val Cys Ala Ser
465                 470                 475                 480

Pro Tyr Thr Cys Gln Val Gln Asn Pro Tyr Tyr Ser Gln Cys Leu
                485                 490                 495
```

<210> SEQ ID NO 34
<211> LENGTH: 249
<212> TYPE: PRT
<213> ORGANISM: H. jecorina GH61A

<400> SEQUENCE: 34

His Gly His Ile Asn Asp Ile Val Ile Asn Gly Val Trp Tyr Gln Ala
1               5                   10                  15

Tyr Asp Pro Thr Thr Phe Pro Tyr Glu Ser Asn Pro Ile Val Val
            20                  25                  30

Gly Trp Thr Ala Ala Asp Leu Asp Asn Gly Phe Val Ser Pro Asp Ala
            35                  40                  45

Tyr Gln Asn Pro Asp Ile Ile Cys His Lys Asn Ala Thr Asn Ala Lys
50                  55                  60

Gly His Ala Ser Val Lys Ala Gly Asp Thr Ile Leu Phe Gln Trp Val
65              70                  75                  80

Pro Val Pro Trp Pro His Pro Gly Pro Ile Val Asp Tyr Leu Ala Asn
            85                  90                  95

Cys Asn Gly Asp Cys Glu Thr Val Asp Lys Thr Thr Leu Glu Phe Phe
            100                 105                 110

Lys Ile Asp Gly Val Gly Leu Leu Ser Gly Gly Asp Pro Gly Thr Trp
            115                 120                 125

Ala Ser Asp Val Leu Ile Ser Asn Asn Asn Thr Trp Val Val Lys Ile
            130                 135                 140

Pro Asp Asn Leu Ala Pro Gly Asn Tyr Val Leu Arg His Glu Ile Ile
145                 150                 155                 160

Ala Leu His Ser Ala Gly Gln Ala Asn Gly Ala Gln Asn Tyr Pro Gln
            165                 170                 175

Cys Phe Asn Ile Ala Val Ser Gly Ser Gly Ser Leu Gln Pro Ser Gly
            180                 185                 190

Val Leu Gly Thr Asp Leu Tyr His Ala Thr Asp Pro Gly Val Leu Ile
            195                 200                 205

Asn Ile Tyr Thr Ser Pro Leu Asn Tyr Ile Ile Pro Gly Pro Thr Val
            210                 215                 220

Val Ser Gly Leu Pro Thr Ser Val Ala Gln Gly Ser Ser Ala Ala Thr
225                 230                 235                 240

Ala Thr Ala Ser Ala Thr Val Pro Gly
            245

<210> SEQ ID NO 35
<211> LENGTH: 249
<212> TYPE: PRT
<213> ORGANISM: Hypocrea rufa
<220> FEATURE:
<221> NAME/KEY: misc_feature
<222> LOCATION: (1)..(249)
<223> OTHER INFORMATION: Endoglucanase IV

<400> SEQUENCE: 35

His Gly His Ile Asn Asp Ile Val Ile Asn Gly Val Trp Tyr Gln Ala
1               5                   10                  15

Tyr Asp Pro Thr Thr Phe Pro Tyr Glu Ser Asn Pro Ile Val Val
            20                  25                  30

Gly Trp Thr Ala Ala Asp Leu Asp Asn Gly Phe Val Ser Pro Asp Ala
            35                  40                  45

Tyr Gln Asn Pro Asp Ile Ile Cys His Lys Asn Ala Thr Asn Ala Lys
50                  55                  60

Gly His Ala Ser Val Lys Ala Arg Asp Thr Ile Leu Phe Gln Trp Val
65              70                  75                  80

Pro Val Pro Trp Pro His Pro Gly Pro Ile Val Asp Tyr Leu Ala Asn
            85                  90                  95

```
Cys Asn Gly Asp Cys Glu Thr Val Asp Lys Thr Thr Leu Glu Phe Phe
            100                 105                 110

Lys Ile Asp Gly Val Gly Leu Leu Ser Gly Gly Asp Pro Gly Thr Trp
            115                 120                 125

Ala Ser Asp Val Leu Ile Ser Asn Asn Asn Thr Trp Val Val Lys Ile
        130                 135                 140

Pro Asp Asn Leu Ala Pro Gly Asn Tyr Val Leu Arg His Glu Ile Ile
145                 150                 155                 160

Ala Leu His Ser Ala Gly Gln Ala Asn Gly Ala Gln Asn Tyr Pro Gln
                165                 170                 175

Cys Phe Asn Ile Ala Val Ser Gly Ser Gly Ser Leu Gln Pro Ser Gly
            180                 185                 190

Val Leu Gly Thr Asp Leu Tyr His Ala Thr Asp Pro Gly Val Pro Ile
            195                 200                 205

Asn Ile Tyr Thr Ser Pro Leu Asn Tyr Ile Ile Pro Gly Pro Thr Val
            210                 215                 220

Val Ser Gly Leu Pro Thr Ser Val Ala Gln Gly Ser Ser Ala Ala Thr
225                 230                 235                 240

Ala Thr Ala Ser Ala Thr Ala Pro Gly
                245

<210> SEQ ID NO 36
<211> LENGTH: 249
<212> TYPE: PRT
<213> ORGANISM: Trichoderma saturnisporum
<220> FEATURE:
<221> NAME/KEY: misc_feature
<222> LOCATION: (1)..(249)
<223> OTHER INFORMATION: Type IV endoglucanase

<400> SEQUENCE: 36

His Gly His Ile Asn Asn Ile Val Ile Asn Gly Val Tyr Tyr Gln Ala
1               5                   10                  15

Tyr Asp Pro Thr Ser Phe Pro Tyr Glu Ser Asn Pro Ile Val Val
            20                  25                  30

Gly Trp Thr Ala Ala Asp Leu Asp Asn Gly Phe Val Ser Pro Asp Ala
            35                  40                  45

Tyr Gly Ser Pro Asp Ile Ile Cys His Lys Asn Ala Thr Asn Ala Lys
        50                  55                  60

Gly His Ala Ser Val Arg Ala Gly Asp Thr Val Leu Phe Gln Trp Val
65                  70                  75                  80

Pro Leu Pro Trp Pro His Pro Gly Pro Ile Val Asp Tyr Leu Ala Asn
                85                  90                  95

Cys Asn Gly Asp Cys Glu Thr Val Asp Lys Thr Ser Leu Glu Phe Phe
            100                 105                 110

Lys Ile Asp Gly Val Gly Leu Ile Ser Gly Gly Asp Pro Gly Asn Trp
            115                 120                 125

Ala Ser Asp Val Leu Ile Ala Asn Asn Asn Thr Trp Val Val Lys Ile
        130                 135                 140

Pro Asp Asp Leu Ala Pro Gly Asn Tyr Val Leu Arg His Glu Ile Ile
145                 150                 155                 160

Ala Leu His Ser Ala Gly Gln Ala Asn Gly Ala Gln Asn Tyr Pro Gln
                165                 170                 175

Cys Phe Asn Leu Ala Val Ser Gly Ser Gly Ser Leu Lys Pro Ser Gly
            180                 185                 190

Val Lys Gly Thr Ala Leu Tyr His Ala Thr Asp Pro Gly Val Leu Ile
```

```
                195                 200                 205
Asn Ile Tyr Thr Ser Pro Leu Asn Tyr Ile Ile Pro Gly Pro Thr Val
            210                 215                 220
Val Ser Gly Leu Pro Thr Ser Val Ala Gln Arg Ser Ser Ala Ala Thr
225                 230                 235                 240
Ala Thr Ala Ser Ala Thr Leu Pro Gly
                245
```

<210> SEQ ID NO 37
<211> LENGTH: 249
<212> TYPE: PRT
<213> ORGANISM: Hypocrea orientalis
<220> FEATURE:
<221> NAME/KEY: misc_feature
<222> LOCATION: (1)..(249)
<223> OTHER INFORMATION: Endoglucanase IV

<400> SEQUENCE: 37

```
His Gly His Ile Asn Asn Ile Val Val Asn Gly Val Tyr Tyr Gln Gly
1               5                   10                  15
Tyr Asp Pro Thr Ser Phe Pro Tyr Glu Ser Asp Pro Ile Val Val
                20                  25                  30
Gly Trp Thr Ala Ala Asp Leu Asp Asn Gly Phe Val Ser Pro Asp Ala
                35                  40                  45
Tyr Gln Ser Pro Asp Ile Ile Cys His Lys Asn Ala Thr Asn Ala Lys
            50                  55                  60
Gly His Ala Ser Val Lys Ala Gly Asp Thr Ile Leu Phe Gln Trp Val
65                  70                  75                  80
Pro Val Pro Trp Pro His Pro Gly Pro Ile Val Asp Tyr Leu Ala Asn
                85                  90                  95
Cys Asn Gly Asp Cys Glu Thr Val Asp Lys Thr Ser Leu Glu Phe Phe
                100                 105                 110
Lys Ile Asp Gly Val Gly Leu Ile Ser Gly Gly Asp Pro Gly Asn Trp
            115                 120                 125
Ala Ser Asp Val Leu Ile Ala Asn Asn Asn Thr Trp Val Val Lys Ile
130                 135                 140
Pro Glu Asp Leu Ala Pro Gly Asn Tyr Val Leu Arg His Glu Ile Ile
145                 150                 155                 160
Ala Leu His Ser Ala Gly Gln Ala Asp Gly Ala Gln Asn Tyr Pro Gln
                165                 170                 175
Cys Phe Asn Leu Ala Val Ser Gly Ser Gly Ser Leu Gln Pro Ser Gly
                180                 185                 190
Val Lys Gly Thr Ala Leu Tyr His Ser Asp Asp Pro Gly Val Leu Ile
            195                 200                 205
Asn Ile Tyr Thr Ser Pro Leu Ala Tyr Thr Ile Pro Gly Pro Ser Val
            210                 215                 220
Val Ser Gly Leu Pro Thr Ser Val Ala Gln Gly Ser Ser Ala Ala Thr
225                 230                 235                 240
Ala Thr Ala Ser Ala Thr Val Pro Gly
                245
```

<210> SEQ ID NO 38
<211> LENGTH: 249
<212> TYPE: PRT
<213> ORGANISM: Trichoderma sp.
<220> FEATURE:
<221> NAME/KEY: misc_feature
<222> LOCATION: (1)..(249)

<223> OTHER INFORMATION: Endoglucanase IV

<400> SEQUENCE: 38

```
His Gly His Ile Asn Asn Ile Val Val Asn Gly Val Tyr Tyr Gln Gly
  1               5                  10                  15
Tyr Asp Pro Thr Ser Phe Pro Tyr Glu Ser Asp Pro Ile Val Val
             20                  25                  30
Gly Trp Thr Ala Ala Asp Leu Asp Asn Gly Phe Val Ser Pro Asp Ala
             35                  40                  45
Tyr Gln Ser Pro Asp Ile Ile Cys His Lys Asn Ala Thr Asn Ala Lys
 50                  55                  60
Gly His Ala Ser Val Lys Ala Gly Asp Thr Ile Pro Leu Gln Trp Val
 65                  70                  75                  80
Pro Val Pro Trp Pro His Pro Gly Pro Ile Val Asp Tyr Leu Ala Asn
             85                  90                  95
Cys Asn Gly Asp Cys Glu Thr Val Asp Lys Thr Ser Leu Glu Phe Phe
                 100                 105                 110
Lys Ile Asp Gly Val Gly Leu Ile Ser Gly Gly Asp Pro Gly Asn Trp
                 115                 120                 125
Ala Ser Asp Val Leu Ile Ala Asn Asn Asn Thr Trp Val Val Lys Ile
             130                 135                 140
Pro Glu Asp Leu Ala Pro Gly Asn Tyr Val Leu Arg His Glu Ile Ile
145                 150                 155                 160
Ala Leu His Ser Ala Gly Gln Ala Asp Gly Ala Gln Asn Tyr Pro Gln
                 165                 170                 175
Cys Phe Asn Leu Ala Val Pro Gly Gly Ser Leu Gln Pro Ser Gly
                 180                 185                 190
Val Lys Gly Thr Ala Leu Tyr His Ser Asp Asp Pro Gly Val Leu Ile
             195                 200                 205
Asn Ile Tyr Thr Ser Pro Leu Ala Tyr Thr Ile Pro Gly Pro Ser Val
             210                 215                 220
Val Ser Gly Leu Pro Thr Ser Val Ala Gln Gly Ser Ser Ala Ala Thr
225                 230                 235                 240
Ala Thr Ala Ser Ala Thr Val Pro Gly
                 245
```

<210> SEQ ID NO 39
<211> LENGTH: 249
<212> TYPE: PRT
<213> ORGANISM: Hypocrea atroviridis
<220> FEATURE:
<221> NAME/KEY: misc_feature
<222> LOCATION: (1)..(249)
<223> OTHER INFORMATION: Glycoside hydrolase family 61 protein

<400> SEQUENCE: 39

```
His Gly His Val Asn Asn Ile Val Val Asn Gly Val Tyr Tyr Gln Gly
  1               5                  10                  15
Tyr Asp Pro Thr Ser Phe Pro Tyr Met Pro Asp Pro Ile Val Val
             20                  25                  30
Gly Trp Thr Ala Ala Asp Thr Asp Asn Gly Phe Val Ser Pro Asp Ala
             35                  40                  45
Tyr Gln Thr Pro Asp Ile Val Cys His Lys Asn Gly Thr Asn Ala Lys
 50                  55                  60
Gly His Ala Ser Val Lys Ala Gly Asp Ser Val Leu Phe Gln Trp Val
 65                  70                  75                  80
```

```
Pro Val Pro Trp Pro His Lys Ser Thr Val Asp Tyr Leu Ala Asn
                 85                  90                  95

Cys Asn Gly Pro Cys Glu Thr Val Asp Lys Thr Thr Leu Glu Phe Phe
            100                 105                 110

Lys Ile Asp Gly Ile Gly Leu Leu Ser Gly Gly Asn Pro Gly Thr Trp
            115                 120                 125

Gly Ser Asp Val Leu Ile Gly Asn Asn Thr Trp Val Ile Gln Ile
130                 135                 140

Pro Glu Asp Leu Gln Thr Gly Asn Tyr Val Leu Arg His Glu Leu Ile
145                 150                 155                 160

Ala Leu His Ser Ala Glu Gln Ala Asp Gly Ala Gln Asn Tyr Pro Gln
                165                 170                 175

Cys Phe Asn Leu Ala Val Thr Gly Thr Gly Ser Leu Gln Pro Ser Gly
                180                 185                 190

Val Leu Ala Thr Asp Leu Tyr His Glu Thr Asp Pro Gly Ile Leu Phe
                195                 200                 205

Asn Ile Tyr Thr Ser Pro Leu Thr Tyr Ile Ile Pro Gly Pro Thr Val
            210                 215                 220

Val Ser Gly Leu Pro Ser Ser Val Ala Gln Ala Ser Ser Ala Ala Thr
225                 230                 235                 240

Ala Thr Ser Ser Ala Thr Val Ser Gly
                245

<210> SEQ ID NO 40
<211> LENGTH: 249
<212> TYPE: PRT
<213> ORGANISM: Hypocrea virens
<220> FEATURE:
<221> NAME/KEY: misc_feature
<222> LOCATION: (1)..(249)
<223> OTHER INFORMATION: Glycoside hydrolase family 61 protein

<400> SEQUENCE: 40

His Gly His Val Asn Asn Ile Val Ile Asn Gly Ala Tyr Tyr Gln Gly
1               5                   10                  15

Tyr Asp Pro Thr Leu Phe Pro Tyr Glu Pro Asn Pro Ile Val Val
                20                  25                  30

Gly Trp Thr Ala Ser Asp Thr Asp Asn Gly Phe Val Ala Pro Asp Ala
            35                  40                  45

Tyr Gln Ser Pro Asp Ile Ile Cys His Arg Asn Ala Thr Asn Ala Arg
        50                  55                  60

Gly His Ala Ser Val Met Ala Gly Ser Ser Val Leu Ile Gln Trp Val
65                  70                  75                  80

Pro Ile Pro Trp Pro His Pro Gly Pro Val Leu Asp Tyr Leu Ala Asn
                85                  90                  95

Cys Asn Gly Asp Cys Glu Thr Val Asp Lys Thr Thr Leu Glu Phe Phe
            100                 105                 110

Lys Ile Asp Gly Ile Gly Leu Ile Ser Gly Asn Pro Gly Arg Trp
            115                 120                 125

Ala Ser Asp Val Leu Ile Gly Asn Asn Gly Thr Trp Val Val Gln Ile
130                 135                 140

Pro Ala Asp Leu Glu Thr Gly Asn Tyr Val Leu Arg His Glu Leu Ile
145                 150                 155                 160

Ala Leu His Ser Ala Gly Ser Val Asp Gly Ala Gln Asn Tyr Pro Gln
                165                 170                 175

Cys Phe Asn Leu Ala Val Thr Gly Thr Gly Ser Leu Gln Pro Thr Gly
```

```
                180               185               190
Val Leu Gly Thr Lys Leu Tyr Gln Glu Ser Asp Pro Gly Ile Leu Phe
            195                 200                 205

Asn Ile Tyr Thr Ser Pro Leu Thr Tyr Thr Ile Pro Gly Pro Thr Val
            210                 215                 220

Val Ser Gly Leu Pro Ser Ser Val Thr Gln Arg Ser Ser Thr Ala Thr
225                 230                 235                 240

Ala Thr Ser Ile Ala Thr Val Pro Gly
                245

<210> SEQ ID NO 41
<211> LENGTH: 250
<212> TYPE: PRT
<213> ORGANISM: Thielavia terrestris
<220> FEATURE:
<221> NAME/KEY: misc_feature
<222> LOCATION: (1)..(250)
<223> OTHER INFORMATION: Glycoside hydrolase family 61 protein

<400> SEQUENCE: 41

His Gly His Val Ser Asn Ile Val Ile Asn Gly Val Ser Tyr Gln Gly
1               5                   10                  15

Tyr Asp Pro Thr Ser Phe Pro Tyr Met Gln Asn Pro Pro Ile Val Val
            20                  25                  30

Gly Trp Thr Ala Ala Asp Thr Asp Asn Gly Phe Val Ala Pro Asp Ala
        35                  40                  45

Phe Ala Ser Gly Asp Ile Ile Cys His Lys Asn Ala Thr Asn Ala Lys
    50                  55                  60

Gly His Ala Val Val Ala Ala Gly Asp Lys Ile Phe Ile Gln Trp Asn
65                  70                  75                  80

Thr Trp Pro Glu Ser His His Gly Pro Val Ile Asp Tyr Leu Ala Ser
                85                  90                  95

Cys Gly Ser Ala Ser Cys Glu Thr Val Asp Lys Thr Lys Leu Glu Phe
            100                 105                 110

Phe Lys Ile Asp Glu Val Gly Leu Val Asp Gly Ser Ser Ala Pro Gly
        115                 120                 125

Val Trp Gly Ser Asp Gln Leu Ile Ala Asn Asn Asn Ser Trp Leu Val
    130                 135                 140

Glu Ile Pro Pro Thr Ile Ala Pro Gly Asn Tyr Val Leu Arg His Glu
145                 150                 155                 160

Ile Ile Ala Leu His Ser Ala Glu Asn Ala Asp Gly Ala Gln Asn Tyr
                165                 170                 175

Pro Gln Cys Phe Asn Leu Gln Ile Thr Gly Thr Gly Thr Ala Thr Pro
            180                 185                 190

Ser Gly Val Pro Gly Thr Ser Leu Tyr Thr Pro Thr Asp Pro Gly Ile
        195                 200                 205

Leu Val Asn Ile Tyr Ser Ala Pro Ile Thr Tyr Thr Val Pro Gly Pro
    210                 215                 220

Ala Leu Ile Ser Gly Ala Val Ser Ile Ala Gln Ser Ser Ser Ala Ile
225                 230                 235                 240

Thr Ala Ser Gly Thr Ala Leu Thr Gly Ser
                245                 250

<210> SEQ ID NO 42
<211> LENGTH: 246
<212> TYPE: PRT
<213> ORGANISM: Neurospora tetrasperma
```

```
<220> FEATURE:
<221> NAME/KEY: misc_feature
<222> LOCATION: (1)..(246)
<223> OTHER INFORMATION: Endoglucanase IV

<400> SEQUENCE: 42
```

| His | Gly | His | Val | Ser | Lys | Val | Ile | Val | Asn | Gly | Val | Glu | Tyr | Gln | Asn |
|---|---|---|---|---|---|---|---|---|---|---|---|---|---|---|---|
| 1 | | | | 5 | | | | | 10 | | | | | 15 | |

| Tyr | Asp | Pro | Thr | Ser | Phe | Pro | Tyr | Asn | Ser | Asn | Pro | Thr | Val | Ile |
|---|---|---|---|---|---|---|---|---|---|---|---|---|---|---|
| | | | 20 | | | | | 25 | | | | | 30 | |

| Gly | Trp | Thr | Ile | Asp | Gln | Lys | Asp | Asn | Gly | Phe | Val | Ser | Pro | Asp | Ala |
|---|---|---|---|---|---|---|---|---|---|---|---|---|---|---|---|
| | | | 35 | | | | | 40 | | | | | 45 | | |

| Phe | Asp | Ser | Gly | Asp | Ile | Ile | Cys | His | Lys | Ser | Ala | Thr | Pro | Ala | Gly |
|---|---|---|---|---|---|---|---|---|---|---|---|---|---|---|---|
| | 50 | | | | | 55 | | | | | 60 | | | | |

| Gly | His | Ala | Thr | Val | Lys | Ala | Gly | Asp | Lys | Ile | Ser | Leu | Gln | Trp | Asp |
|---|---|---|---|---|---|---|---|---|---|---|---|---|---|---|---|
| 65 | | | | | 70 | | | | | 75 | | | | | 80 |

| Gln | Trp | Pro | Glu | Ser | His | Lys | Gly | Pro | Val | Ile | Asp | Tyr | Leu | Ala | Ala |
|---|---|---|---|---|---|---|---|---|---|---|---|---|---|---|---|
| | | | | 85 | | | | | 90 | | | | | 95 | |

| Cys | Asp | Gly | Asp | Cys | Glu | Ser | Val | Asp | Lys | Thr | Ala | Leu | Lys | Phe | Phe |
|---|---|---|---|---|---|---|---|---|---|---|---|---|---|---|---|
| | | | 100 | | | | | 105 | | | | | 110 | | |

| Lys | Ile | Asp | Gly | Ala | Gly | Tyr | Asp | Ala | Thr | Asn | Gly | Trp | Ala | Ser | Asp |
|---|---|---|---|---|---|---|---|---|---|---|---|---|---|---|---|
| | | 115 | | | | | 120 | | | | | 125 | | | |

| Val | Leu | Ile | Lys | Asp | Gly | Asn | Ser | Trp | Val | Val | Glu | Ile | Pro | Glu | Asn |
|---|---|---|---|---|---|---|---|---|---|---|---|---|---|---|---|
| 130 | | | | | 135 | | | | | 140 | | | | | |

| Ile | Lys | Pro | Gly | Asn | Tyr | Val | Leu | Arg | His | Glu | Ile | Ile | Ala | Leu | His |
|---|---|---|---|---|---|---|---|---|---|---|---|---|---|---|---|
| 145 | | | | | 150 | | | | | 155 | | | | | 160 |

| Ser | Ala | Gly | Gln | Ala | Asn | Gly | Ala | Gln | Asn | Tyr | Pro | Gln | Cys | Phe | Asn |
|---|---|---|---|---|---|---|---|---|---|---|---|---|---|---|---|
| | | | | 165 | | | | | 170 | | | | | 175 | |

| Leu | Lys | Val | Glu | Gly | Ser | Gly | Ser | Thr | Val | Pro | Ala | Gly | Val | Ala | Gly |
|---|---|---|---|---|---|---|---|---|---|---|---|---|---|---|---|
| | | | 180 | | | | | 185 | | | | | 190 | | |

| Thr | Glu | Leu | Tyr | Lys | Ala | Thr | Asp | Ala | Gly | Ile | Leu | Phe | Asp | Ile | Tyr |
|---|---|---|---|---|---|---|---|---|---|---|---|---|---|---|---|
| | | 195 | | | | | 200 | | | | | 205 | | | |

| Lys | Asn | Asp | Ile | Ser | Tyr | Pro | Val | Pro | Gly | Pro | Ser | Leu | Ile | Ala | Gly |
|---|---|---|---|---|---|---|---|---|---|---|---|---|---|---|---|
| 210 | | | | | 215 | | | | | 220 | | | | | |

| Ala | Ser | Ser | Ser | Ile | Ala | Gln | Ser | Lys | Met | Ala | Ala | Thr | Ala | Thr | Ala |
|---|---|---|---|---|---|---|---|---|---|---|---|---|---|---|---|
| 225 | | | | | 230 | | | | | 235 | | | | | 240 |

| Ser | Ala | Thr | Leu | Pro | Gly |
|---|---|---|---|---|---|
| | | | | 245 | |

```
<210> SEQ ID NO 43
<211> LENGTH: 246
<212> TYPE: PRT
<213> ORGANISM: Neurospora tetrasperma
<220> FEATURE:
<221> NAME/KEY: misc_feature
<222> LOCATION: (1)..(246)
<223> OTHER INFORMATION: Cat Domain

<400> SEQUENCE: 43
```

| His | Gly | His | Val | Ser | Lys | Val | Ile | Val | Asn | Gly | Val | Glu | Tyr | Gln | Asn |
|---|---|---|---|---|---|---|---|---|---|---|---|---|---|---|---|
| 1 | | | | 5 | | | | | 10 | | | | | 15 | |

| Tyr | Asp | Pro | Thr | Ser | Phe | Pro | Tyr | Asn | Ser | Asn | Pro | Thr | Val | Ile |
|---|---|---|---|---|---|---|---|---|---|---|---|---|---|---|
| | | | 20 | | | | | 25 | | | | | 30 | |

| Gly | Trp | Thr | Ile | Asp | Gln | Lys | Asp | Asn | Gly | Phe | Val | Ser | Pro | Asp | Ala |
|---|---|---|---|---|---|---|---|---|---|---|---|---|---|---|---|
| | | | 35 | | | | | 40 | | | | | 45 | | |

| Phe | Asp | Ser | Gly | Asp | Ile | Ile | Cys | His | Lys | Ser | Ala | Thr | Pro | Ala | Gly |
|---|---|---|---|---|---|---|---|---|---|---|---|---|---|---|---|
| | 50 | | | | | 55 | | | | | 60 | | | | |

```
Gly His Ala Thr Val Lys Ala Gly Asp Lys Ile Ser Leu Gln Trp Asp
65                  70                  75                  80

Gln Trp Pro Glu Ser His Lys Gly Pro Val Ile Asp Tyr Leu Ala Ala
                85                  90                  95

Cys Asp Gly Asp Cys Glu Ser Val Asp Lys Thr Ala Leu Lys Phe Phe
                100                 105                 110

Lys Ile Asp Gly Ala Gly Tyr Asp Ala Thr Asn Gly Trp Ala Ser Asp
            115                 120                 125

Val Leu Ile Lys Asp Gly Asn Ser Trp Val Val Ile Pro Glu Asn
130                 135                 140

Ile Lys Pro Gly Asn Tyr Val Leu Arg His Glu Ile Ile Ala Leu His
145                 150                 155                 160

Ser Ala Gly Gln Ala Asn Gly Ala Gln Asn Tyr Pro Gln Cys Phe Asn
                165                 170                 175

Leu Lys Val Glu Gly Ser Gly Ser Thr Val Pro Ala Gly Val Ala Gly
                180                 185                 190

Thr Glu Leu Tyr Lys Ala Thr Asp Ala Gly Ile Leu Phe Asp Ile Tyr
            195                 200                 205

Lys Asn Asp Ile Ser Tyr Pro Val Pro Gly Pro Ser Leu Ile Ala Gly
210                 215                 220

Ala Ser Ser Ile Ala Gln Ser Lys Met Ala Ala Thr Ala Thr Ala
225                 230                 235                 240

Ser Ala Thr Leu Pro Gly
                245

<210> SEQ ID NO 44
<211> LENGTH: 250
<212> TYPE: PRT
<213> ORGANISM: Thielavia heterothallica
<220> FEATURE:
<221> NAME/KEY: misc_feature
<222> LOCATION: (1)..(250)
<223> OTHER INFORMATION: Glycoside hydrolase family 61 protein

<400> SEQUENCE: 44

His Gly His Val Thr Asn Ile Val Ile Asn Gly Val Ser Tyr Gln Asn
1               5                   10                  15

Phe Asp Pro Phe Thr His Pro Tyr Met Gln Asn Pro Pro Thr Val Val
            20                  25                  30

Gly Trp Thr Ala Ser Asn Thr Asp Asn Gly Phe Val Gly Pro Glu Ser
            35                  40                  45

Phe Ser Ser Pro Asp Ile Ile Cys His Lys Ser Ala Thr Asn Ala Gly
50                  55                  60

Gly His Ala Val Val Ala Ala Gly Asp Lys Val Phe Ile Gln Trp Asp
65                  70                  75                  80

Thr Trp Pro Glu Ser His His Gly Pro Val Ile Asp Tyr Leu Ala Asp
                85                  90                  95

Cys Gly Asp Ala Gly Cys Glu Lys Val Asp Lys Thr Thr Leu Lys Phe
                100                 105                 110

Phe Lys Ile Ser Glu Ser Gly Leu Leu Asp Gly Thr Asn Ala Pro Gly
            115                 120                 125

Lys Trp Ala Ser Asp Thr Leu Ile Ala Asn Asn Ser Trp Leu Val
130                 135                 140

Gln Ile Pro Pro Asn Ile Ala Pro Gly Asn Tyr Val Leu Arg His Glu
145                 150                 155                 160

Ile Ile Ala Leu His Ser Ala Gly Gln Gln Asn Gly Ala Gln Asn Tyr
```

```
                    165                 170                 175
Pro Gln Cys Phe Asn Leu Gln Val Thr Gly Ser Gly Thr Gln Lys Pro
            180                 185                 190

Ser Gly Val Leu Gly Thr Glu Leu Tyr Lys Ala Thr Asp Ala Gly Ile
        195                 200                 205

Leu Ala Asn Ile Tyr Thr Ser Pro Val Thr Tyr Gln Ile Pro Gly Pro
    210                 215                 220

Ala Ile Ile Ser Gly Ala Ser Ala Val Gln Gln Thr Thr Ser Ala Ile
225                 230                 235                 240

Thr Ala Ser Ala Ser Ala Ile Thr Gly Ser
                245                 250

<210> SEQ ID NO 45
<211> LENGTH: 246
<212> TYPE: PRT
<213> ORGANISM: Neurospora crassa
<220> FEATURE:
<221> NAME/KEY: misc_feature
<222> LOCATION: (1)..(246)
<223> OTHER INFORMATION: Endoglucanase IV

<400> SEQUENCE: 45

His Gly His Val Ser Lys Val Ile Val Asn Gly Val Glu Tyr Gln Asn
1               5                   10                  15

Tyr Asp Pro Thr Ser Phe Pro Tyr Asn Ser Asn Pro Pro Thr Val Ile
            20                  25                  30

Gly Trp Thr Ile Asp Gln Lys Asp Asn Gly Phe Val Ser Pro Asp Ala
        35                  40                  45

Phe Asp Ser Gly Asp Ile Ile Cys His Lys Ser Ala Lys Pro Ala Gly
    50                  55                  60

Gly His Ala Thr Val Lys Ala Gly Asp Lys Ile Ser Leu Gln Trp Asp
65                  70                  75                  80

Gln Trp Pro Glu Ser His Lys Gly Pro Val Ile Asp Tyr Leu Ala Ala
                85                  90                  95

Cys Asp Gly Asp Cys Glu Ser Val Asp Lys Thr Ala Leu Lys Phe Phe
            100                 105                 110

Lys Ile Asp Gly Ala Gly Tyr Asp Ala Thr Asn Gly Trp Ala Ser Asp
        115                 120                 125

Thr Leu Ile Lys Asp Gly Asn Ser Trp Val Val Glu Ile Pro Glu Ser
    130                 135                 140

Ile Lys Pro Gly Asn Tyr Val Leu Arg His Glu Ile Ile Ala Leu His
145                 150                 155                 160

Ser Ala Gly Gln Ala Asn Gly Ala Gln Asn Tyr Pro Gln Cys Phe Asn
                165                 170                 175

Leu Lys Val Glu Gly Ser Gly Ser Thr Val Pro Ala Gly Val Ala Gly
            180                 185                 190

Thr Glu Leu Tyr Lys Ala Thr Asp Ala Gly Ile Leu Phe Asp Ile Tyr
        195                 200                 205

Lys Asn Asp Ile Ser Tyr Pro Val Pro Gly Pro Ser Leu Ile Ala Gly
    210                 215                 220

Ala Ser Ser Ser Ile Ala Gln Ser Lys Met Ala Ala Thr Ala Thr Ala
225                 230                 235                 240

Ser Ala Thr Leu Pro Gly
                245

<210> SEQ ID NO 46
```

```
<211> LENGTH: 243
<212> TYPE: PRT
<213> ORGANISM: Sordaria macrospora
<220> FEATURE:
<221> NAME/KEY: misc_feature
<222> LOCATION: (1)..(243)
<223> OTHER INFORMATION: Cat Domain

<400> SEQUENCE: 46

His Gly His Val Ser Lys Val Ile Val Asn Gly Val Glu Tyr Gln Asn
1               5                   10                  15

Tyr Asp Pro Ala Val Phe Pro Tyr Leu Ser Asn Pro Pro Thr Val Ile
            20                  25                  30

Gly Trp Thr Ala Asp Gln Lys Asp Asn Gly Phe Val Ser Pro Asp Ala
        35                  40                  45

Phe Gly Thr Pro Asp Ile Ile Cys His Arg Ser Ala Thr Pro Ala Gly
    50                  55                  60

Gly His Ala Thr Val Lys Ala Gly Asp Lys Ile Ser Leu Lys Trp Asp
65                  70                  75                  80

Pro Val Trp Pro Asp Ser His Lys Gly Pro Val Ile Asp Tyr Leu Ala
                85                  90                  95

Ala Cys Asn Gly Asp Cys Glu Thr Val Asp Lys Thr Ser Leu Arg Phe
            100                 105                 110

Phe Lys Ile Asp Gly Ala Gly Tyr Asn Asn Gly Val Trp Ala Ala Asp
        115                 120                 125

Ala Leu Val Asn Asn Gly Asn Ser Trp Leu Val Gln Ile Pro Ala Asp
    130                 135                 140

Leu Lys Pro Gly Asn Tyr Val Leu Arg His Glu Ile Ile Ala Leu His
145                 150                 155                 160

Gly Ala Gly Ser Ala Asn Gly Ala Gln Ala Tyr Pro Gln Cys Phe Asn
                165                 170                 175

Leu Lys Val Glu Gly Ser Gly Asn Asn Leu Pro Ser Gly Val Pro Leu
            180                 185                 190

Tyr Lys Ala Thr Asp Ala Gly Ile Leu Phe Asn Met Tyr Gln Asn Asp
        195                 200                 205

Phe Thr Tyr Pro Val Pro Gly Pro Ala Leu Ile Ala Gly Ala Val Ser
    210                 215                 220

Ser Ile Pro Gln Ser Ser Ser Ala Ala Thr Thr Ala Ser Ala Thr
225                 230                 235                 240

Val Pro Gly

<210> SEQ ID NO 47
<211> LENGTH: 249
<212> TYPE: PRT
<213> ORGANISM: Gaeumannomyces graminis var. tritici
<220> FEATURE:
<221> NAME/KEY: misc_feature
<222> LOCATION: (1)..(249)
<223> OTHER INFORMATION: Endoglucanase IV

<400> SEQUENCE: 47

His Gly His Val Ser Asn Ile Val Val Asn Gly Val Phe Tyr Pro Gly
1               5                   10                  15

Tyr Asp Val Thr Lys Tyr Pro Trp Gln Pro Asn Ala Pro Thr Val Val
            20                  25                  30

Gly Trp Ser Ala Thr Asn Thr Asp Asn Gly Phe Val Glu Pro Asn Asn
        35                  40                  45

Phe Gly His Pro Asp Ile Ile Cys His Arg Gly Ala Gln Pro Ala Lys
```

```
                    50                  55                  60
Gly His Ala Arg Val Arg Ala Gly Asp Lys Ile Leu Gln Trp Asp
 65                  70                  75                  80

Thr Trp Pro Glu Ser His Lys Gly Pro Val Leu Asp Tyr Leu Ala Arg
                 85                  90                  95

Cys Pro Gly Asp Cys Glu Thr Val Asp Lys Thr Ala Leu Arg Phe Phe
            100                 105                 110

Lys Ile Gly Glu Gly Ser Tyr Ile Ser Gly Ala Ala Pro Gly His Trp
            115                 120                 125

Ala Ala Asp Val Leu Leu Gly Asn Gly Phe Ser Trp Val Val Gln Ile
        130                 135                 140

Pro Glu Asp Val Ala Pro Gly Asn Tyr Val Leu Arg His Glu Ile Ile
145                 150                 155                 160

Ala Leu His Gly Ser Pro Asn Pro Asn Gly Ala Gln Ala Tyr Pro Gln
                165                 170                 175

Cys Phe Asn Leu Glu Ile Ser Gly Ser Gly Ser Arg Gln Pro Ala Gly
            180                 185                 190

Val Ala Gly Thr Ser Leu Tyr Arg Ala Gly Asp Pro Gly Ile His Phe
            195                 200                 205

Pro Leu Tyr Asn Ser Pro Ile Val Tyr Pro Val Pro Gly Pro Ala Leu
        210                 215                 220

Ile Pro Gly Val Pro Ser Thr Val Ala Gln Val Ser Thr Arg Ala Thr
225                 230                 235                 240

Ala Thr Ser Ser Pro Phe Leu Pro Gly
                245
```

<210> SEQ ID NO 48
<211> LENGTH: 249
<212> TYPE: PRT
<213> ORGANISM: Nectria haematococca
<220> FEATURE:
<221> NAME/KEY: misc_feature
<222> LOCATION: (1)..(249)
<223> OTHER INFORMATION: Putative uncharacterized protein

<400> SEQUENCE: 48

```
His Gly His Val Thr Gln Val Ile Ile Asn Gly Val Ala Tyr Gly Gly
 1               5                  10                  15

Tyr Leu Ser Thr Ser Phe Pro Leu Gln Arg Lys Pro Pro Val Val Leu
                20                  25                  30

Gly Trp Thr Ile Glu Gln Arg Asp Asn Gly Phe Val Ser Pro Asp Lys
            35                  40                  45

Tyr Asp His Pro Asp Ile Ile Cys His Arg Asp Ala Thr Pro Ala Gln
 50                  55                  60

Gly His Val Gln Val Ala Gly Asp Thr Ile Thr Ile Lys Trp Ser
 65                  70                  75                  80

Ser Trp Pro Glu Asn His Arg Gly Pro Val Met Asp Tyr Leu Ala Asn
                85                  90                  95

Cys Asn Gly Pro Cys Glu Thr Val Asp Lys Thr Lys Leu Glu Phe Phe
            100                 105                 110

Lys Ile Asp Gly Met Gly Leu Ile Ser Gln Asp Arg Pro Gly Lys Tyr
            115                 120                 125

Ala Asp Gly Ala Leu Arg Glu Asn Gly Tyr Thr Trp Ser Val Arg Ile
        130                 135                 140

Pro Ser Asn Ile Ala Pro Gly Asn Tyr Val Leu Arg His Glu Ile Ile
145                 150                 155                 160
```

```
Ala Leu His Ser Gly Leu Glu Arg Asn Gly Ala Gln Asn Tyr Pro Gln
            165                 170                 175

Cys Phe Asn Leu Lys Ile Thr Gly Ser Gly Ser Asp Asn Pro Pro Gly
            180                 185                 190

Tyr Leu Gly Thr Glu Leu Tyr Asp Ala Asn Asp Pro Gly Ile Leu Val
            195                 200                 205

Asn Ile Tyr Gly Asn Leu Pro Asn Tyr Gln Val Pro Gly Pro Thr Ile
            210                 215                 220

Val Ser Gly Gly Val Ser Ser Val Arg Gln Ser Pro Ser Arg Ala Thr
225                 230                 235                 240

Thr Thr Ala Lys Cys Thr Thr Arg Ser
            245

<210> SEQ ID NO 49
<211> LENGTH: 249
<212> TYPE: PRT
<213> ORGANISM: Fusarium pseudograminearum
<220> FEATURE:
<221> NAME/KEY: misc_feature
<222> LOCATION: (1)..(249)
<223> OTHER INFORMATION: Cat Domain

<400> SEQUENCE: 49

His Gly His Val Asp Glu Ile Ile Val Asn Gly Val Ser Tyr Gln Gly
1               5                   10                  15

Tyr Gly Ser Thr Asp Phe Pro Tyr Met Gln Asp Pro Pro Val Val Ala
            20                  25                  30

Gly Trp Thr Ile Glu Gln Ala Asp Asn Gly Phe Val Ser Pro Asp Lys
            35                  40                  45

Tyr Asp Asp Pro Asp Ile Ile Cys His Arg Asp Ala Thr Pro Ala Lys
        50                  55                  60

Gly His Ile Glu Leu Ala Ala Gly Asp Thr Leu Thr Leu Arg Trp Ser
65                  70                  75                  80

Gly Trp Pro Glu Asn His Ser Gly Pro Ile Leu Asn Tyr Leu Ala Asn
            85                  90                  95

Cys Asn Gly Pro Cys Glu Arg Val Asp Lys Thr Lys Leu Glu Phe Phe
            100                 105                 110

Lys Ile Asp Gly Leu Gly Leu Leu Glu Gln Gly Thr Pro Gly Arg Tyr
            115                 120                 125

Ala Asp Lys Val Leu Gln Asp Asn Gly Asp Arg Trp Asn Val Arg Ile
            130                 135                 140

Pro Lys Asn Ile Ala Pro Gly Asn Tyr Val Leu Arg His Glu Ile Ile
145                 150                 155                 160

Ala Leu His Asn Ala Leu Asp Lys Gly Ala Gln Asn Tyr Pro Gln
            165                 170                 175

Cys Phe Asn Leu Lys Ile Thr Gly Asp Gly Ser Asp Ser Pro Ser Gly
            180                 185                 190

Tyr Leu Gly Thr Glu Leu Tyr Asp Ala Ala Asp Pro Gly Ile Leu Val
            195                 200                 205

Asn Val Tyr Ser Ser Ser Val Asp Tyr Glu Val Pro Gly Pro Thr Ile
            210                 215                 220

Cys Glu Gly Gly Val Ser Ser Val Glu Gln Lys Pro Ser Glu Ala Thr
225                 230                 235                 240

Thr Thr Ala Lys Cys Thr Thr Arg Tyr
            245
```

-continued

```
<210> SEQ ID NO 50
<211> LENGTH: 249
<212> TYPE: PRT
<213> ORGANISM: Gibberella zeae
<220> FEATURE:
<221> NAME/KEY: misc_feature
<222> LOCATION: (1)..(249)
<223> OTHER INFORMATION: Cat Domain

<400> SEQUENCE: 50

His Gly His Val Asp Glu Ile Ile Val Asn Gly Val Ser Tyr Gln Gly
1               5                   10                  15

Tyr Gly Ser Thr Asp Phe Pro Tyr Met Gln Asp Pro Pro Val Val Ala
            20                  25                  30

Gly Trp Thr Ile Glu Gln Ala Asp Asn Gly Phe Val Ser Pro Asp Lys
        35                  40                  45

Tyr Asp Asp Pro Asp Ile Ile Cys His Arg Asp Ala Thr Pro Ala Lys
    50                  55                  60

Gly His Ile Glu Leu Ala Ala Gly Asp Thr Leu Thr Leu Arg Trp Ser
65                  70                  75                  80

Gly Trp Pro Glu Asn His Ser Gly Pro Ile Leu Asn Tyr Leu Ala Asn
                85                  90                  95

Cys Asn Gly Pro Cys Glu Arg Val Asp Lys Thr Lys Leu Glu Phe Phe
            100                 105                 110

Lys Ile Asp Gly Leu Gly Leu Leu Glu Gln Gly Thr Pro Gly Arg Tyr
        115                 120                 125

Ala Asp Lys Val Leu Gln Asp Asn Gly Asp Arg Trp Asn Val Arg Ile
    130                 135                 140

Pro Lys Asn Ile Ala Pro Gly Asn Tyr Val Leu Arg His Glu Ile Ile
145                 150                 155                 160

Ala Leu His Asn Ala Leu Asp Lys Gly Gly Ala Gln Asn Tyr Pro Gln
                165                 170                 175

Cys Phe Asn Leu Lys Ile Thr Gly Asp Gly Ser Asp Ser Pro Ser Gly
            180                 185                 190

Tyr Leu Gly Thr Glu Leu Tyr Asp Ala Ala Asp Pro Gly Ile Leu Val
        195                 200                 205

Asn Val Tyr Ser Ser Ser Val Asp Tyr Glu Val Pro Gly Pro Thr Ile
    210                 215                 220

Cys Glu Gly Gly Val Ser Ser Val Glu Gln Lys Pro Ser Glu Ala Thr
225                 230                 235                 240

Thr Thr Ala Lys Cys Thr Thr Arg Tyr
                245

<210> SEQ ID NO 51
<211> LENGTH: 37
<212> TYPE: PRT
<213> ORGANISM: H. jecorina GH61A
<220> FEATURE:
<221> NAME/KEY: misc_feature
<222> LOCATION: (1)..(37)
<223> OTHER INFORMATION: Carb bind domain

<400> SEQUENCE: 51

Pro Thr Gln Thr Leu Tyr Gly Gln Cys Gly Gly Ser Gly Tyr Ser Gly
1               5                   10                  15

Pro Thr Arg Cys Ala Pro Pro Ala Thr Cys Ser Thr Leu Asn Pro Tyr
            20                  25                  30

Tyr Ala Gln Cys Leu
```

```
<210> SEQ ID NO 52
<211> LENGTH: 37
<212> TYPE: PRT
<213> ORGANISM: Hypocrea virens
<220> FEATURE:
<221> NAME/KEY: misc_feature
<222> LOCATION: (1)..(37)
<223> OTHER INFORMATION: Glycoside hydrolase family 61 protein

<400> SEQUENCE: 52

Pro Ser Gln Thr Leu Tyr Gly Gln Cys Gly Gly Ser Gly Tyr Ser Gly
1               5                   10                  15

Pro Thr Ile Cys Ala Ser Pro Ala Val Cys Ser Thr Leu Asn Pro Tyr
            20                  25                  30

Tyr Ala Gln Cys Leu
            35

<210> SEQ ID NO 53
<211> LENGTH: 37
<212> TYPE: PRT
<213> ORGANISM: Thielavia terrestris
<220> FEATURE:
<221> NAME/KEY: misc_feature
<222> LOCATION: (1)..(37)
<223> OTHER INFORMATION: Glycoside hydrolase family 28 protein

<400> SEQUENCE: 53

Gly Val Gln Ser Glu Tyr Gly Gln Cys Gly Gly Ser Gly Tyr Ser Gly
1               5                   10                  15

Pro Thr Ala Cys Ala Ala Pro Tyr Ala Cys Ser Thr Leu Asn Pro Tyr
            20                  25                  30

Tyr Ala Gln Cys Leu
            35

<210> SEQ ID NO 54
<211> LENGTH: 37
<212> TYPE: PRT
<213> ORGANISM: Hypocrea atroviridis
<220> FEATURE:
<221> NAME/KEY: misc_feature
<222> LOCATION: (1)..(37)
<223> OTHER INFORMATION: Glycoside hydrolase family 45 protein

<400> SEQUENCE: 54

Gly Thr Gln Ser Leu Tyr Gly Gln Cys Gly Gly Thr Gly Trp Ala Gly
1               5                   10                  15

Pro Thr Ala Cys Ala Pro Pro Ala Thr Cys Lys Val Leu Asn Gln Tyr
            20                  25                  30

Tyr Ser Gln Cys Leu
            35

<210> SEQ ID NO 55
<211> LENGTH: 37
<212> TYPE: PRT
<213> ORGANISM: Neosartorya fumigata
<220> FEATURE:
<221> NAME/KEY: misc_feature
<222> LOCATION: (1)..(37)
<223> OTHER INFORMATION: Endoglucanase, putative

<400> SEQUENCE: 55

Ala Thr Gln Thr Leu Tyr Gly Gln Cys Gly Gly Ser Gly Trp Thr Gly
1               5                   10                  15
```

```
Pro Thr Ala Cys Ala Ser Gly Ala Thr Cys Lys Val Leu Asn Pro Tyr
            20                  25                  30

Tyr Ser Gln Cys Leu
        35

<210> SEQ ID NO 56
<211> LENGTH: 37
<212> TYPE: PRT
<213> ORGANISM: Aspergillus terreus
<220> FEATURE:
<221> NAME/KEY: misc_feature
<222> LOCATION: (1)..(37)
<223> OTHER INFORMATION: Putative uncharacterized protein

<400> SEQUENCE: 56

Gly Ser Gln Thr Val Tyr Gly Gln Cys Gly Gly Thr Gly Trp Thr Gly
1               5                   10                  15

Pro Thr Ala Cys Val Ala Ser Ala Thr Cys Thr Thr Leu Asn Pro Tyr
            20                  25                  30

Tyr Ala Gln Cys Leu
        35

<210> SEQ ID NO 57
<211> LENGTH: 37
<212> TYPE: PRT
<213> ORGANISM: Hypocrea jecorina
<220> FEATURE:
<221> NAME/KEY: misc_feature
<222> LOCATION: (1)..(37)
<223> OTHER INFORMATION: Cip1 carb bind domain

<400> SEQUENCE: 57

Pro Thr Gln Thr His Tyr Gly Gln Cys Gly Gly Ile Gly Tyr Ser Gly
1               5                   10                  15

Pro Thr Val Cys Ala Ser Gly Thr Thr Cys Gln Val Leu Asn Pro Tyr
            20                  25                  30

Tyr Ser Gln Cys Leu
        35

<210> SEQ ID NO 58
<211> LENGTH: 37
<212> TYPE: PRT
<213> ORGANISM: Hypocrea rufa
<220> FEATURE:
<221> NAME/KEY: misc_feature
<222> LOCATION: (1)..(37)
<223> OTHER INFORMATION: Exoglucanase 1

<400> SEQUENCE: 58

Pro Thr Gln Thr His Tyr Gly Gln Cys Gly Gly Ile Gly Tyr Ser Gly
1               5                   10                  15

Pro Thr Val Cys Ala Ser Gly Ser Thr Cys Gln Val Leu Asn Pro Tyr
            20                  25                  30

Tyr Ser Gln Cys Leu
        35

<210> SEQ ID NO 59
<211> LENGTH: 37
<212> TYPE: PRT
<213> ORGANISM: Hypocrea virens
<220> FEATURE:
<221> NAME/KEY: misc_feature
<222> LOCATION: (1)..(37)
<223> OTHER INFORMATION: Glycoside hydrolase family 7 protein
```

```
<400> SEQUENCE: 59

Pro Thr Gln Thr His Tyr Gly Gln Cys Gly Gly Ile Gly Tyr Ser Gly
1               5                   10                  15

Pro Thr Gln Cys Val Ser Gly Thr Thr Cys Gln Val Leu Asn Pro Tyr
            20                  25                  30

Tyr Ser Gln Cys Leu
        35

<210> SEQ ID NO 60
<211> LENGTH: 37
<212> TYPE: PRT
<213> ORGANISM: Hypocrea atroviridis
<220> FEATURE:
<221> NAME/KEY: misc_feature
<222> LOCATION: (1)..(37)
<223> OTHER INFORMATION: Glycoside hydrolase family 5 protein

<400> SEQUENCE: 60

Gln Thr Gln Thr Val Trp Gly Gln Cys Gly Gly Gln Gly Tyr Ser Gly
1               5                   10                  15

Pro Thr Asn Cys Ala Ser Gly Ser Ala Cys Ser Thr Leu Asn Pro Tyr
            20                  25                  30

Tyr Ala Gln Cys Ile
        35

<210> SEQ ID NO 61
<211> LENGTH: 37
<212> TYPE: PRT
<213> ORGANISM: Neosartorya fischeri
<220> FEATURE:
<221> NAME/KEY: misc_feature
<222> LOCATION: (1)..(37)
<223> OTHER INFORMATION: Glycosyl hydrolase family 45 protein

<400> SEQUENCE: 61

Ala Thr Gln Thr Leu Tyr Gly Gln Cys Gly Gly Ser Gly Trp Thr Gly
1               5                   10                  15

Pro Thr Ala Cys Ala Ser Gly Ala Thr Cys Lys Val Leu Asn Ser Tyr
            20                  25                  30

Tyr Ser Gln Cys Leu
        35

<210> SEQ ID NO 62
<211> LENGTH: 37
<212> TYPE: PRT
<213> ORGANISM: Trichoderma koningii
<220> FEATURE:
<221> NAME/KEY: misc_feature
<222> LOCATION: (1)..(37)
<223> OTHER INFORMATION: Exoglucanase 1

<400> SEQUENCE: 62

Pro Thr Gln Ser His Tyr Gly Gln Cys Gly Gly Ile Gly Tyr Ser Gly
1               5                   10                  15

Pro Thr Val Cys Ala Ser Gly Thr Thr Cys Gln Val Leu Asn Pro Tyr
            20                  25                  30

Tyr Ser Gln Cys Leu
        35

<210> SEQ ID NO 63
<211> LENGTH: 36
<212> TYPE: PRT
```

-continued

<213> ORGANISM: Colletotrichum graminicola
<220> FEATURE:
<221> NAME/KEY: misc_feature
<222> LOCATION: (1)..(36)
<223> OTHER INFORMATION: Glycosyl hydrolase family 61

<400> SEQUENCE: 63

Pro Thr Gln Lys Met Tyr Gly Gln Cys Gly Gly Val Ala Tyr Met Gly
1               5                   10                  15
Pro Thr Gln Cys Pro Ala Tyr Ala Thr Cys Ser Thr Val Asn Pro Tyr
            20                  25                  30
Tyr Ala Gln Cys
        35

<210> SEQ ID NO 64
<211> LENGTH: 36
<212> TYPE: PRT
<213> ORGANISM: Colletotrichum graminicola
<220> FEATURE:
<221> NAME/KEY: misc_feature
<222> LOCATION: (1)..(36)
<223> OTHER INFORMATION: Glycosyl hydrolase family 61

<400> SEQUENCE: 64

Gln Pro Leu Tyr Gly Gln Cys Gly Gly Leu Asn Trp Pro Pro Glu Ser
1               5                   10                  15
Pro Thr Glu Cys Val Pro Gly Ala Arg Cys Ser Thr Ile Asn Pro Tyr
            20                  25                  30
Tyr Ala Gln Cys
        35

<210> SEQ ID NO 65
<211> LENGTH: 37
<212> TYPE: PRT
<213> ORGANISM: Arthrobotrys oligospora
<220> FEATURE:
<221> NAME/KEY: misc_feature
<222> LOCATION: (1)..(37)
<223> OTHER INFORMATION: Putative uncharacterized protein

<400> SEQUENCE: 65

Pro Leu Gln Ser Lys Trp Gly Gln Cys Gly Gly Val Gly Tyr Thr Gly
1               5                   10                  15
Ala Ser Val Cys Ser Pro Thr Ala Thr Cys Ser Thr Leu Asn Pro Tyr
            20                  25                  30
Tyr Ala Gln Cys Leu
        35

<210> SEQ ID NO 66
<211> LENGTH: 37
<212> TYPE: PRT
<213> ORGANISM: Trichoderma harzianum
<220> FEATURE:
<221> NAME/KEY: misc_feature
<222> LOCATION: (1)..(37)
<223> OTHER INFORMATION: Cellobiohydrolase

<400> SEQUENCE: 66

Ala Thr Gln Thr His Tyr Gly Gln Cys Gly Gly Thr Gly Trp Thr Gly
1               5                   10                  15
Pro Thr Arg Cys Ala Ser Gly Phe Thr Cys Gln Val Leu Asn Pro Phe
            20                  25                  30
Tyr Ser Gln Cys Leu
        35

<210> SEQ ID NO 67
<211> LENGTH: 37
<212> TYPE: PRT
<213> ORGANISM: Penicillium sp.
<220> FEATURE:
<221> NAME/KEY: misc_feature
<222> LOCATION: (1)..(37)
<223> OTHER INFORMATION: Endoglucanase

<400> SEQUENCE: 67

Ala Thr Gln Thr His Tyr Gly Gln Cys Gly Gly Met Ser Tyr Thr Gly
1               5                   10                  15

Pro Thr Val Cys Ala Ser Pro Tyr Thr Cys Gln Val Gln Asn Pro Tyr
            20                  25                  30

Tyr Ser Gln Cys Leu
        35

<210> SEQ ID NO 68
<211> LENGTH: 323
<212> TYPE: PRT
<213> ORGANISM: Hypocrea rufa
<220> FEATURE:
<221> NAME/KEY: misc_feature
<222> LOCATION: (1)..(323)
<223> OTHER INFORMATION: Endoglucanase IV

<400> SEQUENCE: 68

His Gly His Ile Asn Asp Ile Val Ile Asn Gly Val Trp Tyr Gln Ala
1               5                   10                  15

Tyr Asp Pro Thr Thr Phe Pro Tyr Glu Ser Asn Pro Pro Ile Val Val
            20                  25                  30

Gly Trp Thr Ala Ala Asp Leu Asp Asn Gly Phe Val Ser Pro Asp Ala
        35                  40                  45

Tyr Gln Asn Pro Asp Ile Ile Cys His Lys Asn Ala Thr Asn Ala Lys
    50                  55                  60

Gly His Ala Ser Val Lys Ala Arg Asp Thr Ile Leu Phe Gln Trp Val
65                  70                  75                  80

Pro Val Pro Trp Pro His Pro Gly Pro Ile Val Asp Tyr Leu Ala Asn
                85                  90                  95

Cys Asn Gly Asp Cys Glu Thr Val Asp Lys Thr Thr Leu Glu Phe Phe
            100                 105                 110

Lys Ile Asp Gly Val Gly Leu Leu Ser Gly Gly Asp Pro Gly Thr Trp
        115                 120                 125

Ala Ser Asp Val Leu Ile Ser Asn Asn Asn Thr Trp Val Val Lys Ile
    130                 135                 140

Pro Asp Asn Leu Ala Pro Gly Asn Tyr Val Leu Arg His Glu Ile Ile
145                 150                 155                 160

Ala Leu His Ser Ala Gly Gln Ala Asn Gly Ala Gln Asn Tyr Pro Gln
                165                 170                 175

Cys Phe Asn Ile Ala Val Ser Gly Ser Gly Ser Leu Gln Pro Ser Gly
            180                 185                 190

Val Leu Gly Thr Asp Leu Tyr His Ala Thr Asp Pro Gly Val Pro Ile
        195                 200                 205

Asn Ile Tyr Thr Ser Pro Leu Asn Tyr Ile Ile Pro Gly Pro Thr Val
    210                 215                 220

Val Ser Gly Leu Pro Thr Ser Val Ala Gln Gly Ser Ser Ala Ala Thr
225                 230                 235                 240

```
Ala Thr Ala Ser Ala Thr Ala Pro Gly Gly Ser Gly Pro Thr Ser
            245                 250                 255

Arg Thr Thr Thr Thr Ala Arg Thr Thr Gln Ala Ser Ser Arg Pro Ser
        260                 265                 270

Ser Thr Pro Pro Ala Thr Thr Ser Ala Pro Ala Gly Gly Pro Thr Gln
        275                 280                 285

Thr Leu Tyr Gly Gln Cys Gly Gly Ser Gly Tyr Ser Gly Pro Thr Arg
        290                 295                 300

Cys Ala Pro Pro Ala Thr Cys Ser Thr Leu Asn Pro Tyr Tyr Ala Gln
305                 310                 315                 320

Cys Leu Asn

<210> SEQ ID NO 69
<211> LENGTH: 325
<212> TYPE: PRT
<213> ORGANISM: Trichoderma saturnisporum
<220> FEATURE:
<221> NAME/KEY: misc_feature
<222> LOCATION: (1)..(325)
<223> OTHER INFORMATION: Type IV endoglucanase

<400> SEQUENCE: 69

His Gly His Ile Asn Asn Ile Val Ile Asn Gly Val Tyr Tyr Gln Ala
1               5                   10                  15

Tyr Asp Pro Thr Ser Phe Pro Tyr Glu Ser Asn Pro Pro Ile Val Val
            20                  25                  30

Gly Trp Thr Ala Ala Asp Leu Asp Asn Gly Phe Val Ser Pro Asp Ala
        35                  40                  45

Tyr Gly Ser Pro Asp Ile Ile Cys His Lys Asn Ala Thr Asn Ala Lys
    50                  55                  60

Gly His Ala Ser Val Arg Ala Gly Asp Thr Val Leu Phe Gln Trp Val
65                  70                  75                  80

Pro Leu Pro Trp Pro His Pro Gly Pro Ile Val Asp Tyr Leu Ala Asn
                85                  90                  95

Cys Asn Gly Asp Cys Glu Thr Val Asp Lys Thr Ser Leu Glu Phe Phe
            100                 105                 110

Lys Ile Asp Gly Val Gly Leu Ile Ser Gly Gly Asp Pro Gly Asn Trp
        115                 120                 125

Ala Ser Asp Val Leu Ile Ala Asn Asn Asn Thr Trp Val Val Lys Ile
    130                 135                 140

Pro Asp Asp Leu Ala Pro Gly Asn Tyr Val Leu Arg His Glu Ile Ile
145                 150                 155                 160

Ala Leu His Ser Ala Gly Gln Ala Asn Gly Ala Gln Asn Tyr Pro Gln
                165                 170                 175

Cys Phe Asn Leu Ala Val Ser Gly Ser Gly Ser Leu Lys Pro Ser Gly
            180                 185                 190

Val Lys Gly Thr Ala Leu Tyr His Ala Thr Asp Pro Gly Val Leu Ile
        195                 200                 205

Asn Ile Tyr Thr Ser Pro Leu Asn Tyr Ile Ile Pro Gly Pro Thr Val
    210                 215                 220

Val Ser Gly Leu Pro Thr Ser Val Ala Gln Arg Ser Ser Ala Ala Thr
225                 230                 235                 240

Ala Thr Ala Ser Ala Thr Leu Pro Gly Gly Gly Ser Pro Pro Gly
                245                 250                 255

Gly Pro Thr Ser Arg Pro Thr Thr Thr Ala Arg Ser Thr Ser Gln Ala
            260                 265                 270
```

```
Ser Ser Arg Pro Ser Pro Ala Thr Thr Ser Ala Pro Ala Gly Gly
        275                 280                 285

Pro Thr Gln Thr Leu Tyr Gly Gln Cys Gly Gly Ser Gly Tyr Ser Gly
290                 295                 300

Pro Thr Arg Cys Ala Pro Pro Ala Thr Val Ser Thr Leu Asn Pro Tyr
305                 310                 315                 320

Tyr Ala Arg Leu Asn
            325

<210> SEQ ID NO 70
<211> LENGTH: 326
<212> TYPE: PRT
<213> ORGANISM: Hypocrea orientalis
<220> FEATURE:
<221> NAME/KEY: misc_feature
<222> LOCATION: (1)..(326)
<223> OTHER INFORMATION: Endoglucanase IV

<400> SEQUENCE: 70

His Gly His Ile Asn Asn Ile Val Val Asn Gly Val Tyr Tyr Gln Gly
1               5                   10                  15

Tyr Asp Pro Thr Ser Phe Pro Tyr Glu Ser Asp Pro Pro Ile Val Val
                20                  25                  30

Gly Trp Thr Ala Ala Asp Leu Asp Asn Gly Phe Val Ser Pro Asp Ala
            35                  40                  45

Tyr Gln Ser Pro Asp Ile Ile Cys His Lys Asn Ala Thr Asn Ala Lys
    50                  55                  60

Gly His Ala Ser Val Lys Ala Gly Asp Thr Ile Leu Phe Gln Trp Val
65                  70                  75                  80

Pro Val Pro Trp Pro His Pro Gly Pro Ile Val Asp Tyr Leu Ala Asn
                85                  90                  95

Cys Asn Gly Asp Cys Glu Thr Val Asp Lys Thr Ser Leu Glu Phe Phe
            100                 105                 110

Lys Ile Asp Gly Val Gly Leu Ile Ser Gly Gly Asp Pro Gly Asn Trp
        115                 120                 125

Ala Ser Asp Val Leu Ile Ala Asn Asn Asn Thr Trp Val Val Lys Ile
    130                 135                 140

Pro Glu Asp Leu Ala Pro Gly Asn Tyr Val Leu Arg His Glu Ile Ile
145                 150                 155                 160

Ala Leu His Ser Ala Gly Gln Ala Asp Gly Ala Gln Asn Tyr Pro Gln
                165                 170                 175

Cys Phe Asn Leu Ala Val Ser Gly Gly Ser Leu Gln Pro Ser Gly
            180                 185                 190

Val Lys Gly Thr Ala Leu Tyr His Ser Asp Asp Pro Gly Val Leu Ile
        195                 200                 205

Asn Ile Tyr Thr Ser Pro Leu Ala Tyr Thr Ile Pro Gly Pro Ser Val
    210                 215                 220

Val Ser Gly Leu Pro Thr Ser Val Ala Gln Gly Ser Ser Ala Ala Thr
225                 230                 235                 240

Ala Thr Ala Ser Ala Thr Val Pro Gly Gly Ser Gly Pro Gly Asn Pro
                245                 250                 255

Thr Ser Lys Thr Thr Thr Thr Ala Arg Thr Thr Gln Ala Ser Ser Ser
            260                 265                 270

Arg Ala Ser Ser Thr Pro Pro Ala Thr Thr Ser Ala Pro Gly Gly Gly
        275                 280                 285
```

```
Pro Thr Gln Thr Leu Tyr Gly Gln Cys Gly Gly Ser Gly Tyr Ser Gly
        290                 295                 300

Pro Thr Arg Cys Ala Pro Pro Ala Thr Cys Ser Thr Leu Asn Pro Tyr
305                 310                 315                 320

Tyr Ala Gln Cys Leu Asn
                325

<210> SEQ ID NO 71
<211> LENGTH: 326
<212> TYPE: PRT
<213> ORGANISM: Trichoderma sp.
<220> FEATURE:
<221> NAME/KEY: misc_feature
<222> LOCATION: (1)..(326)
<223> OTHER INFORMATION: Endoglucanase IV

<400> SEQUENCE: 71

His Gly His Ile Asn Asn Ile Val Val Asn Gly Val Tyr Tyr Gln Gly
 1               5                  10                  15

Tyr Asp Pro Thr Ser Phe Pro Tyr Glu Ser Asp Pro Ile Val Val
             20                  25                  30

Gly Trp Thr Ala Ala Asp Leu Asp Asn Gly Phe Val Ser Pro Asp Ala
         35                  40                  45

Tyr Gln Ser Pro Asp Ile Ile Cys His Lys Asn Ala Thr Asn Ala Lys
     50                  55                  60

Gly His Ala Ser Val Lys Ala Gly Asp Thr Ile Pro Leu Gln Trp Val
 65                  70                  75                  80

Pro Val Pro Trp Pro His Pro Gly Pro Ile Val Asp Tyr Leu Ala Asn
                 85                  90                  95

Cys Asn Gly Asp Cys Glu Thr Val Asp Lys Thr Ser Leu Glu Phe Phe
            100                 105                 110

Lys Ile Asp Gly Val Gly Leu Ile Ser Gly Gly Asp Pro Gly Asn Trp
        115                 120                 125

Ala Ser Asp Val Leu Ile Ala Asn Asn Asn Thr Trp Val Val Lys Ile
    130                 135                 140

Pro Glu Asp Leu Ala Pro Gly Asn Tyr Val Leu Arg His Glu Ile Ile
145                 150                 155                 160

Ala Leu His Ser Ala Gly Gln Ala Asp Gly Ala Gln Asn Tyr Pro Gln
                165                 170                 175

Cys Phe Asn Leu Ala Val Pro Gly Ser Gly Ser Leu Gln Pro Ser Gly
            180                 185                 190

Val Lys Gly Thr Ala Leu Tyr His Ser Asp Asp Pro Gly Val Leu Ile
        195                 200                 205

Asn Ile Tyr Thr Ser Pro Leu Ala Tyr Thr Ile Pro Gly Pro Ser Val
    210                 215                 220

Val Ser Gly Leu Pro Thr Ser Val Ala Gln Gly Ser Ser Ala Ala Thr
225                 230                 235                 240

Ala Thr Ala Ser Ala Thr Val Pro Gly Gly Ser Pro Gly Asn Pro
                245                 250                 255

Thr Ser Lys Thr Thr Thr Thr Ala Arg Thr Thr Gln Ala Ser Ser Ser
            260                 265                 270

Arg Ala Ser Ser Thr Pro Pro Ala Thr Thr Ser Ala Pro Gly Gly Gly
        275                 280                 285

Pro Thr Gln Thr Leu Tyr Gly Gln Cys Gly Gly Ser Gly Tyr Ser Gly
    290                 295                 300

Pro Thr Arg Cys Ala Pro Pro Ala Thr Cys Ser Thr Leu Asn Pro Tyr
```

```
305                 310                 315                 320
Tyr Ala Gln Cys Leu Asn
                325

<210> SEQ ID NO 72
<211> LENGTH: 328
<212> TYPE: PRT
<213> ORGANISM: Hypocrea atroviridis
<220> FEATURE:
<221> NAME/KEY: misc_feature
<222> LOCATION: (1)..(328)
<223> OTHER INFORMATION: Glycoside hydrolase family 61 protein

<400> SEQUENCE: 72

His Gly His Val Asn Ile Val Val Asn Gly Val Tyr Tyr Gln Gly
1               5                   10                  15

Tyr Asp Pro Thr Ser Phe Pro Tyr Met Pro Asp Pro Ile Val Val
                20                  25                  30

Gly Trp Thr Ala Ala Asp Thr Asp Asn Gly Phe Val Ser Pro Asp Ala
                35                  40                  45

Tyr Gln Thr Pro Asp Ile Val Cys His Lys Asn Gly Thr Asn Ala Lys
        50                  55                  60

Gly His Ala Ser Val Lys Ala Gly Asp Ser Val Leu Phe Gln Trp Val
65                  70                  75                  80

Pro Val Pro Trp Pro His Lys Ser Thr Val Val Asp Tyr Leu Ala Asn
                85                  90                  95

Cys Asn Gly Pro Cys Glu Thr Val Asp Lys Thr Thr Leu Glu Phe Phe
                100                 105                 110

Lys Ile Asp Gly Ile Gly Leu Leu Ser Gly Gly Asn Pro Gly Thr Trp
        115                 120                 125

Gly Ser Asp Val Leu Ile Gly Asn Asn Asn Thr Trp Val Ile Gln Ile
        130                 135                 140

Pro Glu Asp Leu Gln Thr Gly Asn Tyr Val Leu Arg His Glu Leu Ile
145                 150                 155                 160

Ala Leu His Ser Ala Glu Gln Ala Asp Gly Ala Gln Asn Tyr Pro Gln
                165                 170                 175

Cys Phe Asn Leu Ala Val Thr Gly Thr Gly Ser Leu Gln Pro Ser Gly
                180                 185                 190

Val Leu Ala Thr Asp Leu Tyr His Glu Thr Asp Pro Gly Ile Leu Phe
        195                 200                 205

Asn Ile Tyr Thr Ser Pro Leu Thr Tyr Ile Ile Pro Gly Pro Thr Val
        210                 215                 220

Val Ser Gly Leu Pro Ser Ser Val Ala Gln Ala Ser Ser Ala Ala Thr
225                 230                 235                 240

Ala Thr Ser Ser Ala Thr Val Ser Gly Gly Gly Gly Ser Ser Thr
                245                 250                 255

Gly Gly Ser Thr Ser Lys Thr Thr Thr Val Val Arg Ser Thr Thr Ser
                260                 265                 270

Val Thr Ser Lys Ala Ser Ser Ser Thr Ala Val Thr Thr Pro Pro Pro
        275                 280                 285

Ala Gly Gly Thr Gln Thr Leu Tyr Gly Gln Cys Gly Gly Ser Gly Tyr
        290                 295                 300

Ser Gly Pro Thr Lys Cys Ala Ser Pro Ala Val Cys Thr Thr Leu Asn
305                 310                 315                 320

Pro Tyr Tyr Ala Gln Cys Leu Asn
                325
```

<210> SEQ ID NO 73
<211> LENGTH: 326
<212> TYPE: PRT
<213> ORGANISM: Hypocrea virens
<220> FEATURE:
<221> NAME/KEY: misc_feature
<222> LOCATION: (1)..(326)
<223> OTHER INFORMATION: Glycoside hydrolase family 61 protein

<400> SEQUENCE: 73

```
His Gly His Val Asn Asn Ile Val Ile Asn Gly Ala Tyr Tyr Gln Gly
1               5                   10                  15

Tyr Asp Pro Thr Leu Phe Pro Tyr Glu Pro Asn Pro Pro Ile Val Val
            20                  25                  30

Gly Trp Thr Ala Ser Asp Thr Asp Asn Gly Phe Val Ala Pro Asp Ala
        35                  40                  45

Tyr Gln Ser Pro Asp Ile Ile Cys His Arg Asn Ala Thr Asn Ala Arg
    50                  55                  60

Gly His Ala Ser Val Met Ala Gly Ser Ser Val Leu Ile Gln Trp Val
65                  70                  75                  80

Pro Ile Pro Trp Pro His Pro Gly Pro Val Leu Asp Tyr Leu Ala Asn
                85                  90                  95

Cys Asn Gly Asp Cys Glu Thr Val Asp Lys Thr Thr Leu Glu Phe Phe
            100                 105                 110

Lys Ile Asp Gly Ile Gly Leu Ile Ser Gly Gly Asn Pro Gly Arg Trp
        115                 120                 125

Ala Ser Asp Val Leu Ile Gly Asn Asn Gly Thr Trp Val Val Gln Ile
    130                 135                 140

Pro Ala Asp Leu Glu Thr Gly Asn Tyr Val Leu Arg His Glu Leu Ile
145                 150                 155                 160

Ala Leu His Ser Ala Gly Ser Val Asp Gly Ala Gln Asn Tyr Pro Gln
                165                 170                 175

Cys Phe Asn Leu Ala Val Thr Gly Thr Gly Ser Leu Gln Pro Thr Gly
            180                 185                 190

Val Leu Gly Thr Lys Leu Tyr Gln Glu Ser Asp Pro Gly Ile Leu Phe
        195                 200                 205

Asn Ile Tyr Thr Ser Pro Leu Thr Tyr Thr Ile Pro Gly Pro Thr Val
    210                 215                 220

Val Ser Gly Leu Pro Ser Ser Val Thr Gln Arg Ser Ser Thr Ala Thr
225                 230                 235                 240

Ala Thr Ser Ile Ala Thr Val Pro Gly Ser Val Ser Thr Gly Gly Thr
                245                 250                 255

Ser Ser Lys Thr Thr Thr Val Pro Arg Ser Thr Ser Ser Ala Thr Thr
            260                 265                 270

Arg Arg Ser Ser Ser Ser Ala Ile Thr Thr Ser Ala Pro Ala Gly Pro
        275                 280                 285

Ser Gln Thr Leu Tyr Gly Gln Cys Gly Gly Ser Gly Tyr Ser Gly Pro
    290                 295                 300

Thr Ile Cys Ala Ser Pro Ala Val Cys Ser Thr Leu Asn Pro Tyr Tyr
305                 310                 315                 320

Ala Gln Cys Leu Thr Arg
                325
```

<210> SEQ ID NO 74
<211> LENGTH: 347

```
<212> TYPE: PRT
<213> ORGANISM: Thielavia terrestris
<220> FEATURE:
<221> NAME/KEY: misc_feature
<222> LOCATION: (1)..(347)
<223> OTHER INFORMATION: Glycoside hydrolase family 61 protein

<400> SEQUENCE: 74

His Gly His Val Ser Asn Ile Val Ile Asn Gly Val Ser Tyr Gln Gly
1               5                   10                  15

Tyr Asp Pro Thr Ser Phe Pro Tyr Met Gln Asn Pro Ile Val Val
            20                  25                  30

Gly Trp Thr Ala Ala Asp Thr Asp Asn Gly Phe Val Ala Pro Asp Ala
            35                  40                  45

Phe Ala Ser Gly Asp Ile Ile Cys His Lys Asn Ala Thr Asn Ala Lys
50                  55                  60

Gly His Ala Val Val Ala Ala Gly Asp Lys Ile Phe Ile Gln Trp Asn
65                  70                  75                  80

Thr Trp Pro Glu Ser His His Gly Pro Val Ile Asp Tyr Leu Ala Ser
            85                  90                  95

Cys Gly Ser Ala Ser Cys Glu Thr Val Asp Lys Thr Lys Leu Glu Phe
            100                 105                 110

Phe Lys Ile Asp Glu Val Gly Leu Val Asp Gly Ser Ser Ala Pro Gly
        115                 120                 125

Val Trp Gly Ser Asp Gln Leu Ile Ala Asn Asn Asn Ser Trp Leu Val
130                 135                 140

Glu Ile Pro Pro Thr Ile Ala Pro Gly Asn Tyr Val Leu Arg His Glu
145                 150                 155                 160

Ile Ile Ala Leu His Ser Ala Glu Asn Ala Asp Gly Ala Gln Asn Tyr
                165                 170                 175

Pro Gln Cys Phe Asn Leu Gln Ile Thr Gly Thr Gly Thr Ala Thr Pro
            180                 185                 190

Ser Gly Val Pro Gly Thr Ser Leu Tyr Thr Pro Thr Asp Pro Gly Ile
            195                 200                 205

Leu Val Asn Ile Tyr Ser Ala Pro Ile Thr Tyr Thr Val Pro Gly Pro
210                 215                 220

Ala Leu Ile Ser Gly Ala Val Ser Ile Ala Gln Ser Ser Ala Ile
225                 230                 235                 240

Thr Ala Ser Gly Thr Ala Leu Thr Gly Ser Ala Thr Ala Pro Ala Ala
            245                 250                 255

Ala Ala Ala Thr Thr Thr Ser Thr Asn Ala Ala Ala Ala Thr
            260                 265                 270

Ser Ala Ala Ala Ala Gly Thr Ser Thr Thr Thr Ser Ala Ala
            275                 280                 285

Ala Val Val Gln Thr Ser Ser Ser Ser Ala Pro Ser Ser Ala
        290                 295                 300

Ala Ala Ala Ala Thr Thr Ala Ala Ala Ser Ala Arg Pro Thr Gly
305                 310                 315                 320

Cys Ser Ser Gly Arg Ser Arg Lys Gln Pro Arg Arg His Ala Arg Asp
            325                 330                 335

Met Val Val Ala Arg Gly Ala Glu Glu Ala Asn
            340                 345

<210> SEQ ID NO 75
<211> LENGTH: 336
<212> TYPE: PRT
```

-continued

```
<213> ORGANISM: Neurospora tetrasperma
<220> FEATURE:
<221> NAME/KEY: misc_feature
<222> LOCATION: (1)..(336)
<223> OTHER INFORMATION: Endoglucanase IV

<400> SEQUENCE: 75
```

| | | | | | | | | | | | | | | | |
|---|---|---|---|---|---|---|---|---|---|---|---|---|---|---|---|
| His | Gly | His | Val | Ser | Lys | Val | Ile | Val | Asn | Gly | Val | Glu | Tyr | Gln | Asn |
| 1 | | | | 5 | | | | | 10 | | | | | 15 | |
| Tyr | Asp | Pro | Thr | Ser | Phe | Pro | Tyr | Asn | Ser | Asn | Pro | Pro | Thr | Val | Ile |
| | | | 20 | | | | | 25 | | | | | 30 | | |
| Gly | Trp | Thr | Ile | Asp | Gln | Lys | Asp | Asn | Gly | Phe | Val | Ser | Pro | Asp | Ala |
| | | | 35 | | | | | 40 | | | | | 45 | | |
| Phe | Asp | Ser | Gly | Asp | Ile | Ile | Cys | His | Lys | Ser | Ala | Thr | Pro | Ala | Gly |
| 50 | | | | | 55 | | | | | 60 | | | | | |
| Gly | His | Ala | Thr | Val | Lys | Ala | Gly | Asp | Lys | Ile | Ser | Leu | Gln | Trp | Asp |
| 65 | | | | | 70 | | | | | 75 | | | | | 80 |
| Gln | Trp | Pro | Glu | Ser | His | Lys | Gly | Pro | Val | Ile | Asp | Tyr | Leu | Ala | Ala |
| | | | | 85 | | | | | 90 | | | | | 95 | |
| Cys | Asp | Gly | Asp | Cys | Glu | Ser | Val | Asp | Lys | Thr | Ala | Leu | Lys | Phe | Phe |
| | | | | 100 | | | | | 105 | | | | | 110 | |
| Lys | Ile | Asp | Gly | Ala | Gly | Tyr | Asp | Ala | Thr | Asn | Gly | Trp | Ala | Ser | Asp |
| | | | 115 | | | | | 120 | | | | | 125 | | |
| Val | Leu | Ile | Lys | Asp | Gly | Asn | Ser | Trp | Val | Val | Glu | Ile | Pro | Glu | Asn |
| | 130 | | | | | 135 | | | | | 140 | | | | |
| Ile | Lys | Pro | Gly | Asn | Tyr | Val | Leu | Arg | His | Glu | Ile | Ile | Ala | Leu | His |
| 145 | | | | | 150 | | | | | 155 | | | | | 160 |
| Ser | Ala | Gly | Gln | Ala | Asn | Gly | Ala | Gln | Asn | Tyr | Pro | Gln | Cys | Phe | Asn |
| | | | | 165 | | | | | 170 | | | | | 175 | |
| Leu | Lys | Val | Glu | Gly | Ser | Gly | Ser | Thr | Val | Pro | Ala | Gly | Val | Ala | Gly |
| | | | | 180 | | | | | 185 | | | | | 190 | |
| Thr | Glu | Leu | Tyr | Lys | Ala | Thr | Asp | Ala | Gly | Ile | Leu | Phe | Asp | Ile | Tyr |
| | | | 195 | | | | | 200 | | | | | 205 | | |
| Lys | Asn | Asp | Ile | Ser | Tyr | Pro | Val | Pro | Gly | Pro | Ser | Leu | Ile | Ala | Gly |
| 210 | | | | | 215 | | | | | 220 | | | | | |
| Ala | Ser | Ser | Ser | Ile | Ala | Gln | Ser | Lys | Met | Ala | Ala | Thr | Ala | Thr | Ala |
| 225 | | | | | 230 | | | | | 235 | | | | | 240 |
| Ser | Ala | Thr | Leu | Pro | Gly | Ala | Thr | Gly | Gly | Ser | Asn | Ser | Pro | Ala | Thr |
| | | | | 245 | | | | | 250 | | | | | 255 | |
| Ser | Ala | Ala | Ala | Ala | Pro | Ala | Pro | Ser | Thr | Thr | Leu | Val | Thr | Ser |  |
| | | | | 260 | | | | | 265 | | | | | 270 | |
| Thr | Lys | Ala | Ala | Ala | Pro | Ala | Thr | Ser | Ala | Ala | Pro | Ala | Ala | Pro | Ala |
| | | | 275 | | | | | 280 | | | | | 285 | | |
| Thr | Ser | Ala | Ala | Ala | Gly | Ser | Gly | Gln | Val | Gln | Ala | Lys | Gln | Thr | Lys |
| | | | 290 | | | | | 295 | | | | | 300 | | |
| Trp | Gly | Gln | Cys | Gly | Gly | Asn | Gly | Tyr | Thr | Gly | Ala | Thr | Glu | Cys | Glu |
| 305 | | | | | 310 | | | | | 315 | | | | | 320 |
| Ser | Gly | Ser | Thr | Cys | Thr | Lys | Tyr | Asn | Asp | Trp | Tyr | Ser | Gln | Cys | Val |
| | | | | 325 | | | | | 330 | | | | | 335 | |

```
<210> SEQ ID NO 76
<211> LENGTH: 336
<212> TYPE: PRT
<213> ORGANISM: Neurospora tetrasperma
<220> FEATURE:
<221> NAME/KEY: misc_feature
<222> LOCATION: (1)..(336)
```

<223> OTHER INFORMATION: Putative uncharacterized protein

<400> SEQUENCE: 76

```
His Gly His Val Ser Lys Val Ile Val Asn Gly Val Glu Tyr Gln Asn
1               5                   10                  15
Tyr Asp Pro Thr Ser Phe Pro Tyr Asn Ser Asn Pro Thr Val Ile
            20                  25                  30
Gly Trp Thr Ile Asp Gln Lys Asp Asn Gly Phe Val Ser Pro Asp Ala
                35                  40                  45
Phe Asp Ser Gly Asp Ile Ile Cys His Lys Ser Ala Thr Pro Ala Gly
    50                  55                  60
Gly His Ala Thr Val Lys Ala Gly Asp Lys Ile Ser Leu Gln Trp Asp
65                  70                  75                  80
Gln Trp Pro Glu Ser His Lys Gly Pro Val Ile Asp Tyr Leu Ala Ala
                85                  90                  95
Cys Asp Gly Asp Cys Glu Ser Val Asp Lys Thr Ala Leu Lys Phe Phe
            100                 105                 110
Lys Ile Asp Gly Ala Gly Tyr Asp Ala Thr Asn Gly Trp Ala Ser Asp
        115                 120                 125
Val Leu Ile Lys Asp Gly Asn Ser Trp Val Val Glu Ile Pro Glu Asn
130                 135                 140
Ile Lys Pro Gly Asn Tyr Val Leu Arg His Glu Ile Ala Leu His
145                 150                 155                 160
Ser Ala Gly Gln Ala Asn Gly Ala Gln Asn Tyr Pro Gln Cys Phe Asn
                165                 170                 175
Leu Lys Val Glu Gly Ser Gly Ser Thr Val Pro Ala Gly Val Ala Gly
            180                 185                 190
Thr Glu Leu Tyr Lys Ala Thr Asp Ala Gly Ile Leu Phe Asp Ile Tyr
        195                 200                 205
Lys Asn Asp Ile Ser Tyr Pro Val Pro Gly Pro Ser Leu Ile Ala Gly
210                 215                 220
Ala Ser Ser Ser Ile Ala Gln Ser Lys Met Ala Ala Thr Ala Thr Ala
225                 230                 235                 240
Ser Ala Thr Leu Pro Gly Ala Thr Gly Gly Ser Asn Ser Pro Ala Thr
                245                 250                 255
Ser Ala Ala Ala Ala Pro Ala Pro Ser Thr Thr Leu Val Thr Ser
            260                 265                 270
Thr Lys Ala Ala Ala Pro Ala Thr Ser Ala Ala Pro Ala Ala Pro Ala
        275                 280                 285
Thr Ser Ala Ala Ala Gly Ser Gly Gln Val Gln Ala Lys Gln Thr Lys
290                 295                 300
Trp Gly Gln Cys Gly Gly Asn Gly Tyr Thr Gly Ala Thr Glu Cys Glu
305                 310                 315                 320
Ser Gly Ser Thr Cys Thr Lys Tyr Asn Asp Trp Tyr Ser Gln Cys Val
                325                 330                 335
```

<210> SEQ ID NO 77
<211> LENGTH: 319
<212> TYPE: PRT
<213> ORGANISM: Thielavia heterothallica
<220> FEATURE:
<221> NAME/KEY: misc_feature
<222> LOCATION: (1)..(319)
<223> OTHER INFORMATION: Glycoside hydrolase family 61 protein

<400> SEQUENCE: 77

His Gly His Val Thr Asn Ile Val Ile Asn Gly Val Ser Tyr Gln Asn
1               5                   10                  15

Phe Asp Pro Phe Thr His Pro Tyr Met Gln Asn Pro Thr Val Val
            20                  25                  30

Gly Trp Thr Ala Ser Asn Thr Asp Asn Gly Phe Val Gly Pro Glu Ser
        35                  40                  45

Phe Ser Ser Pro Asp Ile Ile Cys His Lys Ser Ala Thr Asn Ala Gly
50                  55                  60

Gly His Ala Val Val Ala Gly Asp Lys Val Phe Ile Gln Trp Asp
65                  70                  75                  80

Thr Trp Pro Glu Ser His His Gly Pro Val Ile Asp Tyr Leu Ala Asp
            85                  90                  95

Cys Gly Asp Ala Gly Cys Glu Lys Val Asp Lys Thr Thr Leu Lys Phe
            100                 105                 110

Phe Lys Ile Ser Glu Ser Gly Leu Leu Asp Gly Thr Asn Ala Pro Gly
            115                 120                 125

Lys Trp Ala Ser Asp Thr Leu Ile Ala Asn Asn Ser Trp Leu Val
130                 135                 140

Gln Ile Pro Pro Asn Ile Ala Pro Gly Asn Tyr Val Leu Arg His Glu
145                 150                 155                 160

Ile Ile Ala Leu His Ser Ala Gly Gln Gln Asn Gly Ala Gln Asn Tyr
                165                 170                 175

Pro Gln Cys Phe Asn Leu Gln Val Thr Gly Ser Gly Thr Gln Lys Pro
            180                 185                 190

Ser Gly Val Leu Gly Thr Glu Leu Tyr Lys Ala Thr Asp Ala Gly Ile
            195                 200                 205

Leu Ala Asn Ile Tyr Thr Ser Pro Val Thr Tyr Gln Ile Pro Gly Pro
210                 215                 220

Ala Ile Ile Ser Gly Ala Ser Ala Val Gln Gln Thr Thr Ser Ala Ile
225                 230                 235                 240

Thr Ala Ser Ala Ser Ala Ile Thr Gly Ser Ala Thr Ala Ala Pro Thr
            245                 250                 255

Ala Ala Thr Thr Thr Ala Ala Ala Ala Thr Thr Thr Thr Thr Ala
            260                 265                 270

Gly Ser Arg Cys Tyr Arg His Ala Leu Asp Arg Arg Leu Ser Phe Phe
            275                 280                 285

Arg Pro Ala Cys Ser Tyr His Arg Cys Arg Tyr Leu Gln Pro Cys Ser
            290                 295                 300

Pro Asp Pro Leu Arg Trp Ser Glu Glu Ala Pro Ser Pro Arg Pro
305                 310                 315

<210> SEQ ID NO 78
<211> LENGTH: 351
<212> TYPE: PRT
<213> ORGANISM: Neurospora crassa
<220> FEATURE:
<221> NAME/KEY: misc_feature
<222> LOCATION: (1)..(351)
<223> OTHER INFORMATION: Endoglucanase IV

<400> SEQUENCE: 78

His Gly His Val Ser Lys Val Ile Val Asn Gly Val Glu Tyr Gln Asn
1               5                   10                  15

Tyr Asp Pro Thr Ser Phe Pro Tyr Asn Ser Asn Pro Thr Val Ile
            20                  25                  30

Gly Trp Thr Ile Asp Gln Lys Asp Asn Gly Phe Val Ser Pro Asp Ala

```
            35                  40                  45
Phe Asp Ser Gly Asp Ile Ile Cys His Lys Ser Ala Lys Pro Ala Gly
 50                  55                  60

Gly His Ala Thr Val Lys Ala Gly Asp Lys Ile Ser Leu Gln Trp Asp
 65                  70                  75                  80

Gln Trp Pro Glu Ser His Lys Gly Pro Val Ile Asp Tyr Leu Ala Ala
                 85                  90                  95

Cys Asp Gly Asp Cys Glu Ser Val Asp Lys Thr Ala Leu Lys Phe Phe
                100                 105                 110

Lys Ile Asp Gly Ala Gly Tyr Asp Ala Thr Asn Gly Trp Ala Ser Asp
            115                 120                 125

Thr Leu Ile Lys Asp Gly Asn Ser Trp Val Val Glu Ile Pro Glu Ser
130                 135                 140

Ile Lys Pro Gly Asn Tyr Val Leu Arg His Glu Ile Ile Ala Leu His
145                 150                 155                 160

Ser Ala Gly Gln Ala Asn Gly Ala Gln Asn Tyr Pro Gln Cys Phe Asn
                165                 170                 175

Leu Lys Val Glu Gly Ser Gly Ser Thr Val Pro Ala Gly Val Ala Gly
            180                 185                 190

Thr Glu Leu Tyr Lys Ala Thr Asp Ala Gly Ile Leu Phe Asp Ile Tyr
        195                 200                 205

Lys Asn Asp Ile Ser Tyr Pro Val Pro Gly Pro Ser Leu Ile Ala Gly
210                 215                 220

Ala Ser Ser Ser Ile Ala Gln Ser Lys Met Ala Ala Thr Ala Thr Ala
225                 230                 235                 240

Ser Ala Thr Leu Pro Gly Ala Thr Gly Gly Ser Asn Ser Pro Ala Thr
                245                 250                 255

Ser Ala Ala Ala Ala Pro Ala Thr Ser Ala Ala Ala Thr Ser
            260                 265                 270

Gln Val Gln Ala Ala Pro Ala Thr Thr Leu Val Thr Ser Thr Lys Ala
            275                 280                 285

Ala Ala Pro Ala Thr Ser Ala Ala Pro Ala Ala Pro Ala Thr Ser
290                 295                 300

Ala Ala Ala Gly Gly Ala Gly Gln Val Gln Ala Lys Gln Thr Lys Trp
305                 310                 315                 320

Gly Gln Cys Gly Gly Asn Gly Phe Thr Gly Pro Thr Glu Cys Glu Ser
                325                 330                 335

Gly Ser Thr Cys Thr Lys Tyr Asn Asp Trp Tyr Ser Gln Cys Val
            340                 345                 350

<210> SEQ ID NO 79
<211> LENGTH: 339
<212> TYPE: PRT
<213> ORGANISM: Gaeumannomyces graminis var. tritici
<220> FEATURE:
<221> NAME/KEY: misc_feature
<222> LOCATION: (1)..(339)
<223> OTHER INFORMATION: Endoglucanase IV

<400> SEQUENCE: 79

His Gly His Val Ser Asn Ile Val Asn Gly Val Phe Tyr Pro Gly
 1               5                  10                  15

Tyr Asp Val Thr Lys Tyr Pro Trp Gln Pro Asn Ala Pro Thr Val Val
                20                  25                  30

Gly Trp Ser Ala Thr Asn Thr Asp Asn Gly Phe Val Glu Pro Asn Asn
            35                  40                  45
```

```
Phe Gly His Pro Asp Ile Ile Cys His Arg Gly Ala Gln Pro Ala Lys
            50              55              60

Gly His Ala Arg Val Arg Ala Gly Asp Lys Ile Leu Leu Gln Trp Asp
 65              70              75                          80

Thr Trp Pro Glu Ser His Lys Gly Pro Val Leu Asp Tyr Leu Ala Arg
                 85              90                      95

Cys Pro Gly Asp Cys Glu Thr Val Asp Lys Thr Ala Leu Arg Phe Phe
             100             105             110

Lys Ile Gly Glu Gly Ser Tyr Ile Ser Gly Ala Ala Pro Gly His Trp
         115             120             125

Ala Ala Asp Val Leu Leu Gly Asn Gly Phe Ser Trp Val Val Gln Ile
         130             135             140

Pro Glu Asp Val Ala Pro Gly Asn Tyr Val Leu Arg His Glu Ile Ile
145             150             155                         160

Ala Leu His Gly Ser Pro Asn Pro Asn Gly Ala Gln Ala Tyr Pro Gln
                 165             170                 175

Cys Phe Asn Leu Glu Ile Ser Gly Ser Gly Ser Arg Gln Pro Ala Gly
             180             185             190

Val Ala Gly Thr Ser Leu Tyr Arg Ala Gly Asp Pro Gly Ile His Phe
         195             200             205

Pro Leu Tyr Asn Ser Pro Ile Val Tyr Pro Val Pro Gly Pro Ala Leu
        210             215             220

Ile Pro Gly Val Pro Ser Thr Val Ala Gln Val Ser Thr Arg Ala Thr
225             230             235                         240

Ala Thr Ser Ser Pro Phe Leu Pro Gly Gly Gly Gly Gly Gly Gly Gly
             245             250             255

Gly Gly Gly Gly Gly Asn Pro Gly Pro Thr Ser Ala Pro Gly Gly Gly
             260             265             270

Asn Gly Gly Gly Gly Gly Gly Gln Gln Pro Pro Gln Thr Thr Thr Ala
             275             280             285

Pro Gly Asn Gly Gly Gly Gly Gly Gly Gly Gly Gly Gly Gly Gly Gly
         290             295             300

Gly Gln Thr Arg Trp Gly Gln Cys Gly Gly Ser Gly Trp Asn Gly Pro
305             310             315                         320

Thr Ala Cys Ala Gln Gly Ala Cys Ser Thr Leu Asn Pro Tyr Tyr Ala
             325             330             335

Gln Cys Val
```